US012799204B2

(12) United States Patent
Luo et al.

(10) Patent No.: US 12,799,204 B2
(45) Date of Patent: Nov. 17, 2026

(54) METHODS FOR TREATING CANCER USING ANTI-CTLA4 ANTIBODIES

(71) Applicant: ADAGENE PTE. LTD., Singapore (SG)

(72) Inventors: Peter Peizhi Luo, Morgan Hill, CA (US); Guizhong Liu, Suzhou (CN); Hua Chang Gong, Suzhou (CN); Songmao Zheng, Suzhou (CN)

(73) Assignee: ADAGENE PTE. LTD., Singapore (SG)

( * ) Notice: Subject to any disclaimer, the term of this patent is extended or adjusted under 35 U.S.C. 154(b) by 492 days.

(21) Appl. No.: 18/553,043

(22) PCT Filed: Mar. 28, 2022

(86) PCT No.: PCT/US2022/022198

§ 371 (c)(1),
(2) Date: Sep. 28, 2023

(87) PCT Pub. No.: WO2022/212286

PCT Pub. Date: Oct. 6, 2022

(65) Prior Publication Data

US 2024/0209091 A1 Jun. 27, 2024

Related U.S. Application Data

(60) Provisional application No. 63/167,111, filed on Mar. 28, 2021.

(51) Int. Cl.
*C07K 16/28* (2006.01)
*A61P 35/04* (2006.01)
*G01N 33/569* (2006.01)

(52) U.S. Cl.
CPC .......... *C07K 16/2818* (2013.01); *A61P 35/04* (2018.01); *G01N 33/56972* (2013.01); *C07K 2317/21* (2013.01); *C07K 2317/24* (2013.01); *C07K 2317/92* (2013.01); *C07K 2317/94* (2013.01); *G01N 2333/705* (2013.01)

(58) Field of Classification Search
CPC .................................................. C07K 16/2818
See application file for complete search history.

(56) References Cited

U.S. PATENT DOCUMENTS

| | | | |
|---|---|---|---|
| 4,399,216 | A | 8/1983 | Axel et al. |
| 4,634,665 | A | 1/1987 | Axel et al. |
| 4,816,567 | A | 3/1989 | Cabilly et al. |
| 5,179,017 | A | 1/1993 | Axel et al. |
| 5,500,362 | A | 3/1996 | Robinson et al. |
| 5,648,237 | A | 7/1997 | Carter |
| 5,677,425 | A | 10/1997 | Axel et al. |
| 5,789,199 | A | 8/1998 | Joly et al. |
| 5,821,337 | A | 10/1998 | Carter et al. |
| 5,840,523 | A | 11/1998 | Simmons et al. |
| 5,959,177 | A | 9/1999 | Hein et al. |
| 5,994,619 | A | 11/1999 | Axel et al. |
| 6,040,498 | A | 3/2000 | Stomp et al. |
| 6,172,197 | B1 | 1/2001 | McCafferty et al. |
| 6,194,551 | B1 | 2/2001 | Idusogie et al. |
| 6,291,158 | B1 | 9/2001 | Bodmer et al. |
| 6,417,429 | B1 | 7/2002 | Hein et al. |
| 6,420,548 | B1 | 7/2002 | Vezina et al. |
| 6,582,915 | B1 | 6/2003 | Stice et al. |
| 6,593,081 | B1 | 7/2003 | McCafferty et al. |
| 6,737,056 | B1 | 5/2004 | Presta |
| 6,765,087 | B1 | 7/2004 | Casterman et al. |
| 7,332,582 | B2 | 2/2008 | Hardy et al. |
| 7,488,802 | B2 | 2/2009 | Collins et al. |
| 7,521,051 | B2 | 4/2009 | Collins et al. |
| 8,008,449 | B2 | 8/2011 | Korman et al. |
| 8,168,757 | B2 | 5/2012 | Finnefrock et al. |
| 8,354,509 | B2 | 1/2013 | Carven et al. |
| 8,383,796 | B2 | 2/2013 | Korman et al. |
| 8,609,089 | B2 | 12/2013 | Langermann et al. |
| 8,735,553 | B1 | 5/2014 | Li et al. |
| 9,683,048 | B2 | 6/2017 | Freeman et al. |
| 10,066,013 | B2 | 9/2018 | Chen et al. |
| 10,357,571 | B2 | 7/2019 | Williams et al. |

(Continued)

FOREIGN PATENT DOCUMENTS

| | | | |
|---|---|---|---|
| AU | 2013202755 | A1 | 5/2013 |
| AU | 2010203353 | B2 | 6/2016 |

(Continued)

OTHER PUBLICATIONS

Abhinandan et al., (2008). "Analysis and improvements to Kabat and structurally correct numbering of antibody variable domains," Mol Immunol, 45:3832-3839.
Adolf-Bryfogle et al., (2015). "PyIgClassify: a database of antibody CDR structural classifications," Nucleic Acids Res, 43:D432-D438.
Al-Lazikani et al., (1997). "Standard conformations for the canonical structures of immunoglobulins," J Mol. Biol., 273:927-948.
Andria et al., (1990). "Diverse VH and VL genes are used to produce antibodies against a defined protein epitope," J. Immunol., 144:2614-2619.
Chester et al., (2018). "Immunotherapy targeting 4-1 BB: mechanistic rationale, clinical results, and future strategies," Blood, 131(1):49-57.
Chichili et al., (2013). "Linkers in the structural biology of protein-protein interactions," Prot. Sci., 22:153-167.
Chothia et al., (1987). "Canonical structures for the hypervariable regions of immunoglobulins," J. Mol. Biol., 196:901-917.
Clynes et al., (1998). "Fc receptors are required in passive and active immunity to melanoma," PNAS (USA), 95:652-656.

(Continued)

*Primary Examiner* — Prema M Mertz
(74) *Attorney, Agent, or Firm* — Morrison & Foerster LLP

(57) ABSTRACT

The present application provides compositions and methods for treating cancers, including cancers that are resistant or refractory to an inhibitor of PD-1 or PD-L1, using an anti-CTLA4 antibody. Biomarkers such as CD8+ effector memory T ($T_{em}$) cells, CD4+ $T_{em}$ cells, regulatory T ($T_{reg}$) cells, and natural killer (NK) cell levels for the methods of treatment described herein are also provided.

20 Claims, 40 Drawing Sheets

Specification includes a Sequence Listing.

(56) References Cited

U.S. PATENT DOCUMENTS

| | | | | |
|---|---|---|---|---|
| 11,078,281 | B2 | 8/2021 | Wang et al. | |
| 11,242,395 | B2 | 2/2022 | Luo et al. | |
| 11,359,016 | B2 * | 6/2022 | Luo | A61K 45/06 |
| 11,692,036 | B2 * | 7/2023 | Luo | A61K 45/06 424/139.1 |
| 2006/0153808 | A1 | 7/2006 | Cristofanilli et al. | |
| 2007/0160619 | A1 | 7/2007 | Nichol et al. | |
| 2009/0304719 | A1 | 12/2009 | Daughtery et al. | |
| 2011/0271358 | A1 | 11/2011 | Freeman et al. | |
| 2015/0079109 | A1 | 3/2015 | Li et al. | |
| 2016/0258025 | A1 | 9/2016 | Klinger et al. | |
| 2016/0311903 | A1 | 10/2016 | West et al. | |
| 2018/0117147 | A1 | 5/2018 | Graziano et al. | |
| 2019/0169245 | A1 | 6/2019 | Williams et al. | |
| 2019/0241662 | A1 | 8/2019 | Luo et al. | |
| 2019/0241886 | A1 | 8/2019 | Luo et al. | |
| 2020/0123621 | A1 | 4/2020 | Bachireddy | |
| 2021/0020264 | A1 | 1/2021 | Stroh et al. | |
| 2021/0047409 | A1 | 2/2021 | Lala et al. | |
| 2021/0206855 | A1 | 7/2021 | Luo et al. | |
| 2021/0207126 | A1 | 7/2021 | Luo et al. | |
| 2022/0204637 | A1 | 6/2022 | Luo et al. | |
| 2024/0141046 | A1 | 5/2024 | Luo et al. | |
| 2024/0150749 | A1 | 5/2024 | Luo et al. | |
| 2024/0209092 | A1 | 6/2024 | Luo et al. | |
| 2025/0326847 | A1 | 10/2025 | Luo et al. | |

FOREIGN PATENT DOCUMENTS

| | | | |
|---|---|---|---|
| CN | 101146553 | A | 3/2008 |
| CN | 102482347 | A | 5/2012 |
| CN | 105296433 | A | 2/2016 |
| CN | 106163556 | A | 11/2016 |
| CN | 107840887 | A | 3/2018 |
| CN | 108271359 | A | 7/2018 |
| CN | 109963873 | A | 7/2019 |
| CN | 110546166 | A | 12/2019 |
| CN | 112352000 | A | 2/2021 |
| CN | 115768525 | A | 3/2023 |
| EP | 368684 | B1 | 3/1994 |
| EP | 338841 | A1 | 3/1995 |
| EP | 616640 | B1 | 9/2004 |
| JP | 2009518446 | A | 5/2009 |
| JP | 2010536370 | A | 12/2010 |
| JP | 2012514982 | A | 7/2012 |
| JP | 2015509952 | A | 4/2015 |
| JP | 2016538240 | A | 12/2016 |
| KR | 1020170036092 | A | 3/2017 |
| WO | WO-1987004462 | A1 | 7/1987 |
| WO | WO-1989001036 | A1 | 2/1989 |
| WO | WO-2002053596 | A2 | 7/2002 |
| WO | WO-2002055106 | A2 | 7/2002 |
| WO | WO-2003002609 | A2 | 1/2003 |
| WO | WO-2003015711 | A2 | 2/2003 |
| WO | WO-2003040170 | A2 | 5/2003 |
| WO | WO-2003048731 | A2 | 6/2003 |
| WO | WO-2003074678 | A2 | 9/2003 |
| WO | WO-2004004771 | A1 | 1/2004 |
| WO | WO-2004016805 | A2 | 2/2004 |
| WO | WO-2004056875 | A1 | 7/2004 |
| WO | WO-2004058821 | A2 | 7/2004 |
| WO | WO-2004072286 | A1 | 8/2004 |
| WO | WO-2004081026 | A2 | 9/2004 |
| WO | WO-2004101790 | A1 | 11/2004 |
| WO | WO-2006066568 | A2 | 6/2006 |
| WO | WO-2006079372 | A1 | 8/2006 |
| WO | WO-2006101692 | A1 | 9/2006 |
| WO | WO-2006121168 | A1 | 11/2006 |
| WO | WO-2006129163 | A1 | 12/2006 |
| WO | WO-2007005874 | A2 | 1/2007 |
| WO | WO-2007059782 | A1 | 5/2007 |
| WO | WO-2008156712 | A1 | 12/2008 |
| WO | WO-2009022215 | A1 | 2/2009 |
| WO | WO-2009025846 | A2 | 2/2009 |
| WO | WO-2009101611 | A1 | 8/2009 |
| WO | WO-2009114335 | A2 | 9/2009 |
| WO | WO-2010027827 | A2 | 3/2010 |
| WO | WO-2010077634 | A1 | 7/2010 |
| WO | WO-2011066342 | A2 | 6/2011 |
| WO | WO-2011066389 | A1 | 6/2011 |
| WO | WO-2013192550 | A2 | 12/2013 |
| WO | WO-2014179664 | A2 | 11/2014 |
| WO | WO-2014194302 | A2 | 12/2014 |
| WO | WO-2015085847 | A1 | 6/2015 |
| WO | WO-2015112800 | A1 | 7/2015 |
| WO | WO-2015112900 | A1 | 7/2015 |
| WO | WO-2016014974 | A2 | 1/2016 |
| WO | WO-2016118629 | A1 | 7/2016 |
| WO | WO-2016130898 | A2 | 8/2016 |
| WO | WO-2016179285 | A1 | 11/2016 |
| WO | WO-2016196237 | A1 | 12/2016 |
| WO | WO-2017106372 | A1 | 6/2017 |
| WO | WO-2017194265 | A1 | 11/2017 |
| WO | WO-2018202649 | A1 | 11/2018 |
| WO | WO-2018209701 | A1 | 11/2018 |
| WO | WO-2018213732 | A1 | 11/2018 |
| WO | WO-2019020774 | A2 | 1/2019 |
| WO | WO-2019036842 | A1 | 2/2019 |
| WO | WO-2019036855 | A1 | 2/2019 |
| WO | WO-2019036856 | A1 | 2/2019 |
| WO | WO-2019148444 | A1 | 8/2019 |
| WO | WO-2019149281 | A1 | 8/2019 |
| WO | WO-2019149282 | A1 | 8/2019 |
| WO | WO-2020139920 | A2 | 7/2020 |
| WO | WO-2020149026 | A1 | 7/2020 |
| WO | WO-2020198672 | A1 | 10/2020 |
| WO | WO-2021228178 | A1 | 11/2021 |
| WO | WO-2022171192 | A1 | 8/2022 |
| WO | WO-2022212286 | A1 | 10/2022 |
| WO | WO-2022218264 | A1 | 10/2022 |

OTHER PUBLICATIONS

Committee for Medicinal Products for Human Use (CHMP). Assessment Report For Yervoy (ipilirnumab). CHMP assessment report EMNCHMP/557664/2011. May 19, 2011(May 19, 2011) pp. 1-71.

Desnoyers et al., (2013). "Tumor-Specific Activation of an EGFR-Targeting Probody Enhances Therapeutic Index," Sci. Transl. Med., 5(207):e144, 25 pages.

Ehrenmann et al., (2010). "IMGT/3Dstructure-DB and IMGT/DomainGapAlign: a database and a tool for immunoglobulins or antibodies, T cell receptors, MHC, IgSF and MhcSF," Nucleic Acids Res., 38:D301-D307.

Extended European Search Report received for European Patent Application No. 19747798.7 mailed on Oct. 19, 2021, 10 pages.

Extended European Search Report received for European Patent Application No. 19748085.8 mailed on Jun. 1, 2022, 12 pages.

Ferrara et al., (2018). "Anti-CTLA-4 immunotherapy does not deplete FOXP3+ regulatory T cells (Tregs) in human cancers—Letter," Clin. Cancer Res, 25(11):3468.

Gazzano-Santoro et al., (1996). "A non-radioactive complement-dependent cytotoxicity assay for anti-CD20 monoclonal antibody," J. Immunol. Methods, 202:163-71.

Gerspach et al., (2006). "Target-selective activation of a TNF prodrug by urokinase-type plasminogen activator (uPA) mediated proteolytic processing at the cell surface," Cancer Immunol Immunother, 55(12):1590-1600.

Ha et al., (2019). "Differential control of human Treg and effector T cells in tumor immunity by Fc-engineered anti-CTLA-4 antibody," PNAS, 116(2):609-618.

He et al., (2017). "Remarkably similar CTLA-4 binding properties of therapeutic ipilimumab and tremelimumab antibodies," Oncotarget, 8:67129-67139.

Honegger et al., (2001)."Yet another numbering scheme for immunoglobulin variable domains: an automatic modeling and analysis tool," Mol Biol., 309:657-670.

Hurwitz et al., (1998). "CTLA-4 blockade synergizes with tumor-derived granulocyte-macrophage colony-stimulating factor for treatment of an experimental mammary carcinoma," Proc Natl Acad Sci USA 95 (17):10067-71.

(56) References Cited

OTHER PUBLICATIONS

Idusogie et al., (2000). "Mapping of the C1q binding site on rituxan, a chimeric antibody with a human IgG1 Fc," J. Immunol., 164:4178-4184.
International Search Report and Written Opinion of the International Searching Authority mailed Apr. 28, 2019, issued for PCT/CN2019/074580, filed Feb. 2, 2019, 15 pages.
International Search Report and Written Opinion of the International Searching Authority mailed May 8, 2019, issued for PCT/CN2019/074581, filed Feb. 2, 2019, 13 pages.
International Search Report and Written Opinion of the International Searching Authority mailed Nov. 6, 2018, issued for PCT/CN2018/075065, filed Feb. 2, 2018, 16 pages.
International Search Report and Written Opinion of the International Searching Authority mailed Nov. 7, 2018, issued for PCT/CN2018/075064, filed Feb. 2, 2018, 17 pages.
Jiang et al., (2004). "Tumor imaging by means of proteolytic activation of cell-penetrating peptides," Proc Natl Acad Sci USA, 101(51):17867-72.
Kabat et al., (1977). "Unusual distributions of amino acids in complementarity-determining (hypervariable) segments of heavy and light chains of immunoglobulins and their possible roles in specificity of antibody-combining sites," J. Biol. Chem., 252:6609-6616.
Ke et al., (1997). "Optimal Subsite Occupancy and Design of a Selective Inhibitor of Urokinase," J Biol Chem 272(33):20456-62.
Kranz et al., (1981). "Restricted reassociation of heavy and light chains from hapten-specific monoclonal antibodies," Proc. Natl. Acad. Sci. USA, 78(9):5807-5811.
Kwon et al., (1997). "Manipulation of T cell costimulatory and inhibitory signals for immunotherapy of prostate cancer," Proc Natl Acad Sci USA, 94(15):8099-103.
Lee et al., (2016). "Structural basis of checkpoint blockade by monoclonal antibodies in cancer immunotherapy," Nat Commun, 7(13354):1-10.
Lefranc et al., (2003). "IMGT unique numbering for immunoglobulin and T cell receptor variable domains and Ig superfamily V-like domains," Dev. Comp. Immu+B249nol., 27:55-77.
Lei et al., (1987). "Characterization of the Erwinia carotovora pelB gene and its product pectate lyase," J. Bacteriol., 169:4379-83.
Lin et al., (2011). "Improved affinity of a chicken single-chain antibody to avian infectious bronchitis virus by site-directed mutagenesis of complementarity-determining region H3," African Journal of Biotechnology, 10(79):18294-18302.
Mariuzza, (1987). "The Structural Basis Of Antigen-Antibody Recognition," Annu. Rev. Biophys. Biophys. Chem., 16:139-159.
McCarthy et al., (2001). "Altering the fine specificity of an anti-Legionella single chain antibody by a single amino acid insertion," J. Immunol. Methods, 251(1-2):137-149. Abstract only.
Palma et al., (2004). "CD137 and CD137 Ligand Constitutively Coexpressed On Human T And B Leukemia Cells Signal Proliferation And Survival," International Journal Of Cancer, 108:390-398.
Ramagopal et al., (2017). "Structural basis for cancer immunotherapy by the first-in-class checkpoint inhibitor ipilimumab," Proc Natl Acad Sci USA 114(21): 4223-4232.
Ravetch et al., (1991). "Fc receptors," Annu. Rev. Immunol., 9:457-92.
Ribas et al., (2007). "Tremelimumab (CP-675, 206), a Cytotoxic T 1-61 Lymphocyte-Associated Antigen 4 Blocking Monoclonal Antibody in Clinical Development for Patients with Cancer," The Oncologist, 12:873-883.
Schwartz et al., (2001). "Structural basis for co-stimulation by the human CTLA-4/B7-2 complex," Nature 410(6828): 604-608.
Sharma et al., (2019; epub 2018). "Anti-CTLA-4 Immunotherapy Does Not Deplete FOXP3+ Regulatory T Cells (Tregs) in Human Cancers," Clin. Cancer Res., 25:1233-1238.
Stamper et al., (2001). "Crystal structure of the B7-1/CTLA-4 complex that inhibits human immune responses," Nature 410(6828): 608-611.
Xu et al., (2012). "Preparation and characterization of a chimeric anti-human CTLA-4 monoclonal antibody," Current Immunology, 5(32):359-364. English Abstract Only.
Yang et al., (1997). "Enhanced induction of antitumor T-cell responses by cytotoxic T lymphocyte-associated molecule-4 blockade: the effect is manifested only at the restricted tumor-bearing stages," Cancer Res 57(18):4036-41.
Zhou et al., (2019). "Is protein context responsible for peptide-mediated interactions," Mol. Omics, 15:280-295.
ClinicalTrials.gov, (2021). "NCT04645069, Record History, ver 3," available online at <https://clinicaltrials.gov/study/NCT04645069?tab=history&a=3#version-content-panel>, 13 pages.
ClinicalTrials.org, (2020). "A Phase 1b/2 Study of ADG116, ADG116 Combined With Anti- PD-1 Antibody or Anti-CD137 Antibody in Solid Tumors Patients, NCT04501276," Available online at <https://clinicaltrials.gov/study/NCT04501276?term=NCT04501276&rank=1&tab=history&a=2#version-content-panel> obtained on May 21, 2021, 15 pages.
Extended European Search Report received for European Patent Application No. 22781974.5 mailed on Feb. 13, 2025, 11 pages.
Fairfax et al., (2020). "Peripheral CD8+ T cell characteristics associated with durable responses to immune checkpoint blockade in patients with metastatic melanoma," Nat Med, 26(2):193-199, 31 pages.
Hack et al., (2020). "Augmenting Anticancer Immunity Through Combined Targeting of Angiogenic and PD-1/PD-LI Pathways: Challenges and Opportunities," Frontiers In Immunology, 11:598877, 24 pages.
He et al., (2017). "Study on the mechanism of action of CTLA-4 therapeutic antibody Ipilimumab," Compilation of abstracts of the 12th National Immunology Academic Conference, pp. 322-323. English Abstract Only.
Ingram et al. (2018). "Anti-CTLA-4 therapy requires an Fc domain for efficacy," Proc Natl Acad Sci USA. 115(15):3912-3917.
International Search Report and Written Opinion received for International Patent Application No. PCT/US2022/022198 mailed on Jun. 24, 2022, 13 pages.
Jenkins et al., (2020). "Abstract 587: Tumor-Activated Fc-Engineered Anti-Ctla-4 Monoclonal Antibody, Xtxi0i, Demonstrates Tumor-Selective Pd And Efficacy In Preclinical Models," J Immunother Cancer, 8(3):A351.
Korman et al., (2017). "Abstract SY09-01: Next generation anti-CTLA-4 antibodies," Cancer Res, 77(13_Supplement):SY09-01, 2 pages.
Liu et al., (2019). "P788: Development of ADG116, a novel antagonist anti-CTLA-4 human antibody for cancer immunotherapy," Journal of Immuno Therapy of Cancer, 7(suppl 1):283, pp. 151-152.
Patnaik et al., (2021). "135P First-in-human phase I trial of SRF617, a potent inhibitor of CD39 activity, as monotherapy or in combination, in patients(pts) with advanced solid tumors," Annals Of Oncology, 32:S1435-S1436.
Perets et al., (2020). "Safety and efficacy of quavonlimab, a novel anti-CTLA-4 antibody (MK-1308), in combination with pembrolizumab in #rst-line advanced non-small-cell lung cancer," Annals of Oncology, 32(3):395-403.
Richardson et al., (2021). "137P Phase I dose-finding study of a novel anti-CTLA-4 antibody ADG116 as monotherapy in patients with advanced solid tumors," Annals of Oncology 32(7): S1436-S1437.
Sharma et al., (2015). "The future of immune checkpoint therapy," Science, 348(6230):56-61.
Simpson et al., (2013). "Fc-dependent depletion of tumor-infiltrating regulatory T cells co-defines the efficacy of anti-CTLA-4 therapy against melanoma," J Exp Med, 210(9):1695-1710.
Ternyila, (2020). "FDA Approves Every-6-Week Pembrolizurnab Dosage," available online <https://www.targetedonc.com/view/fda-approves-every-6-week-pembrolizumab-dosage>, 2 pages.
US Food & Drug Administration, (2020). "FDA approves new dosing regimen for pembrolizumab," available online at <https://www.fda.gov/drugs/resources-information-approved-drugs/fda-approves-new-dosing-regimen-pembrolizumab>, 2 pages.

(56) References Cited

OTHER PUBLICATIONS

Zimmer et al., (2017). "Ipilimumab alone or in combination with nivolumab after progression on anti-PD-1 therapy in advanced melanoma," Eur J Cancer, 75:47-55.
Ahmadzadeh et al., (2009). "Tumor antigen-specific CD8 T cells infiltrating the tumor express high levels of PD-1 and are functionally impaired," Blood, 114:1537-1544.
Angal et al., (1993). "A single amino acid substitution abolishes the heterogeneity of chimeric mouse/human (IgG4) antibody," Mol. Imunol., 30:105-108.
Clackson et al., (1991). "Making antibody fragments using phage display libraries," Nature, 352:624-628.
Clinicaltrials.org, (2025). "ADG126 in Combination With Pembrolizumab in Patients With Advanced/Metastatic Solid Tumors, NCT05405595," Available online at <https://www.clinicaltrials.gov/study/NCT05405595>, 18 pages.
Dong et al., (2002). "Tumor-associated B7-H1 promotes T-cell apoptosis: a potential mechanism of immune evasion," Nat Med., 8(8):793-800.
Gao et al., (2009). "Overexpression of PD-L1 significantly associates with tumor aggressiveness and postoperative recurrence in human hepatocellular carcinoma," Clinical Cancer Research, 15:971-979.
Ghebeh et al., (2006). "The B7-H1 (PD-L1) T lymphocyte-inhibitory molecule is expressed in breast cancer patients with infiltrating ductal carcinoma: correlation with important high-risk prognostic factors," Neoplasia, 8:190-198.
Ghebeh et al., (2008). "Foxp3+ Tregs and B7-H1+/PD-1+ T lymphocytes co-infiltrate the tumor tissues of high-risk breast cancer patients: implication for immunotherapy," BMC Cancer, 8:57, 12 pages.
Hamanishi et al., (2007). "Programmed cell death 1 ligand 1 and tumor-infiltrating Cds+ T lymphocytes are prognostic factors of human ovarian cancer," Proc. Natl. Acad. Sci. USA, 104:3360-3365.
Hino et al., (2010). "Tumor cell expression of programmed cell death-1 is a prognostic factor for malignant melanoma," Cancer, 116(7):1757-66.
Inman et al., (2007). "PD-L1 (B7-H1) expression by urothelial carcinoma of the bladder and ECG-induced granulomata: associations with localized stage progression," Cancer, 109:1499-1505.
Kumar et al., (2021). "Beyond the single average tumor: understanding IO combinations using a clinical QSP model that incorporates heterogeneity in patient response," CPT Pharmacomet Syst Pharmacol, 10:684-695.
Marks et al., (1991). "By-passing immunization. Human antibodies from V-gene libraries displayed on phage," J. Mol. Biol., 222:581-597.
Nakanishi et al., (2007). "Overexpression of B7-H1 (PD-L1) significantly associates with tumor grade and postoperative prognosis in human urothelial cancers," Cancer Immunol Immunother, 56:1173-1182.
Nomi et al., (2007). "Clinical significance and therapeutic potential of the programmed death-1 ligand/programmed death-1 pathway in human pancreatic cancer," Clinical Cancer Research, 13:2151-2157.
Ohigashi et al., (2005). "Clinical significance of programmed death-1 ligand-1 and programmed death-1 ligand-2 expression in human esophageal cancer," Clin. Cancer Research, 11:2947-2953.
Park et al., (2023). "Abstract 105: Fecal microbiota transplantation combined with anti-PD-1 inhibitor for unresectable or metastatic solid cancers refractory to anti-PD-1 inhibitor," Journal of Clinical Oncology, 41(16_suppl).
Presta, (2005). "Selection, design, and engineering of therapeutic antibodies," J. Allergy Clin. Immunol., 116:731-6.
Rowshanravan et al., (2018). "CTLA4: a moving target in immunotherapy," Blood, 131:58-67.
Schuurman et.al., (2001). "The inter-heavy chain disulfide bonds of IgG4 are in equilibrium with intra-chain disulfide bonds," Mol. Immunol., 38:1-8.
Sharpe et al., (2007). "The function of programmed cell death 1 and its ligands in regulating autoimmunity and infection," Nature Immunology, 8:239-245.
Shimauchi et al., (2007). "Augmented expression of programmed death-1 in both neoplasmatic and non-neoplastic CD4+ T-cells in adult T-cell Leukemia/ Lymphoma," Int. J. Cancer, 121:2585-2590.
Thompson et al., (2006). "Significance of B7-H1 overexpression in kidney cancer," Clinical genitourin Cancer, 5:206-211.
Thompson et al., (2007). "PD-1 is expressed by tumor infiltrating cells and is associated with poor outcome for patients with renal carcinoma," Clinical Cancer Research, 15:1757-1761.
WHO Drug Information, (2013). "International Nonproprietary Names for Pharmaceutical Substances (INN): Iambrolizumab," WHO Drug Information, 27(2):161-162.
WHO Drug Information, (2013). "International Nonproprietary Names for Pharmaceutical Substances (INN): nivolumab," WHO Drug Information, 27(1):68-69.
Wolchok et al., (2017). "Overall Survival with Combined Nivolumab and Ipilimumab in Advanced Melanoma," N Engl J Med, 377(14):1345-1356.
Yang et al., (2008). "PD-1 interaction contributes to the functional suppression of T-cell responses to human uveal melanoma cells in vitro," Invest Ophthalmol Vis Sci., 49(6):2518-2525.
Adagene, (Apr. 13, 2021). "Adagene Presents Preclinical Data from Lead SAFEbody™ Program, ADG126, at the American Association for Cancer Research (AACR) Annual Meeting 2021," available online at <https://investor.adagene.com/news-releases/news-release-details/adagene-presents-preclinical-data-lead-safebodytm-program-adg126/>, 2 pages.
Adagene, (Apr. 18, 2023). "Adagene Presents Clinical Data for Anti-CTLA-4 SAFEbody® ADG126 Reinforcing Best-in-Class Safety Profile at Repeat Doses and Showing Early Efficacy Profile in Advanced/Metastatic Solid Tumors," available online at <https://investor.adagene.com/news-releases/news-release-details/adagene-presents-clinical-data-anti-ctla-4-safebodyr-adg126/>, 2 pages.
Adagene, (Apr. 23, 2025). "Adagene Announces Upcoming Poster Presentation on Masked Anti-CTLA-4 SAFEbody® ADG126 (Muzastotug) at American Society of Clinical Oncology (ASCO) Annual Meeting," available online at <https://investor.adagene.com/node/8076/pdf>, 1 page.
Adagene, (Dec. 16, 2022). "Adagene Announces Clinical Trial Collaboration to Evaluate Anti-CTLA-4 SAFEbody@ ADG126 in Combination with Roche's Standard-of-Care for First-Line Advanced Liver Cancer," available online at <https://investor.adagene.com/news-releases/news-release-details/adagene-announces-clinical-trial-collaboration-evaluate-anti>, 2 pages.
Adagene, (Feb. 9, 2024). "Adagene Announces Progress and Expansion of Clinical Collaboration Program for Masked, Anti-CTLA-4 SAFEbody® ADG126 (muzastotug) in Combination with KEYTRUDA® (pembrolizumab) to Demonstrate Further Efficacy in Patients with Metastatic Microsatellite-stable (MSS) Colorectal Cancer (CRC)," available online at <https://investor.adagene.com/news-releases/news-release-details/adagene-announces-progress-and-expansion-clinical-collaboration/>, 2 pages.
Adagene, (Jan. 27, 2022). "Adagene Announces First Patient Dosed with Novel, Proprietary Combination of Anti-CD137 Agonist, ADG106, and Anti-CTLA-4 Monoclonal Antibody, ADG116," available online at <https://investor.adagene.com/news-releases/news-release-details/adagene-announces-first-patient-dosed-novel-proprietary/>, 2 pages.
Adagene, (Jan. 27, 2025). "Adagene Announces Updated Data from Phase 1b/2 Study of Muzastotug in Combination with KEYTRUDA® (pembrolizumab) in Colorectal Cancer at ASCO Gastrointestinal Cancers Symposium," available online at <https://investor.adagene.com/news-releases/news-release-details/adagene-announces-updated-data-phase-1b2-study-muzastotug/>, 2 pages.
Adagene, (Jan. 4, 2024). "Adagene To Present Interim Results of Masked anti-CTLA-4 SAFEbody® ADG126 (muzastotug) in Combination with Pembrolizumab in MSS CRC at ASCO-GI Symposium," available online at <https://www.theglobeandmail.com/investing/markets/stocks/ADAG/pressreleases/23112344/adagene-to-present-interim-results-of-masked-anti-ctla-4-safebody-adg126-muzastotug-in-combination-with-pembrolizumab-in-mss-crc-at-asco-gi-symposium/>, 1 page.

(56) References Cited

OTHER PUBLICATIONS

Adagene, (Jan. 9, 2023). "Adagene Announces Interim Data Demonstrating Safety and Confirmed Clinical Responses of Anti-CTLA-4 SAFEbody® ADG126 up to 10 mg/kg with Repeat Cycles in Combination with Anti-PD-1 Therapy from Dose Escalation Portion of Phase 1b/2 Trial," available online at <https://investor.adagene.com/news-releases/news-release-details/adagene-announces-interim-data-demonstrating-safety-and>, 1 page.
Adagene, (Janury 21, 2025). "Adagene to Announce Updated Data from Phase 1b/2 Study of Muzastotug in Combination with KEYTRUDA® (pembrolizumab) in Colorectal Cancer at ASCO Gastrointestinal Cancers Symposium," available online at <https://investor.adagene.com/news-releases/news-release-details/adagene-announce-updated-data-phase-1b2-study-muzastotug/>, 2 pages.
Adagene, (Jul. 12, 2024). "Adagene Announces Poster Presentation on Masked Anti-CTLA-4 SAFEbody® ADG126 (muzastotug) in Combination with Pembrolizumab in MSS CRC at Upcoming European Society for Medical Oncology (ESMO) Congress in September," available online at <https://investor.adagene.com/news-releases/news-release-details/adagene-announces-poster-presentation-masked-anti-ctla-4>, 1 page.
Adagene, (Jul. 22, 2021). "Adagene Announces Clinical Trial Collaboration With Merck to Advance Two Anti-CTLA-4 Monoclonal Antibody Programs (ADG116 and ADG126) in Combination Therapy with KEYTRUDA® (pembrolizumab)," available online at <https://investor.adagene.com/news-releases/news-release-details/adagene-announces-clinical-trial-collaboration-merck-advance-two>, 2 pages.
Adagene, (Mar. 14, 2023). "Adagene Announces Poster Presentations on Anti-CTLA-4 SAFEbody®, ADG126, at Upcoming American Association for Cancer Research (AACR) Annual Meeting in April," available online at <https://investor.adagene.com/news-releases/news-release-details/adagene-announces-poster-presentation-optimal-dose-selection/>, 1 page.
Adagene, (Mar. 16, 2022). "Adagene Announces FDA Clearance to Proceed with Phase 1b/2 Trial of Anti-CTLA-4 ADG126 SAFEbody@ in Combination Therapy With Anti-PD-1 Antibody Pembrolizumab," available online at <https://investor.adagene.com/news-releases/news-release-details/adagene-announces-fda-clearance-proceed-phase-1b2-trial-anti/>, 1 page.
Adagene, (Mar. 29, 2021). "Adagene Announces Clinical Advancement for ADG116," available online at <https://investor.adagene.com/news-releases/news-release-details/adagene-announces-clinical-advancement-adg116>, 2 pages.
Adagene, (May 22, 2025). "Adagene Announces Updated Data from Phase 1b/2 Study of Muzastotug (ADG126) in Combination with KEYTRUDA® (pembrolizumab) in Colorectal Cancer at the American Society of Clinical Oncology (ASCO) Annual Meeting," available online at <https://investor.adagene.com/news-releases/news-release-details/adagene-announces-updated-data-phase-1b2-study-muzastotug-adg126>, 2 pages.
Adagene, (Nov. 22, 2021). "Adagene Announces Poster Presentations of Clinical Data for Two Novel Antibody Programs at ESMO Immuno-Oncology Congress 2021," available online at <https://www.biospace.com/adagene-announces-poster-presentations-of-clinical-data-for-two-novel-antibody-programs-at-esmo-immuno-oncology-congress-2021>, 2 page.
Adagene, (Nov. 3, 2023). "Adagene Presents Data Demonstrating the Best-in-Class Therapeutic Index for Masked Anti-CTLA-4 SAFEbody® ADG126 at SITC 2023," available online at <https://investor.adagene.com/node/7591/pdf>, 2 pages.
Adagene, (Nov. 7, 2024). "Adagene Presents Two Posters with New Insights on Increased Therapeutic Index for Masked Anti-CTLA-4 SAFEbody® ADG126 (Muzastotug) and Data Reinforcing Clinical Safety and Efficacy for ADG126 as Monotherapy and in Combination with Anti-PD-1 Therapy at Society for Immunotherapy of Cancer (SITC) 39th Annual Meeting," available online at <https://investor.adagene.com/news-releases/news-release-details/adagene-presents-two-posters-new-insights-increased-therapeutic/>, 3 pages.
Adagene, (Oct. 11, 2022). "Adagene Announces Poster Presentations on Anti-CTLA-4 NEObody™, ADG116, at Upcoming Society for Immunotherapy of Cancer's (SITC) Annual Meeting in November," available online at <https://investor.adagene.com/news-releases/news-release-details/adagene-announces-poster-presentations-anti-ctla-4- neobodytm/>, 2 page.
Adagene, (Oct. 12, 2023). "Adagene Announces Poster Presentation on Optimal Dose Selection for Masked Anti-CTLA-4 SAFEbody® ADG126 at Upcoming Society for Immunotherapy of Cancer (SITC) 38th Annual Meeting," available online at <https://investor.adagene.com/news-releases/news-release-details/adagene-announces-poster-presentation-optimal-dose-selection/>, 1 page.
Adagene, (Oct. 9, 2024). "Adagene Announces Upcoming Poster Presentations on Masked Anti-CTLA-4 SAFEbody® ADG126 (Muzastotug) at Society for Immunotherapy of Cancer (SITC) 39th Annual Meeting," available online at <https://investor.adagene.com/news-releases/news-release-details/adagene-announces-upcoming-poster-presentations-masked-anti-ctla/>, 2 pages.
Adagene, (Sep. 10, 2022). "Adagene Presents Interim Monotherapy Data at ESMO 2022 Showing Compelling Safety, Anti-Tumor Activity and Pharmacokinetics of Masked, Anti-CTLA-4 SAFEbody® ADG126 in Patients with Advanced Tumors," available online at <https://investor.adagene.com/news-releases/news-release-details/adagene-presents-interim-monotherapy-data-esmo-2022-showing/>, 2 pages.
Adagene, (Sep. 16, 2024). "Adagene Presents Results at ESMO Congress that Show Best-in-Class Therapeutic Potential for Anti-CTLA-4 SAFEbody® ADG126 (Muzastotug) in Combination with KEYTRUDA® (Pembrolizumab) in Advanced/Metastatic Microsatellite-stable (MSS) Colorectal Cancer (CRC)," available online at <https://investor.adagene.com/news-releases/news-release-details/adagene-presents-results-esmo-congress-show-best-class-8>, 3 pages.
Adagene, (Sep. 5, 2025). "Adagene's ADG126 to be Highlighted in Two Presentations at the 2025 Chinese Society of Clinical Oncology (CSCO) Meeting in Jinan, China," available online at <https://investor.adagene.com/news-releases/news-release-details/adagenes-adg126-be-highlighted-two-presentations-2025-chinese>, 2 pages.
Ariyapperuma et al., (2023). "Poster: Interim Results of a Phase 1b/2 Study of ADG126 (a Masked anti-CTLA-4 SAFEbody®) Monotherapy and in Combination with Toripalimab (an anti-PD-1 Antibody) in Patients (pts) with Advanced / Metastatic Solid Tumors," AACR 2023, Abstract No. CT227, 1 page.
Fakih et al., (2026). "Poster: Ph1b evaluation of ADG126 (muzastotug, an anti-CTLA-4 masking antibody) pembrolizumab (Pembro) IO doublet in combination with fruquintinib (Fruq) in advanced and metastatic microsatellite stable colorectal cancer," AACR 2026, Abstract No. CT083, 1 page.
Li et al., (2023). "Poster CT233: Initial Results of a Phase 1b/2 Study of ADG126 (a Masked Anti CTLA 4 SAFEbody ®) in Combination with Pembrolizumab (an Anti PD 1 Antibody) in Patients with Advanced/Metastatic Solid Tumors," AACR 2023, 1 page.
Li et al., (2024). "Poster 127: Results of a Phase 1b/2 Study of ADG126 (a Masked Anti-CTLA-4 SAFEbody®) in Combination with Pembrolizumab (Pembro) in Patients with Metastatic Microsatellite-stable (MSS) Colorectal Cancer (CRC)," Asco Gi 2024, 1 page.
Li et al., (2024). "Poster 578P: Increased Therapeutic Index of Muzastotug (ADG126), a Masked Anti-CTLA-4 Antibody, in Combination with Pembrolizumab (Pembro) Enables Significant Clinical Benefits and Supports Further Clinical Development in Patients with Metastatic MSS CRC," ESMO 2024, Abstract No. 6055, 1 page.
Li et al., (2024). "Poster: Phase 1b/2, Multicenter Dose Escalation and Expansion Study of Muzastotug (ADG126, a Masked Anti-CTLA-4 SAFEbody®) in Combination with Pembrolizumab in Advanced/Metastatic MSS CRC," SITC 2024, Abstract No. 744, 1 page.
Li et al., (2025). "Poster 248: Safety and Efficacy of ADG126 (an Anti-CTLA-4 Masking Antibody) in Combination with Pembrolizumab: Updated Results of Phase 1b/2 Study in Advanced MSS CRC, "ASCO 2025, Abstract No. 3579, 1 page.

(56) References Cited

OTHER PUBLICATIONS

Li et al., (2025). "Poster: Update of Phase 1b/2 Study of Muzastotug (ADG126, an Anti-CTLA-4 SAFEbody®) in Combination with Pembrolizumab in Advanced/Metastatic MSS CRC," ASCO GI 2025, Abstract No. 129, 1 page.
Li et al., (2026). "Poster: Results from the phase 1b/2 Morpheus Liver study in patients with unresectable locally advanced or metastatic hepatocellular carcinoma (HCC): muzastotug (ADG126: masked anti-CTLA-4 Ab) combination arm," AACR 2026, Abstract No. CTO54, 1 page.
Li, (2025). "2025 ASCO Data Presentation: Safety and Efficacy of ADG126 (an Anti-CTLA-4 Masking Antibody) in Combination with Pembrolizumab: Updated Results of Phase 1b/2 Study in Advanced MSS CRC," ASCO 2025, 16 pages.
Liu et al., (2019). "Poster P788: Development of a novel antagonist anti-CTLA-4 antibody for cancer immunotherapy," SITC 2019, 1 page.
Liu et al., (2021). "Poster: A Novel Anti-CTLA-4 Checkpoint Inhibitor Prodrug to Address On-target Off-tumor Toxicity for Cancer Immunotherapy," 2021 AACR Annual Conference, Abstract No. 1853, 1 page.
Park et al., (2022). "Poster: A Phase 1b/2 Study of a Novel Anti-CTLA-4 NEObodyTM ADG116 Monotherapy and in Combination with Toripalimab (TORI; Anti-PD-1 Antibody) in Patients with Advanced / Metastatic Solid Tumors," SITC 2022, Abstract No. 753, 1 page.
Richardson et al., (2021). "Poster: Phase 1 dose-finding study of a novel anti-CTLA-4 antibody ADG116 as monotherapy in patients with advanced solid tumors," ESMO IO 2021, Abstract No. 394, 1 page.
Richardson et al., (2022). "Abstract e17601: Phase 1 study of ADG126, a novel masked anti-CTLA-4 SAFEbody, that combines tumor-localized activation with strong Treg depletion and soft ligand blocking in patients with advanced solid tumors," Gynecological Cancer, 40(suppl 16):e17601, 1 page.
Richardson et al., (2022). "Poster 741P: Phase 1 Results Demonstrate Highly Differentiated Safety and PK Profile of ADG126, a Masked anti-CTLA-4 SAFEbody® in Patients with Advanced Solid Tumors," ESMO 2022, 1 page.
Tolcher et al., (2022). "Poster 773: A Phase 1b/2, Open-Label, Dose Escalation and Expansion Study of an Anti-CTLA-4 NEOBodyTM ADG116 in Combination with Pembrolizumab (Anti-PD-1 Antibody) in Patients with Advanced/Metastatic Solid Tumors: A Preliminary Update," SITC 2022, 1 page.
Zheng et al., (2023). "Poster 847: Optimal Dose Selection of ADG126 (Masked Anti- CTLA-4 SAFEbody®) with Significantly Widened Therapeutic Index Compared to Ipilimumab in Combination with anti-PD-1 Antibodies Informed by QSP Modeling," SITC 2023, 1 page.
Zheng et al., (2024). "Poster: Deciphering Improved Clinical Therapeutic Index (TI) of Muzastotug (ADG126), a Masked Anti-CTLA-4 SAFEbody® over its Unmasked Form (ADG116) as Monotherapy or in Combination with anti-PD-1 Therapy (Toripalimab)," SITC 2024, Abstract No. 506, 1 page.

* cited by examiner $$\frac{dC_1}{dt} = -(K_{10}+K_{12})C_1+K_{21}C_2$$

$$\frac{dC_2}{dt} = K_{12}C_1-K_{21}C_2$$

| Theta | Estimate* | SE | RSE | 95% CI* |
|---|---|---|---|---|
| V1 L/kg | **0.0393** | 0.0025 | 6.3% | 0.034 - 0.044 |
| V2 L/kg | **0.03** | 0.0081 | 26.9% | 0.014 - 0.046 |
| CL L/day/kg | **0.00194** | 0.0001 | 3.4% | 0.002 - 0.002 |
| Q L/day/kg | **0.00261** | 0.0001 | 3.9% | 0.002 - 0.003 |

| Subject ID | Dose (mg/kg) | Prior tx # | Prior IO # | Duration (day) | Dose # |
|---|---|---|---|---|---|
| 1 | 0.003 | 2 | Pembro | 37 | 2 |
| 2 | 0.01 | 11 | 0 | 87 | 3 |
| 3 | 0.03 | 5 | Nivo | 29 | 2 |
| 4 | 0.03 | 2 | Pembro | 128 | 4 |
| 5 | 0.03 | 5 | 0 | 24 | 1 |
| 6 | 0.1 | 8 | 0 | 22 | 1 |
| 7 | 0.1 | 4 | Nivo | 43 | 2 |
| 8 | 0.1 | 1 | 0 | 33 | 2 |
| 9 | 0.3 | 2 | 0 | 84 | 4 |
| 10 | 0.3 | 4 | 0 | 31 | 2 |
| 11 | 0.3 | 3 | 0 | 48 | 3 |
| 12 | 1 | 5 | 0 | 40 | 2 |
| 13 | 1 | 2 | 0 | 174 | 5 |

| Subject ID | Dose (mg/kg) | Prior tx # | Prior IO # | Duration (day) | Dose # |
|---|---|---|---|---|---|
| 14 | 1 | 7 | 0 | 85 | 4 |
| 15 | 3 | 3 | Pembro | 37 | 2 |
| 16 | 3 | 7 | 0 | 40 | 2 |
| 17 | 3 | 4 | 0 | 13 | 1 |
| 18 | 3 | 4 | 0 | 87 | 4 |
| 19 | 6 | 3 | 0 | 116+* | 4+ |
| 20 | 6 | 3 | 0 | 39 | 2 |
| 21 | 6 | 5 | 0 | 45 | 3 |
| 22 | 10 | 3 | 0 | 38+* | 2+ |
| 23 | 10 | 3 | Nivo, 2x | 37 | 2 |
| 24 | 10 | 2 | 0 | 36 | 2 |
| 25 | 6 (Exp) | 2 | 0 | 34+* | 2+ |

* Still on treatment

FIG. 15B

Treg depletion and CD8/Treq ratios in the tumor-infiltrating lymphocytes (TIL) of treated MC38 tumors in the *hCTLA4* knock-in background

METHODS FOR TREATING CANCER USING ANTI-CTLA4 ANTIBODIES

CROSS-REFERENCE TO RELATED APPLICATIONS

This application is a national stage application under 35 U.S.C. § 371 of International Patent Application No. PCT/US2022/022198, filed Mar. 28, 2022, which claims priority to U.S. Provisional Patent Application No. 63/167,111, filed Mar. 28, 2021, the contents of each of which are hereby incorporated herein by reference in their entirety for all purposes.

FIELD OF THE INVENTION

The present application is in the field of cancer therapeutics, and relates to compositions and methods for treating cancers using antibodies that bind to human CTLA4.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695402001300SEQLIST.TXT, date recorded: Sep. 28, 2023, size: 98,651 bytes).

BACKGROUND

CTLA4 is a member of the immunoglobulin (Ig) superfamily of proteins that acts to downregulate T-cell activation and maintain immunogenic homeostasis. It has been shown that in vivo antibody-mediated blockade of CTLA4 enhanced anti-cancer immune responses in a syngeneic murine prostate cancer model (Kwon et al. (1997) Proc Natl Acad Sci USA, 94(15):8099-103). In addition, blockade of CTLA4 function was shown to enhance anti-tumor T cell responses at various stages of tumor growth in tumor-bearing mice (Yang et al. (1997) Cancer Res 57(18):4036-41; Hurwitz et al. (1998) Proc Natl Acad Sci USA 95 (17):10067-7). However, the development of antibody-based therapeutics suitable for human use remains difficult, as translation from pre-clinical animal models to human safety is often poor. Accordingly, a need exists for anti-CTLA4 antibodies that are cross-reactive among different species, such as humans and experimental animals (e.g., mouse, monkey, rat, etc.), to concurrently enable animal model studies and provide suitable human therapeutic candidates. In addition, a need exists for the development of safer anti-CTLA4 antibodies that are only active in certain contexts, such as in the protease-rich tumor microenvironment.

BRIEF SUMMARY

The present application provides methods for treating cancer with an anti-CTLA4 antibody, and methods of using biomarkers (e.g., pharmacodynamic biomarkers) for determining responsiveness of a patient to an anti-CTLA4 antibody treatment, for adjusting dosage and dosing schedule of the treatment, and for monitoring prognosis of the treatment.

Accordingly, in one aspect, provided herein is a method of treating a cancer in a subject, comprising: (a) administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, (b) subsequently determining a level of one or more biomarkers selected from the group consisting of IL-1β, IL-2, IL-6, IL-10, interferon (IFN)-γ, tumor necrosis factor (TNF)-α, soluble CTLA4 (sCTLA4), soluble PD-L1 (sPD-L1), soluble CD25 (sCD25), CXCL11, FoxP3, Ki67, CD8+ T cells, CD4+ T cells, CD8+ effector memory T ($T_{em}$) cells, CD4+ $T_{em}$ cells, regulatory T ($T_{reg}$) cells, a ratio of CD8+ $T_{em}$ cells to $T_{reg}$ cells, a ratio of CD4+ $T_{em}$ cells to $T_{reg}$ cells, NK cells and B cells in a sample of the subject. In some embodiments, an increase or decrease of the one or more biomarkers after administration of the anti-CTLA4 antibody compared to the baseline level of the one or more biomarkers indicates an increased likelihood that the subject has an effective response to the CTLA4 antibody. In some embodiments, wherein the sample has an increase or decrease of the one or more biomarkers after administration of the anti-CTLA4 antibody compared to the baseline level of the one or more biomarkers, the method further comprises administering to the subject a further cycle of an effective amount of the anti-CTLA4 antibody.

In another aspect, provided herein is a method of providing a prognosis for a subject who has been administered with an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108; the method comprising determining a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells in a sample of the subject, wherein an increase or decrease of the one or more biomarkers after administration of the anti-CTLA4 antibody compared to the baseline level of the one or more biomarkers indicates an increased likelihood that the subject has an effective response to the CTLA4 antibody.

In some embodiments according to any one of the methods described above, the one or more biomarkers comprise one or more biomarkers selected from the group consisting of CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, an increase in the level of CD8+ T cells, CD4+ T cells, CD8+ $T_{reg}$ cells, CD4+ $T_{em}$ cells, a ratio of CD8+ $T_{reg}$ cells to $T_{reg}$ cells, a ratio of CD4+ $T_{em}$ cells to $T_{reg}$ cells, NK cells and B cells after administration of the anti-CTLA4 antibody compared to the baseline level of the one or more biomarkers indicates an increased likelihood that the subject has an effective response to the CTLA4 antibody. In some embodiments, the one or more biomarkers comprise CD8+ $T_{em}$ cells. In some embodiments, the one or more biomarkers comprise CD4+ $T_{em}$ cells. In some embodiments, the one or more biomarkers comprise NK cells. In some embodiments, the one or more biomarkers comprise a ratio of CD8+ $T_{em}$ cells to $T_{reg}$ cells. In some embodiments, the one or more biomarkers comprise a ratio of CD4+ $T_{em}$ cells to $T_{reg}$ cells. In some embodiments, the one or more biomarkers comprise $T_{reg}$ cells. In some embodiments, a decrease in the level of $T_{reg}$ cells after administration of the anti-CTLA4 antibody compared to the baseline level of $T_{reg}$ cells indicates an increased likelihood that the subject has an effective response to the CTLA4 antibody.

In some embodiments according to any one of the methods described above, the sample is a blood sample. In some embodiments, the sample is a tumor biopsy sample.

In some embodiments according to any one of the methods described above, the cancer is resistant or refractory to a prior therapy, wherein the prior therapy is an inhibitor of CTLA4, PD-1, or a PD-1 ligand. In some embodiments, the subject is resistant to or has relapsed from a prior therapy, wherein the prior therapy is an inhibitor of CTLA4, PD-1, or a PD-1 ligand. In some embodiments, the prior therapy is an inhibitor of CTLA4, such as ipilimumab. In some embodiments, the prior therapy is an inhibitor of PD-1, such as an anti-PD-1 antibody, for example, pembrolizumab. In some embodiments, the prior therapy is an inhibitor of a PD-1 ligand (e.g., PD-L1), for example an anti-PD-L1 antibody. In some embodiments, the prior therapy includes both an inhibitor of CTLA4 and am inhibitor of PD-1. In some embodiments, the prior therapy includes both an inhibitor of CTLA4 and am inhibitor of PD-L1. In some of the foregoing embodiments, the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100. In some of the foregoing embodiments, the anti-CTLA4 antibody comprises a human IgG1 Fc region, such as a wildtype IgG1 Fc region or a variant that has enhanced ADCC activity. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580.

Another aspect of the present application provides a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the cancer is resistant or refractory to a prior therapy, wherein the prior therapy is an inhibitor of CTLA4, PD-1, or a PD-1 ligand. In some embodiments, the present application provides a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the subject is resistant to or has relapsed from a prior therapy, wherein the prior therapy is an inhibitor of CTLA4, PD-1, or a PD-1 ligand. In some embodiments, the prior therapy is an inhibitor of CTLA4, such as ipilimumab. In some embodiments, the prior therapy is an inhibitor of PD-1, such as an anti-PD-1 antibody, for example, pembrolizumab. In some embodiments, the prior therapy is an inhibitor of a PD-1 ligand (e.g., PD-L1), for example an anti-PD-L1 antibody.

In some embodiments according to any one of the methods described above, the cancer is liver cancer, a cancer of the digestive system (e.g., colon cancer, colorectal cancer), lung cancer, bone cancer, heart cancer, brain cancer, kidney cancer, bladder cancer, a hematological cancer (e.g., leukemia), skin cancer, breast cancer, thyroid cancer, pancreatic cancer, a head and/or neck cancer, an eye-related cancer, a male reproductive system cancer (e.g., prostate cancer, testicular cancer), or a female reproductive system cancer (e.g., uterine cancer, cervical cancer). In some embodiments, the cancer is a solid cancer. In some embodiments, the cancer is urothelial carcinoma. In some embodiments, the cancer is advanced-stage cancer. In some embodiments, the cancer is metastatic cancer.

In some embodiments according to any one of the methods described above, the anti-CTLA4 antibody is administered at a dose of about 0.001 mg/kg to about 20 mg/kg. In other embodiments according to any one of the methods described above, the anti-CTLA4 antibody is administered at a dose of about 0.001 mg/kg to about 10 mg/kg. In some embodiments, the anti-CTLA4 antibody is administered at a dose of at least about 0.03 mg/kg. In some embodiments, the anti-CTLA4 antibody is administered at a dose of at least about 6 mg/kg. In some embodiments, the anti-CTLA4 antibody is administered at a dose of about 0.03 mg/kg, 0.1 mg/kg, 0.3 mg/kg, 1.0 mg/kg, 3.0 mg/kg, 6.0 mg/kg, 10.0 mg/kg, 15 mg/kg or 20 mg/kg. In some embodiments, the anti-CTLA4 antibody is administered intravenously. In some embodiments, the anti-CTLA4 antibody is administered subcutaneously. In some embodiments, the anti-CTLA4 antibody is administered about once every three weeks. In some embodiments, the subject receives at least 4 cycles of treatment with the anti-CTLA4 antibody. In some embodiments, the subject further receives a maintenance treatment comprising administering to the subject an effective amount of the anti-CTLA4 antibody about once every four weeks to about once every twelve weeks (e.g., once every 4, 6, 8, 10, or 12 weeks).

Another aspect of the present application provides a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the anti-CTLA4 antibody is administered at a dose of at least 6 mg/kg.

In some embodiments according to any one of the methods described above, the anti-CTLA4 antibody is administered at a dose of about 6 mg/kg (e.g., 6 mg/kg).

In some embodiments, the anti-CTLA4 antibody is administered at a dose of about 10 mg/kg (e.g., 10 mg/kg).

In some embodiments, the anti-CTLA4 antibody is administered at a dose of about 3 mg/kg (e.g., 3 mg/kg) once every three weeks. In some embodiments, the anti-CTLA4 antibody is administered at a dose of about 6 mg/kg (e.g., 6 mg/kg) once every three weeks. In some embodiments, the anti-CTLA4 antibody is administered at a dose of about 10 mg/kg (e.g., 10 mg/kg) once every three weeks. In some embodiments, the anti-CTLA4 antibody is administered at a dose of about 10 mg/kg (e.g., 10 mg/kg) once every three weeks. In some embodiments, the anti-CTLA4 antibody is administered at a dose of about 15 mg/kg (e.g., 15 mg/kg) once every three weeks. In some embodiments, the anti-CTLA4 antibody is administered at a dose of about 20 mg/kg (e.g., 15 mg/kg) once every three weeks. In some embodiments, the cancer is urothelial carcinoma. In some of the foregoing embodiments, the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100. In some of the foregoing embodiments, the anti-CTLA4 antibody comprises a human IgG1 Fc region, such as a wildtype IgG1 Fc region or a variant that has enhanced ADCC activity. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580.

In some embodiments according to any one of the methods described above, the subject is human.

In some embodiments according to any one of the methods described above, the anti-CTLA4 antibody is cross-reactive with a CTLA4 polypeptide from at least one non-human animal selected from the group consisting of cynomolgus monkey, mouse, rat, and dog. In some embodiments, the antibody binds to cynomolgus monkey CTLA4 and mouse CTLA4. In some embodiments, the antibody binds to human CTLA4, cynomolgus monkey CTLA4, mouse CTLA4, rat CTLA4, and/or dog CTLA4 with a dissociation constant ($K_D$) of about 350 nM or less (e.g., about 300 nM or less, about 200 nM or less, about 100 nM or less, about 50 nM or less, or about 10 nM or less). In some embodiments, the $K_D$ is measured by surface plasmon resonance (SPR). In some embodiments, binding of the antibody to CTLA4 induces antibody-dependent cell cytotoxicity (ADCC) against a CTLA4-expressing cell. In some embodiments, binding of the antibody to CTLA4 induces ADCC against a Treg cell. In some embodiments, binding of the anti-CTLA4 antibody described herein induces antibody-dependent cell cytotoxicity (ADCC) against a CTLA4-expressing human cell or a human Treg cell, wherein the ADCC activity of the anti-CTL4 antibody is higher than the ADCC activity of ipilimumab in vitro, and wherein both antibodies comprise wild type human IgG1 Fc region. In some embodiments, binding of the anti-CTLA4 antibody described herein induces antibody-dependent cell cytotoxicity (ADCC) against a CTLA4-expressing human cell or a human Treg cell, wherein the ADCC activity of the anti-CTLA4 antibody is two times or higher than the ADCC activity of ipilimumab in vitro, and wherein both antibodies comprise wild type human IgG1 Fc region. In some embodiments, the EC50 of the anti-CTL4 antibody ADCC activity is 50% or less than the EC50 of ipilimumab ADCC activity in vitro. In some embodiments, the anti-CTLA4 antibody depletes Treg cells selectively in tumor microenvironment (e.g., reducing percentage of Treg cells in tumor infiltrating lymphocytes), as compared to PBMC or spleen in a mouse cancer model.

In some embodiments according to any one of the methods described above, the antibody specifically binds to an epitope comprising amino acid residues at a ligand binding site of human CTLA4, such as CD80 and/or CD86 binding site of human CTLA4. In some embodiments, the antibody specifically binds to an epitope similar to a ligand binding site of human CTLA4, such as CD80 and/or CD86 binding site of human CTLA4. In some embodiments, the anti-CTLA4 antibody blocks binding of CD80 and/or CD86 to human CTLA4. In some embodiments, the anti-CTLA4 antibody has an IC50 higher than the IC50 of ipilimumab for blocking binding of CD80 and/or CD86 to human CTLA4. In some embodiments, the anti-CTLA4 antibody has an IC50 that is 3.5 times or higher (including 3.9 times or higher) than the IC50 of ipilimumab for blocking binding of CD80 and/or CD86 to human CTLA4 in an assay that CD86 or CD80 is plate bound and CTLA4 is in solution or CTLA4 displayed on cell surface.

In some embodiments according to any one of the methods described above, the antibody comprises a heavy chain variable region and a light chain variable region, a) wherein the heavy chain variable region comprises an HVR-H1, an HVR-H2, and an HVR-H3, wherein the HVR-H1 comprises an amino acid sequence according to a formula selected from the group consisting of: Formula (I): X1TFSX2YX3IHWV (SEQ ID NO: 1), wherein X1 is F or Y, X2 is D or G, and X3 is A, G, or W; Formula (II): YSIX1SGX2X3WX4WI (SEQ ID NO: 2), wherein X1 is S or T, X2 is H or Y, X3 is H or Y, and X4 is A, D, or S; and Formula (III): FSLSTGGVAVX1WI (SEQ ID NO: 3), wherein X1 is G or S; wherein the HVR-H2 comprises an amino acid sequence according to a formula selected from the group consisting of: Formula (IV): IGX1IX2HSGSTYYSX3SLKSRV (SEQ ID NO: 4), wherein X1 is D or E, X2 is S or Y, and X3 is P or Q; Formula (V): IGX1ISPSX2GX3TX4YAQKFQGRV (SEQ ID NO: 5), wherein X1 is I or W, X2 is G or S, X3 is G or S, and X4 is K or N; and Formula (VI): VSX1ISGX2GX3X4TYYADSVKGRF (SEQ ID NO: 6), wherein X1 is A, G, or S, X2 is S or Y, X3 is G or S, and X4 is S or T; and wherein the HVR-H3 comprises an amino acid sequence according to a formula selected from the group consisting of: Formula (VII): ARX1X2X3X4FDX5 (SEQ ID NO: 7), wherein X1 is G, R, or S, X2 is A, I, or Y, X3 is D, V, or Y, X4 is A, E, or Y, and X5 is I or Y; Formula (VIII): ARX1GX2GYFDX3 (SEQ ID NO: 8), wherein X1 is D or L, X2 is F or Y, and X3 is V or Y; Formula (IX): ARX1X2X3X4AX5X6FDY (SEQ ID NO: 9), wherein X1 is L or R, X2 is I or P, X3 is A or Y, X4 is S or T, X5 is T or Y, and X6 is A or Y; Formula (X): ARDX1X2X3GSSGYYX4GFDX5 (SEQ ID NO: 10), wherein X1 is I or V, X2 is A or H, X3 is P or S, X4 is D or Y, and X5 is F or V; and b) wherein the light chain variable region comprises an HVR-L1, an HVR-L2, and an HVR-L3, wherein the HVR-L1 comprises an amino acid sequence according to a formula selected form the group consisting of: Formula (XI): RASQX1X2X3SX4LX5 (SEQ ID NO: 11), wherein X1 is G or S, X2 is I or V, X3 is G or S, X4 is S or Y, and X5 is A or N; Formula (XII): RASQX1VX2X3RX4LA (SEQ ID NO: 12), wherein X1 is S or T, X2 is F, R, or S, X3 is G or S, and X4 is F or Y; and Formula (XIII): RASX1SVDFX2GX3SFLX4 (SEQ ID NO: 13), wherein X1 is E or Q, X2 is D, F, H, or Y, X3 is F, I, or K, and X4 is A, D, or H; wherein the HVR-L2 comprises an amino acid sequence according to Formula (XIV): X1ASX2X3X4X5GX6 (SEQ ID NO: 14), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of: Formula (XV): YCX1X2X3X4X5X6PX7T (SEQ ID NO: 15), wherein X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y; Formula (XVT): YCQQX1X2X3WPPWT (SEQ ID NO: 16), wherein X1 is S or Y, X2 is D or Y, and X3 is Q or Y; and Formula (XVII): YCQX1YX2SSPPX3YT (SEQ ID NO: 17), wherein X1 is H or Q, X2 is T or V, and X3 is E or V. In some embodiments, the HVR-H1 comprises an amino acid sequence selected from the group consisting of SEQ ID NOS: 18-29, the HVR-H2 comprises an amino acid sequence selected from the group consisting of SEQ ID NOS: 30-39, the HVR-H3 comprises an amino acid sequence selected from the group consisting of SEQ ID NOS: 40-52, the HVR-L1 comprises an amino acid sequence selected from the group consisting of SEQ ID NOS: 53-65, the HVR-L2 comprises an amino acid sequence selected from the group consisting of SEQ ID NOS: 66-69, and the HVR-L3 comprises an amino acid sequence selected from the group consisting of SEQ ID NOS: 70-81. In some embodiments, the antibody comprises: a) an HVR-H1 comprising the amino acid sequence of SEQ ID NO: 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70; b) an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71; c) an HVR-H1 comprising the amino acid sequence of SEQ ID NO: 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72; d) an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73; e) an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74; f) an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75; g) an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76; h) an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77; i) an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78; j) an HVR-H1 comprising the amino acid sequence of SEQ ID NO: 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79; k) an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80; l) an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81; or m) an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77. In some embodiments, the heavy chain variable region comprises an amino acid sequence selected from the group consisting of SEQ ID NOS: 82-94, and/or the light chain variable region comprises an amino acid sequence selected from the group consisting of SEQ ID NOS: 95-107. In some embodiments, the antibody comprises: a) a heavy chain variable region comprising the amino acid sequence of SEQ ID NO: 82 or a variant thereof having at least about 90% (e.g., at least about 92%, 95%, 98%, 99% or more) sequence identity to the amino acid sequence of SEQ ID NO: 82, and a light chain variable region comprising the amino acid sequence of SEQ ID NO: 95 or a variant thereof having at least about 90% (e.g., at least about 92%, 95%, 98%, 99% or more) sequence identity to the amino acid sequence of SEQ ID NO: 95; b) a heavy chain variable region comprising the amino acid sequence of SEQ ID NO: 83 or a variant thereof having at least about 90% (e.g., at least about 92%, 95%, 98%, 99% or more) sequence identity to the amino acid sequence of SEQ ID NO: 83, and a light chain variable region comprising the amino acid sequence of SEQ ID NO: 96 or a variant thereof having at least about 90% (e.g., at least about 92%, 95%, 98%, 99% or more) sequence identity to the amino acid sequence of SEQ ID NO: 96; c) a heavy chain variable region comprising the amino acid sequence of SEQ ID NO: 84 or a variant thereof having at least about 90% (e.g., at least about 92%, 95%, 98%, 99% or more) sequence identity to the amino acid sequence of SEQ ID NO: 84, and a light chain variable region comprising the amino acid sequence of SEQ ID NO: 97 or a variant thereof having at least about 90% (e.g., at least about 92%, 95%, 98%, 99% or more) sequence identity to the amino acid sequence of SEQ ID NO: 97; d) a heavy chain variable region comprising the amino acid sequence of SEQ ID NO: 85 or a variant thereof having at least about 90% (e.g., at least about 92%, 95%, 98%, 99% or more) sequence identity to the amino acid sequence of SEQ ID NO: 85, and a light chain variable region comprising the amino acid sequence of SEQ ID NO: 98 or a variant thereof having at least about 90% (e.g., at least about 92%, 95%, 98%, 99% or more) sequence identity to the amino acid sequence of SEQ ID NO: 98; e) a heavy chain variable region comprising the amino acid sequence of SEQ ID NO: 86 or a variant thereof having at least about 90% (e.g., at least about 92%, 95%, 98%, 99% or more) sequence identity to the amino acid sequence of SEQ ID NO: 86, and a light chain variable region comprising the amino acid sequence of SEQ ID NO: 99 or a variant thereof having at least about 90% (e.g., at least about 92%, 95%, 98%, 99% or more) sequence identity to the amino acid sequence of SEQ ID NO: 99; f) a heavy chain variable region comprising the amino acid sequence of SEQ ID NO: 87 or a variant thereof having at least about 90% (e.g., at least about 92%, 95%, 98%, 99% or more) sequence identity to the amino acid sequence of SEQ ID NO: 87, and a light chain variable region comprising the amino acid sequence of SEQ ID NO: 100 or a variant thereof having at least about 90% (e.g., at least about 92%, 95%, 98%, 99% or more) sequence identity to the amino acid sequence of SEQ ID NO: 100; g) a heavy chain variable region comprising the amino acid sequence of SEQ ID NO: 88 or a variant thereof having at least about 90% (e.g., at least about 92%, 95%, 98%, 99% or more) sequence identity to the amino acid sequence of SEQ ID NO: 88, and a light chain variable region comprising the amino acid sequence of SEQ ID NO: 101 or a variant thereof having at least about 90% (e.g., at least about 92%, 95%, 98%, 99% or more) sequence identity to the amino acid sequence of SEQ ID NO: 101; h) a heavy chain variable region comprising the amino acid sequence of SEQ ID NO: 89 or a variant thereof having at least about 90% (e.g., at least about 92%, 95%, 98%, 99% or more) sequence identity to the amino acid sequence of SEQ ID NO: 89, and a light chain variable region comprising the amino acid sequence of SEQ ID NO: 102 or a variant thereof having at least about 90% (e.g., at least about 92%, 95%, 98%, 99% or more) sequence identity to the amino acid sequence of SEQ ID NO: 102; i) a heavy chain variable region comprising the amino acid sequence of SEQ ID NO: 90 or a variant thereof having at least about 90% (e.g., at least about 92%, 95%, 98%, 99% or more) sequence identity to the amino acid sequence of SEQ ID NO: 90, and a light chain variable region comprising the amino acid sequence of SEQ ID NO: 103 or a variant thereof having at least about 90% (e.g., at least about 92%, 95%, 98%, 99% or more) sequence identity to the amino acid sequence of SEQ ID NO: 103; j) a heavy chain variable region comprising the amino acid sequence of SEQ ID NO: 91 or a variant thereof having at least about 90% (e.g., at least about 92%, 95%, 98%, 99% or more) sequence identity to the amino acid sequence of SEQ ID NO: 91, and a light chain variable region comprising the amino acid sequence of SEQ ID NO: 104 or a variant thereof having at least about 90% (e.g., at least about 92%, 95%, 98%, 99% or more) sequence identity to the amino acid sequence of SEQ ID NO: 104; k) a heavy chain variable region comprising the amino acid sequence of SEQ ID NO: 92 or a variant thereof having at least about 90% (e.g., at least about 92%, 95%, 98%, 99% or more) sequence identity to the amino acid sequence of SEQ ID NO: 92, and a light chain variable region comprising the amino acid sequence of SEQ ID NO: 105 or a variant thereof having at least about 90% (e.g., at least about 92%, 95%, 98%, 99% or more) sequence identity to the amino acid sequence of SEQ ID NO: 105; l) a heavy chain variable region comprising the amino acid sequence of SEQ ID NO: 93 or a variant thereof having at least about 90% (e.g., at least about 92%, 95%, 98%, 99% or more) sequence identity to the amino acid sequence of SEQ ID NO: 93, and a light chain variable region comprising the amino acid sequence of SEQ ID NO: 106 or a variant thereof having at least about 90% (e.g., at least about 92%, 95%, 98%, 99% or more) sequence identity to the amino acid sequence of SEQ ID NO: 106; or m) a heavy chain variable region comprising the amino acid sequence of SEQ ID NO: 94 or a variant thereof having at least about 90% (e.g., at least about 92%, 95%, 98%, 99% or more) sequence identity to the amino acid sequence of SEQ ID NO: 94, and a light chain variable region comprising the amino acid sequence of SEQ ID NO: 107 or a variant thereof having at least about 90% (e.g., at least about 92%, 95%, 98%, 99% or more) sequence identity to the amino acid sequence of SEQ ID NO: 107.

In some embodiments according to any one of the methods described above, the anti-CTLA4 antibody described herein comprises a heavy chain variable region and a light chain variable region, wherein one, two, three, four, five, or six HVRs of the antibody comprise a HVR sequence shown in Table A. In some embodiments, the anti-CTLA4 antibody comprises a heave chain variable region comprising an HVR-H1, an HVR-H2, and an HVR-H3, wherein the HVR-H1 comprises the amino acid sequence of SEQ ID NO: 23, or the HVR-H2 comprises the amino acid sequence of SEQ ID NO: 35, or the HVR-H3 comprises the amino acid sequence of SEQ ID NO: 45. In some embodiments, the anti-CTLA4 antibody comprises a light chain variable region comprising an HVR-L1, an HVR-L2, and an HVR-L3, wherein the HVR-L1 comprises the amino acid sequence of SEQ ID NO: 58, or the HVR-L2 comprises the antibody comprises the amino acid sequence of SEQ ID NO: 66, or the HVR-L3 comprises the amino acid sequence of SEQ ID NO: 75. In some embodiments, the anti-CTLA4 antibody comprises (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, one, two, three, four, five or six of the HVRs of the antibody may comprise one, two or three conservative amino acid substitutions in the HVRs. In some embodiments, the anti-CTLA4 antibody comprises (b) a heavy chain variable region comprising the amino acid sequence of SEQ ID NO: 87 or an amino acid sequence having at least 90% (e.g., 91%, 92%, 93%, 95%, 96%, 97%, 98%, or 99%) sequence identity to the amino acid sequence of SEQ ID NO: 87, and/or a light chain variable region comprising the amino acid sequence of SEQ ID NO: 100 or an amino acid sequence having at least 90% (e.g., 91%, 92%, 93%, 95%, 96%, 97%, 98%, or 99%) sequence identity to the amino acid sequence of SEQ ID NO: 100.

In some embodiments according to anyone of the methods described above, the antibody is a human antibody. In some embodiments, the antibody comprises an IgG1, IgG2, IgG3, or IgG4 Fc region (such as human IgG1, IgG2, IgG3, or IgG4 Fc region). In some embodiments, the antibody comprising a human IgG1 or a variant that has enhanced ADCC activity. In some embodiments, the antibody comprises a human IgG1 with reduced fucosylation (or non-fucosylated).

In some embodiments according to any one of the methods described above, the method further comprises administering to the subject an effective amount of at least one additional therapeutic agent. In some embodiments, the at least one additional therapeutic agent is selected from the group consisting of viral gene therapy, immune checkpoint inhibitors, target therapies, radiation therapies, vaccination therapies, and chemotherapies. In some embodiments, the method comprises administering to the subject an effective amount of the anti-CTLA4 antibody described herein prior to a surgery or after a surgery to remove the tumor in the subject.

It is to be understood that one, some, or all of the properties of the various embodiments described above and herein may be combined to form other embodiments of the present application. These and other aspects of the present application will become apparent to one of skill in the art. These and other embodiments of the present application are further described by the detailed description that follows.

BRIEF DESCRIPTION OF THE DRAWINGS

FIG. 9A shows (from left to right) the % change in $CD8^+$ $T_{EM}$/Treg ratio, the % change in $CD8^+$ $T_{EM}$ cells, and the % change in $T_{reg}$ cells for subject 6102-003 at a 0.1 mg/kg dose. FIG. 9B shows (from left to right) the % change in $CD8^+$ $T_{EM}$/Treg ratio, the % change in $CD8^+$ $T_{EM}$ cells, and the % change in $T_{reg}$ cells for subject 6101-004 at a 0.1 mg/kg dose. FIG. 9C shows (from left to right) the % change in $CD8^+$ $T_{EM}$/Treg ratio, the % change in $CD8^+$ $T_{EM}$ cells, and the % change in $T_{reg}$ cells for subject 6101-005 at a 0.3 mg/kg dose. In each plot, the x-axis shows the time of sampling, and the y-axis shows the percentage change relative to baseline.

FIG. 12A shows goodness-of-fit plots. FIG. 12B shows a diagnostic plot.

FIGS. 15A-15D show information regarding the ongoing study. FIG. 15A describes the dosing schedule of the study. FIG. 15B shows information regarding the subjects of the ongoing study and provides information regarding the amount and duration of TY21580 dosing for each. FIG. 15C shows the increase in CD8+ T cells in Subject #23 between C1D1 predose and C2D1. FIG. 15D shows treatment-related adverse events patients of the study have experienced.

FIG. 17A shows the change in relative abundance of IFN-γ to baseline in patients treated with TY21580. The x-axis shows the dose cohorts, the y-axis shows the percent change, and the lines represent values from different subjects. FIG. 17B shows the change in relative abundance of IFN-γ between baseline and C1D2 in patients treated with TY21580. The x-axis shows the dose cohorts, the y-axis shows the percent change, and the lines represent values from different subjects. FIG. 17C shows the scatter dot plot of percent change in IFN-γ from C1D2 relative to baseline in patients treated with TY21580. The x-axis shows the dose cohorts, the y-axis shows the percent change, and the dots represent values from different subjects.

FIG. 18A shows the change in relative abundance of TNFα to baseline in patients treated with TY21580. The x-axis shows the dose cohorts, the y-axis shows the percent change, and the lines represent values from different subjects. FIG. 18B shows the scatter dot plot of percent change in TNFα from C1D2 relative to baseline treated with TY21580. The x-axis shows the dose cohorts, the y-axis shows the percent change, and the dots represent values from different subjects.

FIG. 19B shows the scatter dot plot of percent change in IL-6 from C1D2 relative to baseline in patients treated with TY21580. The x-axis shows the dose cohorts, the y-axis shows the percent change, and the dots represent values from different subjects.

FIGS. 20A and 20B show changes of IL-10 in patients treated with TY21580. FIG. 20A shows the change in relative abundance of IL-10 to baseline in patients treated with TY21580. The x-axis shows the dose cohorts, the y-axis shows the percent change, and the lines represent values from different subjects. FIG. 20B shows the scatter dot plot of percent change in IL-10 from C1D2 relative to baseline in patients treated with TY21580. The x-axis shows the dose cohorts, the y-axis shows the percent change, and the dots represent values from different subjects.

FIG. 21A shows the abundance of sPD-L1 in patients treated with TY21580. The x-axis shows the dose cohorts, the y-axis shows the concentration of sPD-L1, and the lines represent values from different subjects. FIG. 21B shows the change in relative abundance of sPD-L1 to baseline in patients treated with TY21580. The x-axis shows the dose cohorts, the y-axis shows the percent change relative to baseline, and the lines represent values from different subjects. FIG. 21C shows the scatter dot plot of percent change in sPD-L1 from C1D8 relative to baseline in patients treated with TY21580. The x-axis shows the dose cohorts, the y-axis shows the percent change, and the dots represent values from different subjects.

FIG. 22A shows the change in relative abundance of sCD25 to baseline in patients treated with TY21580. The x-axis shows the dose cohorts, the y-axis shows the percent change, and the lines represent values from different subjects. FIG. 22B shows the scatter dot plot of percent change in sCD25 from C1D8 relative to baseline in patients treated with TY21580. The x-axis shows the dose cohorts, the y-axis shows the percent change, and the dots represent values from different subjects.

FIG. 23A shows the change in relative abundance of CXCL-11 to baseline in patients treated with TY21580. The x-axis shows the dose cohorts, the y-axis shows the percent change, and the lines represent values from different subjects. FIG. 23B shows the scatter dot plot of percent change in CXCL-11 from C1D8 relative to baseline in patients treated with TY21580. The x-axis shows the dose cohorts, the y-axis shows the percent change, and the dots represent values from different subjects.

FIG. 24A shows the change in CD4+ T cell levels relative to baseline in patients treated with TY21580 over time. The x-axis shows the dose cohorts, the y-axis shows the change in absolute cell level per L relative to baseline, and the lines represent values from different subjects. Values from several patients are highlighted (#4, #19, #22, #23). FIG. 24B shows the percent change in absolute CD4+ T cell levels on C1D8 relative to baseline in patients treated with TY21580. The x-axis shows the dose cohorts, the y-axis shows the percent change, and the dots represent values from different subjects. FIG. 24C shows the change in absolute count of CD4+ T cells from baseline to C1D8 in patients treated with TY21580. The x-axis shows the time point, the y-axis shows the absolute count per μL, and the lines represent values from different subjects. FIG. 24D shows the shows the percent change in absolute CD4+ T cell levels on C1D15 relative to baseline in patients treated with TY21580. The x-axis shows the dose cohorts, the y-axis shows the percent change, and the dots represent values from different subjects. FIG. 24E shows the change in absolute count of CD4+ CD8− T cells from baseline to C1D15 in patients treated with TY21580. The x-axis shows the time point, the y-axis shows the absolute count per μL, and the lines represent values from different subjects.

FIG. 25A shows the change in CD8+ T cell levels relative to baseline in patients treated with TY21580 over time. The x-axis shows the dose cohorts, the y-axis shows the change in absolute cell level per μL relative to baseline, and the lines represent values from different subjects. Values from several patients are highlighted (#4, #19, #22, #23). FIG. 25B shows the percent change in absolute CD8+ T cell levels on C1D8 relative to baseline in patients treated with TY21580. The x-axis shows the dose cohorts, the y-axis shows the percent change, and the dots represent values from different subjects. FIG. 25C shows the change in absolute count of CD8+ T cells from baseline to C1D8 in patients treated with TY21580. The x-axis shows the time point, the y-axis shows the absolute count per μL, and the lines represent values from different subjects. FIG. 25D shows the percent change in absolute CD8+ T cell levels on C1D15 relative to baseline in patients treated with TY21580. The x-axis shows the dose cohorts, the y-axis shows the percent change, and the dots represent values from different subjects. FIG. 25E shows the change in absolute count of CD8+ T cells from baseline to C1D15 in patients treated with TY21580. The x-axis shows the time point, the y-axis shows the absolute count per μL, and the lines represent values from different subjects.

FIG. 26A shows the change in absolute count of NK cells on C1D8 relative to baseline in patients treated with TY21580. The x-axis shows the time point, the y-axis shows the absolute count per μL, and the lines represent values from different subjects. FIG. 26B shows the change in absolute count of NK cells on C1D15 relative to baseline in patients treated with TY21580. The x-axis shows the time point, the y-axis shows the absolute count per μL, and the lines represent values from different subjects.

DETAILED DESCRIPTION

I. Definitions

Figure 1:
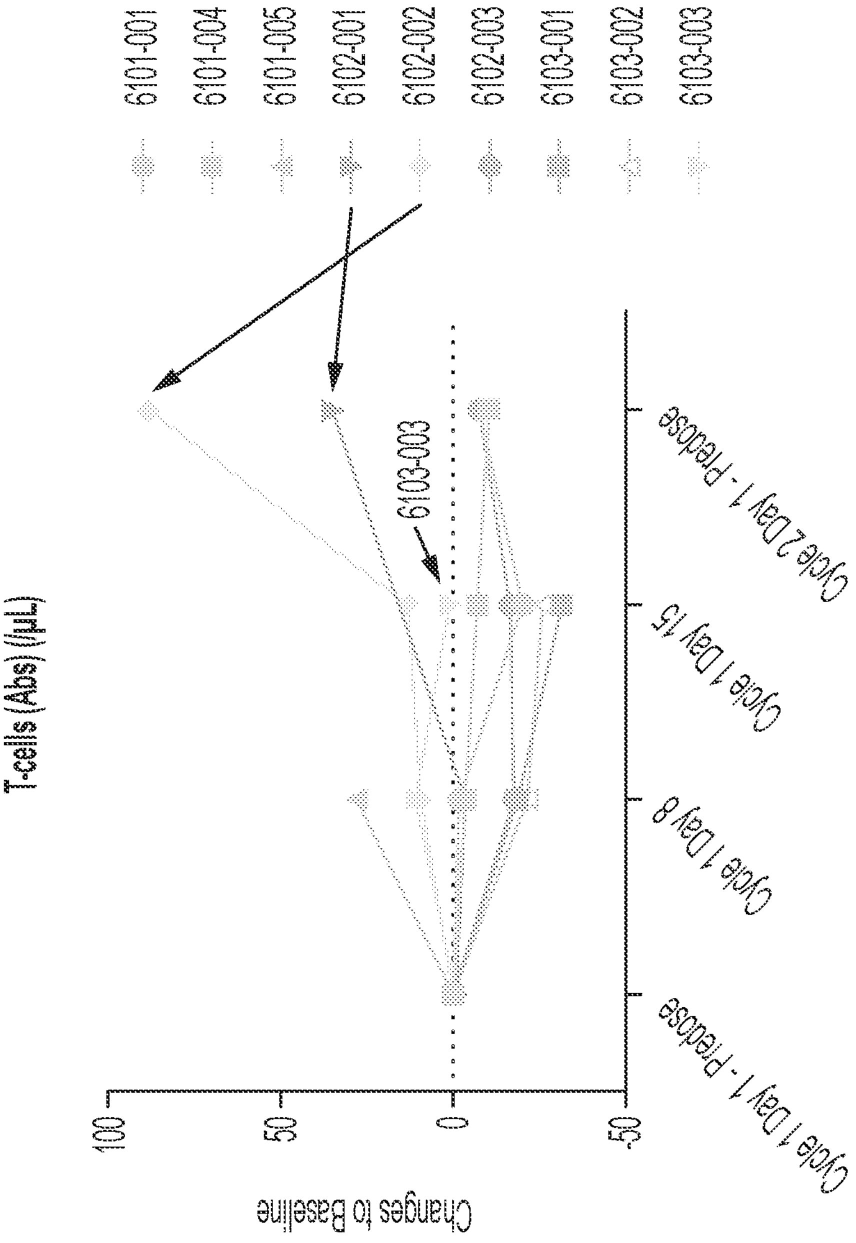
FIG. 1 shows the change in T cell levels relative to baseline in patients treated with the anti-CTLA4 antibody TY21580 over time. The x-axis shows the time of sampling, the y-axis shows the % change in absolute T cell counts per μL relative to baseline, and the lines represent values from different subjects.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Generally, nomenclatures used in connection with, and techniques of, antibody engineering, immunotherapy, cell and tissue culture, molecular biology, immunology, microbiology, genetics and protein and nucleic acid chemistry described herein are those well-known and commonly used in the art.

The term "antibody" is used herein in the broadest sense and specifically covers monoclonal antibodies (including full length monoclonal antibodies), polyclonal antibodies, multispecific antibodies (e.g., bispecific antibodies, trispecific antibodies), and antibody fragments (e.g., Fab, Fab', Fab'-SH, $F(ab')_2$, Fv and/or a single-chain variable fragment or scFv) so long as they exhibit the desired biological activity.

In some embodiments, the term "antibody" refers to an antigen-binding protein (i.e., immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain (CH1). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed hyper-variable regions (HVR) based on structural and sequence analysis. HVRs are interspersed with regions that are more conserved, termed framework regions (FW) (see e.g., Chen et al. (1999) J. Mol. Biol. (1999) 293, 865-881). Each $V_H$ and $V_L$ is composed of three HVRs and four FWs, arranged from amino-terminus to carboxy-terminus in the following order: FW-1_HVR-1_FW-2_HVR-2_FW-3_HVR-3_FW4. Throughout the present application, the three HVRs of the heavy chain are referred to as HVR-H1, HVR-H2, and HVR-H3. Similarly, the three HVRs of the light chain are referred to as HVR-L1, HVR-L2, and HVR-L3.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45: 3832-3839 (2008); Lefranc M. P. et al., *Dev. Comp. Immunol.,* 27: 55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs as defined by each of the above-cited references, are set forth below in Table I as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present invention and for possible inclusion in one or more claims herein.

TABLE I

CDR DEFINITIONS

| | Kabat[1] | Chothia[2] | MacCallum[3] | IMGT[4] | AHo[5] |
|---|---|---|---|---|---|
| VH CDR1 | 31-35 | 26-32 | 30-35 | 27-38 | 25-40 |
| VH CDR2 | 50-65 | 53-55 | 47-58 | 56-65 | 58-77 |
| VH CDR3 | 95-102 | 96-101 | 93-101 | 105-117 | 109-137 |
| VL CDR1 | 24-34 | 26-32 | 30-36 | 27-38 | 25-40 |
| VL CDR2 | 50-56 | 50-52 | 46-55 | 56-65 | 58-77 |
| VL CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids (see e.g., Fundamental Immunology Ch. 7 (Paul, W., ed., 2$^{nd}$ ed. Raven Press, N.Y). (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated a (alpha), 6 (delta), E (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antibody derivative" or "derivative" of an antibody refers to a molecule that is capable of binding to the same antigen (e.g., CTLA4) that the antibody binds to and comprises an amino acid sequence of the antibody linked to an additional molecular entity. The amino acid sequence of the antibody that is contained in the antibody derivative may be a full-length heavy chain, a full-length light chain, any portion or portions of a full-length heavy chain, any portion or portions of the full-length light chain of the antibody, any other fragment(s) of an antibody, or the complete antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional molecular entity by chemical coupling, genetic fusion, noncovalent association, or otherwise. The term "antibody derivative" also encompasses chimeric antibodies, humanized antibodies, and molecules that are derived from modifications of the amino acid sequences of a CTLA4 antibody, such as conservation amino acid substitutions, additions, and insertions.

The term "antigen-binding fragment" or "antigen binding portion" of an antibody refers to one or more portions of an antibody that retain the ability to bind to the antigen that the antibody bonds to (e.g., CTLA4). Examples of "antigen-binding fragments" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., *Nature* 341:544-546 (1989)), which consists of a $V_H$ domain; and (vi) an isolated complementarity determining region (CDR).

The term "CTLA4" is used in the present application, and includes the human CTLA4 (e.g., UniProt accession number P16410), as well as variants, isoforms, and species homologs thereof (e.g., mouse CTLA4 (UniProt accession number P09793), rat CTLA4 (UniProt accession number Q9Z1A7), dog CTLA4 (UniProt accession number Q9XSI1), cynomolgus monkey CTLA4 (UniProt accession number G7PL88), etc.). Accordingly, an anti-CTLA4 antibody, as defined and disclosed herein, may also bind CTLA4 from species other than human. In other cases, an anti-CTLA4 antibody may be completely specific for the human CTLA4 and may not exhibit species or other types of cross-reactivity.

The term "CTLA4 antibody" refers to an antibody, as defined herein, capable of binding to human CTLA4.

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography, 2-dimensional nuclear magnetic resonance, deuterium and hydrogen exchange in combination with mass spectrometry, or site-directed mutagenesis, or all methods used in combination with computational modeling of antigen and its complex structure with its binding antibody and its variants (see e.g., Epitope Mapping Protocols in Methods in Molecular Biology, Vol. 66, G. E. Morris, Ed. (1996)). Once a desired epitope of an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (0-linkage), and threonine (0-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; O-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system, which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; human cells (e.g., HEK293F cells, HEK293T cells; or human tissues or hybridoma cells, yeast cells, insect cells (e.g., S2 cells), bacterial cells (e.g., *E. coli* cells) and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "humanized antibody" refers to a chimeric antibody that contains amino acid residues derived from human antibody sequences. A humanized antibody may contain some or all of the CDRs or HVRs from a non-human animal or synthetic antibody while the framework and constant regions of the antibody contain amino acid residues derived from human antibody sequences.

The term "illustrative antibody" refers to any one of the antibodies described in the disclosure and designated as those listed in Tables A and B, and any antibodies comprising the 6 HVRs and/or the VH and VLs of the antibodies listed in Tables A and B. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art.

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998). An exemplary assay for assessing ADCC activity is provided in the examples herein.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 BI and WO 1999/51642. See also, e.g., Idusogie et al. J. Immunol. 164: 4178-4184 (2000).

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see e.g., Flatman et al., J. Chromatogr. B 848:79-87 (2007).

The term "$K_a$" refers to the association rate constant of a particular antibody-antigen interaction, where the term "$k_d$" refers to the dissociation rate constant of a particular antibody-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (μM) dissociation constant. $K_D$ values for antibodies can be determined using methods well established in the art. One method for determining the $K_D$ of an antibody is by using surface plasmon resonance, typically using a biosensor system such as a BIACORE® system. For example, an assay procedure using the BIACORE™ system (BIAcore assay) is described in at least Example 3 of the present application.

The term "mammal" refers to any animal species of the Mammalia class. Examples of mammals include: humans; laboratory animals such as rats, mice, hamsters, rabbits, non-human primates, and guinea pigs; domestic animals such as cats, dogs, cattle, sheep, goats, horses, and pigs; and captive wild animals such as lions, tigers, elephants, and the like.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see e.g., Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucleic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

As used herein, the term "binds", "binds to", "specifically binds" "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 M, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "treat", "treating", or "treatment", with reference to a certain disease condition in a mammal, refers causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "prevent" or "preventing," with reference to a certain disease condition in a mammal, refers to preventing or delaying the onset of the disease, or preventing the manifestation of clinical or subclinical symptoms thereof.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vector is capable of autonomous replication in a host cell into which it is introduced (e.g., bacterial vectors having a bacterial origin of replication and episomal mammalian vectors). Another specific type of vector capable of directing the expression of expressible foreign nucleic acids to which they are operatively linked is commonly referred to as "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors." Other examples of "vectors" may include display vectors (e.g., vectors that direct expression and display of an encoded polypeptide on the surface of a virus or cell (such as a bacterial cell, yeast cell, insect cell, and/or mammalian cell).

As used herein, a "subject", "patient", or "individual" may refer to a human or a non-human animal. A "non-human animal" may refer to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In some embodiments, the subject, patient, or individual is a human.

An "effective amount" refers to at least an amount effective, at dosages and for periods of time necessary, to achieve one or more desired or indicated effects, including a therapeutic or prophylactic result. An effective amount can be provided in one or more administrations. For purposes of the present application, an effective amount of antibody, drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition (e.g., an effective amount as administered as a monotherapy or combination therapy). Thus, an "effective amount" may be considered in the context of administering one or more therapeutic agents, and a single agent may be considered to be given in an effective amount if, in conjunction with one or more other agents, a desirable result may be or is achieved.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

As used herein, the term "biomarker" or "marker" refers generally to a molecule (e.g., pre-mRNA, mRNA, protein, etc.) or cell population (e.g., effector memory T cell or $T_{reg}$ cell, or regulatory T cell or $T_{reg}$ cell), the level of which in or on a subject's tissue (e.g., tumor), or in case of a molecule, secreted by the subject's tissue or cell, can be detected by known methods (or methods disclosed herein) and is predictive or can be used to predict (or aid prediction) for a subject's sensitivity to, and in some embodiments, to predict (or aid prediction) a subject's responsiveness to, treatment regimens (e.g., treatments with an anti-CTLA4 antibody).

As used herein, the term "sample", refers to a composition that is obtained or derived from a subject of interest that contains a cellular and/or other molecular entity that is to be characterized and/or identified, for example based on physical, biochemical, chemical and/or physiological characteristics.

As used herein, the term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells. Optionally, the tissue or cell sample is obtained from a disease tissue or organ. The tissue sample may contain compounds, which are not naturally intermixed with the tissue in nature such as preservatives, anticoagulants, buffers, fixatives, nutrients, antibiotics, or the like. As used herein, a "reference value" or "reference level" may be an absolute value; a relative value; a value that has an upper and/or lower limit; a range of values; an average value; a median value; a mean value; or a value as compared to a particular level or baseline level.

As used herein, a "baseline level" or "baseline value" refers to a level or a value of a subject before the subject begins a treatment, such as an anti-CTLA4 antibody treatment.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of biomarker analysis or protocol, one may use the results of the biomarker level analysis or protocol to determine whether a specific therapeutic regimen should be performed. With respect to the embodiment of biomarker level analysis or protocol, one may use the results of the biomarker level analysis or protocol to determine whether a specific therapeutic regimen should be performed.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A patient who "does not have an effective response" to treatment refers to a patient who does not have any one of extending survival (including overall survival and progression free survival); resulting in an objective response (including a complete response or a partial response); or improving signs or symptoms of cancer.

The methods and techniques of the present application are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

As used herein, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present application described herein include "comprising," "consisting," and "consisting essentially of" aspects and embodiments.

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Treatment

The present application provides methods for treating cancers in a subject using an anti-CTLA4 antibody that specifically binds to human CTLA4. Any one of the anti-CTLA4 antibodies (including full-length antibodies and antigen-binding fragments thereof) in Section IV "Anti-CTLA4 Antibodies" may be used in the methods described herein.

In some embodiments, there is provided a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the cancer is resistant or refractory to a prior therapy, wherein the prior therapy is an inhibitor of CTLA4, PD-1, or a PD-1 ligand. In some embodiments, the cancer is a solid cancer, such as advanced-stage and/or metastatic cancer. In some embodiments, the cancer is urothelial carcinoma.

In some embodiments, there is provided a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the cancer is resistant or refractory to a different anti-CTLA4 antibody, such as ipilimumab. In some embodiments, the cancer is a solid cancer, such as advanced-stage and/or metastatic cancer. In some embodiments, the cancer is urothelial carcinoma.

In some embodiments, there is provided a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the cancer is resistant or refractory to an inhibitor of PD-1 or a PD-1 ligand (e.g., PD-L1 or PD-L2). In some embodiments, the cancer is a solid cancer, such as advanced-stage and/or metastatic cancer. In some embodiments, the cancer is urothelial carcinoma.

In some embodiments, there is provided a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the cancer is resistant or refractory to an anti-PD-1 antibody, such as pembrolizumab. In some embodiments, the cancer is a solid cancer, such as advanced-stage and/or metastatic cancer. In some embodiments, the cancer is urothelial carcinoma.

In some embodiments, there is provided a method of treating a cancer in a subject, wherein the cancer is resistant or refractory to an inhibitor of CTLA-4, PD-1 or a PD-1 ligand (e.g., PD-L1 or PD-L2), comprising administering to the subject an effective amount of an anti-CTLA4 antibody, wherein the antibody comprises: (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the cancer is resistant or refractory to an anti-PD-1 antibody, such as pembrolizumab. In some embodiments, the cancer is resistant or refractory to a different anti-CTLA4 antibody, such as ipilimumab. In some embodiments, the cancer is resistant or refractory to an anti-PD-L1 antibody. In some embodiments, the cancer is a solid cancer, such as advanced-stage and/or metastatic cancer. In some embodiments, the cancer is urothelial carcinoma. In some embodiments, the antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100. In some embodiments, the antibody comprises a human IgG1 Fc region, such as a wildtype IgG1 Fc region or a variant that has enhanced ADCC activity. In some embodiments, the antibody is TY21580.

In some embodiments, there is provided a method of treating a cancer in a subject, comprising administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and wherein the anti-CTLA4 antibody is administered at a dose of at least about 6 mg/kg (e.g., 6 mg/kg or 10 mg/kg). In some embodiments, the anti-CTLA4 antibody comprises: (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100. In some embodiments, the antibody comprises a human IgG1 Fc region, such as a wildtype IgG1 Fc region or a variant that has enhanced ADCC activity. In some embodiments, the antibody is TY21580. In some embodiments, the anti-CTLA4 antibody is administered about once every three weeks. In some embodiments, the anti-CTLA4 antibody is administered intravenously.

In some embodiments, there is provided a method of treating a cancer in a subject, comprising administering to the subject: (a) an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, and (b) an effective amount of an anti-PD-1 antibody. In some embodiments, the anti-PD-1 antibody is pembrolizumab, a biosimilar thereof, or a derivative thereof. In some embodiments, the anti-PD-1 antibody is toripalimab, a biosimilar thereof, or a derivative thereof. In some embodiments, the anti-CTLA4 antibody comprises: (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100. In some embodiments, the antibody comprises a human IgG1 Fc region, such as a wildtype IgG1 Fc region or a variant that has enhanced ADCC activity. In some embodiments, the antibody is TY21580. In some embodiments, the anti-CTLA4 antibody is administered at a dose of at least about 6 mg/kg (e.g., 6 mg/kg or 10 mg/kg). In some embodiments, the anti-CTLA4 antibody is administered about once every three weeks. In some embodiments, the anti-CTLA4 antibody is administered intravenously. In some embodiments, the cancer is resistant or refractory to an inhibitor of CTLA-4, PD-1 or a PD-1 ligand (e.g., PD-L1 or PD-L2). In some embodiments, the cancer is a solid cancer, such as advanced-stage and/or metastatic cancer. In some embodiments, the cancer is urothelial carcinoma. Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of therapy can be employed, including for example, measurement of response through radiological imaging.

The anti-CTLA4 antibodies and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art. In some embodiments, the anti-CTLA4 antibody is administered intravenously.

In some embodiments, the anti-CTLA4 antibody is administered at a dose of no more than any one of 20 mg/kg, 15 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, 0.01 mg/kg, 0.003 mg/kg, or 0.001 mg/kg. In some embodiments, the dose of the anti-CTLA4 antibody is within any one of the following ranges, wherein the ranges have an upper limit of any one of: 20 mg/kg, 15 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, or 0.003 mg/kg, and an independently selected lower limit of any one of 15 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, 0.01 mg/kg, 0.003 mg/kg or 0.001 mg/kg, and wherein the lower limit is less than the upper limit. In some embodiments, the anti-CTLA4 antibody is administered at a dose of any one of about 0.03 mg/kg to about 20 mg/kg, about 0.1 mg/kg to about 20 mg/kg, about 0.3 mg/kg to about 20 mg/kg, about 1 mg/kg to about 20 mg/kg, about 5 mg/kg to about 20 mg/kg, about 0.03 mg/kg to about 10 mg/kg, about 0.1 mg/kg to about 10 mg/kg, about 0.3 mg/kg to about 10 mg/kg, about 1 mg/kg to about 10 mg/kg, about 3 mg/kg to about 10 mg/kg, about 5 mg/kg to about 10 mg/kg, about 0.03 mg/kg to about 0.1 mg/kg, about 0.1 mg/kg to about 0.3 mg/kg, about 0.3 mg/kg to about 1 mg/kg, about 1 mg/kg to about 3 mg/kg, about 3 mg/kg to about 5 mg/kg, about 0.1 mg/kg to about 3 mg/kg, or about 1 mg/kg to about 5 mg/kg. The doses described herein may refer to a suitable dose for a human, or an equivalent dose for the specific species of the subject. In some embodiments, the anti-CTLA4 antibody is administered at a dose equivalent to about 0.03 mg/kg to about 10 mg/kg, or about 0.03 mg/kg to about 20 mg/kg. such as about 0.03 mg/kg, about 0.1 mg/kg, about 0.3 mg/kg, about 1.0 mg/kg, about 3.0 mg/kg, about 6.0 mg/kg, about 10 mg/kg, about 15 mg/kg, or about 20 mg/kg for a human subject.

In some embodiments where the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90%/o sequence identity to the amino acid sequence of SEQ ID NO: 100, the anti-CTLA4 antibody is administered at a dose of between about 0.5 mg/kg to about 10 mg/kg once every three weeks, about 1 mg/kg to about 10 mg/kg once every three weeks, about 3 mg/kg to about 20 mg/kg once every three weeks, about 3 mg/kg to about 15 mg/kg once every three weeks, about 6 mg/kg to about 15 mg/kg once every three weeks, or from abut 6 mg/kg to about 10 mg/kg once every three weeks. In some such embodiments, the anti-CTLA4 antibody is administered at a dose of about 0.5 mg/kg once every three weeks. In some such embodiments, the anti-CTLA4 antibody is administered at a dose of about 1 mg/kg once every three weeks. In some such embodiments, the anti-CTLA4 antibody is administered at a dose of about 3 mg/kg once every three weeks. In other such embodiments, the anti-CTLA4 antibody is administered at a dose of about 6 mg/kg once every three weeks. In other such embodiments, the anti-CTLA4 antibody is administered at a dose of about 10 mg/kg once every three weeks. In some of the foregoing embodiments, the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580. In some of the foregoing embodiments, the anti CTLA4 antibody is administered to a patient with melanoma, non-small cell lung cancer, renal cell carcinoma, or hepatocellular carcinoma. In other of the foregoing embodiments, the anti CTLA4 antibody is administered to a patient with a MSI-H or dMMR cancer. In other of the foregoing embodiments, the anti CTLA4 antibody is administered to a patient with a cancer that has metastasized. In some of the foregoing embodiments, the anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In some embodiments where the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100, the anti-CTLA4 antibody is administered at a first higher dose (e.g., between about 10 mg/kg and about 20 mg) for at least one treatment cycle (as defined herein) followed by a lower dose (e.g., between about 0.5 mg/kg to about 10 mg/kg, about 0.5 mg/kg to about 6 mg/kg, or about 3 mg/kg to about 10 mg/kg) in subsequent cycles. In some such embodiments, the anti-CTLA4 antibody is administered at a dose of about 10 mg/kg for at least one treatment cycle (e.g., one to three treatment cycles) and at a dose of about 6 mg/kg in subsequent treatment cycles. In other such embodiments, the anti-CTLA4 antibody is administered at a dose of about 10 mg/kg for at least one treatment cycle (e.g., one to three treatment cycles) and at a dose of about 3 mg/kg in subsequent treatment cycles. In other such embodiments, the anti-CTLA4 antibody is administered at a dose of about 15 mg/kg for at least one treatment cycle (e.g., one to three treatment cycles) and at a dose of about 10 mg/kg in subsequent treatment cycles. In other such embodiments, the anti-CTLA4 antibody is administered at a dose of about 20 mg/kg for at least one treatment cycle (e.g., one to three treatment cycles) and at a dose of about 10 mg/kg in subsequent treatment cycles. In some of the foregoing embodiments, the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580. In some of the foregoing embodiments, the anti CTLA4 antibody is administered to a patient with melanoma, non-small cell lung cancer, renal cell carcinoma, or hepatocellular carcinoma. In other of the foregoing embodiments, the anti CTLA4 antibody is administered to a patient with a MSI-H or dMMR cancer. In other of the foregoing embodiments, the anti CTLA4 antibody is administered to a patient with a cancer that has metastasized. In some of the foregoing embodiments, the anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In some embodiments where the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100, the anti-CTLA4 antibody is administered at a dose that provides a steady state concentration of from about 50 nM to about 700 nM in systemic circulation when measured at the last day of a dosing cycle (i.e., serum trough concentration). For instance, if the dosing cycle is once every three weeks, the serum trough concentration is measured on day 21 (i.e., after 504 hours) of the dosing cycle. If the dosing cycle is once every four weeks (i.e., after 672 hours), the serum trough concentration is measured on day 28 of the dosing cycle. In some embodiments, the anti-CTLA4 antibody is administered at a dose that provides a steady state serum trough concentration of from about 100 nM to about 500 nM. In other embodiments, the anti-CTLA4 antibody is administered at a dose that provides a steady state serum trough concentration of from about 100 nM to about 400 nM. In other embodiments, the anti-CTLA4 antibody is administered at a dose that provides a steady state serum trough concentration of from about 100 nM to about 200 nM. In other embodiments, the anti-CTLA4 antibody is administered at a dose that provides a steady state serum trough concentration of from about 150 nM to about 400 nM. In other embodiments, the anti-CTLA4 antibody is administered at a dose that provides a steady state serum trough concentration of from about 150 nM to about 450 nM. In some of the foregoing embodiments, the anti-CTLA4 antibody is administered once every three weeks. In some of the foregoing embodiments, the anti-CTLA4 antibody is administered once every four weeks. In some of the foregoing embodiments, the anti-CTLA4 antibody is administered once every two weeks. In some of the foregoing embodiments, the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580. In some of the foregoing embodiments, the anti CTLA4 antibody is administered to a patient with melanoma, non-small cell lung cancer, renal cell carcinoma, or hepatocellular carcinoma. In other of the foregoing embodiments, the anti CTLA4 antibody is administered to a patient with a MSI-H or dMMR cancer. In other of the foregoing embodiments, the anti CTLA4 antibody is administered to a patient with a cancer that has metastasized. In some of the foregoing embodiments, the anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In some embodiments where the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100, the anti-CTLA4 antibody is administered at a dose that provides a concentration of from about 100 nM to about 2,000 nM in systemic circulation when measured after one week (i.e., 168 hours) of a dosing schedule. In some embodiments, the anti-CTLA4 antibody is administered at a dose that provides a concentration of from about 150 nM to about 1,500 nM in systemic circulation when measured after one week (i.e., 168 hours) of a dosing schedule. In other embodiments, the anti-CTLA4 antibody is administered at a dose that provides a concentration of from about 150 nM to about 1,000 nM in systemic circulation when measured after one week (i.e., 168 hours) of a dosing schedule. In other embodiments, the anti-CTLA4 antibody is administered at a dose that provides a concentration of from about 1,000 nM to about 2,000 nM in systemic circulation when measured after one week (i.e., 168 hours) of a dosing schedule. In other embodiments, the anti-CTLA4 antibody is administered at a dose that provides a concentration of from about 150 nM to about 500 nM in systemic circulation when measured after one week (i.e., 168 hours) of a dosing schedule. other embodiments, the anti-CTLA4 antibody is administered at a dose that provides a concentration of greater than about 150 nM when measured after one week (i.e., 168 hours) of a dosing schedule. In some of the foregoing embodiments, the anti-CTLA4 antibody is administered once every three weeks. In some of the foregoing embodiments, the anti-CTLA4 antibody is administered once every four weeks. In some of the foregoing embodiments, the anti-CTLA4 antibody is administered once every two weeks. In some of the foregoing embodiments, the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580. In some of the foregoing embodiments, the anti CTLA4 antibody is administered to a patient with melanoma, non-small cell lung cancer, renal cell carcinoma, or hepatocellular carcinoma. In other of the foregoing embodiments, the anti CTLA4 antibody is administered to a patient with a MSI-H or dMMR cancer. In other of the foregoing embodiments, the anti CTLA4 antibody is administered to a patient with a cancer that has metastasized. In some of the foregoing embodiments, the anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In some embodiments where the anti-CTLA4 antibody comprises a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100, the anti-CTLA4 antibody is administered at a dose that results in a steady state $AUC_{(0-\infty)}$ of from about 500,000 day*ng/mL to about 2,500,000 day*ng/mL. In some embodiments, the anti-CTLA4 antibody is administered at a dose that results in a steady state $AUC_{(0-\infty)}$ of from about 500,000 day*ng/mL to about 1,500,000 day*ng/mL. In some embodiments, the anti-CTLA4 antibody is administered at a dose that results in a steady state $AUC_{(0-\infty)}$ of from about 500,000 day*ng/mL to about 1,000,000 day*ng/mL. In some embodiments, the anti-CTLA4 antibody is administered at a dose that results in a steady state $AUC_{(0-\infty)}$ of from about 500,000 day*ng/mL to about 1,000,000 day*ng/mL. In some embodiments, the anti-CTLA4 antibody is administered at a dose that results in a steady state $AUC_{(0-\infty)}$ of from about 1,500,000 day*ng/mL to about 2,000,000 day*ng/mL. In some embodiments, the anti-CTLA4 antibody is administered at a dose that results in a steady state $AUC_{(0-\infty)}$ of from about 2,000,000 day*ng/mL to about 2,500,000 day*ng/mL. In some embodiments, the steady state $AUC_{(0-\infty)}$ is achieved by administering the anti-CTLA4 antibody once every three weeks. In some embodiments, the steady state $AUC_{(0-\infty)}$ is achieved by administering the anti-CTLA4 antibody once every four weeks. In some embodiments, the steady state $AUC_{(0-\infty)}$ is achieved by administering the anti-CTLA4 antibody once every five weeks. In some embodiments, the steady state $AUC_{(0-\infty)}$ is achieved by administering the anti-CTLA4 antibody once every two weeks. In some of the foregoing embodiments, the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the anti-CTLA4 antibody comprises a heavy chain comprising the amino acid sequence of SEQ ID NO: 125 and a light chain comprising the amino acid sequence of SEQ ID NO: 127. In some of the foregoing embodiments, the anti-CTLA4 antibody comprises a heavy chain comprising the amino acid sequence of SEQ ID NO: 126 and a light chain comprising the amino acid sequence of SEQ ID NO: 127. In some of the foregoing embodiments, the anti-CTLA4 antibody is TY21580. In some of the foregoing embodiments, the anti CTLA4 antibody is administered to a patient with melanoma, non-small cell lung cancer, renal cell carcinoma, or hepatocellular carcinoma. In other of the foregoing embodiments, the anti CTLA4 antibody is administered to a patient with a MSI-H or dMMR cancer. In other of the foregoing embodiments, the anti CTLA4 antibody is administered to a patient with a cancer that has metastasized. In some of the foregoing embodiments, the anti-CTLA4 antibody is administered to a patient that is resistant or refractory to prior cancer therapy, including other anti-CTLA4 antibodies, anti-PD-1 antibodies, anti PD-L1 antibodies, or combinations thereof.

The effective amount of the anti-CTLA4 antibody may be administered in a single dose or in multiple doses. For methods that comprises administration of the anti-CTLA4 antibody in multiple doses, exemplary dosing frequencies include, but are not limited to, weekly, weekly without break, weekly for two out of three weeks, weekly for three out of four weeks, once every three weeks, once every two weeks, monthly, every six months, yearly, etc. In some embodiments, the anti-CTLA4 antibody is administered about weekly, once every 2 weeks, once every 3 weeks, once every 6 weeks, or once every 12 weeks. In some embodiments, the intervals between each administration are less than about any of 3 years, 2 years, 12 months, 11 months, 10 months, 9 months, 8 months, 7 months, 6 months, 5 months, 4 months, 3 months, 2 months, 1 month, 4 weeks, 3 weeks, 2 weeks, or 1 week. In some embodiments, the intervals between each administration are more than about any of 1 week, 2 weeks, 3 weeks, 4 weeks, 1 month, 2 months, 3 months, 4 months, 5 months, 6 months, 7 months, 8 months, 9 months, 10 months, 11 months, 12 months, 2 years, or 3 years. In some embodiments, there is no break in the dosing schedule.

In some embodiments, the anti-CTLA4 antibody is administered at a low frequency, for example, any one of no more frequent than once per week, once every other week, once per three weeks, once per month, once per 2 months, once per 3 months, once per 4 months, once per 5 months, once per 6 months, once per 7 months, once per 8 months, once per 9 months, once per 10 months, once per 11 months, once per year, or less. In some embodiments, the anti-CTLA4 antibody is administered in a single dose. In some embodiments, the anti-CTLA4 antibody is administered about once every three weeks.

In some embodiments, the anti-CTLA4 antibody is administered for 2 or more cycles, such as about any one of 2, 3, 4, 5, 6, 7, 8, 9, 10, 11, 12, or more cycles. In some embodiments, the anti-CTLA4 antibody is administered for at least 4 cycles.

In some embodiments, the treatment comprises an initial phase and a subsequent maintenance phase. In some embodiments, the anti-CTLA4 antibody is administered less frequently in the maintenance phase than in the initial phase. In some embodiments, the anti-CTLA4 antibody is administered at the same frequently in the maintenance phase as in the initial phase. In some embodiments, the treatment comprises an initial phase wherein the anti-CTLA4 antibody is administered about once every three weeks for at least 4 cycles, and a maintenance phase wherein the anti-CTLA4 antibody is administered about once every 4 weeks to once every 12 weeks, such as once every 4 weeks, once every 6 weeks, once every 8 weeks, once every 10 weeks, or once every 12 weeks. In some embodiments, the dosing frequency in the maintenance phase is adjusted depending on one or more biomarkers, such as $T_{reg}$ cells, CD8+ $T_{em}$ cells, CD4+$T_{em}$ cells, a ratio of CD8+ $T_{em}$ cells to $T_{reg}$ cells, a ratio of CD4+ $T_{em}$ cells to $T_{reg}$ cells, and/or NK cells. For example, if the subject shows an increase in the ratio of CD8+ $T_{em}$ cells to $T_{reg}$ cells after receiving the anti-CTLA4 antibody, the subject may be further administered an anti-CTLA4 antibody at about every 4 weeks.

The administration of the anti-CTLA4 antibody can be extended over an extended period of time, such as from about a week to about a month, from about a month to about a year, from about a year to about several years. In some embodiments, the anti-CTLA4 antibody is administered over a period of at least any of about 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 1 year, 2 years, 3 years, 4 years, or more.

The methods described herein are useful for treating a variety of cancers. In some embodiments, the cancer is a solid cancer. In some embodiments, the cancer is a liquid cancer. A variety of cancers where CTLA4 is implicated, whether malignant or benign and whether primary or secondary, may be treated or prevented with a method provided by the disclosure. Exemplary cancers include, but are not limited to, liver cancer, a cancer of the digestive system (e.g., colon cancer, colorectal cancer), lung cancer, bone cancer, heart cancer, brain cancer, kidney cancer, bladder cancer, a hematological cancer (e.g., leukemia), skin cancer, breast cancer, thyroid cancer, pancreatic cancer, a head and/or neck cancer, an eye-related cancer, a male reproductive system cancer (e.g., prostate cancer, testicular cancer), or a female reproductive system cancer (e.g., uterine cancer, cervical cancer). In some embodiments, the cancer is kidney cancer, such as renal cell carcinoma, or urothelial carcinoma.

In some embodiments, the subject has been previously treated with a prior therapy. In some embodiments, the subject has previously received any one of 1, 2, 3, 4, or more prior therapies. In some embodiments, the subject has exhausted all other available therapies. In some embodiments, the subject is unresponsive or resistant to a prior therapy. In some embodiments, the subject has disease reoccurrence subsequent to a prior therapy. In some embodiments, the subject is refractory to a prior therapy. In some embodiments, the subject has failed a prior therapy within about 1 year, 6 months, 3 months or less. In some embodiments, the subject has not previously received a prior therapy.

In some embodiments, the subject has been previously treated with a standard therapy for the cancer. In some embodiments, the subject is unresponsive or resistant to a standard therapy. In some embodiments, the subject has disease reoccurrence subsequent to a standard therapy. In some embodiments, the subject is refractory to a standard therapy. In some embodiments, the subject has failed a standard therapy within about 1 year, 6 months, 3 months or less. In some embodiments, the subject has not previously received a standard therapy. In some embodiments, the subject has refused or is ineligible for a standard therapy.

In some embodiments, the prior therapy (e.g., standard therapy) is selected from the group consisting of viral gene therapy, immunotherapy, targeted therapy, radiation therapy, and chemotherapy. In some embodiments, the prior therapy is an immune checkpoint inhibitor. In some embodiments, the prior therapy is an inhibitor of CTLA4, PD-1, or a PD-1 ligand (e.g., PD-L1 or PD-L2). In some embodiments, the prior therapy is an inhibitor of CTLA4, such as an anti-CTLA4 antibody that is different from the anti-CTLA4 antibodies described herein. In some embodiments, the prior therapy is ipilimumab. In some embodiments, the prior therapy is an inhibitor of CTLA4 (e.g., an anti-CTLA4 antibody) and an inhibitor of PD-1 (e.g., an anti-PD-1 antibody). In some embodiments, the prior therapy is an inhibitor of CTLA4 (e.g., an anti-CTLA4 antibody) and an inhibitor of PD-1 ligand (e.g., an anti-PD-L1 antibody or an anti-PD-L2 antibody).

In some embodiments, the prior therapy is an inhibitor of PD-1 or a PD-1 ligand, including a PD-1 binding antagonist, a PDL1 binding antagonist and a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the inhibitor of PD-1 is a molecule that inhibits the binding of PD-1 to its ligand binding partners. In some embodiments, the inhibitor of a PD-1 ligand is an inhibitor of PD-L1 and/or PD-L2. In some embodiments, the inhibitor of PD-L1 is a molecule that inhibits the binding of PDL1 to its binding partners. In some embodiments, a PD-L2 binding partner is PD-1 and/or B7-1. In some embodiments, the inhibitor of a PD-1 ligand is a molecule that inhibits the binding of PD-L2 to its binding partners. In some embodiments, a PD-L2 binding partner is PD-1. The inhibitor may be an antibody, an antigen binding fragment thereof, an immunoadhesin, a fusion protein, or oligopeptide.

In some embodiments, the inhibitor of PD-1 is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the inhibitor of PD-1 is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the inhibitor of PD-1 is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342. In some embodiments, the anti-PD-1 antibody is nivolumab (CAS Registry Number: 946414-94-4). In some embodiments, the anti-PD-1 antibody is pembrolizumab (CAS Registry Number: 1374853-91-4).

In some embodiments, the inhibitor of PD-L1 is anti-PD-L1 antibody. In some embodiments, the inhibitor of PD-L1 is selected from the group consisting of YW243.55.S70, MPDL3280A, MDX-1105, and MEDI4736. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MEDI4736 is an anti-PD-L1 antibody described in WO2011/066389 and US2013/034559. Examples of anti-PD-L1 antibodies useful for the methods of this application, and methods for making thereof are described in PCT patent application WO 2010/077634 A1 and U.S. Pat. No. 8,217,149, which are incorporated herein by reference.

Prior therapies (e.g., standard therapies) also encompass surgery to remove a tumor and radiation therapy. Exemplary radiation therapies include, but are not limited to, ionizing (electromagnetic) radiotherapy (e.g., X-rays or gamma rays)

and particle beam radiation therapy (e.g., high linear energy radiation). The source of radiation can be external or internal to the subject.

The methods described herein are useful for various aspects of cancer treatment. In some embodiments, there is provided a method of inhibiting cell proliferation (such as tumor growth) in an individual, comprising administering to the individual an effective amount of any one of the anti-CTLA4 antibodies described herein. In some embodiments, at least about 10% (including for example at least about any of 20%, 30%, 40%, 60%, 70%, 80%, 90%, 95% or more) cell proliferation is inhibited.

In some embodiments, there is provided a method of inhibiting tumor metastasis in an individual, comprising administering to the individual an effective amount of any one of the anti-CTLA4 antibodies described herein. In some embodiments, at least about 10% (including for example at least about any of 20%, 30%, 40%, 60%, 70%, 80%, 90%, 95% or more) metastasis is inhibited.

In some embodiments, there is provided a method of reducing (such as eradicating) pre-existing tumor metastasis (such as metastasis to the lymph node) in an individual, comprising administering to the individual an effective amount of any one of the anti-CTLA4 antibodies described herein. In some embodiments, at least about 10% (including for example at least about any of 20%, 30%, 40%, 60%, 70%, 80%, 90%, 95% or more) metastasis is reduced.

In some embodiments, there is provided a method of reducing incidence or burden of preexisting tumor metastasis (such as metastasis to the lymph node) in an individual, comprising administering to the individual an effective amount of any one of the anti-CTLA4 antibodies described herein.

In some embodiments, there is provided a method of reducing tumor size in an individual, comprising administering to the individual an effective amount of any one of the anti-CTLA4 antibodies described herein. In some embodiments, the method reduces tumor size by at least about 100 (including for example at least about any of 20%, 30%, 40%, 60%, 70%, 80%, 90%, 95% or more).

In some embodiments, there is provided a method of prolonging time to disease progression of cancer in an individual, comprising administering to the individual an effective amount of any one of the anti-CTLA4 antibodies described herein. In some embodiments, the method prolongs the time to disease progression by at least any of 1, 2, 3, 4, 5, 6, 7, 8, 9, 10, 11, 12, 16, 20, 24, 28, 32, 36, or more weeks.

In some embodiments, there is provided a method of prolonging survival (e.g., overall survival or progression-free survival) of an individual having cancer, comprising administering to the individual an effective amount of any one of the anti-CTLA4 antibodies described herein. In some embodiments, the method prolongs the survival of the individual by at least any of 1, 2, 3, 4, 5, 6, 7, 8, 9, 10, 11, 12, 18, or 24 months.

In some embodiments, there is provided a method of alleviating one or more symptoms in an individual having cancer, comprising administering to the individual an effective amount of any one of the anti-CTLA4 antibodies described herein.

In some embodiments, there is provided a method of improving the quality of life in an individual having cancer, comprising administering to the individual an effective amount of any one of the anti-CTLA4 antibodies described herein.

The anti-CTLA4 antibody may be administered alone as monotherapy, or administered in combination with one or more additional therapeutic agents or therapies. In some embodiment, anti-CTLA4 antibody is administered in combination with one or more additional therapeutic agents for separate, sequential or simultaneous administration. The term "additional therapeutic agent" refers to any therapeutic agent other than an anti-CTLA4 antibody provided by the disclosure. In some embodiments, there is provided a combination therapy for treating cancer in a subject, which comprises administering to the subject a therapeutically effective amount of an anti-CTLA4 antibody described herein in combination with one or more additional therapeutic agents. In some embodiments, anti-CTLA4 antibody is administered in combination with one or more additional therapeutic agents comprising chemotherapeutic agents, immunotherapeutic agents, and/or hormone therapeutic agents. In some embodiments, the one or more additional therapeutic agents are selected from the group consisting of selected from the group consisting of viral gene therapy, immune checkpoint inhibitors, targeted therapies, radiation therapies, and chemotherapies.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Examples of particular chemotherapeutic agents include: (1) alkylating agents, such as chlorambucil (LEUKERAN®), mcyclophosphamide (CYTOXAN®), ifosfamide (IFEX®), mechlorethamine hydrochloride (MUSTARGEN), thiotepa (THIOPLEX®), streptozotocin (ZANOSAR®), carmustine (BICNU®, GLIADEL WAFER®), lomustine (CEENU®), and dacarbazine (DTIC-DOME®); (2) alkaloids or plant vinca alkaloids, including cytotoxic antibiotics, such as doxorubicin (ADRIAMYCIN®), epirubicin (ELLENCE®, PHARMORUBICIN®), daunorubicin (CERUBIDINE®, DAUNOXOME®), nemorubicin, idarubicin (IDAMYCIN PFS®, ZAVEDOS®), mitoxantrone (DHAD®, NOVANTRONE®), dactinomycin (actinomycin D, COSMEGEN®), plicamycin (MITHRACIN®), mitomycin (MUTAMYCIN®), and bleomycin (BLENOXANE®), vinorelbine tartrate (NAVELBINE®), vinblastine (VELBAN®), vincristine (ONCOVIN®), and vindesine (ELDISINE®); (3) antimetabolites, such as capecitabine (XELODA®), cytarabine (CYTOSAR-U®), fludarabine (FLUDARA®), gemcitabine (GEMZAR®), hydroxyurea (HYDRA®), methotrexate (FOLEX®, MEXATE, TREXALL®), nelarabine (ARRANON®), trimetrexate (NEUTREXIN®), and pemetrexed (ALIMTA®); (4) Pyrimidine antagonists, such as 5-fluorouracil (5-FU); capecitabine (XELODA®), raltitrexed (TOMUDEX®), tegafur-uracil (UFTORAL®), and gemcitabine (GEMZAR®); (5) taxanes, such as docetaxel (TAXOTERE®), paclitaxel (TAXOL®); (6) platinum drugs, such as cisplatin (PLATINOL®) and carboplatin (PARAPLATIN®), and oxaliplatin (ELOXATIN®); (7) topoisomerase inhibitors, such as irinotecan (CAMPTOSAR®), topotecan (HYCAMTIN®), etoposide (ETOPOPHOS®, VEPESSID®, TOPOSAR®), and teniposide (VUMON®); (8) epipodophyllotoxins (podophyllotoxin derivatives), such as etoposide (ETOPOPHOS®, VEPESSID®, TOPOSAR®); (9) folic acid derivatives, such as leucovorin (WELLCOVORIN®); (10) nitrosoureas, such as carmustine (BICNU®), lomustine (CEENU®); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA®), erlotinib (TARCEVA®), bortezomib (VELCADE®), imatinib mesylate (GLEEVEC®), genefitinib, lapatinib, sorafenib, thalidomide, sunitinib (SUTENT®), axitinib, rituximab (RITUXAN, MABTHERA®), trastuzumab (HERCEPTIN®), cetuximab (ERBITUX®), bevacizumab (AVASTIN®), and ranibizumab (LUCENTIS®), lym-1 (ONCOLYM®), antibodies to insulin-like growth factor-1 receptor (IGF-1R) that are disclosed in WO2002/053596); (12) angiogenesis inhibitors, such as bevacizumab (AVASTIN®), suramin (GERMANIN®), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE®).

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxID, GMXX, and NeuVax; and antibodies such as alemtuzumab (CAMPATH®), bevacizumab (AVASTIN®), cetuximab (ERBITUX®), gemtuzunab ozogamicin (MYLOTARG®), ibritumomab tiuxetan (ZEVALIN®), panitumumab (VECTIBIX®), rituximab (RITUXAN®, MABTHERA®), trastuzumab (HERCEPTIN®), tositumomab (BEXXAR®), ipilimumab (YERVOY®), tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX®), toremifene (FARESTON®), fulvestrant (FASLODEX®), anastrozole (ARIMIDEX®), exemestane (AROMASIN®), letrozole (FEMARA®), megestrol acetate (MEGACE®), goserelin (ZOLADEX®), and leuprolide (LUPRON®). The anti-CTLA4 antibodies of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

In some embodiments, the additional therapeutic agent is one or more of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-KIR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNα, GM-CSF, a chimeric antigen receptor, adoptively transferred T cells, an anti-cancer vaccine, and an oncolytic virus. In some embodiments, the additional therapeutic agent is an anti-PD-1 antibody. In some embodiments, the additional therapeutic agent is an anti-PD-1 antibody.

The combination therapy for treating cancer also encompasses the combination of an anti-CTLA4 antibody with surgery to remove a tumor. The anti-CTLA4 antibody may be administered to the mammal before, during, or after the surgery.

The combination therapy for treating cancer also encompasses combination of an anti-CTLA4 antibody with radiation therapy, such as ionizing (electromagnetic) radiotherapy (e.g., X-rays or gamma rays) and particle beam radiation therapy (e.g., high linear energy radiation). The source of radiation can be external or internal to the mammal. The anti-CTLA4 antibody may be administered to the mammal before, during, or after the radiation therapy.

Also provided are compositions of any one of the anti-CTLA4 antibodies described herein for use in the methods described in this section, and use of the anti-CTLA4 antibodies in the manufacture of a medicament for treating cancer (such as a solid cancer, e.g., urothelial carcinoma).

III. Biomarkers

The present application also provides biomarkers, which can be used in conjunction with any one of the methods of treatment described herein. Suitable biomarkers include IL-1β, IL-2, IL-6, interferon (IFN)-γ, tumor necrosis factor (TNF)-α, soluble CTLA4 (sCTLA4), soluble PD-L1 (sPD-L1), soluble CD25 (sCD25), CXCL11, FoxP3, Ki67, CD8+ T cells, CD4+ T cells, CD8+ effector memory T ($T_{em}$) cells, CD4+ $T_{em}$ cells, regulatory T ($T_{reg}$) cells, a ratio of CD8+ $T_{em}$ cells to $T_{reg}$ cells, a ratio of CD4+ $T_{em}$ cells to $T_{reg}$ cells, NK cells and B cells.

In some embodiments, there is provided a method of treating or delaying progression of cancer in a subject by administering an effective amount of an anti-CTLA4 antibody based on a level of one or more biomarkers selected from the group consisting of IL-10, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+$T_{em}$ cells to $T_{reg}$ cells, NK cells and B cells in one or more samples obtained from the subject. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells.

In some embodiments, there is provided a method of determining whether a subject is likely to respond to a therapy comprising an anti-CTLA4 antibody by determining a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{reg}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells in one or more samples obtained from the subject. In some embodiments, there is provided a method of treating or delaying progression of cancer in a subject by administering an effective amount of an anti-CTLA4 antibody after it has been determined that the subject is likely to respond to the anti-CTLA4 antibody. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to Treg cells. In some embodiments, the one or more biomarkers comprises NK cells.

In some embodiments, there is provided a method of selecting a subject to receive or not to receive a therapy comprising an anti-CTLA4 antibody based on a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to Treg cells, a ratio of CD4+ $T_{em}$ cells to $T_{reg}$ cells, NK cells and B cells in one or more samples obtained from the subject. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, the one or more biomarkers comprises CD8+$T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells.

In some embodiments, there is provided a method of predicting responsiveness and/or monitoring treatment and/or responsiveness of a subject to a therapy comprising an anti-CTLA4 antibody by determining a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells in one or more samples obtained from the subject. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to Treg cells. In some embodiments, the one or more biomarkers comprises NK cells.

In some embodiments, there is provided a method of positively and/or negatively stratifying patients into particular treatment regimen groups based upon a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to Treg cells, a ratio of CD4+ $T_{em}$ cells to $T_{reg}$ cells, NK cells and B cells in one or more samples obtained from the patients. In some embodiments, the treatment comprises administration of an anti-CTLA4 antibody. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells.

In some embodiments, there is provided an assay for determining a level of one or more biomarkers selected from the group consisting of IL-1β, IL-2, IL-6, IL-10, IFN-γ, TNF-α, sCTLA4, sPD-L1, sCD25, CXCL11, FoxP3, Ki67, CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells in one or more samples obtained from the subject. In some embodiments, the assay is a flow cytometry assay. In some embodiments, the assay is an immunohistochemistry (IHC) assay. In some embodiments, the assay is a multiplex IHC assay capable of detecting two or more biomarkers. In some embodiments, the assay is an immunoassay, such as a Meso Scale Discovery (MSD) assay. In some embodiments, the one or more biomarkers comprise CD8+ T cells, CD4+ T cells, CD8+ $T_{em}$ cells, CD4+ $T_{em}$ cells, $T_{reg}$ cells, a ratio of CD8+$T_{em}$ cells to $T_{reg}$ cells, a ratio of CD4+ $T_{em}$ cells to $T_{reg}$ cells, NK cells and B cells. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells.

In some embodiments, there is provided a method of treating a cancer in a subject, comprising: (a) administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108, (b) subsequently determining a level of one or more biomarkers selected from the group consisting of CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells, B cells in a sample of the subject. In some embodiments, an increase of the level of one or more biomarkers selected from the group consisting of CD8+ T cells, CD4+ T cells, CD8+ $T_{em}$ cells, CD4+ $T_{em}$ cells, a ratio of CD8+ $T_{em}$ cells to $T_{reg}$ cells, a ratio of CD4+ $T_{em}$ cells to $T_{reg}$ cells, NK cells and B cells after administration of the anti-CTLA4 antibody compared to the baseline level of the one or more biomarkers indicates an increased likelihood that the subject has an effective response to the CTLA4 antibody. In some embodiments, a decrease of the level of $T_{reg}$ cells after administration of the anti-CTLA4 antibody compared to the baseline level of the $T_{reg}$ cells indicates an increased likelihood that the subject has an effective response to the CTLA4 antibody. In some embodiments, the cancer is a solid cancer, such as advanced-stage and/or metastatic cancer. In some embodiments, the cancer is urothelial carcinoma. In some embodiments, the cancer is resistant or refractory to a prior therapy, wherein the prior therapy is an inhibitor of CTLA4 (e.g., ipilimumab), PD-1 (e.g., pembrolizumab), or a PD-1 ligand. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells. In some embodiments, the antibody is TY21580.

In some embodiments, there is provided a method of treating a cancer in a subject, comprising: (a) administering to the subject an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108; (b) subsequently determining a level of one or more biomarkers selected from the group consisting of CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells in a sample of the subject; and (c) wherein the sample has an increase of the level of one or more biomarkers selected from the group consisting of CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells and B cells after administration of the anti-CTLA4 antibody compared to the baseline level of the one or more biomarkers, and/or the sample has a decrease of the level of $T_{reg}$ cells after administration of the anti-CTLA4 antibody compared to the baseline level of the $T_{reg}$ cells, administering to the subject a further cycle of an effective amount of the anti-CTLA4 antibody. In some embodiments, the cancer is a solid cancer, such as advanced-stage and/or metastatic cancer. In some embodiments, the cancer is urothelial carcinoma. In some embodiments, the cancer is resistant or refractory to a prior therapy, wherein the prior therapy is an inhibitor of CTLA4 (e.g., ipilimumab), PD-1 (e.g., pembrolizumab), or a PD-1 ligand. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells. In some embodiments, the antibody is TY21580.

In some embodiments, there is provided a method of providing a prognosis for a subject who has been administered with an effective amount of an anti-CTLA4 antibody, wherein the antibody specifically binds to an epitope comprising amino acid residues Y105 and L106 of human CTLA4 but does not comprise residue I108, wherein the numbering of the amino acid residues is according to SEQ ID NO: 108; the method comprising determining a level of one or more biomarkers selected from the group consisting of CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells, B cells in a sample of the subject, wherein: (a) an increase of the level of one or more biomarkers selected from the group consisting of CD8+ T cells, CD4+ T cells, CD8+ $T_{em}$ cells, CD4+ $T_{em}$ cells, a ratio of CD8+ $T_{em}$ cells to $T_{reg}$ cells, a ratio of CD4+ $T_{em}$ cells to $T_{reg}$ cells, NK cells and B cells after administration of the anti-CTLA4 antibody compared to the baseline level of the one or more biomarkers indicates an increased likelihood that the subject has an effective response to the CTLA4 antibody; and/or (b) a decrease of the level of $T_{reg}$ cells after administration of the anti-CTLA4 antibody compared to the baseline level of the $T_{reg}$ cells indicates an increased likelihood that the subject has an effective response to the CTLA4 antibody. In some embodiments, the cancer is a solid cancer, such as advanced-stage and/or metastatic cancer. In some embodiments, the cancer is urothelial carcinoma. In some embodiments, the cancer is resistant or refractory to a prior therapy, wherein the prior therapy is an inhibitor of CTLA4 (e.g., ipilimumab), PD-1 (e.g., pembrolizumab), or a PD-1 ligand. In some embodiments, the one or more biomarkers comprises CD8+ $T_{em}$ cells. In some embodiments, the one or more biomarkers comprises CD4+ $T_{em}$ cells. In some embodiments, the one or more biomarkers comprises $T_{reg}$ cells. In some embodiments, the one or more biomarkers comprises a ratio of CD8+ $T_{em}$ cells to $T_{reg}$ cells. In some embodiments, the one or more biomarkers comprises a ratio of CD4+ $T_{em}$ cells to $T_{reg}$ cells. In some embodiments, the one or more biomarkers comprises NK cells. In some embodiments, the antibody is TY21580.

In some embodiments, the biomarker is a cell population, such as tumor infiltrating T cells, CD8+ T cells, CD4+ T cells, CD8+ $T_{reg}$ cells, CD4+ $T_{reg}$ cells, NK cells and/or B cells, or a ratio between two cell populations such as a ratio of CD8+ $T_{em}$ cells to $T_{reg}$ cells, or a ratio of CD4+ $T_{em}$ cells to $T_{reg}$ cells. Suitable methods for determining levels of cell populations in a sample are known in the art, including, for example, fluorescence-activated cell sorting (FACS). In some embodiments, the sample is a blood sample. In some embodiments, the sample is a tumor sample. In some embodiments, the T cells are tumor infiltrating T cells.

In some embodiments, the method comprises determining the level of $T_{em}$ cells in a sample. In some embodiments, the $T_{em}$ cells are CD8+ $T_{em}$ cells. In some embodiments, the $T_{em}$ cells are CD4+ $T_{em}$ cells. In some embodiments, the $T_{em}$ cells are CD45RO+ CCR7− L-selectin-T cells. In some embodiments, the $T_{em}$ cells have intermediate to high expression of CD44. In some embodiments, the level of $T_{em}$ cells (e.g., CD8+ $T_{em}$ cells or CD4+ $T_{em}$ cells) increases by at least about 10%, 20%, 30%, 50%, 60%, 70%, 80%, 90%, 100%, 150%, 2 fold, 3 fold, 4 fold, 5 fold or more in a subject likely to respond to the anti-CTLA4 antibody treatment after the subject receives an anti-CTLA4 antibody than the baseline level, e.g., before the subject receives the anti-CTLA4 antibody. In some embodiments, a low level of $T_{em}$ cells prior to receiving an anti-CTLA4 antibody in a subject compared to a reference level (e.g., a level of $T_{em}$ cells of a healthy subject) indicates that the subject is likely to respond to the anti-CTLA4 antibody treatment. In some embodiments, the low level is no more than any one of 90%, 80%, 70%, 60%, 50%, 40%, 30%, 20%, 10% or less than the reference level.

In some embodiments, the method comprises determining the level of $T_{reg}$ cells in a sample. In some embodiments, the $T_{reg}$ cells are CD4+ CD25+ FOXP3+ T cells. In some embodiments, a decrease in the level of $T_{reg}$ cells after receiving an anti-CTLA4 antibody in a subject compared to a baseline level indicates that the subject is likely to respond to the anti-CTLA4 antibody treatment, e.g., the subject is likely to have stable disease or partial response. In some embodiments, the level of $T_{reg}$ cells decreases by at least about 10%, 20%, 30%, 50%, 60%, 70%, 80%, 90% or more in a subject likely to respond to the anti-CTLA4 antibody treatment after the subject receives an anti-CTLA4 antibody than before the subject receives the anti-CTLA4 antibody.

In some embodiments, the method comprises determining a ratio of the level of $T_{em}$ cells to the level of $T_{reg}$ cells, such as a ratio of the level of CD8+ $T_{em}$ cells to the level of $T_{reg}$ cells, and/or a ratio of the level of CD8+ $T_{em}$ cells to the level of $T_{reg}$ cells after administration of the anti-CTLA4 antibody. In some embodiments, an increase in the ratio of CD8+ $T_{em}$ cells to $T_{reg}$ cells after receiving an anti-CTLA4 antibody in a subject compared to a baseline level indicates that the subject is likely to respond to the anti-CTLA4 antibody treatment, e.g., the subject is likely to have stable disease or partial response. In some embodiments, the ratio of CD8+ $T_{em}$ cells to $T_{reg}$ cells increases by at least about 10%, 20%, 30%, 50%, 60%, 70%, 80%, 90% or more in a subject likely to respond to the anti-CTLA4 antibody treatment after the subject receives an anti-CTLA4 antibody than before the subject receives the anti-CTLA4 antibody. In some embodiments, an increase in the ratio of CD4+ $T_{em}$ cells to $T_{reg}$ cells after receiving an anti-CTLA4 antibody in a subject compared to a baseline level indicates that the subject is likely to respond to the anti-CTLA4 antibody treatment, e.g., the subject is likely to have stable disease or partial response. In some embodiments, the ratio of CD4+ $T_{reg}$ cells to $T_{reg}$ cells increases by at least about 10%, 20%, 30%, 50%, 60%, 70%, 80%, 90% or more in a subject likely to respond to the anti-CTLA4 antibody treatment after the subject receives an anti-CTLA4 antibody than before the subject receives the anti-CTLA4 antibody.

In some embodiments, the method comprises determining the level of NK cells in a sample, such as a blood sample, e.g., peripheral blood sample. In some embodiments, an increase in the level of NK cells after receiving an anti-CTLA4 antibody in a subject compared to the baseline level of NK cells indicates an increased likelihood that the subject has an effective response to the CTLA4 antibody, e.g., the subject is likely to have stable disease or partial response. In some embodiments, the level of NK cells increases by at least about 10%, 20%, 30%, 50%, 60%, 70%, 80%, 90% or more in a subject likely to respond to the anti-CTLA4 antibody treatment after the subject receives an anti-CTLA4 antibody than before the subject receives the anti-CTLA4 antibody. In some embodiments, a low level of NK cells prior to receiving an anti-CTLA4 antibody in a subject compared to a reference level (e.g., a level of NK cells of a healthy subject) indicates that the subject is likely to respond to the anti-CTLA4 antibody treatment. In some embodiments, the low level is no more than any one of 90%, 80%, 70%, 60%, 50%, 40%, 30%, 20%, 10% or less than the reference level.

In some embodiments, the level of a biomarker in a sample is measured by determining the level of RNA transcript expression of the biomarker. Suitable methods of measuring RNA transcript levels in a sample are known in the art, including, for example, by Northern blot analysis, nuclease protection assays, in situ hybridization, PCR analysis (e.g., qPCR, RT-PCR, RT-qPCR, etc.), and next generation sequencing (e.g., RNAseq). In some embodiments, the level of transcript expression of the biomarker is measured by RT-PCR, in situ hybridization, and/or RNAseq.

In some embodiments, the level of a biomarker in a sample is measured by determining the level of protein expression of the biomarker. Suitable methods of measuring protein expression in a sample are known in the art, including, for example, immunoassays (e.g., Meso Scale Discovery or MSD assay), immunohistochemistry (IHC), PET imaging, Western blotting, enzyme-linked immunosorbent assays (ELISAs), flow cytometry, and mass spectrometry. In some embodiments, the level of protein expression of the biomarker is measured by immunoassay, Western blotting, ELISA, IHC, and/or flow cytometry.

In some embodiments, the level of one or more biomarkers is measured in one or more (e.g., one or more, two or more, three or more, four or more, etc.) samples obtained from a subject. Any suitable sample in the form of tissues and/or fluids that are known or believed to contain diseased cells and/or the target of interest may be used in the methods described herein, including, for example, sputum, pleural fluid, lymph fluid, bone marrow, blood, plasma, serum, urine, tissue samples (samples known or expected to contain cancer cells), tumor samples, tumor biopsies, etc. In some embodiments, the sample is a blood sample. In some embodiments, the sample is a serum sample. In some embodiments, the sample is a tumor sample. In some embodiments, the sample is a tumor biopsy. In some embodiments, the sample comprises one or more cancer cells.

Methods of obtaining suitable tissue and/or fluid samples (e.g., methods that are appropriate for obtaining a representative sample from a particular type, location, disease tissue, etc.) are well known to one of ordinary skill in the art, including, for example, by resection, bone marrow biopsy or bone marrow aspiration, endoscopic biopsy or endoscopic aspiration (e.g., cystoscopy, bronchoscopy, colonoscopy, etc.), needle biopsy or needle aspiration (e.g., fine needle aspiration, core needle biopsy, vacuum-assisted biopsy, image-guided biopsy, etc.) skin biopsy (e.g., shave biopsy, punch biopsy, incisional biopsy, excisional biopsy, etc.), various other surgical tissue (e.g., tumor tissue) biopsy and/or excision strategies, and fluid collections (e.g., collecting urine, blood, serum, plasma, sputum, etc.).

In some embodiments, the one or more samples obtained from the subject are enriched for diseased (e.g., cancerous) cells. Methods of enriching a tissue or fluid preparation for diseased (e.g., cancerous) cells are known in the art, including, for example, by separating diseased (e.g., cancerous) cells from normal cells by flow cytometry. In some embodiments, the level of one or more biomarkers is measured in the enriched samples. In some embodiments, the level of one or more biomarkers is measured in samples that have not been enriched or otherwise altered after isolation.

In some embodiments, the one or more samples are fixed (i.e. preserved) by conventional methodology (See e.g., "Manual of Histological Staining Method of the Armed Forces Institute of Pathology," 3rd edition (1960) Lee G. Luna, HT (ASCP) Editor, The Blakston Division McGraw-Hill Book Company, New York; *The Armed Forces Institute*

*of Pathology Advanced Laboratory Methods in Histology and Pathology* (1994) Ulreka V. Mikel, Editor, Armed Forces Institute of Pathology, American Registry of Pathology, Washington, D.C.). The choice of a fixative may be determined by one of ordinary skill in the art for the purpose for which the sample is to be analyzed. The length of fixation will depend upon the size and type of the tissue sample and the fixative used (e.g., neutral buffered formalin, paraformaldehyde, etc.), as will be appreciated by one of ordinary skill in the art. In some embodiments, the level of one or more biomarkers is measured in a sample that is fixed. In some embodiments, the level of one or more biomarkers is measured in samples that have not been fixed or otherwise altered after isolation.

In some embodiments, one or more samples are obtained from the subject prior to administration with an anti-CTLA4 antibody. In some embodiments, one or more samples are obtained from the subject after administration of a first and/or subsequent dose of an anti-CTLA4 antibody. In some embodiments, one or more samples are obtained from the subject after completion of an anti-CTLA4 antibody therapy. In some embodiments, one or more samples are obtained from the subject, prior to, during, and after completion of an anti-CTLA4 antibody therapy.

In some embodiments, the method comprises comparing the level of a biomarker in a sample obtained from a subject to a reference level of the biomarker. In some embodiments, the reference level is the level of the biomarker in a reference sample (e.g., a reference cell (such as a cell line, including but not limited to Raji (ATCC, CC-86) or Daudi (ATCC, CCL-213) cell lines), a corresponding sample taken from one or more patients determined to be responsive to anti-CTLA4 antibody therapy, a corresponding sample taken from one or more patients determined to be non-responsive to anti-CTLA4 antibody therapy, a corresponding adjacent normal tissue, etc.). In some embodiments, the reference level is measured in the reference sample using the same method as was used to measure the level of the biomarker in the subject's sample. In some embodiments, the reference level is measured in the reference sample using a different method than was used to measure the level of the biomarker in the subject's sample.

In some embodiments, the reference level is a pre-determined level of a biomarker (e.g., the average level of the biomarker in a database of diseased samples (such as tissue biopsies or serum samples) isolated from multiple reference patients; the average level of the biomarker in a database of samples (such as tissue biopsies or serum samples) isolated from multiple healthy reference patients; etc.).

In some embodiments, the reference level is a baseline level of the biomarker before the subject is administered the anti-CTLA4 antibody.

In some embodiments, the reference level of a biomarker refers to a detectable level of expression. That is to say, in some embodiments, the level of a biomarker measured in the sample obtained from the subject is considered to be lower than a reference level when the level of the biomarker in the sample is undetectable, e.g., below the limit of detection.

In some embodiments, the level of a biomarker measured in the sample obtained from the subject is considered to be lower than the reference level when the level of the biomarker in the sample is at least about 25% lower than the reference level. For example, the level of a biomarker measured in the sample obtained from the subject is considered to be lower than the reference level when the level of the biomarker in the sample is at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the reference level. In some embodiments, the level of a biomarker measured in the sample obtained from the subject is considered to be lower than the reference level when the level of the biomarker in the sample is at least about 1-fold lower than the reference level. For example, the level of a biomarker measured in the sample obtained from the subject is considered to be lower than the reference level when the level of the biomarker in the sample is at least about 1-fold, at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5 fold, at least about 8-fold, at least about 8.5-fold, at least about 9-fold, at least about 9.5-fold, at least about 10-fold, at least about 100-fold, or at least about 1000-fold lower than the reference level. In some embodiments, the level of a biomarker in the sample obtained from the subject is below the limit of detection. In some embodiments, the level of a biomarker measured in the sample obtained from the subject is considered to be lower than the reference level when the level of the biomarker in the sample is below the limit of detection while the reference level is above the limit of detection, is detectable, and/or is not zero. In some embodiments, a level is considered to be below the limit of detection when the level does not give an appreciable signal, a detectable signal, and/or is not significantly different than an appropriate negative control when performing an assay for measuring the level of a biomarker (e.g., below the limit of detection of an assay measuring RNA transcript expression of the biomarker (such as RT-PCR, in situ hybridization, and/or next generation sequencing), below the limit of detection of an assay measuring protein expression of a biomarker (such as an immunoassay, PET imaging, Western blotting, ELISA, immunohistochemistry, and/or flow cytometry), etc.).

In some embodiments, a subject is administered an effective amount of an anti-CTLA4 antibody when the level of a biomarker in a sample obtained from the subject is lower than the reference level. In some embodiments, a subject is determined to be likely to respond to an anti-CTLA4 antibody when the level of the biomarker in a sample obtained from the subject is lower than the reference level. In some embodiments, a subject is administered an effective amount of an anti-CTLA4 antibody after the subject has been determined to be likely to respond to the anti-CTLA4 antibody. In some embodiments, a subject having cancer is selected for treatment with an anti-CTLA4 when the level of the biomarker in a sample obtained from the subject is lower than the reference level. In some embodiments, a subject is positively stratified for enrollment into an anti-CTLA4 antibody therapy when the level of a biomarker in a sample obtained from the subject is lower than the reference level.

In some embodiments, the level of a biomarker measured in the sample obtained from the subject is considered to be higher than the reference level when the level of the biomarker in the sample is at least about 5% higher than the reference level. For example, the level of a biomarker measured in the sample obtained from the subject is considered to be higher than the reference level when the level of the biomarker in the sample is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% higher than the reference level. In some embodiments, the level of a biomarker measured in the sample obtained from the subject is considered to be higher than the reference level when the level of the biomarker in the sample is at least about 1-fold higher than the reference level. For example, the level of a biomarker measured in the sample obtained from the subject is considered to be higher than the reference level when the level of the biomarker in the sample is at least about 1-fold, at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5 fold, at least about 8-fold, at least about 8.5-fold, at least about 9-fold, at least about 9.5-fold, at least about 10-fold, at least about 100-fold, or at least about 1000-fold higher than the reference level. In some embodiments, the level of a biomarker in the reference sample is below the limit of detection. In some embodiments, the level of a biomarker measured in the sample obtained from the subject is considered to be higher than the reference level when the level of the biomarker in the sample is above the limit of detection, is detectable, and/or is not zero while the level of the biomarker in the reference sample is below the limit of detection. In some embodiments, a level is considered to be below the limit of detection when the level does not give an appreciable signal, a detectable signal, and/or is not significantly different than an appropriate negative control when performing an assay for measuring the level of a biomarker (e.g., below the limit of detection of an assay measuring RNA transcript expression of the biomarker (such as RT-PCR, in situ hybridization, and/or next generation sequencing), below the limit of detection of an assay measuring protein expression of the biomarker (such as an immunoassay, PET imaging, Western blotting, ELISA, immunohistochemistry, and/or flow cytometry), etc.).

In some embodiments, a subject is administered an effective amount of an anti-CTLA4 antibody when the level of a biomarker in a sample obtained from the subject is higher than the reference level. In some embodiments, a subject is determined to be likely to respond to an anti-CTLA4 antibody when the level of a biomarker in a sample obtained from the subject is higher than the reference level. In some embodiments, a subject is administered an effective amount of an anti-CTLA4 antibody after the subject has been determined to be likely to respond to the anti-CTLA4 antibody. In some embodiments, a subject having cancer is selected for treatment with an anti-CTLA4 antibody when the level of expression of a biomarker in a sample obtained from the subject is higher than the reference level. In some embodiments, a subject is positively stratified for enrollment into an anti-CTLA4 antibody therapy when the level of a biomarker in a sample obtained from the subject is higher than the reference level.

In some embodiments, the method comprises determining the level of a biomarker at two or more time points during the course of the anti-CTLA4 antibody treatment. In some embodiments, the method comprises determining the level of a biomarker (e.g., CD8+ Ta cells, CD4+ $T_{em}$ cells, a ratio between CD8+ $T_{em}$ cells to $T_{reg}$ cells, a ratio between CD4+ $T_{em}$ cells to $T_{reg}$ cells, NK cells) in a sample obtained from the subject prior to the administration of the anti-CTLA4 antibody. In some embodiments, the method comprises determining the level of a biomarker in a sample obtained from the subject after the administration of the anti-CTLA4 antibody. In some embodiments, the method comprises determining the level of a biomarker in a sample obtained from the subject after each cycle of anti-CTLA4 antibody treatment. In some embodiments, the method comprises determining a ratio ("induction ratio") between the difference in the level of the biomarker after administration of the anti-CTLA4 antibody (C2) and the level of the biomarker before administration of the anti-CTLA4 antibody (C1) and the level of the biomarker before administration of the anti-CTLA4 antibody (C1): (C2-C1)/C1. In some embodiments, an induction ratio of at least about any one of 50%, 1, 2, 3, 4, 5, 6, 7, 8, 9, 10 or more indicates a high likelihood of responding to the anti-CTLA4 antibody treatment, i.e., having stable disease (SD) or partial response (PR) after the treatment.

IV. Anti-CTLA4 Antibodies

The method described herein comprise administration of an anti-CTLA4 antibody that specifically binds to human CTLA4, including CTLA4 antibodies, antigen-binding fragments of the CTLA4 antibodies, and derivatives of the CTLA4 antibodies. Exemplary anti-CTLA4 antibodies have been described, for example, in International Publication No. WO2019149281A1, which is incorporated herein by reference in its entirety.

In some embodiments, the anti-CTLA4 antibody is any one of the antibodies described herein, including antibodies described with reference to specific amino acid sequences of HVRs, variable regions (VL, VH), and light and heavy chains (e.g., IgG1, IgG2, IgG4). In some embodiments, the antibodies are human antibodies. In some embodiments, the antibodies are humanized antibodies and/or chimeric antibodies. In some embodiments, the anti-CTLA4 antibody binds to human CTLA4, and have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (f) activates human PBMCs (e.g., stimulates secretion of IL-2 and/or IFNγ); (g) are capable of inhibiting tumor cell growth; (h) have therapeutic effect on a cancer; and (i) block binding of human CTLA4 to human CD80 and/or human CD86. In some embodiments, the anti-CTLA4 antibodies described herein have lower activity in blocking binding of CD80 and/or CD86 to human CTLA4 as compared to ipilimumab in an assay wherein either when human CD80 and/or CD86 are immobilized (or plate bound) or when human CTLA4 protein is present on cell surface. In some embodiments, the anti-CTLA4 antibodies described herein deplete $T_{reg}$ cells selectively in tumor microenvironment as compared to $T_{reg}$ depletions in PBMC or spleen. In some embodiments, the anti-CTLA4 antibodies described herein have higher $T_{reg}$ depletion activity in tumor microenvironment as compared to ipilimumab. Also provided herein are one or more anti-CTLA4 antibodies or antigen-binding fragments that cross-compete for binding to human CTLA4 with one or more of the antibodies or antigen-binding fragments described herein.

In some embodiments, the antibodies or antigen-binding fragments bind to human, cynomolgus monkey, mouse, rat, and/or dog CTLA4 with a $K_D$ of about 500 nM or less (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the antibodies or antigen-binding fragments bind to human, cynomolgus monkey, mouse, rat, and/or dog CTLA4 with a $K_D$ of about 350 nM or less. In some embodiments, the antibodies or antigen-binding fragments bind to human CTLA4 with a $K_D$ of about 100 nM or less. In some embodiments, the antibodies or antigen-binding fragments bind to human CTLA4 with a $K_D$ of about 50 nM or less. In some embodiments, the antibodies or antigen-binding fragments bind to human CTLA4 with a $K_D$ of about 10 nM or less. Methods of measuring the $K_D$ of an antibody or antigen-binding fragment may be carried out using any method known in the art, including for example, by surface plasmon resonance, an ELISA, isothermal titration calorimetry, a filter binding assay, an EMSA, etc. In some embodiments, the $K_D$ is measured by surface plasmon resonance or an ELISA (see e.g., Example 3 below).

In some embodiments, the antibodies or antigen-binding fragments described herein have antagonist activity on human CTLA4. In some embodiments, the antibodies or antigen-binding fragments repress one or more activities of human CTLA4 when a cell (e.g., a human cell) expressing human CTLA4 is contacted by the antibody or antigen binding fragment (e.g., CTLA4 blockade as measured by an increase in a reporter gene signal using a CLA4 blockage reporter gene assay).

In some embodiments, the antibodies or antigen-binding fragments are cross-reactive with monkey (e.g., cynomolgus monkey), mouse, rat, and/or dog CTLA4. In some embodiments, the antibodies or antigen-binding fragments are cross-reactive with monkey CTLA4. In some embodiments, the antibodies or antigen-binding fragments are cross-reactive with mouse CTLA4. In some embodiments, the antibodies or antigen-binding fragments are cross-reactive with rat CTLA4. In some embodiments, the antibodies or antigen-binding fragments are cross-reactive with dog CTLA4. In some embodiments, the antibodies or antigen binding fragments are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, rat, and dog CTLA4. In some embodiments, the antibodies or antigen binding fragments are cross-reactive if the antibodies or antigen-binding fragments binds to a non-human CTLA4 molecule with a $K_D$ less than about 500 nM (e.g., less than about 1 nM, less than about 10 nM, less than about 25 nM, less than about 50 nM, less than about 75 nM, less than about 100 nM, less than about 150 nM, less than about 200 nM, less than about 250 nM, less than about 300 nM, less than about 350 nM, etc.). Methods of measuring antibody cross-reactivity are known in the art, including, without limitation, surface plasmon resonance, an ELISA, isothermal titration calorimetry, a filter binding assay, an EMSA, etc. In some embodiments, the cross-reactivity is measured by ELISA.

In some embodiments, the antibodies induce ADCC effects against a CTLA4 expressing cell (e.g., against CTLA4-expressing human cells such as Tregs) after the antibody binds to the cell-expressed CTLA4. Methods of measuring ADCC effects (e.g., in vitro methods) are known in the art. In some embodiments, the antibodies induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control or ipilimumab).

In some embodiments, the antibodies or antigen-binding fragments are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the antibodies or antigen-binding fragments relative to corresponding tumor cells not contacted with the antibodies or antigen-binding fragments (or relative to corresponding tumor cells contacted with an isotype control antibody). In some embodiments, the antibodies or antigen-binding fragments are capable of reducing tumor volume in a subject when the subject is administered the antibodies or antigen-binding fragments. In some embodiments, the antibodies or antigen-binding fragments are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the antibodies or antigen-binding fragments; as compared to a corresponding tumor in a subject administered an isotype control antibody). Methods of monitoring tumor cell growth/proliferation, tumor volume, and/or tumor inhibition are known in the art.

In some embodiments, the antibodies or antigen-binding fragments have therapeutic effect on a cancer. In some embodiments, the antibodies or antigen-binding fragments reduce one or more signs or symptoms of a cancer. In some embodiments, a subject suffering from a cancer goes into partial or complete remission when administered the antibodies or antigen-binding fragments.

In another aspect, the disclosure provides isolated antibodies that compete or cross-compete for binding to human CTLA4 with any of the illustrative antibodies of the disclosure, such as TY21585, TY21586, TY21587, TY21588, TY21589, TY21580, TY21591, TY21686, TY21687, TY21689, TY21680, TY21691, and/or TY21692. In a particular embodiment, the present application provides isolated antibodies that compete or cross-compete for binding to the same epitope on the human CTLA4 with any of the illustrative antibodies of the disclosure. The ability of an antibody to compete or cross-compete for binding with another antibody can be determined using standard binding assays known in the art, such as BIAcore analysis, ELISA assays, or flow cytometry. For example, one can allow an illustrative antibody of the disclosure to bind to human CTLA4 under saturating conditions and then measure the ability of the test antibody to bind to the CTLA4. If the test antibody is able to bind to the CTLA4 at the same time as the illustrative antibody, then the test antibody binds to a different epitope as the illustrative antibody. However, if the test antibody is not able to bind to the CTLA4 at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

In some embodiments, the antibodies or antigen-binding fragments block the binding between CTLA4 and one or more of its binding partners (e.g., human CTLA4 and human CD80, human CTLA4 and human CD86). In some embodiments, the antibodies or antigen-binding fragments block the binding between CTLA4 and its ligand in vitro. In some embodiments, the antibody or antigen-binding fragment has a half maximal inhibitory concentration ($IC_{50}$) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for blocking binding of CTLA4 to CD80 and/or CD86. In some embodiments, the antibody or antigen-binding fragment has a half maximal inhibitory concentration ($IC_{50}$) of about 100 nM or less for blocking binding of CTLA4 to CD80 and/or CD86. In some embodiments, the antibody or antigen-binding fragment completely blocks binding of human CTLA4 to CD80 and/or CD86 when provided at a concentration of about 100 nM or greater (e.g., about 100 nM or greater, about 500 nM or greater, about 1 μM or greater, about 10 μM or greater, etc.). As used herein, the term "complete blocking" or "completely blocks" refers to the antibody or antigen-binding fragment's ability to reduce binding between a first protein and a second protein by at least about 80% (e.g., at least about 80%, at least about 85%, at least about 90%, at least about 95%, at least about 99%, etc.). Methods of measuring the ability of an antibody or antigen-binding fragment to block binding of a first protein (e.g., human CTLA4) and a second protein (e.g., human CD80 or human CD86) are known in the art, including, without limitation, via BIAcore analysis, ELISA assays, and flow cytometry. In some embodiments, the anti-CTLA4 antibodies described herein have lower activity in blocking ligand binding than ipilimumab.

In some embodiments, the anti-CTLA4 antibody binds human CTLA4 with a $K_D$ of 1000 nM or less (e.g., 50 nM or less, 10 nM or less) as measured by surface plasmon resonance. In some embodiments, the antibody is cross-reactive with at least one non-human species selected from cynomolgus monkey, mouse, rat, and dog.

In some embodiments, the anti-CTLA4 antibody specifically binds to an epitope similar to a ligand binding site of human CTLA4. In some embodiments, the antibody specifically binds to an epitope similar to CD80 binding site of human CTLA4. In some embodiments, the antibody specifically binds to an epitope similar to CD86 binding site of human CTLA4. In some embodiments, the antibody specifically binds to an epitope comprising one or more amino acid residues in a ligand binding site (e.g., CD80 and/or CD86 binding site) of human CTLA4. In some embodiments, the antibody specifically binds to an epitope on human CTLA4 that is different from the epitope of ipilimumab. In some embodiments, the epitope does not comprise amino acid residues in the CC' loop motif of human CTLA4. In some embodiments, the epitope does not comprise amino acid residue L106 or I108 of human CTLA4. In some embodiments, the antibody specifically binds to an epitope comprising amino acid residues Y105 and L106, but not I108 of human CTLA4, wherein the numbering of the amino acid residues is according to (SEQ ID NO: 108)
```
KAMHVAQPAVVLASSRGIASFVCEYASPGKATEVRVTVLRQADSQVT

EVCAATYMMGNELTFLDDSICTGTSSGNQVNLTIQGLRAMDTGLYIC

KVELMYPPPYYLGIGNGTQIYVIDPE
```

In some embodiments, the anti-CTLA4 antibody comprising a heavy chain variable region and a light chain variable region, a) where the heavy chain variable region comprises an HVR-H1, an HVR-H2, and an HVR-H3, where the HVR-H1 comprises an amino acid sequence according to a formula selected from: Formula (I): X1TFSX2YX3IHWV (SEQ ID NO: 1), where X1 is F or Y, X2 is D or G, and X3 is A, G, or W; Formula (II): YSIX1SGX2X3WX4WI (SEQ ID NO: 2), where X1 is S or T, X2 is H or Y, X3 is H or Y, and X4 is A, D, or S; and Formula (III): FSLSTGGVAVX1WI (SEQ ID NO: 3), where X1 is G or S; the HVR-H2 comprises an amino acid sequence according to a formula selected from: Formula (IV): IGX1IX2HSGSTYYSX3SLKSRV (SEQ ID NO: 4), where X1 is D or E, X2 is S or Y, and X3 is P or Q; Formula (V): IGX1ISPSX2GX3TX4YAQKFQGRV (SEQ ID NO: 5), where X1 is I or W, X2 is G or S, X3 is G or S, and X4 is K or N; and Formula (VI): VSX1ISGX2GX3X4TYYADSVKGRF (SEQ ID NO: 6), where X1 is A, G, or S, X2 is S or Y, X3 is G or S, and X4 is S or T; and the HVR-H3 comprises an amino acid sequence according to a formula selected from: Formula (VII): ARX1X2X3X4FDX5 (SEQ ID NO: 7), where X1 is G, R, or S, X2 is A, 1, or Y, X3 is D, V, or Y, X4 is A, E, or Y, and X5 is I or Y; Formula (VIII): ARX1GX2GYFDX3 (SEQ ID NO: 8), where X1 is D or L, X2 is F or Y, and X3 is V or Y; Formula (IX): ARX1X2X3X4AX5X6FDY (SEQ ID NO: 9), where X1 is L or R, X2 is I or P, X3 is A or Y, X4 is S or T, X5 is T or Y, and X6 is A or Y; and Formula (X): ARDX1X2X3GSSGYYX4GFDX5 (SEQ ID NO: 10), where X1 is I or V, X2 is A or H, X3 is P or S, X4 is D or Y, and X5 is F or V; and/or b) where the light chain variable region comprises an HVR-L1, an HVR-L2, and an HVR-L3, where the HVR-L1 comprises an amino acid sequence according to a formula selected from: Formula (XI): RASQX1X2X3SX4LX5 (SEQ ID NO: 11), where X1 is G or S, X2 is I or V, X3 is G or S, X4 is S or Y, and X5 is A or N; Formula (XII): RASQX1VX2X3RX4LA (SEQ ID NO: 12), where X1 is S or T, X2 is F, R, or S, X3 is G or S, and X4 is F or Y; and Formula (XIII): RASX1SVDFX2GX3SFLX4 (SEQ ID NO: 13), where X1 is E or Q, X2 is D, F, H, or Y, X3 is F, I, or K, and X4 is A, D, or H; the HVR-L2 comprises an amino acid sequence according to Formula (XIV): X1ASX2X3X4X5GX6 (SEQ ID NO: 14), where X1 is A or D, X2 is N, S, or T, X3 is L or R, X4 is A, E, or Q, X5 is S or T, and X6 is I or V; and the HVR-L3 comprises an amino acid sequence according to a formula selected from: Formula (XV): YCX1X2X3X4X5X6PX7T (SEQ ID NO: 15), where X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y; Formula (XVI): YCQQX1X2X3WPPWT (SEQ ID NO: 16), where X1 is S or Y, X2 is D or Y, and X3 is Q or Y; and Formula (XVII): YCQX1YX2SSPPX3YT (SEQ ID NO: 17), where X1 is H or Q, X2 is T or V, and X3 is E or V.

In some embodiments, the antibody comprises: a) an HVR-H1 comprising an amino acid sequence selected from SEQ ID NOS: 18-29; an HVR-H2 comprising an amino acid sequence selected from SEQ ID NOS. 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69 and an HVR-L3 comprising an amino acid sequence selected from SEQ ID NOS: 70-81. In some embodiments, the antibody comprises one, two, three, four, five, or all six of the HVRs shown for any of the exemplary antibodies described in Table A below.

TABLE A anti-CTLA4 HVR sequences

| Ab name: | HVR-H1 | HVR-H2 | HVR-H3 | HVR-L1 | HVR-L2 | HVR-L3 |
|---|---|---|---|---|---|---|
| TY21585 | FTFSDYAIHWV (SEQ ID NO: 18) | IGIISPSSGSTNYAQKFQGRV (SEQ ID NO: 30) | ARDIHSGSSGYYYGFDV (SEQ ID NO: 40) | RASESVDFFGISFLA (SEQ ID NO: 53) | DASNRATGI (SEQ ID NO: 66) | YCQHYTSSPPVYT (SEQ ID NO: 70) |
| TY21586 | YSITSGYYWAWI (SEQ ID NO: 19) | VSSISGSGSTTYYADSVKGRF (SEQ ID NO: 31) | ARDGFGYFDY (SEQ ID NO: 41) | SASSSVSYVY (SEQ ID NO: 54) | DASSLESGV (SEQ ID NO: 67) | YCVQGLQTPWT (SEQ ID NO: 71) |
| TY21587 | FTFSDYGIHWV (SEQ ID NO: 20) | IGEIYHSGSTYYSPSLKSRV (SEQ ID NO: 32) | ARDVAPGSSGYYDGFDF (SEQ ID NO: 42) | RASQGIGSSLA (SEQ ID NO: 55) | DASNRATGI (SEQ ID NO: 66) | YCQQYDQWPPWT (SEQ ID NO: 72) |
| TY21588 | YSISSGYHWDWI (SEQ ID NO: 21) | VSGISGYGGSTYYADSVKGRF (SEQ ID NO: 33) | ARHSYYGSGNFDY (SEQ ID NO: 43) | RASESVDFFGKSFLH (SEQ ID NO: 56) | DASNLETGV (SEQ ID NO: 68) | YCQQSYSWPPT (SEQ ID NO: 73) |
| TY21589 | FTFSDYWIHWV (SEQ ID NO: 22) | IGWISPSGGGTKYAQKFQGRV (SEQ ID NO: 34) | ARGAYEFDY (SEQ ID NO: 44) | RASQSVSSRFLA (SEQ ID NO: 57) | DASNRATGI (SEQ ID NO: 66) | YCQQSYPTPLT (SEQ ID NO: 74) |
| TY21580 | YSISSGYHWSWI (SEQ ID NO: 23) | LARIDWDDDKYYSTSLKSRL (SEQ ID NO: 35) | ARSYVYFDY (SEQ ID NO: 45) | RASQSVRGRFLA (SEQ ID NO: 58) | DASNRATGI (SEQ ID NO: 66) | YCQQSSSWPPT (SEQ ID NO: 75) |
| TY21591 | FSLSTGGVAVSWI (SEQ ID NO: 24) | IGEIYHSGSTYYSPSLKSRV (SEQ ID NO: 32) | ARRIATATYFDY (SEQ ID NO: 46) | RASQTVFSRYLA (SEQ ID NO: 59) | DASNRATGI (SEQ ID NO: 66) | YCQQSYYWPPWT (SEQ ID NO: 76) |
| TY21686 | FSLSTGGVAVGWI (SEQ ID NO: 25) | VSAISGYGSTTYYADSVKGRF (SEQ ID NO: 36) | ARLPYSAYAFDY (SEQ ID NO: 47) | RASQGVSSYLA (SEQ ID NO: 60) | AASTLQSGV (SEQ ID NO: 69) | YCQHHYGTPLT (SEQ ID NO: 77) |
| TY21687 | FTFSGYAIHWV (SEQ ID NO: 26) | IGIISPSGGGTKYAQKFQGRV (SEQ ID NO: 37) | ARHPFAY (SEQ ID NO: 48) | RASQSVDFYGISFLD (SEQ ID NO: 61) | DASNRATGI (SEQ ID NO: 66) | YCQQYVSSPPEYT (SEQ ID NO: 78) |
| TY21689 | YTFSGYGIHWV (SEQ ID NO: 27) | IGEIYHSGSTYYSPSLKSRV (SEQ ID NO: 32) | ARRIDAFDI (SEQ ID NO: 49) | RASQSVDFDGFSFLH (SEQ ID NO: 62) | DASSLESGV (SEQ ID NO: 67) | YCQQRDSWPYT (SEQ ID NO: 79) |
| TY21680 | YTFSGYAIHWV (SEQ ID NO: 28) | IGIISPSGGGTKYAQKFQGRV (SEQ ID NO: 37) | ARLYDVAY (SEQ ID NO: 50) | RASQSVDFHGKSFLH (SEQ ID NO: 63) | DASSLESGV (SEQ ID NO: 67) | YCEQSLEVPFT (SEQ ID NO: 80) |
| TY21691 | FTFSDYAIHWV (SEQ ID NO: 18) | IGIISPSGGSTKYAQKFQGRV (SEQ ID NO: 38) | ARLGYGYFDV (SEQ ID NO: 51) | RASQSVDFYGISFLH (SEQ ID NO: 64) | DASSLESGV (SEQ ID NO: 67) | YCVQALQLPLT (SEQ ID NO: 81) |
| TY21692 | YSITSGHYWSWI (SEQ ID NO: 29) | IGDISHSGSTYYSQSLKSRV (SEQ ID NO: 39) | ARGSRTGYFDY (SEQ ID NO: 52) | RASQSISSYLN (SEQ ID NO: 65) | DASNLETGV (SEQ ID NO: 68) | YCQHHYGTPLT (SEQ ID NO: 77) |

In some embodiments, the antibody comprises an HVR-H1 comprising the amino acid sequence of SEQ ID NO. 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70. In some embodiments, the antibody comprises an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71. In some embodiments, the antibody comprises an HVR-H1 comprising the amino acid sequence of SEQ ID NO. 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72. In some embodiments, the antibody comprises an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73. In some embodiments, the antibody comprises an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74. In some embodiments, the antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the antibody comprises an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76. In some embodiments, the antibody comprises an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77. In some embodiments, the antibody comprises an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78. In some embodiments, the antibody comprises an HVR-H1 comprising the amino acid sequence of SEQ ID NO. 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79. In some embodiments, the antibody comprises an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80. In some embodiments, the antibody comprises an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81. In some embodiments, the antibody comprises an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77.

In some embodiments, the antibody comprises: a) a heavy chain variable region comprising an amino acid sequence selected from SEQ ID NOS: 82-94, and/or b) a light chain variable region comprising an amino acid sequence selected from SEQ ID NOS: 95-107. In some embodiments, the antibody comprises a heavy chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 82-94, and/or a light chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 95-107. In some embodiments, the antibody comprises a heavy chain variable region and a light chain variable region of any of the exemplary antibodies described in Table B below. In some embodiments, the antibody comprises one, two, or all three HVRs of the heavy chain variable region, and/or one, two, or all three HVRs of the light chain variable region shown for any of the exemplary antibodies described in Table B below.

TABLE B anti-CTLA4 variable region amino acid sequences

| Ab name: | VH: | VL: |
|---|---|---|
| TY21585 | EVQLVESGGGLVQPGGSLRLSCAASGFTFSDY AIHWVRQAPGKGLEWIGIISPSSGSTNYAQKF QGRVTISRDNSKNTLYLQLNSLRAEDTAVYYC ARDIHSGSSGYYYGFDVWGQGTLVTVSS (SEQ ID NO: 82) | DIQLTQSPSSLSASVGDRVTITCRASESVDFF GISFLAWYQQKPGKAPKLLIYDASNRATGI PSRFSGSGSGTDFTLTISSLQPEDFATYYCQ HYTSSPPVYTFGQGTKVEIKR (SEQ ID NO: 95) |
| TY21586 | EVQLVESGGGLVQPGGSLRLSCAASGYSITSG YYWAWIRQAPGKGLEWVSSISGSGSTTYYAD SVKGRFTISRDNSKNTLYLQLNSLRAEDTAVY YCARDGFGYFDYWGQGTLVTVSS (SEQ ID NO: 83) | DIQLTQSPSSLSASVGDRVTITCSASSSVSYV YWYQQKPGKAPKLLIYDASSLESGVPSRFS GSGSGTDFTLTISSLQPEDFATYYCVQGLQT PWTFGQGTKVEIKR (SEQ ID NO: 96) |
| TY21587 | EVQLVESGGGLVQPGGSLRLSCAASGFTFSDY GIHWVRQAPGKGLEWIGEIYHSGSTYYSPSLK SRVTISRDNSKNTLYLQLNSLRAEDTAVYYCA RDVAPGSSGYYDGFDFWGQGTLVTVSS (SEQ ID NO: 84) | DIQLTQSPSSLSASVGDRVTITCRASQGIGSS LAWYQQKPGKAPKLLIYDASNRATGIPSRF SGSGSGTDFTLTISSLQPEDFATYYCQQYDQ WPPWTFGQGTKVEIKR (SEQ ID NO: 97) |
| TY21588 | EVQLVESGGGLVQPGGSLRLSCAASGYSISSG YHWDWIRQAPGKGLEWVSGISGYGGSTYYA DSVKGRFTISRDNSKNTLYLQLNSLRAEDTAV YYCARHSYYGSGNFDYWGQGTLVTVSS (SEQ ID NO: 85) | DIQLTQSPSSLSASVGDRVTITCRASESVDFF GKSFLHWYQQKPGKAPKLLIYDASNLETG VPSRFSGSGSGTDFTLTISSLQPEDFATYYC QQSYSWPPTFGQGTKVEIKR (SEQ ID NO: 98) |
| TY21589 | EVQLVESGGGLVQPGGSLRLSCAASGFTFSDY WIHWVRQAPGKGLEWIGWISPSGGGTKYAQK FQGRVTISRDNSKNTLYLQLNSLRAEDTAVYY CARGAYEFDYWGQGTLVTVSS (SEQ ID NO: 86) | DIQLTQSPSSLSASVGDRVTITCRASQSVSS RFLAWYQQKPGKAPKLLIYDASNRATGIPS RFSGSGSGTDFTLTISSLQPEDFATYYCQQS YPTPLTFGQGTKVEIKR (SEQ ID NO: 99) |
| TY21580 | EVQLVESGGGLVQPGGSLRLSCAASGYSISSG YHWSWIRQAPGKGLEWLARIDWDDDKYYST SLKSRLTISRDNSKNTLYLQLNSLRAEDTAVYY CARSYVYFDYWGQGTLVTVSS (SEQ ID NO: 87) | DIQLTQSPSSLSASVGDRVTITCRASQSVRG RFLAWYQQKPGKAPKLLIYDASNRATGIPS RFSGSGSGTDFTLTISSLQPEDFATYYCQQS SSWPPTFGQGTKVEIKR (SEQ ID NO: 100) |
| TY21591 | EVQLVESGGGLVQPGGSLRLSCAASGFSLSTG GVAVSWIRQAPGKGLEWIGEIYHSGSTYYSPS LKSRVTISRDNSKNTLYLQLNSLRAEDTAVYY CARRIATATYFDYWGQGTLVTVSS (SEQ ID NO: 88) | DIQLTQSPSSLSASVGDRVTITCRASQTVFS RYLAWYQQKPGKAPKLLIYDASNRATGIPS RFSGSGSGTDFTLTISSLQPEDFATYYCQQS YYWPPWTFGQGTKVEIKR (SEQ ID NO: 101) |
| TY21686 | EVQLVESGGGLVQPGGSLRLSCAASGFSLSTG GVAVGWIRQAPGKGLEWVSAISGYGSTTYYA DSVKGRFTISRDNSKNTLYLQLNSLRAEDTAV YYCARLPYSAYAFDYWGQGTLVTVSS (SEQ ID NO: 89) | DIQLTQSPSSLSASVGDRVTITCRASQGVSS YLAWYQQKPGKAPKLLIYAASTLQSGVPSR FSGSGSGTDFTLTISSLQPEDFATYYCQHHY GTPLTFGQGTKVEIKR (SEQ ID NO: 102) |
| TY21687 | EVQLVESGGGLVQPGGSLRLSCAASGFTFSGY AIHWVRQAPGKGLEWIGIISPSGGGTKYAQKF QGRVTISRDNSKNTLYLQLNSLRAEDTAVYYC ARHPFAYWGQGTLVTVSS (SEQ ID NO: 90) | DIQLTQSPSSLSASVGDRVTITCRASQSVDE YGISFLDWYQQKPGKAPKLLIYDASNRATG IPSRFSGSGSGTDFTLTISSLQPEDFATYYCQ QYVSSPPEYTFGQGTKVEIKR (SEQ ID NO: 103) |
| TY21689 | EVQLVESGGGLVQPGGSLRLSCAASGYTFSGY GIHWVRQAPGKGLEWIGEIYHSGSTYYSPSLK SRVTISRDNSKNTLYLQLNSLRAEDTAVYYCA RRIDAFDIWGQGTLVTVSS (SEQ ID NO: 91) | DIQLTQSPSSLSASVGDRVTITCRASQSVDF DGFSFLHWYQQKPGKAPKLLIYDASSLESG VPSRFSGSGSGTDFTLTISSLQPEDFATYYC QQRDSWPYTFGQGTKVEIKR (SEQ ID NO: 104) |
| TY21680 | EVQLVESGGGLVQPGGSLRLSCAASGYTFSGY AIHWVRQAPGKGLEWIGIISPSGGGTKYAQKF QGRVTISRDNSKNTLYLQLNSLRAEDTAVYYC ARLYDVAYWGQGTLVTVSS (SEQ ID NO: 92) | DIQLTQSPSSLSASVGDRVTITCRASQSVDF HGKSFLHWYQQKPGKAPKLLIYDASSLES GVPSRFSGSGSGTDFTLTISSLQPEDFATYY CEQSLEVPFTFGQGTKVEIKR (SEQ ID NO: 105) |
| TY21691 | EVQLVESGGGLVQPGGSLRLSCAASGFTFSDY AIHWVRQAPGKGLEWIGIISPSGGSTKYAQKF QGRVTISRDNSKNTLYLQLNSLRAEDTAVYYC ARLGYGYFDVWGQGTLVTVSS (SEQ ID NO: 93) | DIQLTQSPSSLSASVGDRVTITCRASQSVDF YGISFLHWYQQKPGKAPKLLIYDASSLESG VPSRFSGSGSGTDFTLTISSLQPEDFATYYC VQALQLPLTFGQGTKVEIKR (SEQ ID NO: 106) |

TABLE B-continued anti-CTLA4 variable region amino acid sequences

| Ab name: | VH: | VL: |
|---|---|---|
| TY21692 | EVQLVESGGGLVQPGGSLRLSCAASGYSITSG HYWSWIRQAPGKGLEWIGDISHSGSTYYSQSL KSRVTISRDNSKNTLYLQLNSLRAEDTAVYYC ARGSRTGYFDYWGQGTLVTVSS (SEQ ID NO: 94) | DIQLTQSPSSLSASVGDRVTITCRASQSISSY LNWYQQKPGKAPKLLIYDASNLETGVPSR FSGSGSGTDFTLTISSLQPEDFATYYCQHHY GTPLTFGQGTKVEIKR (SEQ ID NO: 107) |

In some embodiments, the antibody comprises a heavy chain variable region comprising the amino acid sequence of SEQ ID NO: 82, and a light chain variable region comprising the amino acid sequence of SEQ ID NO: 95. In some embodiments, the antibody comprises a heavy chain variable region comprising the amino acid sequence of SEQ ID NO: 83, and a light chain variable region comprising the amino acid sequence of SEQ ID NO: 96. In some embodiments, the antibody comprises a heavy chain variable region comprising the amino acid sequence of SEQ ID NO: 84, and a light chain variable region comprising the amino acid sequence of SEQ ID NO: 97. In some embodiments, the antibody comprises a heavy chain variable region comprising the amino acid sequence of SEQ ID NO: 85, and a light chain variable region comprising the amino acid sequence of SEQ ID NO: 98. In some embodiments, the antibody comprises a heavy chain variable region comprising the amino acid sequence of SEQ ID NO: 86, and a light chain variable region comprising the amino acid sequence of SEQ ID NO: 99. In some embodiments, the antibody comprises a heavy chain variable region comprising the amino acid sequence of SEQ ID NO: 87, and a light chain variable region comprising the amino acid sequence of SEQ ID NO: 100. In some embodiments, the antibody comprises a heavy chain variable region comprising the amino acid sequence of SEQ ID NO: 88, and a light chain variable region comprising the amino acid sequence of SEQ ID NO: 101. In some embodiments, the antibody comprises a heavy chain variable region comprising the amino acid sequence of SEQ ID NO: 89, and a light chain variable region comprising the amino acid sequence of SEQ ID NO: 102. In some embodiments, the antibody comprises a heavy chain variable region comprising the amino acid sequence of SEQ ID NO: 90, and a light chain variable region comprising the amino acid sequence of SEQ ID NO: 103. In some embodiments, the antibody comprises a heavy chain variable region comprising the amino acid sequence of SEQ ID NO: 91, and a light chain variable region comprising the amino acid sequence of SEQ ID NO: 104. In some embodiments, the antibody comprises a heavy chain variable region comprising the amino acid sequence of SEQ ID NO: 92, and a light chain variable region comprising the amino acid sequence of SEQ ID NO: 105. In some embodiments, the antibody comprises a heavy chain variable region comprising the amino acid sequence of SEQ ID NO: 93, and a light chain variable region comprising the amino acid sequence of SEQ ID NO: 106. In some embodiments, the antibody comprises a heavy chain variable region comprising the amino acid sequence of SEQ ID NO: 94, and a light chain variable region comprising the amino acid sequence of SEQ ID NO: 107.

In some embodiments, an antibody of the present application cross-competes for binding to human CTLA4 with an antibody comprising: a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, an antibody of the present application cross-competes for binding to human CTLA4 with an antibody comprising one, two, three, four, five, or all six of the HVRs shown for any of the exemplary antibodies described in Table A. In some embodiments, an antibody of the present application cross-competes for binding to human CTLA4 with an antibody comprising: a) a heavy chain variable region comprising an amino acid sequence selected from SEQ ID NOS: 82-94; and/or b) a light chain variable region comprising an amino acid sequence selected from SEQ ID NOS: 95-107. In some embodiments, an antibody of the present application cross-competes for binding to human CTLA4 with an antibody comprising a VH and/or VL shown for any of the exemplary antibodies described in Table B.

The CTLA4 antibodies described herein may be in any class, such as IgG, IgM, IgE, IgA, or IgD. In some embodiments, the CTLA4 antibodies are in the IgG class, such as IgG1, IgG2, IgG3, or IgG4 subclass. A CTLA4 antibody can be converted from one class or subclass to another class or subclass using methods known in the art. An exemplary method for producing an antibody in a desired class or subclass comprises the steps of isolating a nucleic acid encoding a heavy chain of a CTLA4 antibody and a nucleic acid encoding a light chain of a CTLA4 antibody, isolating the sequence encoding the $V_H$ region, ligating the $V_H$ sequence to a sequence encoding a heavy chain constant region of the desired class or subclass, expressing the light chain gene and the heavy chain construct in a cell, and collecting the CTLA4 antibody. Antibodies of the present application may be monoclonal antibodies or polyclonal antibodies. Antibodies of the present application may be monospecific antibodies or multispecific (e.g., bispecific, trispecific, etc.) antibodies. In some embodiments, the CTLA4 antibodies described herein may include one or more Fc mutations (e.g., that modulate (increase or decrease) ADCC or CDC activities). Any suitable Fc mutations known in the art may be used in the CTLA4 antibodies of the present application.

In some embodiments, the anti-CTLA4 antibody comprises a heavy chain comprising the amino acid sequence EVQLVESGGGLVQPGGSLRLSCAASGYSIS-SGYHWSWIRQAPGKGLEWLARIDWDDDKYYSTSL KSRLTISRDNSKNTLYLQLNSLRAEDTAVYY-CARSYVYFDYWGQGTLVTVSSASTKGPSVFPLA PSSKSTSGGTAALGCLVKDYFPEPVTVSWNSGALT-SGVHTFPAVLQSSGLYSLSSVVTVPSSSL GTQTYICNVNHKPSNTKVDKKVEPKSCDKTH- TCPPCPAPELLGGPSVFLFPPKPKDTLMISRTP EVTCVVVDVSHEDPE- VKFNWYVDGVEVHNAKTKPREEQYN- STYRVVSVLTVLHQDWLNGKEYKC KVSNKALPA- PIEKTISKAKGQPREPQVYTLPPSRDELTKNQVSLTC- LVKGFYPSDIAVEWESNG QPEN- NYKTTPPVLDSDGSFFLYSK- LTVDKSRWQQGNVFSCSVMHEALHNHYTQKSLSL- SPG (SEQ ID NO:125) and a light chain comprising the amino acid sequence DIQLTQSPSSLSASVGDRVTIT- CRASQSVRGRFLAWYQQKPGKAPKLLIYDASNRAT- GIPSRFS GSGSGTDFTLTISSLQPEDFATYYCQQSSS- WPPTFGQGTKVEIKRTVAAPSVFIFPPSDEQLKS GTASVVCLLNNFYPREAKVQWKVD- NALQSGNSQESVTEQDSKDSTYSLSSTLTL- SKADYEKHKV YACEVTHQGLSSPVTKSFNRGEC (SEQ ID NO:127). In some embodiments, the anti-CTLA4 antibody comprises a heavy chain comprising the amino acid sequence EVQLVESGGGLVQPGGSLRLSCAASGY- SISSGYHWSWIRQAPGKGLEWLAR- IDWDDDKYYSTSL KSRLTISRDNSKNTLYLQLNSL- RAEDTAVYYCARSYVYFDYWGQGTLVTVSSASTK- GPSVFPLA PSSKSTSGGTAALGCLVKDYF- PEPVTVSWNSGALTSGVHTFPAVLQSSGLYS- LSSVVTVPSSSL GTQTYICNVNHKPSNTKVDKKVE- PKSCDKTHTCPPCPAPELLGGPSVFLFPPKPKDTLMIS- RTP EVTCVVVDVSHEDPE- VKFNWYVDGVEVHNAKTKPREEQYN- STYRVVSVLTVLHQDWLNGKEYKC KVSNKALPA- PIEKTISKAKGQPREPQVYTLPPSRDELTKNQVSLTC- LVKGFYPSDIAVEWESNG QPEN- NYKTTPPVLDSDGSFFLYSK- LTVDKSRWQQGNVFSCSVMHEALHNHYTQKSLSL- SPGK (SEQ ID NO:126) and a light chain comprising the amino acid sequence DIQLTQSPSSLSASVGDRVTIT- CRASQSVRGRFLAWYQQKPGKAPKLLIYDASNRAT- GIPSRFS GSGSGTDFTLTISSLQPEDFATYYCQQSSS- WPPTFGQGTKVEIKRTVAAPSVFIFPPSDEQLKS GTASVVCLLNNFYPREAKVQWKVD- NALQSGNSQESVTEQDSKDSTYSLSSTLTL- SKADYEKHKV YACEVTHQGLSSPVTKSFNRGEC (SEQ ID NO:127). In some embodiments, the anti-CTLA4 antibody refers to a mix of antibody species, wherein each antibody species has a light chain comprising the amino acid sequence of SEQ ID NO: 127 and a heavy chain comprising either the amino acid sequence of SEQ ID NO: 125 or 126.

In some embodiments, the anti-CTLA4 antibody comprises a heavy chain comprising the amino acid sequence EVQLVESGGGLVQPGGSLRLS- CAASGFTFSDYAIHWVRQAPGKGLEWIGIISPSGGST- KYAQKF QGRVTISRDNSKNTLYLQLNSLRAED- TAVYYCARLGYGYFDVWGQGTLVTVSSASTKGPS- VFPL APSSKSTSGGTAALGCLVKDYF- PEPVTVSWNSGALTSGVHTFPAVLQSSGLYS- LSSVVTVPSSS LGTQTYICNVNHKPSNTKVDKKVE- PKSCDKTHTCPPCPAPELLGGPSVFLFPPKPKDTLMIS- RT PEVTCVVVDVSHEDPE- VKFNWYVDGVEVHNAKTKPREEQYN- STYRVVSVLTVLHQDWLNGKEYK CKVSNKALPA- PIEKTISKAKGQPREPQVYTLPPSRDELTKNQVSLTC- LVKGFYPSDIAVEWESN GQPEN- NYKTTPPVLDSDGSFFLYSK- LTVDKSRWQQGNVFSCSVMHEALHNHYTQKSLSL- SPG (SEQ ID NO:128) and a light chain comprising the amino acid sequence DIQLTQSPSSLSASVGDRVTIT- CRASQSVDFYGISFLHWYQQKPGKAPKLLIYDAS- SLESGVPS RFSGSGSGTDFTLTISSLQPEDFA- TYYCVQALQLPLTFGQGTKVEIKRTVAAPSVFIFPPSD- EQ LKSGTASVVCLLNNFYPREAKVQWKVD- NALQSGNSQESVTEQDSKDSTYSLSSTLTLSKADYEK HKVYACEVTHQGLSSPVTKSFNRGEC (SEQ ID NO:130). In some embodiments, the anti-CTLA4 antibody comprises a heavy chain comprising the amino acid sequence EVQLVESGGGLVQPGGSLRLS- CAASGFTFSDYAIHWVRQAPGKGLEWIGIISPSGGST- KYAQKF QGRVTISRDNSKNTLYLQLNSLRAED- TAVYYCARLGYGYFDVWGQGTLVTVSSASTKGPS- VFPL APSSKSTSGGTAALGCLVKDYF- PEPVTVSWNSGALTSGVHTFPAVLQSSGLYS- LSSVVTVPSSS LGTQTYICNVNHKPSNTKVDKKVE- PKSCDKTHTCPPCPAPELLGGPSVFLFPPKPKDTLMIS- RT PEVTCVVVDVSHEDPE- VKFNWYVDGVEVHNAKTKPREEQYN- STYRVVSVLTVLHQDWLNGKEYK CKVSNKALPA- PIEKTISKAKGQPREPQVYTLPPSRDELTKNQVSLTC- LVKGF-YPSDIAVEWESN GQPEN- NYKTTPPVLDSDGSFFLYSK- LTVDKSRWQQGNVFSCSVMHEALHNHYTQKSLSL- SPGK (SEQ ID NO:129) and a light chain comprising the amino acid sequence DIQLTQSPSSLSASVGDRVTIT- CRASQSVDFYGISFLHWYQQKPGKAPKLLIYDAS- SLESGVPS RFSGSGSGTDFTLTISSLQPEDFA- TYYCVQALQLPLTFGQGTKVEIKRTVAAPSVFIFPPSD- EQ LKSGTASVVCLLNNFYPREAKVQWKVD- NALQSGNSQESVTEQDSKDSTYSLSSTLTLSKADYEK HKVYACEVTHQGLSSPVTKSFNRGEC (SEQ ID NO:130). In some embodiments, the anti-CTLA4 antibody refers to a mix of antibody species, wherein each antibody species has a light chain comprising the amino acid sequence of SEQ ID NO: 130 and a heavy chain comprising either the amino acid sequence of SEQ ID NO: 128 or 129.

In some embodiments, the anti-CTLA4 antibody comprises a heavy chain comprising the amino acid sequence EVQLVESGGGLVQPGGSLRLSCAASGYSITSGYY- WAWIRQAPGKGLEWVSSISGSGSTTYYADS VKGRFTISRDNSKNTLYLQLNSLRAEDTAVYY- CARDGFGYFDYWGQGTLVTVSSASTKGPSVFP LAPSSKSTSGGTAALGCLVKDYF- PEPVTVSWNSGALTSGVHTFPAVLQSSGLYS- LSSVVTVPSS SLGTQTYICNVNHKPSNTKVDKKVE- PKSCDKTHTCPPCPAPELLGGPSVFLFPPKPKDTLMI- SR TPEVTCVVVDVSHEDPE- VKFNWYVDGVEVHNAKTKPREEQYN- STYRVVSVLTVLHQDWLNGKEY KCKVSNKALPA- PIEKTISKAKGQPREPQVYTLPPSRDELTKNQVSLTC- LVKGFYPSDIAVEWES NGQPEN- NYKTTPPVLDSDGSFFLYSK- LTVDKSRWQQGNVFSCSVMHEALHNHYTQKSLSL- SPG (SEQ ID NO:131) and a light chain comprising the amino acid sequence DIQLTQSPSSL- SASVGDRVTITCSASSSVSYVYWYQQKPGKAPKLLIY- DASSLESGVPSRFSGS GSGTDFTLTISSLQPEDFA- TYYCVQGLQTPWTFGQGTKVEIKRTVAAPSVFIFPP- SDEQLKSGT ASVVCLLNNFYPREAKVQWKVD- NALQSGNSQESVTEQDSKDSTYSLSSTLTL- SKADYEKHKVYA CEVTHQGLSSPVTKSFNRGEC (SEQ ID NO:133). In some embodiments, the anti-CTLA4 antibody comprises a heavy chain comprising the amino acid sequence EVQLVESGGGLVQPGGSLRLS- CAASGYSITSGYYWAWIRQAPGKGLEWVSSISGSG- STTYYADS VKGRFTISRDNSKNTLYLQLNSLRAED- TAVYYCARDGFGYFDYWGQGTLVTVSSASTKGPSVFP LAPSSKSTSGGTAALGCLVKDYF- PEPVTVSWNSGALTSGVHTFPAVLQSSGLYS- LSSVVTVPSS SLGTQTYICNVNHKPSNTKVDKKVE- PKSCDKTHTCPPCPAPELLGGPSVFLFPPKPKDTLMISR TPEVTCVVVDVSHEDPE- VKFNWYVDGVEVHNAKTKPREEQYN- STYRVVSVLTVLHQDWLNGKEY KCKVSNKALPA- PIEKTISKAKGQPREPQVYTLPPSRDELTKNQVSLTC- LVKGFYPSDIAVEWES NGQPEN- NYKTTPPVLDSDGSFFLYSK- LTVDKSRWQQGNVFSCSVMHEALHNHYTQKSLSL- SPGK (SEQ ID NO:132) and a light chain comprising the amino acid sequence DIQLTQSPSSL- SASVGDRVTITCSASSSVSYVYWYQQKPGKAPKLLIY- DASSLESGVPSRFSGS GSGTDFTLTISSLQPEDFA- TYYCVQGLQTPWTFGQGTKVEIKRTVAAPSVFIFPP- SDEQLKSGT ASVVCLLNNFYPREAKVQWKVD- NALQSGNSQESVTEQDSKDSTYSLSSTLTL- SKADYEKHKVYA CEVTHQGLSSPVTKSFNRGEC (SEQ ID NO:133). In some embodiments, the anti-CTLA4 antibody refers to a mix of antibody species, wherein each antibody species has a light chain comprising the amino acid sequence of SEQ ID NO: 133 and a heavy chain comprising either the amino acid sequence of SEQ ID NO: 131 or 132.

In some embodiments, the anti-CTLA4 antibody comprises a heavy chain comprising the amino acid sequence EVQLVESGGGLVQPGGSLRLSCAASGFTFSG- YAIHWVRQAPGKGLEWIGIISPSGGGTKYAQKF QGRVTISRDNSKNTLYLQLNSLRAEDTAVYYCARHP- FAYWGQGTLVTVSSASTKGPSVFPLAPS SKST- SGGTAALGCLVKDYFPEPVTVSWNSGALT- SGVHTFPAVLQSSGLYSLSSVVTVPSSSLGT QTYICNVNHKPSNTKVDKKVEPKSCDKTHTCPPCPA- PELLGGPSVFLFPPKPKDTLMISRTPEV TCVVVDVSHEDPEVKFNWYVDGVEVHNAKTKPRE- EQYNSTYRVVSVLTVLHQDWLNGKEYKCKV SNKA- LPAPIEKTISKAKGQPREPQVYTLPPSRDELT- KNQVSLTCLVKGFYPSDIAVEWESNGQP ENNYKTTPPVLDSDGSFFLYSK- LTVDKSRWQQGNVFSCSVMHEALHNHYTQKSLSL- SPG (SEQ ID NO:134) and a light chain comprising the amino acid sequence DIQLTQSPSSLSASVGDRVTIT- CRASQSVDFYGISFLDWYQQKPGKAPKLLIYDASN- RATGIPS RFSGSGSGTDFTLTISSLQPEDFA- TYYCQQYVSSPPEYTFGQGTKVEIKRTVAAPSVFIFP- PSD EQLKSGTASVVCLLNNFYPREAKVQWKVD- NALQSGNSQESVTEQDSKDSTYSLSSTLTLSKADY EKHKVYACEVTHQGLSSPVTKSFNRGEC (SEQ ID NO:136). In some embodiments, the anti-CTLA4 antibody comprises a heavy chain comprising the amino acid sequence EVQLVESGGGLVQPGGSLRLS- CAASGFTFSGYAIHWVRQAPGKGLEWIGIISPSGGGT- KYAQKF QGRVTISRDNSKNTLYLQLNSLRAED- TAVYYCARHPFAYWGQGTLVTVSSASTKGPSVFPL- APS SKSTSGGTAALGCLVKDYFPEPVTVSWNSGALT- SGVHTFPAVLQSSGLYSLSSVVTVPSSSLGT QTYICNVNHKPSNTKVDKKVEPKSCDKTHTCPPCPA- PELLGGPSVFLFPPKPKDTLMISRTPEV TCVVVDVSHEDPEVKFNWYVDGVEVHNAKTKPRE- EQYNSTYRVVSVLTVLHQDWLNGKEYKCKV SNKA- LPAPIEKTISKAKGQPREPQVYTLPPSRDELT- KNQVSLTCLVKGFYPSDIAVEWESNGQP ENNYKTTPPVLDSDGSFFLYSK- LTVDKSRWQQGNVFSCSVMHEALHNHYTQKSLSL- SPGK (SEQ ID NO:135) and a light chain comprising the amino acid sequence DIQLTQSPSSLSASVGDRVTIT- CRASQSVDFYGISFLDWYQQKPGKAPKLLIYDASN- RATGIPS RFSGSGSGTDFTLTISSLQPEDFA- TYYCQQYVSSPPEYTFGQGTKVEIKRTVAAPSVFIFP- PSD EQLKSGTASVVCLLNNFYPREAKVQWKVD- NALQSGNSQESVTEQDSKDSTYSLSSTLTLSKADY EKHKVYACEVTHQGLSSPVTKSFNRGEC (SEQ ID NO:136). In some embodiments, the anti-CTLA4 antibody refers to a mix of antibody species, wherein each antibody species has a light chain comprising the amino acid sequence of SEQ ID NO: 136 and a heavy chain comprising either the amino acid sequence of SEQ ID NO: 134 or 135.

In some embodiments, the anti-CTLA4 antibody comprises a heavy chain comprising the amino acid sequence EVQLVESGGGLVQPGGSLRLSCAASGYTFSG- YAIHWVRQAPGKGLEWIGIISPSGGGTKYAQKF QGRVTISRDNSKNTLYLQLNSLRAEDTAVYYCAR- LYDVAYWGQGTLVTVSSASTKGPSVFPLAP SSKST- SGGTAALGCLVKDYFPEPVTVSWNSGALT- SGVHTFPAVLQSSGLYSLSSVVTVPSSSLG TQTYICNVNHKPSNTKVDKKVEPKSCDKTH- TCPPCPAPELLGGPSVFLFPPKPKDTLMISRTPE VTCVVVDVSHEDPE- VKFNWYVDGVEVHNAKTKPREEQYN- STYRVVSVLTVLHQDWLNGKEYKCK VSNKALPA- PIEKTISKAKGQPREPQVYTLPPSRDELTKNQVSLTC- LVKGFYPSDIAVEWESNGQ PEN- NYKTTPPVLDSDGSFFLYSK- LTVDKSRWQQGNVFSCSVMHEALHNHYTQKSLSL- SPG (SEQ ID NO:137) and a light chain comprising the amino acid sequence DIQLTQSPSSLSASVGDRVTIT- CRASQSVDFHGKSFLHWYQQKPGKAPKLLIYDAS- SLESGVPS RFSGSGSGTDFTLTISSLQPEDFA- TYYCEQSLEVPFTFGQGTKVEIKRTVAAPSVFIFPPS- DEQ LKSGTASVVCLLNNFYPREAKVQWKVD- NALQSGNSQESVTEQDSKDSTYSLSSTLTLSKADYEK HKVYACEVTHQGLSSPVTKSFNRGEC (SEQ ID NO:139). In some embodiments, the anti-CTLA4 antibody comprises a heavy chain comprising the amino acid sequence EVQLVESGGGLVQPGGSLRLS- CAASGYTFSGYAIHWVRQAPGKGLEWIGI- ISPSGGGTKYAQKF QGRVTISRDNSKNTLYLQLNSL- RAEDTAVYYCARLYDVAYWGQGTLVTVSSASTKGP- SVFPLAP SSKSTSGGTAALGCLVKDYF- PEPVTVSWNSGALTSGVHTFPAVLQSSGLYS- LSSVVTVPSSSLG TQTYICNVNHKPSNTKVDKKVE- PKSCDKTHTCPPCPAPELLGGPSVFLFPPKPKDTLMIS- RTPE VTCVVVDVSHEDPE- VKFNWYVDGVEVHNAKTKPREEQYN- STYRVVSVLTVLHQDWLNGKEYKCK VSNKALPA- PIEKTISKAKGQPREPQVYTLPPSRDELTKNQVSLTC- LVKGFYPSDIAVEWESNGQ PEN- NYKTTPPVLDSDGSFFLYSK- LTVDKSRWQQGNVFSCSVMHEALHNHYTQKSLSL- SPGK (SEQ ID NO:138) and a light chain comprising the amino acid sequence DIQLTQSPSSLSASVGDRVTIT- CRASQSVDFHGKSFLHWYQQKPGKAPKLLIYDAS- SLESGVPS RFSGSGSGTDFTLTISSLQPEDFA- TYYCEQSLEVPFTFGQGTKVEIKRTVAAPSVFIFPPS- DEQ LKSGTASVVCLLNNFYPREAKVQWKVD- NALQSGNSQESVTEQDSKDSTYSLSSTLTLSKADYEK HKVYACEVTHQGLSSPVTKSFNRGEC (SEQ ID NO:139). In some embodiments, the anti-CTLA4 antibody refers to a mix of antibody species, wherein each antibody species has a light chain comprising the amino acid sequence of SEQ ID NO: 139 and a heavy chain comprising either the amino acid sequence of SEQ ID NO: 137 or 138.

In some embodiments, the anti-CTLA4 antibody is an antigen-binding fragment of an anti-CTLA4 antibody. the antigen-binding fragments of a CTLA4 antibody include: (i) a Fab fragment, which is a monovalent fragment consisting of the $V_L$, $V_H$, $C_L$ and $C_H1$ domains; (ii) a $F(ab')_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody (see e.g., Bird et al. (1988) Science 242:423-426; Huston et al. (1988) Proc. Natl. Acad. Sci. USA 85:5879-5883).

In some embodiments, the anti-CTLA4 antibody is a derivative of any one of the anti-CTLA4 antibodies described herein. In some embodiments, the antibody derivative is derived from modifications of the amino acid sequences of an illustrative antibody (e.g., a "parent antibody") of the present application while conserving the overall molecular structure of the parent antibody amino acid sequence. Amino acid sequences of any regions of the parent antibody chains may be modified, such as framework regions, HVR regions, or constant regions. Types of modifications include substitutions, insertions, deletions, or combinations thereof, of one or more amino acids of the parent antibody.

In some embodiments, the antibody derivative comprises a $V_L$ or $V_H$ region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 82-107 In some embodiments, the antibody derivative comprises an HVR-H1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 18-29. In some embodiments, the antibody derivative comprises an HVR-H2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 30-39. In some embodiments, the antibody derivative comprises an HVR-H3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 40-52. In some embodiments, the antibody derivative comprises an HVR-L1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 53-65. In some embodiments, the antibody derivative comprises an HVR-L2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 66-69. In some embodiments, the antibody derivative comprises an HVR-L3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 70-81.

In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOS: 18-107.

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the HVRs, framework regions, or constant regions. In one embodiment, the present application provides an antibody derivative that contains the $V_H$ and $V_L$ HVR sequences of an illustrative antibody of this disclosure, yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kaba et al., Sequences of Proteins of Immunological Interest, Fifth Edition, U.S. Department of Health and Human Services, NIH Publication No. 91-3242 (1991); Tomlinson et al., *J. Mol. Biol.* 227:776-798 (1992); and Cox et al., *Eur. J. Immunol.* 24:827-836 (1994)). Framework sequences that may be used in constructing an antibody derivative include those that are structurally similar to the framework sequences used by illustrative antibodies of the disclosure For example, the HVR-H1, HVR-H2, and HVR-H3 sequences, and the HVR-L1, HVR-L2, and HVR-L3 sequences of an illustrative antibody can be grafted onto framework regions that have the identical sequence as that found in the germline immunoglobulin gene from which the framework sequence derive, or the HVR sequences can be grafted onto framework regions that contain one or more mutations as compared to the germline sequences.

In some embodiments, the antibody derivative is a chimeric antibody, which comprises an amino acid sequence of an illustrative antibody of the disclosure. In one example, one or more HVRs from one or more illustrative antibodies are combined with HVRs from an antibody from a non-human animal, such as mouse or rat. In another example, all of the HVRs of the chimeric antibody are derived from one or more illustrative antibodies. In some particular embodiments, the chimeric antibody comprises one, two, or three HVRs from the heavy chain variable region and/or one, two, or three HVRs from the light chain variable region of an illustrative antibody. Chimeric antibodies can be generated using conventional methods known in the art.

Another type of modification is to mutate amino acid residues within the HVR regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within an HVR region are altered. In some embodiments, the antibody derivative comprises 1, 2, 3, or 4 amino acid substitutions in the heavy chain HVRs and/or in the light chain HVRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the heavy chain HVR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "back mutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another case, the Fc hinge region of an antibody is mutated to decrease the biological half-life of the antibody.

Furthermore, an antibody of the present application may be modified to alter its potential glycosylation site or pattern in accordance with routine experimentation known in the art. In another aspect, the present application provides a derivative of a CTLA4 antibody that contains at least one mutation in a variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present application provides a derivative of a CTLA4 antibody having a potential N-linked glycosylation site at asparagine in the heavy chain variable region, wherein the potential N-linked glycosylation site in one heavy chain variable region is removed. In another embodiment, the present application provides a derivative of a CTLA4 antibody having a potential N-linked glycosylation site at asparagine in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

Methods of Making

Antibodies of the present application can be produced by techniques known in the art, including conventional monoclonal antibody methodology e.g., the standard somatic cell hybridization technique (See e.g., Kohler and Milstein, *Nature* 256:495 (1975), viral or oncogenic transformation of B lymphocytes, or recombinant antibody technologies.

Hybridoma production is a very well-established procedure. The common animal system for preparing hybridomas is the murine system. Immunization protocols and techniques for isolation of immunized splenocytes for fusion are known in the art. Fusion partners (e.g., murine myeloma cells) and fusion procedures are also known. One well-known method that may be used for making human CTLA4 antibodies provided by the present application involves the use of a XenoMouse™ animal system. XenoMouse™ mice are engineered mouse strains that comprise large fragments of human immunoglobulin heavy chain and light chain loci and are deficient in mouse antibody production (see e.g., Green et al., (1994) Nature Genetics 7:13-21; WO2003/040170). The animal is immunized with a CTLA4 antigen. The CTLA4 antigen is isolated and/or purified CTLA4. It may be a fragment of CTLA4, such as the extracellular domain of CTLA4. Immunization of animals can be carried out by any method known in the art (see e.g., Harlow and Lane, Antibodies: A Laboratory Manual, New York: Cold Spring Harbor Press, 1990). Methods for immunizing non-human animals such as mice, rats, sheep, goats, pigs, cattle and horses are well known in the art (see e.g., Harlow and Lane, supra, and U.S. Pat. No. 5,994,619). The CTLA4 antigen may be administered with an adjuvant to stimulate the immune response. Exemplary adjuvants include complete or incomplete Freund's adjuvant, RIBI (muramyl dipeptides) or ISCOM (immunostimulating complexes). After immunization of an animal with a CTLA4 antigen, antibody-producing immortalized cell lines are prepared from cells isolated from the immunized animal. After immunization, the animal is sacrificed and lymph node and/or splenic B cells are immortalized. Methods of immortalizing cells include, but are not limited to, transferring them with oncogenes, inflecting them with the oncogenic virus cultivating them under conditions that select for immortalized cells, subjecting them to carcinogenic or mutating compounds, fusing them with an immortalized cell, e.g., a myeloma cell, and inactivating a tumor suppressor gene (see e.g., Harlow and Lane, supra). If fusion with myeloma cells is used, the myeloma cells preferably do not secrete immunoglobulin polypeptides (a non-secretory cell line). Immortalized cells are screened using CTLA4, a portion thereof, or a cell expressing CTLA4. CTLA4 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

Antibodies of the present application may also be prepared using phage display or yeast display methods. Such display methods for isolating human antibodies are established in the art (see e.g., Knappik, et al. (2000) J. Mol. Biol. 296, 57-86; Feldhaus et al. (2003) Nat Biotechnol 21:163-170).

In some embodiments, the anti-CTLA4 antibody is prepared by expressing one or more nucleic acids encoding the anti-CTLA4 antibody or polypeptide chains thereof in a host cell. In some embodiments, the one or more nucleic acids is a DNA or RNA, and may or may not contain intronic sequences. Typically, the nucleic acid is a cDNA molecule.

Nucleic acids of the disclosure can be obtained using any suitable molecular biology techniques. For antibodies expressed by hybridomas, cDNAs encoding the light and heavy chains of the antibody made by the hybridoma can be obtained by PCR amplification or cDNA cloning techniques. For antibodies obtained from an immunoglobulin gene library (e.g., using phage display techniques), the nucleic acid encoding the antibody can be recovered from the library.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG4 or IgG2 constant region without ADCC effect. The IgG4 constant region sequence can be any of the various alleles or allotypes known to occur among different individuals. These allotypes represent naturally occurring amino acid substitution in the IgG4 constant regions. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al., *Science* 242:423-426 (1988); Huston et al., *Proc. Natl. Acad. Sci. USA* 85:5879-5883 (1988); and McCafferty et al., *Nature* 348:552-554 (1990)).

In some embodiments, there is provided a vector that comprises a nucleic acid molecule described herein. In some embodiments, the vector is an expression vector or a display vector (e.g., a viral display vector, a bacterial display vector, a yeast display vector, an insect display vector, a mammalian display vector, etc.). The nucleic acid molecule may encode a portion of a light chain or heavy chain (such as a CDR or a HVR; a light or heavy chain variable region), a full-length light or heavy chain, polypeptide that comprises a portion or full-length of a heavy or light chain, or an amino acid sequence of an antibody derivative or antigen-binding fragment. In some embodiments, the vector is an expression vector useful for the expression of an anti-CTLA4 antibody. In some embodiments, provided herein are vectors, wherein a first vector comprises a polynucleotide sequence encoding a heavy chain variable region as described herein, and a second vector comprises a polynucleotide sequence encoding a light chain variable region as described herein. In some embodiments, a single vector comprises polynucleotides encoding a heavy chain variable region as described herein and a light chain variable region as described herein.

To express an anti-CTLA4 antibody of the disclosure, DNAs encoding partial or full-length light and heavy chains are inserted into expression vectors such that the DNA molecules are operatively linked to transcriptional and translational control sequences. In this context, the term "operatively linked" means that an antibody gene is ligated into a vector such that transcriptional and translational control sequences within the vector serve their intended function of regulating the transcription and translation of the DNA molecule. The expression vector and expression control sequences are chosen to be compatible with the expression host cell used. The antibody light chain gene and the antibody heavy chain gene can be inserted into separate vectors, or both genes can be inserted into the same expression vector. The antibody genes are inserted into the expression vector by any suitable methods (e.g., ligation of complementary restriction sites on the antibody gene fragment and vector, or homologous recombination-based DNA ligation). The light and heavy chain variable regions of the antibodies described herein can be used to create full-length antibody genes of any antibody isotype and subclass by inserting them into expression vectors already encoding heavy chain constant and light chain constant regions of the desired isotype and subclass such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody sequences, the expression vectors of the disclosure typically carry regulatory sequences that control the expression of the antibody sequences in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR promoter system, which contains sequences from the SV40 early promoter and the long terminal repeat of human T cell leukemia virus type I (Takebe, Y. et al. (1988) *Mol. Cell. Biol.* 8:466-472).

In addition to the antibody chain genes and regulatory sequences, the expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by any suitable techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the disclosure in either prokaryotic or eukaryotic host cells, expression of antibodies in eukaryotic cells, and typically mammalian host cells, is most typical.

The present application further provides a host cell containing a nucleic acid molecule provided by the present application. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Methods of introducing a recombinant nucleic acid into a host cell are known in the art, including, for example, by calcium phosphate transfection, DEAE, dextran mediated transfection, electroporation or phage infection.

Suitable prokaryotic hosts for transformation include *E. coli, Bacillus subtilis, Salmonella typhimurium* and various species within the genera *Pseudomonas, Streptomyces*, and *Staphylococcus*.

Suitable eukaryotic hosts for transformation include yeast, insect (e.g., S2 cells), and mammalian cells. Mammalian host cells for expressing an anti-CTLA4 antibody of the disclosure include, for example, Chinese Hamster Ovary (CHO) cells (including dhfr-CHO cells, described in Urlaub and Chasin, *Proc. Natl. Acad. Sci. USA* 77:4216-4220 (1980); Sharp, *J. Mol. Biol.* 159:601-621 (1982)), NSO myeloma cells, COS cells, HEK293F cells, HEK293Tcells, and Sp2 cells. In particular, for use with NSO myeloma or CHO cells, another expression system is the GS (glutamine synthetase) gene expression system disclosed in WO 87/04462, WO 89/01036 and EP 338,841. In some embodiments, antibodies of the present application are produced in CHO cells. In some embodiments, antibodies of the present application are modified, and do not include a C-terminal lysine residue (e.g., the C-terminal lysine residue of an antibody heavy chain described herein is removed (such as before or during antibody production)). When expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using any suitable protein purification methods known in the art (e.g., protein A chromatography and/or ion exchange chromatography).

V. Pharmaceutical Compositions, Kits, and Articles of Manufacture

In other aspects, the present application provides a composition comprising any one of the anti-CTLA4 antibodies described herein. In some embodiments, the composition is a pharmaceutical composition comprising the anti-CTLA4 antibody and a pharmaceutically acceptable carrier. The compositions can be prepared by conventional methods known in the art.

The term "pharmaceutically acceptable carrier" refers to any inactive substance that is suitable for use in a formulation for the delivery of an active agent (e.g., the anti-CTLA4 antibody). A carrier may be an anti-adherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride. The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering an anti-CTLA4 antibody is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the antibody into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of an anti-CTLA4 antibody included in the composition will vary depending upon a number of factors, such as the specific anti-CTLA4 antibody and carriers used, dosage form, and desired release and pharmacodynamic characteristics. The amount of an anti-CTLA4 antibody in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the anti-CTLA4 antibody, one or more additional therapeutic agents may be included in the composition. Examples of additional therapeutic agents are described herein in the "Methods of Treatment" section. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent, which produces a therapeutic effect, but may be a lesser amount as well.

In some embodiments, there is provided an article of manufacture comprising materials useful for the treatment of a cancer. The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a cancer, described herein, and may have a sterile access port (for example, the container may be an intravenous solution bag or a vial having a stopper pierceable by a hypodermic injection needle). Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a cancer. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a cancer described herein, optionally in combination with the articles of manufacture. Kits of the present application include one or more containers comprising any one of the compositions described herein (or unit dosage form and/or article of manufacture). In some embodiments, the kit further comprises other agents (e.g., one or more additional therapeutic agents) and/or instructions for use in accordance with any of the methods described herein. The kit may further comprise a description of selection of individuals suitable for treatment. Instructions supplied in the kits of the present application are typically written instructions on a label or package insert (e.g., a paper sheet included in the kit), but machine-readable instructions (e.g., instructions carried on a magnetic or optical storage disk) are also acceptable.

For example, in some embodiments, there is provided a kit comprising a pharmaceutical composition comprising any one of the anti-CTLA4 antibodies described herein and a pharmaceutically acceptable carrier; and instructions for administering the pharmaceutical composition to a subject having a cancer. In some embodiments, the kit further comprises a pharmaceutical composition comprising an additional therapeutic agent, such as a chemotherapeutic agent. In some embodiments, the kit comprises one or more assays or reagents thereof for determining a level of one or more biomarkers described herein (e.g., CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells, B cells).

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

EXAMPLES

The invention can be further understood by reference to the following examples, which are provided by way of illustration and are not meant to be limiting.

Example 1. Phase 1, Open-Label, Dose Escalation Study of TY21580 in Patients with Advanced/Metastatic Solid Tumors The following example describes an ongoing phase 1 clinical trial to assess the safety and tolerability of TY21580, an anti-cytotoxic T-lymphocyte-associated protein 4 (CTLA4) fully human immunoglobulin G (IgG)1 monoclonal antibody (see ClinicalTrials.gov Identifier: NCT04501276).

TY21580. TY21580 is a fully human ligand-blocking anti-CTLA-4 mAb that target a conserved epitope with broad species cross-reactivity for translational fidelity. Without being bound by any theory or hypothesis, TY21580 was observed to have softer CTLA-4 ligand blocking and stronger ADCC for depleting regulatory T-cells than ipilimumab. In a head-to-head in vivo efficacy study, TY21580 was observed to have at least a five-fold greater preclinical antitumor activity in comparison with ipilimumab. In preclinical studies, TY21580 was well tolerated in rats and cynomolgus monkeys in four-week repeat-dose GLP toxicology studies at doses up to 30 mg/kg, and demonstrated an encouraging antitumor response in multiple immune-competent mouse tumor models in a dose-dependent manner both as a single agent (showing initial response at 0.02 mg/kg, and complete response at 0.1 mg/kg for tumor size of ~100 $mm^3$ in H22 liver cancer model) and in combination with other therapies. Without being bound by any theory or hypothesis, TY21580 balances safety and efficacy through a novel mechanism of action; TY21580 maintains its original physiological function via partial blocking of CTLA-4 ligand binding, and in conjunction, depletes $T_{regs}$ in the tumor microenvironment via strong antibody-dependent cellular cytotoxicity (ADCC).

Objectives. The primary objectives of the study are to assess the safety and tolerability of TY21580 administered intravenously (IV) at escalating dose levels in adults with advanced/metastatic solid tumors, and to determine the maximum tolerated dose (MTD) and decide upon a recommended Phase 2 dose (RP2D) for TY21580. Secondary objectives of the study are to assess the pharmacokinetic (PK) profile of TY21580; to assess dose proportionality of key PK parameters (AUC, $C_{max}$); to assess the immunogenicity of TY21580; and to characterize the relationship between immunogenicity (anti-drug antibody (ADA) positivity) and PK, safety and efficacy parameters; to assess the preliminary antitumor activity of TY21580. An exploratory objective of the study is to assess pharmacodynamic biomarkers (including but not limited to cytokines (IL-1β, IL-2, IL-6, IL-10, interferon (IFN)-γ and tumor necrosis factor (TNF)-α), plasma proteins (sCTLA4, sPD-L1, sCD25, CXCL11), immune cells (tumor infiltrating immune ($T_{reg}$), CD8+ $T_{EM}$, Ki67), and tissue biomarkers (FoxP3, IFNγ, PD-L1) for TY21580.

Methodology. This is a Phase 1, open-label, dose escalation study in patients with advanced/metastatic solid tumors. The anticipated number of patients in Phase 1 is up to approximately 60 patients and is not driven by statistical considerations. The actual total number of patients is determined by the composite elements of this protocol, the dose escalation and dose level expansion criteria, the observed dose-limiting toxicities (DLTs)—present or absent, any objective evidence of antitumor activity, and other clinical safety data that is collectively taken together. Safety oversight is provided by a Safety Review Committee (SRC) comprised of the Principal Investigator (PI), the medical monitors and the Sponsor.

All potential study candidates provide informed consent and undergo Screening procedures before participating in the study. After a Screening period of up to 28 days, qualified patients are enrolled to receive their assigned dose regimen of TY21580. TY21580 is administered intravenously (IV) over 60-90 minutes with planned doses every 3 weeks (Q3W) for the first 4 cycles. If no intolerable toxicities occur during the first consecutive 4 treatment cycles, administration of TY21580 may continue every 12 weeks (Q12W) for a total duration of up to 2 years.

A treatment cycle is 21 days with one IV dose of TY21580 administered on Day 1. DLTs are evaluated during the initial 21 days. Toxicities are assessed using the National Cancer Institute Common Terminology Criteria for Adverse Events (NCI CTCAE) v5.0. Patients are treated on study with TY21580 until documented confirmed disease progression according to RECIST v1.1 and/or iRECIST, development of significant toxicity, withdrawal of consent, or other discontinuation/withdrawal reason; whichever occurs first. During the study, patients are evaluated for safety and toxicity, PK, immunogenicity, objective response, DOR, PFS, OS and pre-specified biomarkers per protocol.

The study utilizes an Accelerated Titration Design (ATD) in the lower dose levels (DL1 and DL2) followed by a traditional 3+3 dose escalation design in the higher dose levels until the RP2D is determined. The starting dose is DLL. The study is conducted using nine potential dose levels administered by IV infusion as shown in Table 1, below.

TABLE 1

Potential TY21580 Dose Levels

| Design | Dose Level (DL)* | Dose, mg/kg | Percent Increase from Previous Dose |
|---|---|---|---|
| Accelerated titration design | DL-1 | 0.001 | — |
| | DL1 | 0.003 | 300% |
| | DL2 | 0.01 | 333% |
| Traditional 3 + 3 design** | DL3 | 0.03 | 300% |
| | DL4 | 0.1 | 333% |
| | DL5 | 0.3 | 300% |
| | DL6 | 1.0 | 333% |
| | DL7 | 3.0 | 300% |
| | DL8 | 6.0 | 200% |
| | DL9 | 10.0 | 166% |

*The proposed doses, schedule(s), and PK time points may be reconsidered and amended during the study based on safety data and observed systemic exposures and as determined by the SRC. DL-1 is a lower titration dose to be used in the event of DLTs or clinically significant grade ≥2 toxicity AEs in DL1.

**If a single patient experiences a DLT or two ≥Grade 2 drug-related toxicities during the 21-day DLT evaluation period, traditional 3 + 3 dose escalation criteria will apply for that dose level with enrollment of additional patients. All subsequent dose levels will then follow traditional 3 + 3 dose escalation criteria.

During the ATD phase, 1 patient per dose level is treated. If the patient experiences a DLT or two ≥Grade 2 drug-related toxicity, the dose level is expanded according to a 3+3 design. From DL3 (0.03 mg/kg) onwards, dose escalation follows a traditional 3+3 design with 3 or 6 patients treated at each dose level, depending upon the incidence of DLTs. Initially, 3 patients are enrolled into the dose level with the sentinel patient treated at least 24 hours before the subsequent patients.

From DL3 (0.03 mg/kg) onwards, dose escalation will follow a traditional 3+3 design with 3 or 6 patients treated at each dose level, depending upon the incidence of DLTs. Initially, 3 patients will be enrolled into the dose level with the sentinel patient treated at least 24 hours before the subsequent patients. Dose escalation decisions will be made by the SRC. Dose escalation rules for traditional 3+3 design are as follows in Table 2, below.

TABLE 2

Dose Escalation Rules for Traditional 3 + 3 Design

| Number of Patients with DLT at a Given Dose Level | Dose Escalation Decision Rule |
|---|---|
| 0 of 3 | Enroll 3 patients at next dose level (next/higher dose level/dose escalation) |
| 1 of 3 | Enroll 3 additional patients at current dose level (current dose) |
| 2 of 3 | Stop enrollment. Enroll 3 more patients at the previous dose level (previous/lower level/dose de-escalation) if only 3 were previously enrolled, or at an intermediate dose level |
| 1 of 6 | Enroll 3 patients at next dose level (next/higher dose level/dose escalation) |
| ≥2 of 6 | Stop enrollment. If at DL-1 or DL1, the study will be stopped. If at DL2 or above, enroll 3 more patients at the previous dose level (previous/lower dose level/dose de-escalation) if only 3 were previously enrolled, or at an intermediate dose level |

The highest potential dose level in this study will not exceed 10 mg/kg as the predetermined maximum administered dose (MAD). Once either the MTD or MAD are reached, the RP2D is determined, including selection and treatment of an intermediate dose level between the pre-specified dose levels. The RP2D is decided upon based primarily on the observation of either the MTD, or by the MAD in the absence of an MTD. Options for consideration for the RP2D will also include dose levels below the MTD or MAD, as well as intermediate doses between the pre-specified dose levels, based on an overall assessment of all safety data, as well as all available PK and pharmacodynamic data, and documented objective response observations during dose escalation. Additional cohorts may be added as expansion cohorts to further evaluate the RP2D.

Intra-patient dose escalation up to the dose level cleared by the SRC is permitted for a patient who has completed at least two cycles of treatment at the originally enrolled dose level.

The treatment may proceed beyond progressive disease by RECIST v1.1 if there is evidence of clinical benefit without worsened tumor-related symptoms and/or unacceptable toxicity. All progressive disease should be confirmed as per iRECIST: a repeat scan will be required, preferably after 4 weeks and no later than 6 weeks. Once disease progression is confirmed as per and/or iRECIST, ongoing treatment is not be allowed. Otherwise, the study treatment may continue for a total duration of up to 2 years, or until disease progression, unacceptable toxicity, or withdrawal of consent; whichever occurs first.

All patients, except those who have withdrawn consents, are followed up for safety follow-up assessments, at 30-day and 90-day from the date of the last dose, as well as for survival, every 12 weeks from the date of the last dose. Patients who discontinue treatment due to intolerable adverse events related to TY21580 are followed up until the adverse events have returned to Grade 0 or 1, or become stable, or until the patient receives new non-protocol treatment. Survival follow-up continues until receipt of another antitumor therapy, patient being lost to follow-up or death, whichever occurs first. The Sponsor may also decide to terminate the study at any time.

Criteria for Eligibility. Patients must meet all of the following inclusion criteria to be eligible for participation in this study:

1) ≥18 years of age at the time of informed consent.
2) Eastern Cooperative Oncology Group (ECOG) performance status 0 or 1 with no deterioration over the previous 2 weeks.
3) Patients with advanced or metastatic solid tumors, confirmed by histopathology, who have progressed after all standard therapies, or for whom no further standard therapy exists. Patients who have declined standard therapy or have no access to standard therapy may be enrolled and the reasons for lack of access need to be documented.
4) Patients who are refractory or relapsed to prior anti-CTLA4 checkpoint inhibitors or anti-Programmed cell death protein 1 (PD-1) will also be recruited if they meet all eligibility criteria.
5) Adequate hematologic function, defined by the following:
   a. Absolute neutrophil count (ANC)≥$1.5\times10^9$/L, without the use of granulocyte colony stimulating factor such as filgrastim within 2 weeks prior to study treatment.
   b. Platelet count ≥$100\times10^9$/L without transfusion within 2 weeks (≤14 days) prior to study treatment. Patients with hepatocellular carcinoma and a platelet count ≥$75\times10^9$/L.
   c. Hemoglobin ≥9 g/dL without transfusion or erythropoietin within 2 weeks (≤14 days) prior to study treatment.
6) Aspartate transaminase (AST) and alanine aminotransferase (ALT)≤3×upper limit of normal (ULN), and total bilirubin ≤1.5×ULN. Exception: Patients who have serum bilirubin increases due to documented underlying Gilbert's Syndrome or familial benign unconjugated hyperbilirubinemia. Patients with hepatocellular carcinoma and hepatic metastases may have AST and ALT up to ≤5×ULN.
7) Adequate renal function defined by either a creatinine clearance ≥60 mL/min (by Cockcroft-Gault formula) or serum creatinine (SCr)<1.5×ULN
8) Coagulation tests, defined by the following:
   a. Activated partial thromboplastin time (aPTT)≤1.5×ULN.
   b. International normalized ratio (INR)≤1.5×ULN. Exception: INR 2 to ≤3×ULN is acceptable for patients on Warfarin anticoagulation.
9) Left ventricular ejection fraction (LVEF)≥50% measured by multiple-gated acquisition (MUGA) or echocardiogram (ECHO).
10) Previous antitumor therapy (including endocrine, chemoradiotherapy/radiotherapy, targeted therapy, or immunotherapy) that has ended at least 4 weeks prior to administration of TY21580. Patients who failed prior anti-CTLA4 checkpoint inhibitors may be considered eligible if they meet all eligibility criteria.
11) Previous adverse events have been improved to baseline or ≤Grade 1 NCI CTCAE v5.0 (except for patients with alopecia).

Exclusion criteria include any one of the following:

1) Pregnant or breastfeeding females.
2) Females of childbearing potential and males whose partners are of childbearing potential who do not agree to the use of two forms of highly effective contraception during the treatment period and for 120 days after the last dose of study drug.
3) Treatment with any investigational drug within 4 weeks prior to the first dose of study drug.
4) Grade ≥3 immune-related AEs (irAEs) or irAE that lead to discontinuation of prior immunotherapy.
5) Untreated or uncontrolled central nervous system (CNS) tumors or metastases with following exceptions:
   a. Clinically stable Magnetic Resonance Imaging (MRI) scans (at least two consecutive scans within 6 months) and no progressive or uncontrolled neurologic symptoms or signs (e.g., seizures, headaches, central nausea/emesis, progressive neurologic deficits) for at least 4 weeks.
   b. Any untreated asymptomatic brain metastases not requiring immediate local or systemic therapy.
6) History of life-threatening hypersensitivity or known to be allergic to protein drugs or recombinant proteins or any ingredients contained in the TY21580 drug formulation
7) Patients with active autoimmune disease or a documented medical history of autoimmune disease or symptoms that required systemic use of pharmacologic dose of corticosteroid and/or immunosuppressant. Exceptions are patients with vitiligo, resolved childhood asthma/atopy, and type I diabetes mellitus or hypothyroidism that can be managed by replacement therapy.
8) Patients requiring systemic treatment with corticosteroids (>15 mg/day prednisone or equivalent) or other immunosuppressive medications within 21 days before the planned first dose of study drug. Inhaled or topical steroids, and adrenal replacement steroid doses ≤15 mg daily prednisone equivalent are permitted in the absence of active autoimmune disease. Ophthalmologic, nasal, inhaled and intra-articular injections of steroids are allowed.

9) Peripheral neuropathy ≥Grade 2.

10) Patients receiving granulocyte colony stimulating factor (G-CSF), granulocyte macrophage colony stimulating factor (GM-CSF), erythropoietin, or blood (red blood cell [RBC] or platelet) transfusion within 14 days prior to the first dose of the study drug.

11) Any evidence of underlying liver dysfunction due to other causes; Any history of significant alcohol abuse, alcoholic or drug-induced hepatitis, or documented nonalcoholic steatohepatitis 12) Active viral (any etiology) hepatitis patient are excluded. Hepatitis B virus (HBV) carriers are ineligible. Cured Hepatitis C (HCV) (negative HCV ribonucleic acid [RNA] test) patients may be enrolled after consulting with the medical monitor.

13) Any uncontrolled active infections requiring systemic antimicrobial treatment (viral, bacterial, or other), or uncontrolled or poorly controlled diabetes as evidenced by Screening (baseline) HgbA-1c≥7.5, asthma, chronic obstructive pulmonary disease (COPD), or other conditions that pose a risk to the patient participating on study.

14) Known human immunodeficiency virus (HIV) positive status.

15) Patients with any type of primary immunodeficiency or autoimmune disorder requiring treatment.

16) Major surgery within 4 weeks prior to the first dose of the study drug.

17) Prior organ allograft transplantations or allogeneic peripheral blood stem cell (PBSC)/bone marrow (BM) transplantation.

18) Clinically significant cardiac conditions, including myocardial infarction within the last six months, uncontrolled angina, viral myocarditis, pericarditis, cerebrovascular accident, or other acute uncontrolled heart disease <3 months prior to the first dose of the study drug; LVEF<50%, New York Heart Association (NYHA) Class III or IV congestive heart failure, or uncontrolled hypertension.

19) Pulmonary embolism or deep vein thrombosis within 3 months prior to the first dose of study drug.

20) Live viral vaccine therapies within 4 weeks prior to the first dose of study drug.

21) Any known, documented, or suspected history of illicit substance abuse.

22) Any other disease or clinically significant abnormality in laboratory parameters, including serious medical or psychiatric illness/condition, which in the judgment of the Investigator might compromise the safety of the patient or integrity of the study, interfere with the patient participation in the trial or compromise the trial objectives.

Safety Evaluations. Safety assessments are carried out during specified periodic physical examination findings, vital signs, ECOG performance status, laboratory variables (e.g., liver tests/monitoring, hematology, coagulation tests, serum chemistry, urine tests and pregnancy test), ECG, and AEs. AEs are graded according to the NCI CTCAE v5.0. Investigators and site personnel are responsible for properly documenting and reporting AEs/SAEs. Prior to dose escalation, the SRC reviews the safety data from the current level after all patients have completed the first cycle of 21 days, to determine whether escalating (or de-escalating) to next dose level should proceed.

Efficacy Evaluations. Tumor assessments for response/progression are performed at baseline, and every 6 weeks (±1 week) for the first 4 cycles. If treatment continues beyond 4 cycles, then assessments are carried out every 9 weeks (±1 week) for the remaining treatment duration thereafter, until disease progression or death, treatment/study discontinuation due to treatment toxicity, loss to follow-up, withdrawal of consent, start of new cancer treatment, or study completion/closure, whichever occurs first. The exploratory evaluation of efficacy is based on tumor assessment by the Investigator per RECIST v1.1 and/or iRECIST.

Pharmacokinetic and Immunogenicity Evaluations. Blood samples are collected from all patients during the first cycle to determine the serum concentration of TY21580. Pharmacokinetic (PK) parameters are monitored more intensively during the first treatment cycle. Starting from the second administration, plasma concentration of TY21580 is collected within 30 minutes before the administration of the drug ($C_{trough}$) and at the end of infusion. The PK sampling time points may be adjusted based on cumulative data. Non-compartmental analysis will be conducted using WinNonlin 6.4 or higher version. PK parameters include, but not limited to $AUC_{0\text{-}21d}$, $AUC_{last}$, $C_{max}$, $T_{max}$, $t_{1/2}$, MRT, $C_L$, $V_d$ are reported. Dose proportionality is also assessed for AUC and $C_{max}$.

Blood samples for ADAs are collected at pre-dose of cycles 1, 2, 3, 4, and every two cycles thereafter if treatment will continue beyond 4 cycles. Additionally, ADA samples are collected at the end of the treatment and at the 30- and day 90-day follow-up visits after the last dose. Neutralization activity is evaluated if ADA is positive.

Results

Interim results of the study are provided in the drawings and are described below.

General Observations

To date, TY21580 has been well tolerated in more than 10 patients in dose escalation up to 0.3 mg/kg, and no dose-limiting toxicity (DLT), or unexpected safety signals including treatment-related serious adverse events (SAEs, i.e., drug related G3 and G4 toxicities), colitis or hepatitis have been observed so far. The terminal half-life of TY21580 was within the normal range of an IgG1 based antibody, which is around 14 days with good exposure.

Figure 2:
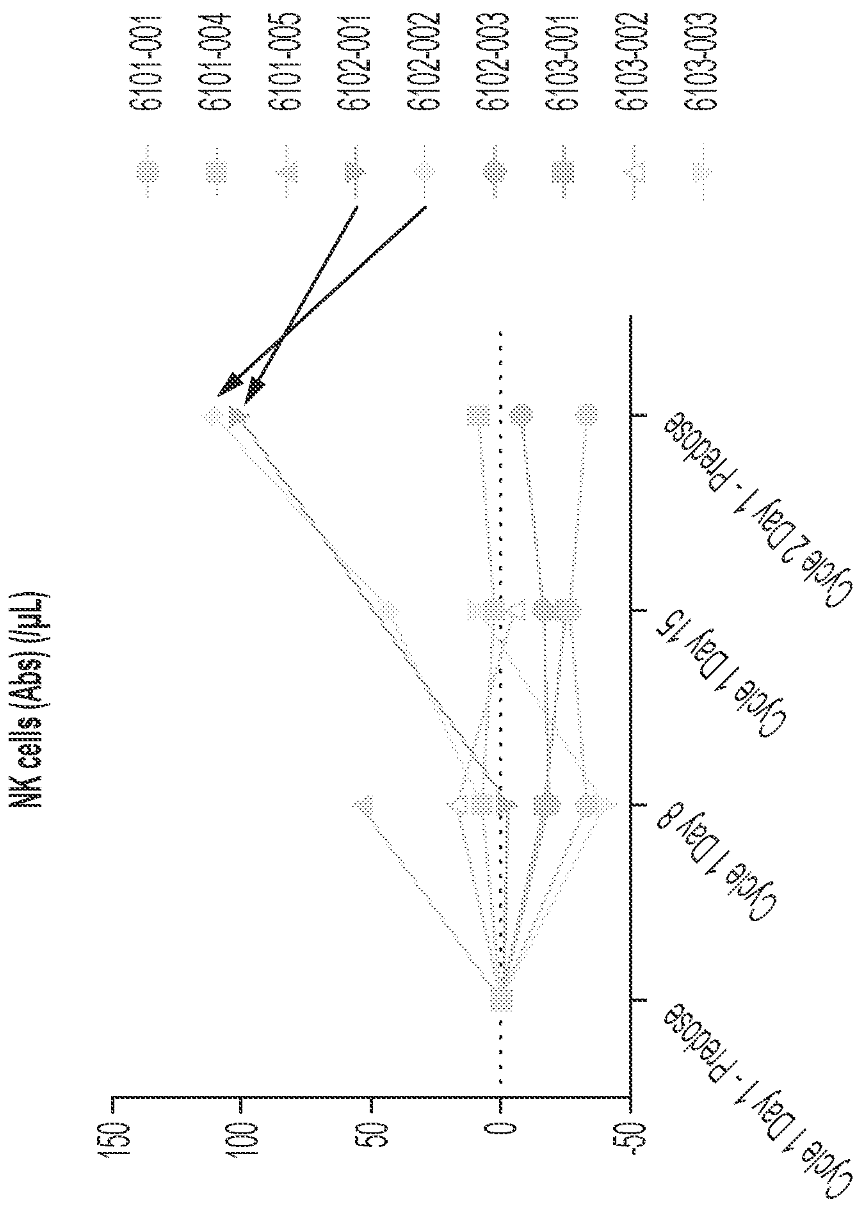
FIG. 2 shows the change in NK cell levels relative to baseline in patients treated with TY21580 over time. The x-axis shows the time of sampling, the y-axis shows the % change in absolute NK cell counts per μL relative to baseline, and the lines represent values from different subjects.
Figure 3:
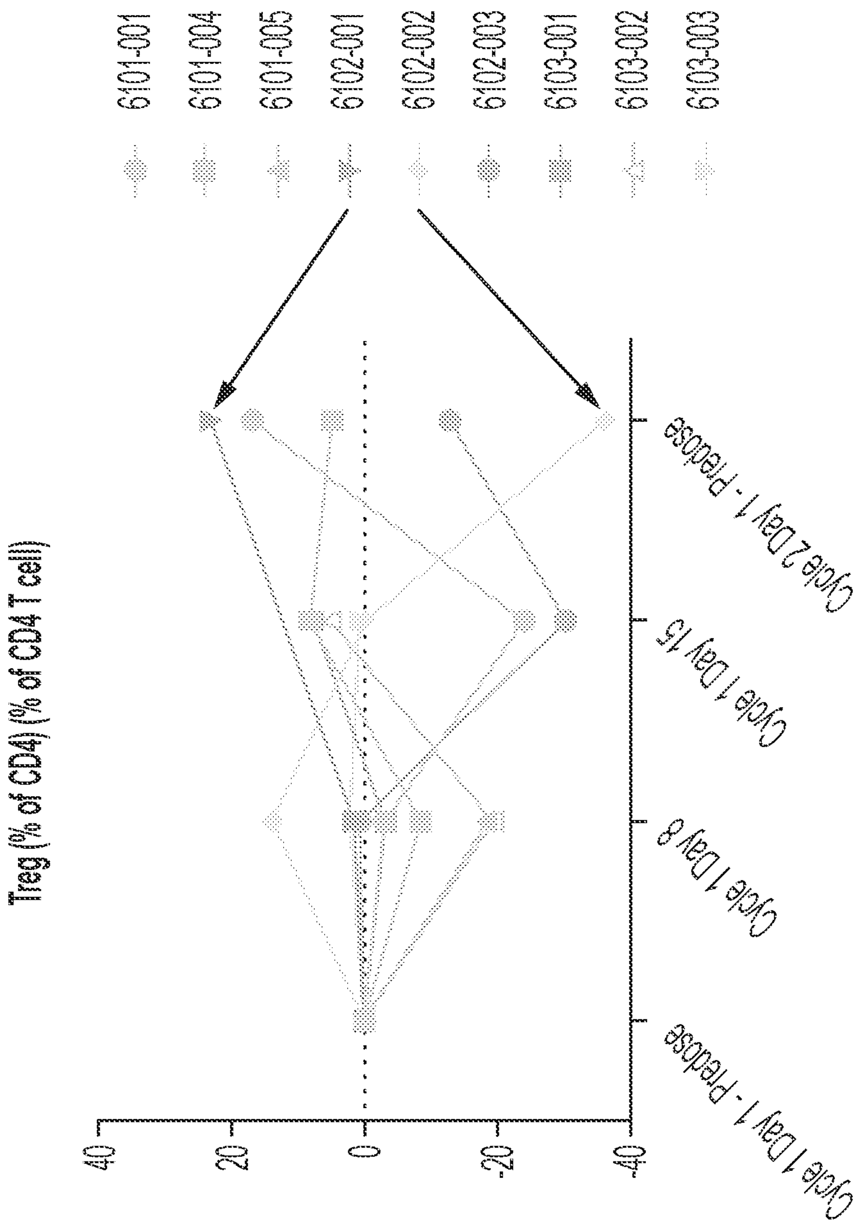
FIG. 3 shows the percentage of $T_{reg}$ cells out of the total CD4+ T cell population in patients treated with TY21580 over time. The x-axis shows the time of sampling, the y-axis shows the % change $T_{reg}$ levels relative to baseline, and the lines represent values from different subjects.
Figure 4:
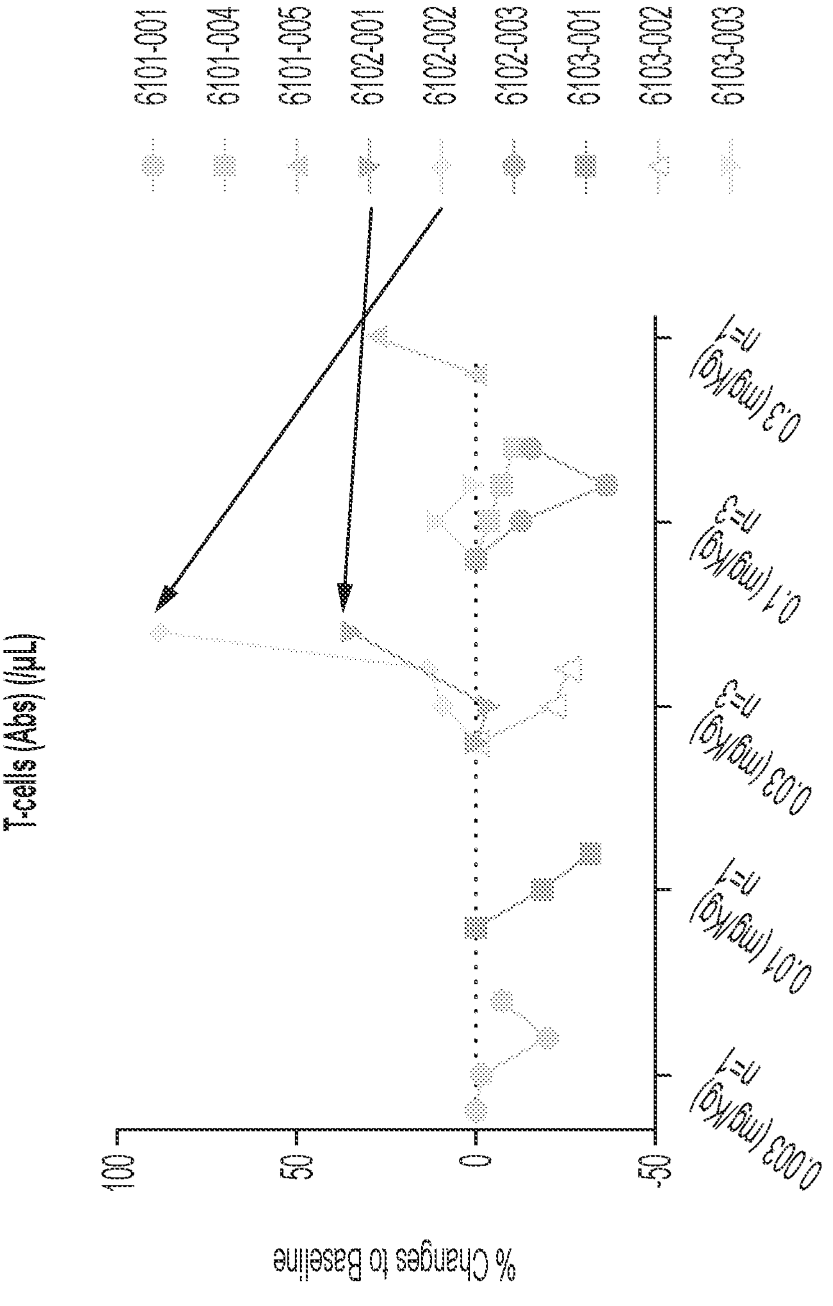
FIG. 4 shows the change in T cell levels relative to baseline in patients treated with TY21580 in different dose cohorts of TY21580. The x-axis shows the dose, the y-axis shows the % change in absolute T cell counts per μL relative to baseline, and the lines represent values from different subjects.
Figure 5:
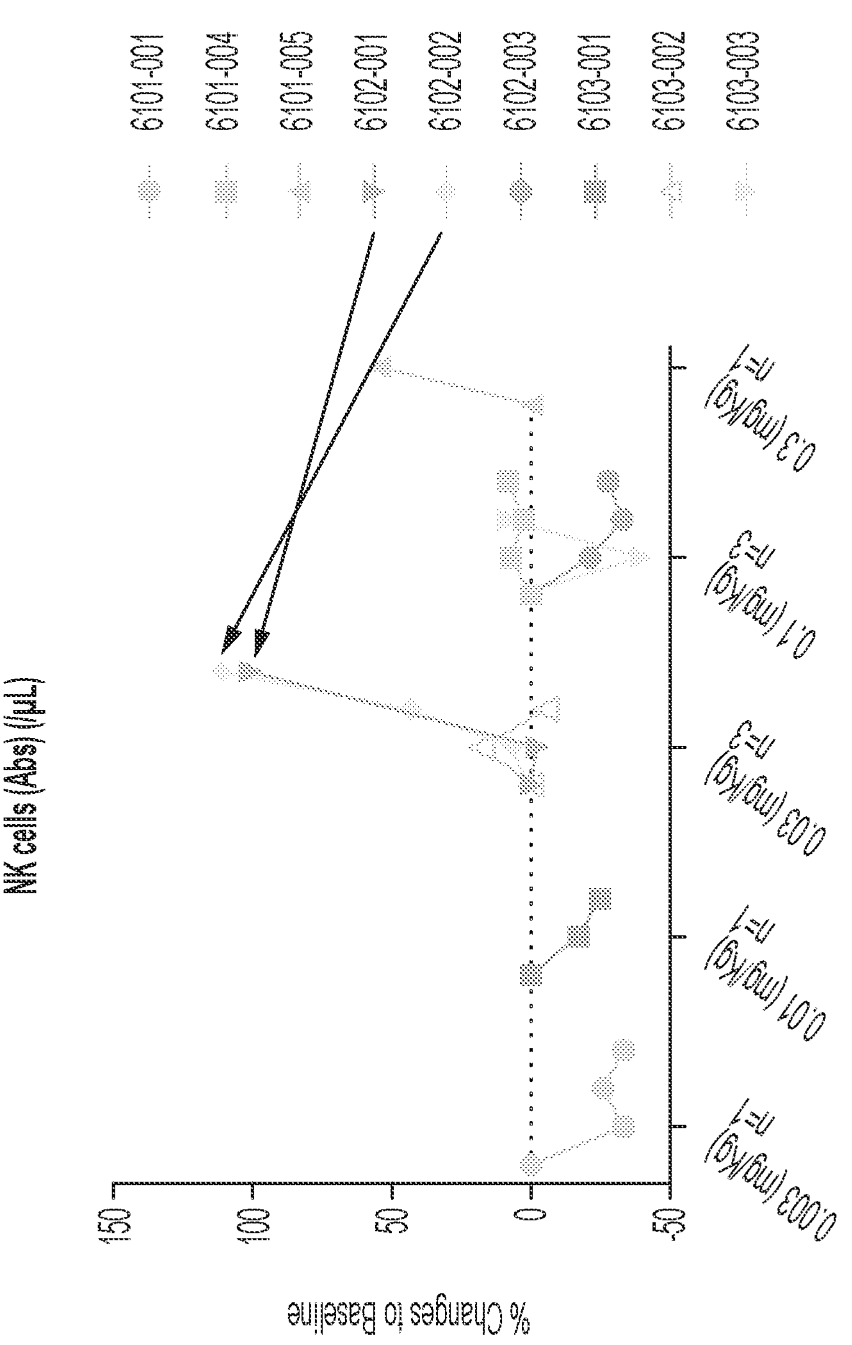
FIG. 5 shows the change in NK cell levels relative to baseline in patients treated with TY21580 in different dose cohorts of TY21580. The x-axis shows the dose, the y-axis shows the % change in absolute NK cell counts per μL relative to baseline, and the lines represent values from different subjects.
Figure 6:
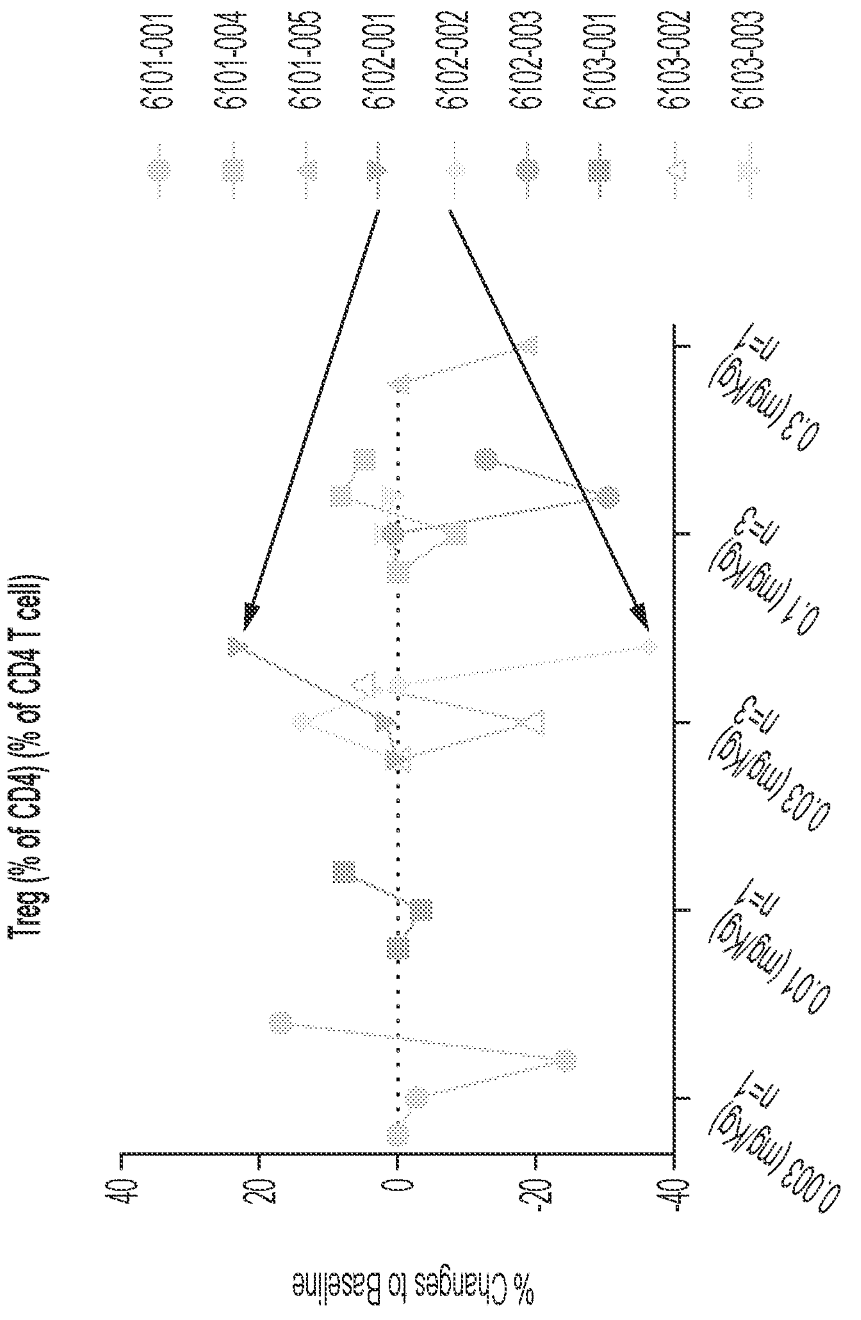
FIG. 6 shows the percentage of $T_{reg}$ cells out of the total CD4+ T cell population in patients treated with TY21580 in different dose cohorts of TY21580. The x-axis shows the dose, the y-axis shows the % change in $T_{reg}$ levels relative to baseline, and the lines represent values from different subjects.
Figure 7:
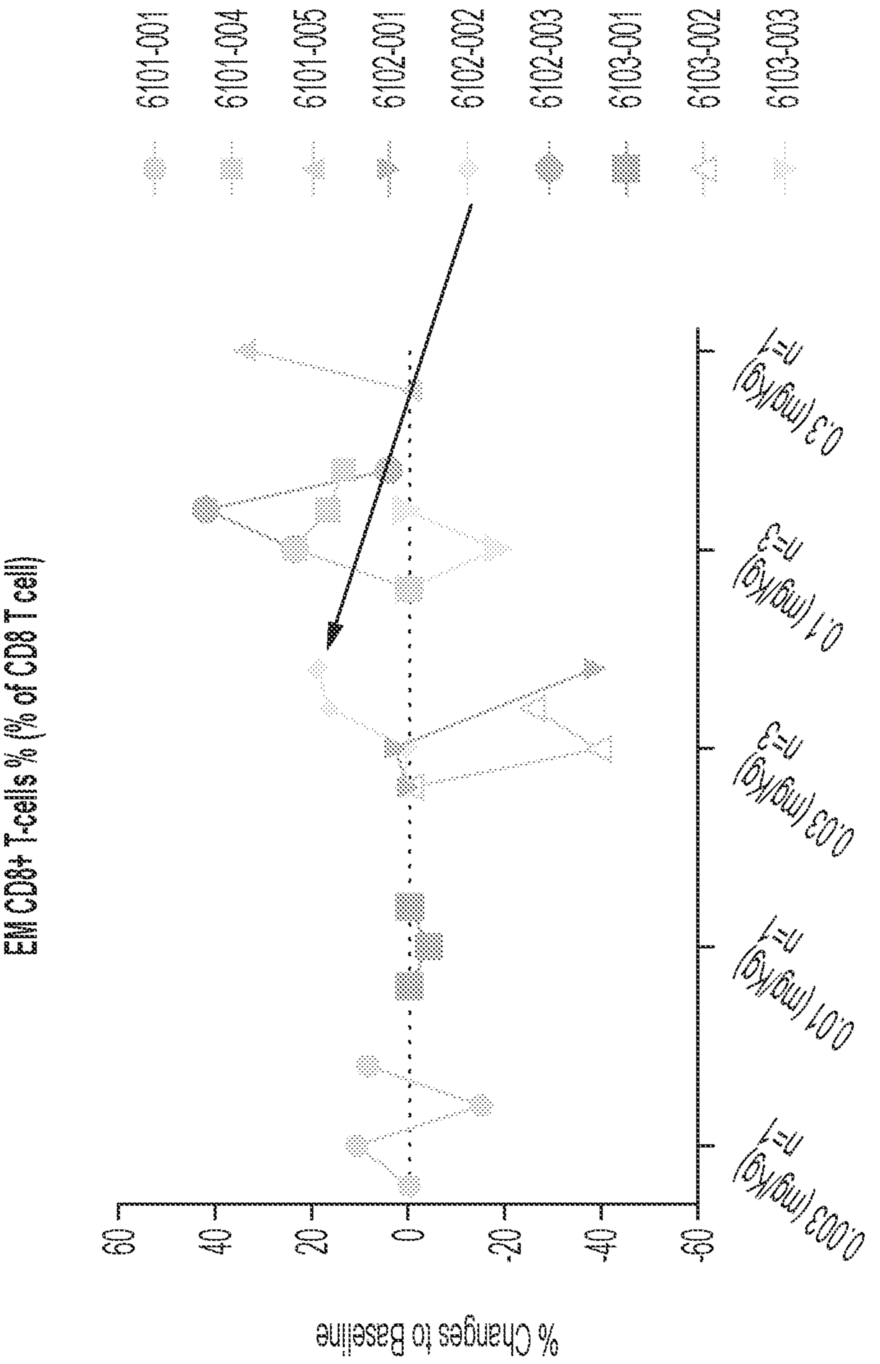
FIG. 7 shows the percentage of effector memory (EM) CD8+ T cells out of the total CD8+ T cell population in patients treated with TY21580 in different dose cohorts of TY21580. The x-axis shows the dose, the y-axis shows the % change in EM CD8+ T cell levels relative to baseline, and the lines represent values from different subjects.
Figure 8:
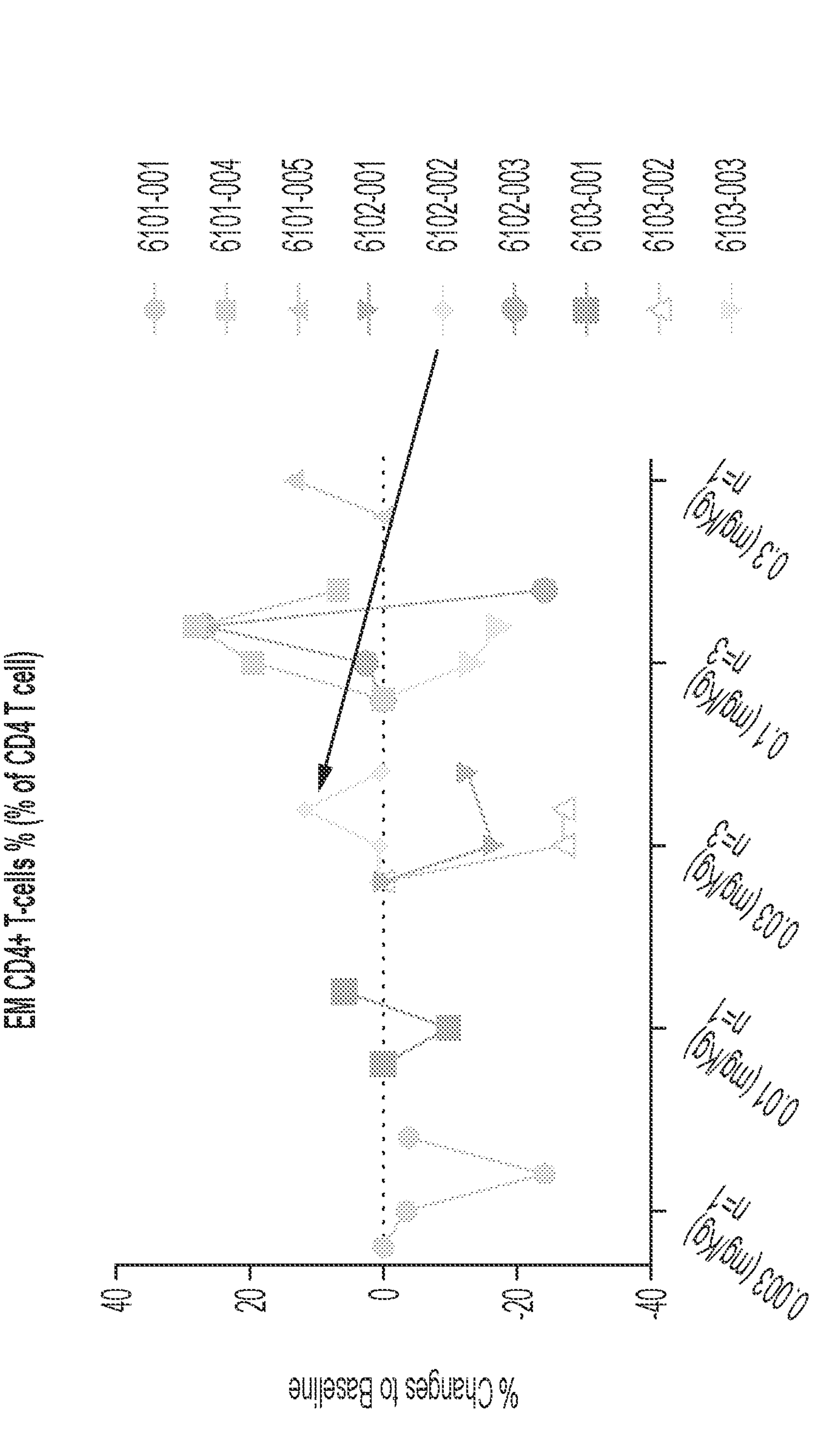
FIG. 8 shows the percentage of EM $CD4^+$ T cells out of the total $CD4^+$ T cell population in patients treated with TY21580 in different dose cohorts of TY21580. The x-axis shows the dose, the y-axis shows the % change in EM $CD4^+$ T cell levels relative to baseline, and the lines represent values from different subjects.
Figure 9A:
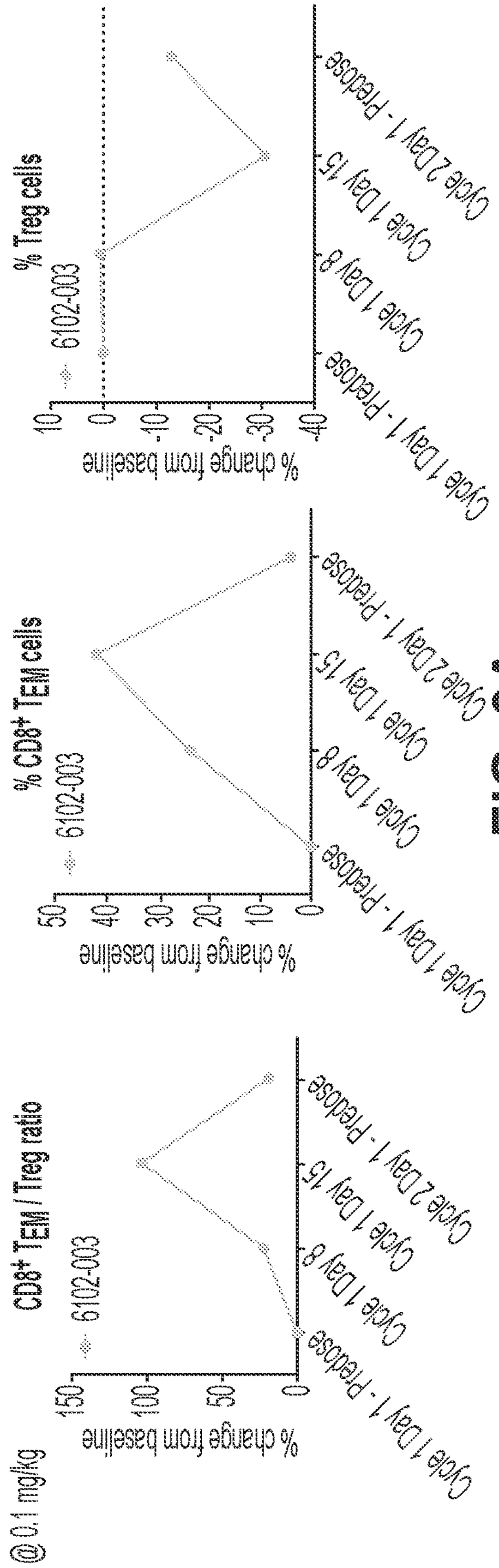
FIGS. 9A-9C show the results of lymphocyte profiling of three subjects at either a 0.1 mg/kg or 0.3 mg/kg dose of TY21580.
Figure 9B:
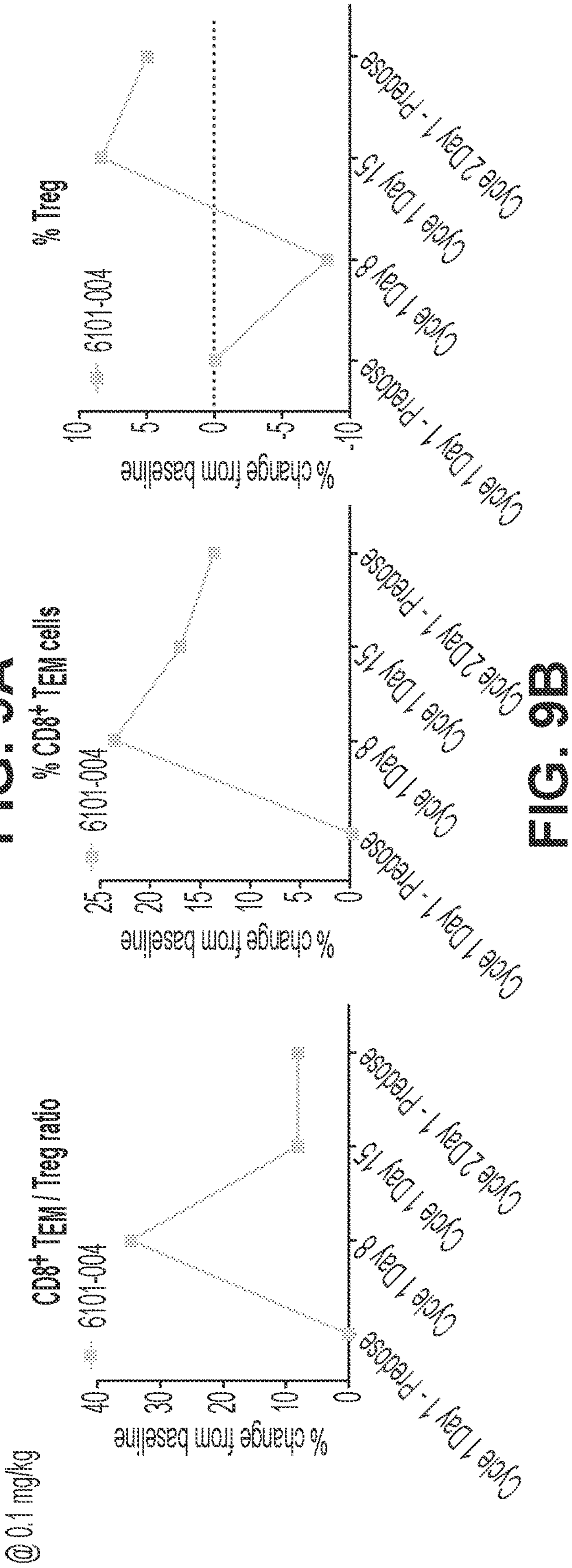
Figure 9C:
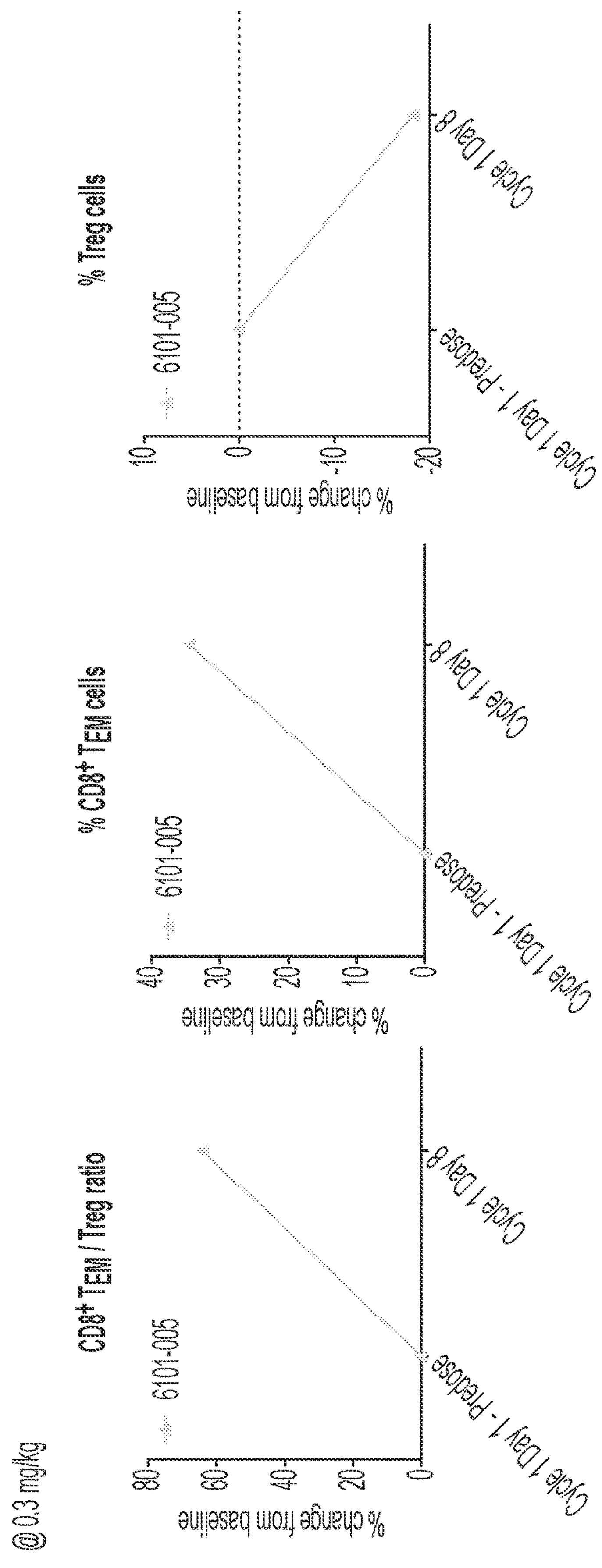

Interim pharmacodynamics (PD) results are presented in FIGS. 1-9C, and FIGS. 13-14. Specifically, TY21580 induced an immune cell response for T cells at dose levels from 0.03 to 0.3 mg/kg doses (FIGS. 1, 4). An effective CD8 and CD4 T cell increase was observed first, followed by a decrease in a dose-dependent way from 0.03, 0.1 and 0.3 mg/kg doses, similar to treatment with anti-PD1 and CD137 antibodies, etc. For certain patients, there was a decrease in the percentage of $T_{reg}$ cells at 0.03. 0.1 and 0.3 mg/kg doses (FIG. 6), and a significant increase in the percentage of CD8+ effector memory T cells (FIG. 7) and CD4+ effector memory T cell (FIG. 8) at 0.03. 0.1 and 0.3 mg/kg doses. Additionally, for these patients, the ratio of CD8+ effector memory T cell/regulatory T cell ($T_{EM}/T_{reg}$) (FIG. 13) and the ratio of CD4+ effector memory T cell/regulatory T cell ($T_{EM}/T_{reg}$) (FIG. 14) showed significant increase. There was an increase in the level of NK and B cells for certain patients (FIGS. 2, 5).

Figure 13:
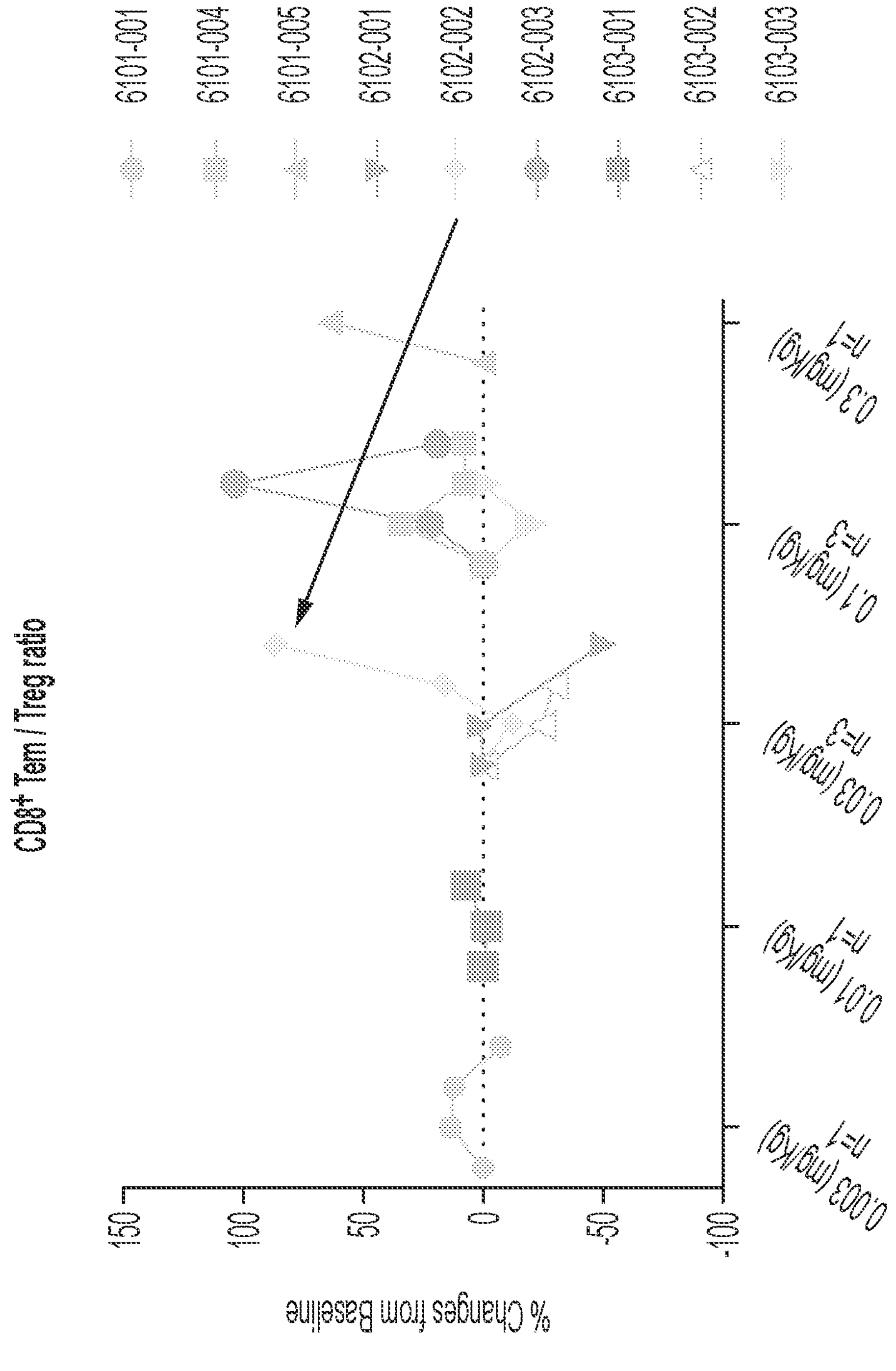
FIG. 13 shows the % change in $CD8^+$ $T_{EM}/T_{reg}$ cell ratio in patients treated with TY21580 in different dose cohorts of TY21580. The x-axis shows the dose, the y-axis shows the percentage, and the lines represent values from different subjects.
Figure 14:
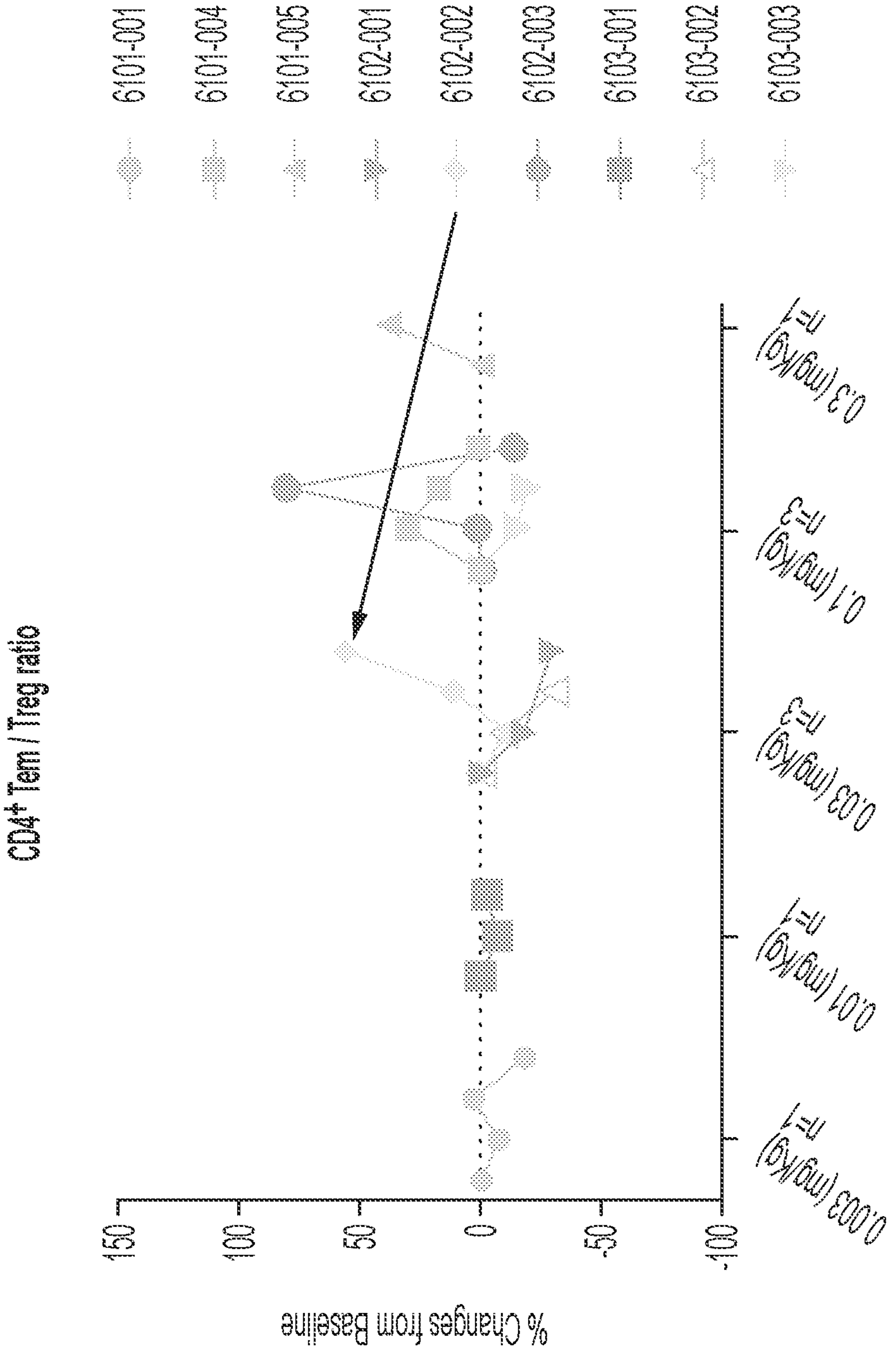
FIG. 14 shows the % change in $CD4^+$ $T_{EM}/T_{reg}$ cell ratio inpatients treated with TY21580 in different dose cohorts of TY21580. The x-axis shows the dose, the y-axis shows the percentage, and the lines represent values from different subjects.

FIGS. 4-6 and 13-14 show the relationship between TY21580 dose and immune cell response. A dose-dependent change in CD8+ $T_{EM}/T_{reg}$ ratio, an important pharmacodynamic (PD) biomarker indicating immune activation, was observed for patients dosed by TY21580 from 0.003 to 0.3 mg/kg (FIG. 13). Similarly, as shown in FIG. 14, there was a dose-dependent change in the CD4$^+$ $T_{EM}/T_{reg}$ ratio. A strong trend in dose-dependent CD8+ $T_{EM}/T_{reg}$ ratio and CD4+$T_{EM}/T_{reg}$ ratio upon TY21580 treatment at doses of 0.003 to 0.3 mg/kg demonstrates that TY21580 can stimulate immune cell effectively at a dose level as low as 0.03 mg/kg. This dose-dependent change in CD8+ $T_{EM}/T_{reg}$ ratio, is a strong clinical proof of mechanism (POM) for TY21580. These results are consistent with preclinical observations that TY21580 would be potent in sensitive tumor model such as H22 at dose as low as 0.02 mg/kg to induce tumor response, and achieve a complete response (CR) at 0.1 mg/kg. In particular, a steady increase in immune cells including CD8+ $T_{EM}/T_{reg}$ ratio was observed for a patient (subject 6103-002) who has received 3 cycles of TY21580 at 0.03 mg/kg after this patient became refractory and resistant to prior pembrolizumab therapy for >25 cycles. The patient developed irAE pruritus. Additionally, subject 6103-003 also developed an irAE Grade 1 rash, at end of treatment on day 22. This Grade 1 treatment-related immune-mediated pruritus was consistent with the mechanism of action by TY21580 treatment.

Monitoring is ongoing to confirm the dose-dependent response of the various biomarkers to TY21580 treatment.

Upon treatment with TY21580, significant increases in absolute T cell and N cell levels, and decreases in the percentage of $T_{reg}$ cells correlates with favorable clinical outcomes. The Phase 1 dose escalation data demonstrates the clinical proof of mechanism for TY21580 in targeting CTLA-4, consistent with preclinical observations for the potency of TY21580 starting from 0.03 to 0.3 mg/kg. It is anticipated that TY21580 has the potential to overcome the limitations of existing anti-CTLA-4 checkpoint inhibitors on the market, and extend the market potential beyond current anti-CTLA-4 inhibitors in both monotherapy and combination settings. The anti-CTLA-4 therapeutics described herein may improve the clinical benefits by expanding clonal diversity, infiltrating into cold tumors, and treating patients resistant/refractory to current immuno-therapies.

Subject 6102-002

Subject 6102-002 was enrolled in the study. Subject 6102-002 was a white male, 60 years of age, with an urothelial carcinoma (kidney), and an ECOG Scale of Performance Status of 0. Subject 6102-002 had previously received 25 cycles of Pembrolizumab plus Epacadostat from Apr. 15, 2018 to Sep. 19, 2019. The subject had showed an initial partial response and then had become refractory and resistant to Pembrolizumab therapy for >25 cycles. Three 0.03 mg/kg doses (2.7+ mg) of TY21580 were administered to subject 6102-002, and the dose was escalated to 0.1 mg/kg on Feb. 24, 2021. Subject 6102-002 will be escalated to higher dose once cleared. Subject 6102-002 developed the immune-related adverse event (irAE) pruritus. This grade 1 drug related immune toxicity at 0.03 mg/kg suggested target modulation at 0.03 mg/kg at an estimated 60% target engagement, and is consistent with the mechanism of action by TY21580 treatment. A summary of the treatment emergent adverse events experienced by subject 6102-002 is provided in Table 3, below.

TABLE 3

Summary of treatment emergent adverse events for subject 6102-002

| Treatment Emergent Adverse Events (TEAEs) | Start | Stop | Grade | Causality | Outcome |
|---|---|---|---|---|---|
| Headache | 2020 Dec. 22 (Day 1) | 2020 Dec. 22 (Day 1) | 1 | Not related | Rec-ed |
| Myalgia | 2021 Jan. 5 (Day 15) | 2021 Jan. 13 (Day 23) | 1 | Not related | Rec-ed |
| Pruritus/ irAE | 2021 Jan. 4 (Day 14) | Ongoing | | Related | Rec-ing |
| Gastro reflux | 2021 Jan. 14 (Day 24) | | 1 | Not related | Rec-ing |

Figure 10:
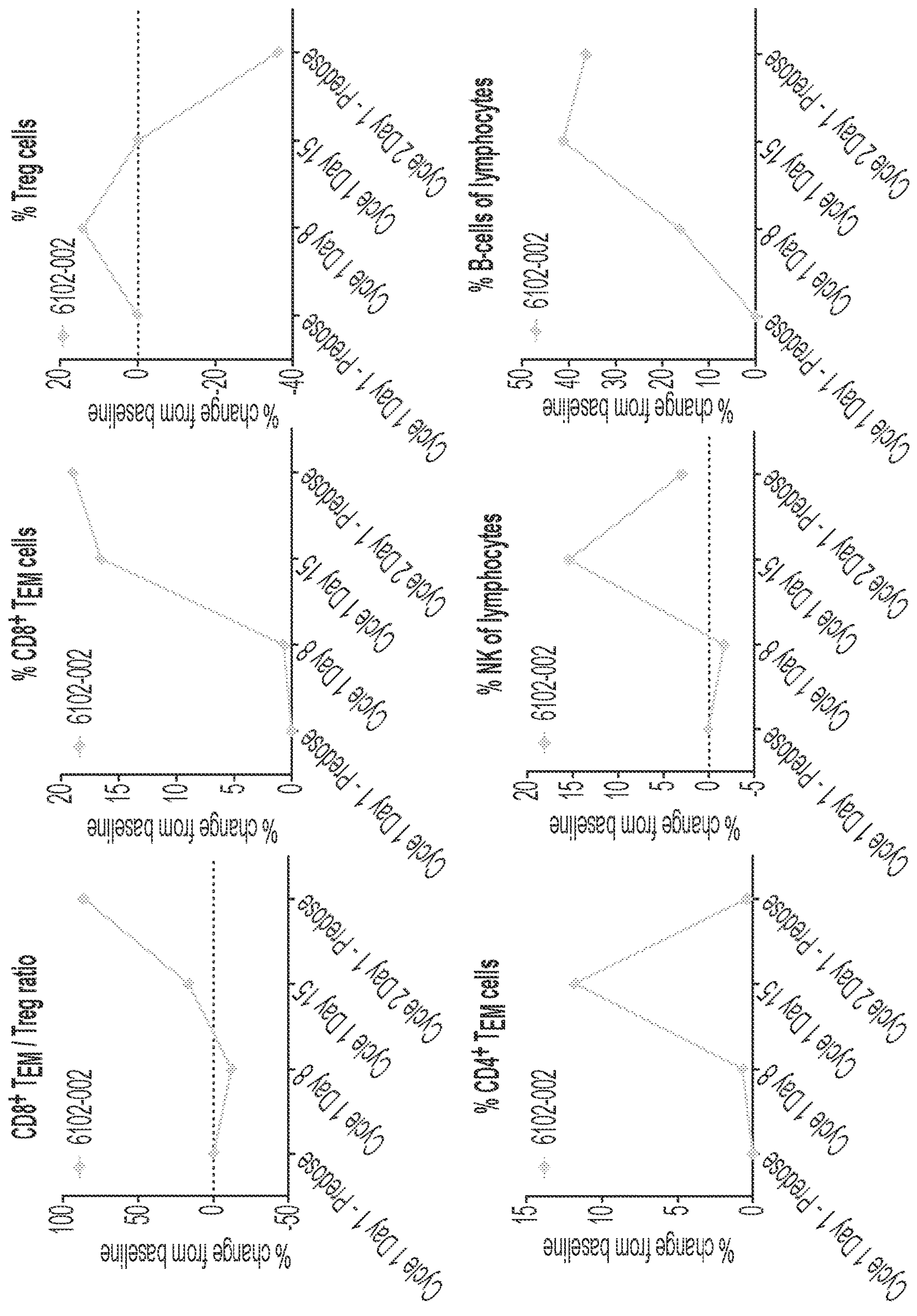
FIG. 10 shows the results of lymphocyte profiling subject 6102-002 at a 0.03 mg/kg dose of TY21580. The plots show (from left to right on the top row) the % change in $CD8^+$ $T_{EM}/T_{reg}$ ratio, the % change in $CD8^+$ $T_{EM}$ cells, and the % change in $T_{reg}$ cells, and (from left to right on the bottom row) the % change in $CD4^+$ $T_{EM}$ cells, the % change in NK cells, and the % change in B cells. In each plot, the x-axis shows the time of sampling, and the y-axis shows the percentage change relative to baseline.

FIG. 10 provides lymphocyte profiling results of subject 6102-002 overtime. As shown in FIG. 10, in subject 6102-002, there was an effective CD8 T cell increase continuously, but CD4 T cells increased first and then decreased at 0.03 mg/kg. In subject 6102-002, $T_{reg}$ cells decreased at 0.03 mg/kg. The CD8+ $T_{EM}/T_{reg}$ ratio showed a significant increase. Further, NK and B cells increased. An analysis of immune cell subpopulation by flow cytometry revealed stimulation of T cells, NK and B cell proliferation, and $T_{reg}$ depletion upon TY21580 treatment, especially for the big increase in CD8$^+$ $T_{EM}/T_{reg}$ ratio. This trend seemed to be followed by patients dosed at 0.1 and 0.3 mg/kg (as described above). PD results for subject 6102-002 are also shown in FIGS. 1-8.

Population Pharmacokinetic (PK) Modeling

Figure 11:
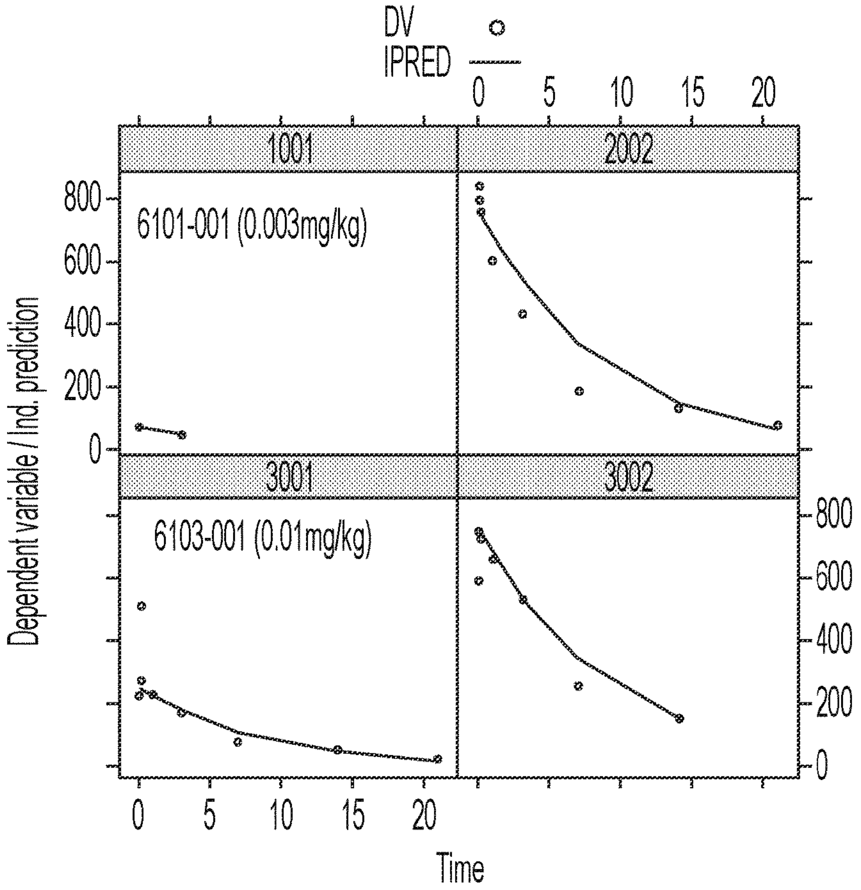
FIG. 11 shows the results of population pharmacokinetic modeling using a 2-compartment model for TY21580 in the phase 1 study.
Figure 11:
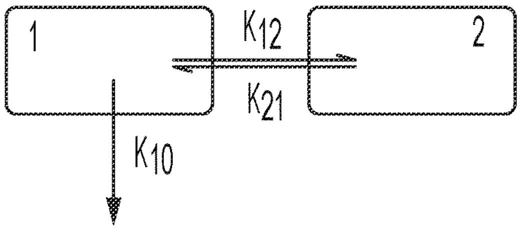
Figure 12A:
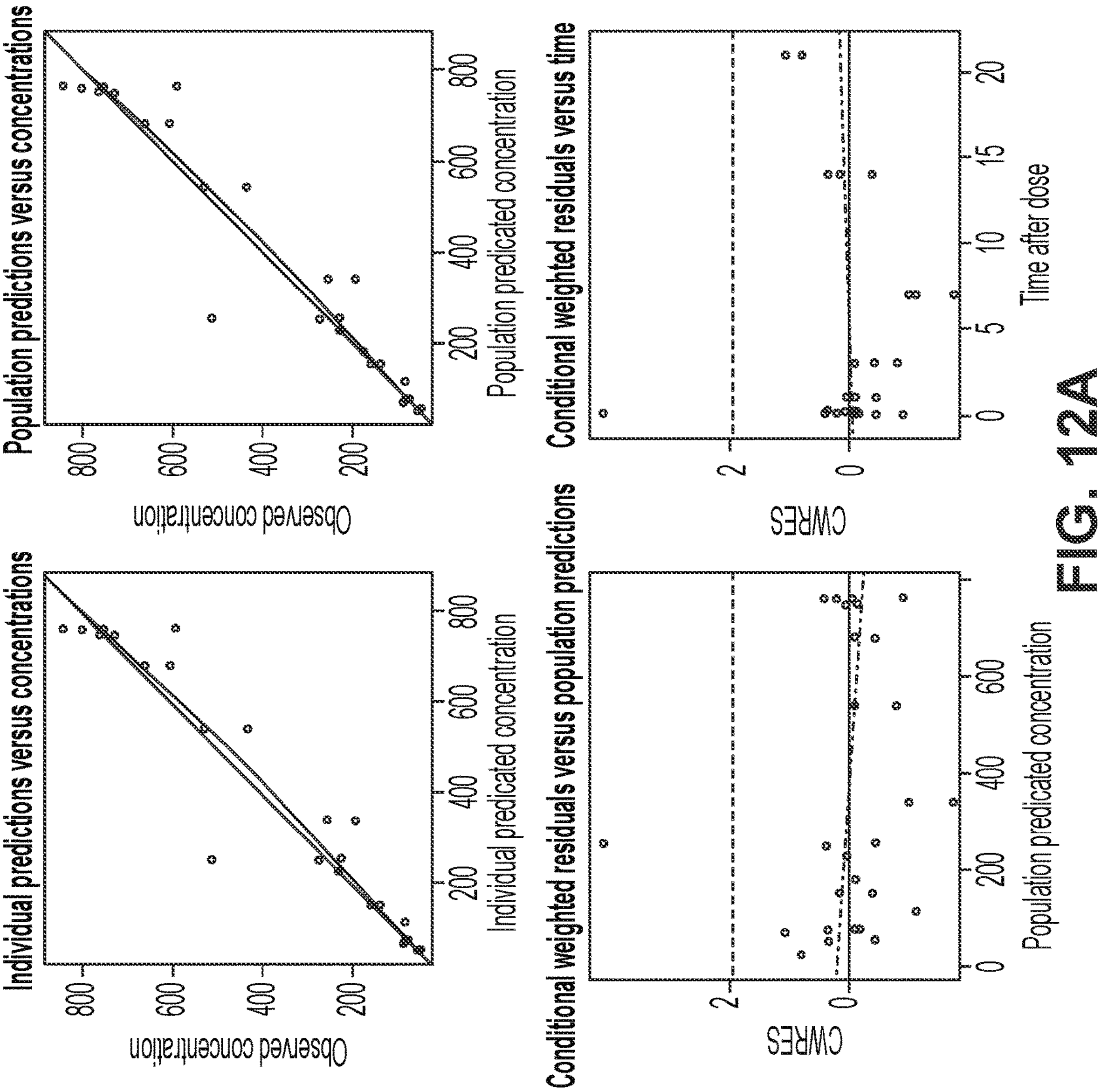
FIGS. 12A-12B show the results of population pharmacokinetic modeling for the phase 1 study.
Figure 12B:
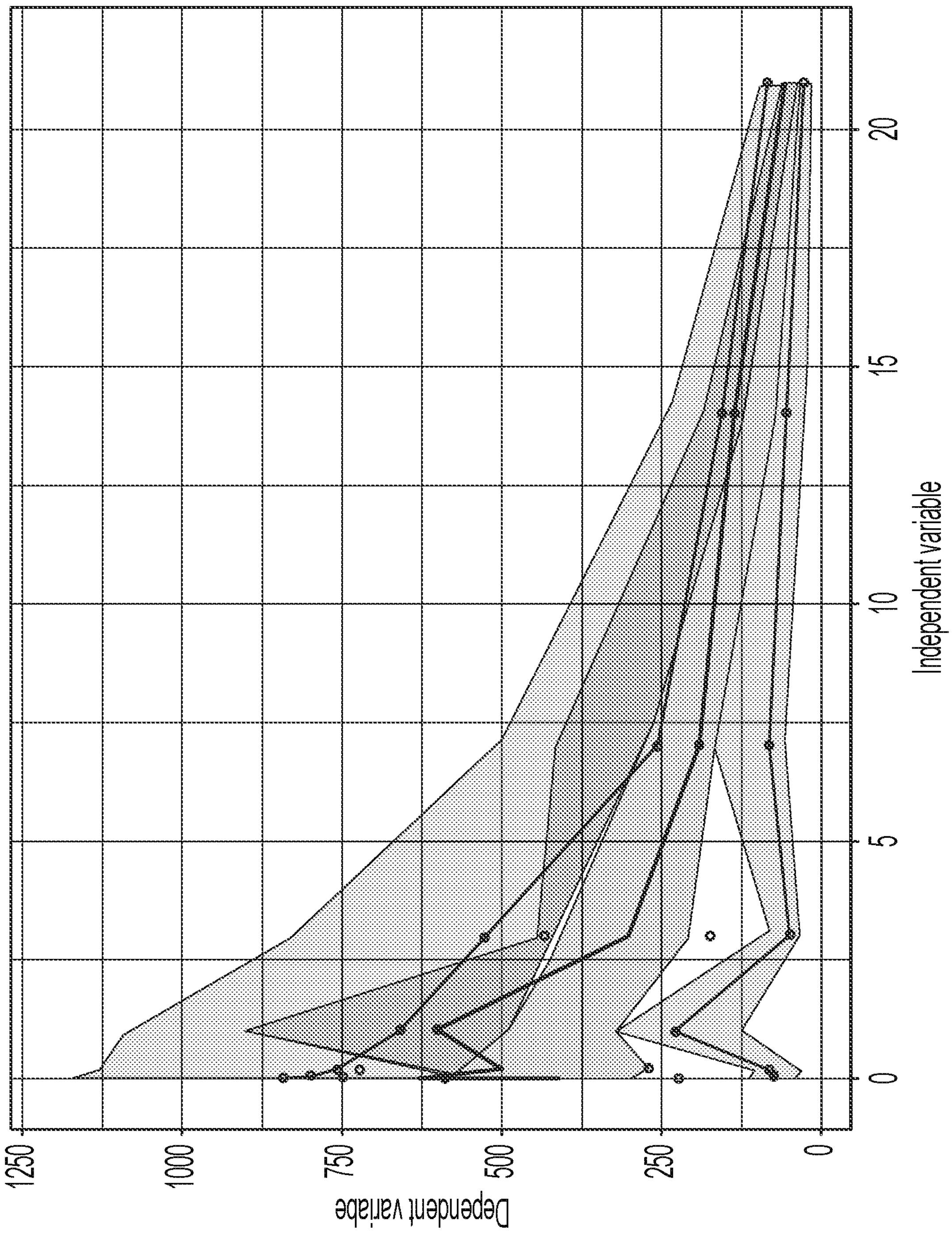

Preliminary PK population modeling was performed for the study. A 2-compartment linear PK model described the current PK data reasonably well across the studied doses (FIG. 11). All PK parameters were estimated with good precision, except for V2 (peripheral volume of distribution). The model-estimated population terminal half-life was ~14 days. The model-estimated population central volume of distribution (V1) was similar to plasma volume (e.g., 40 mL/kg). Goodness-of-fit plots were generated (FIGS. 12A-12B). The fit of the model was reasonably good based on the diagnostic plots. Additional emerging PK data is used to refine the parameter estimates in real-time.

A second interim analysis of the ongoing study are provided in the drawings and are described below.

Clinical Summary

Figure 15A:
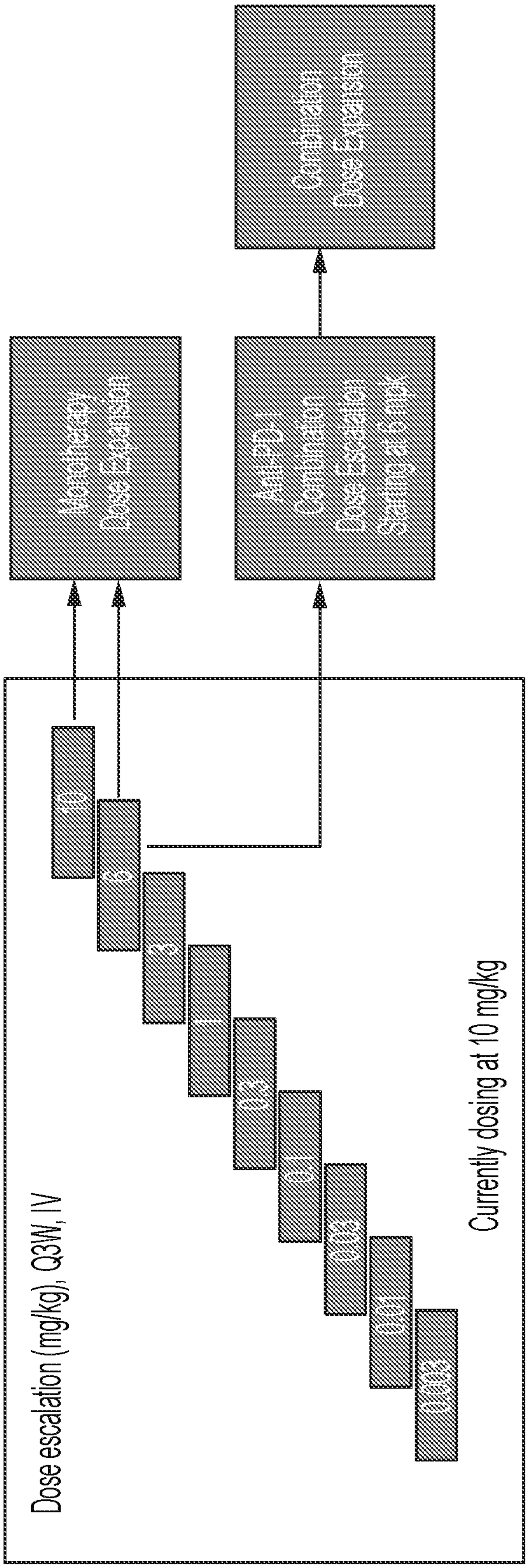
Figure 15C:
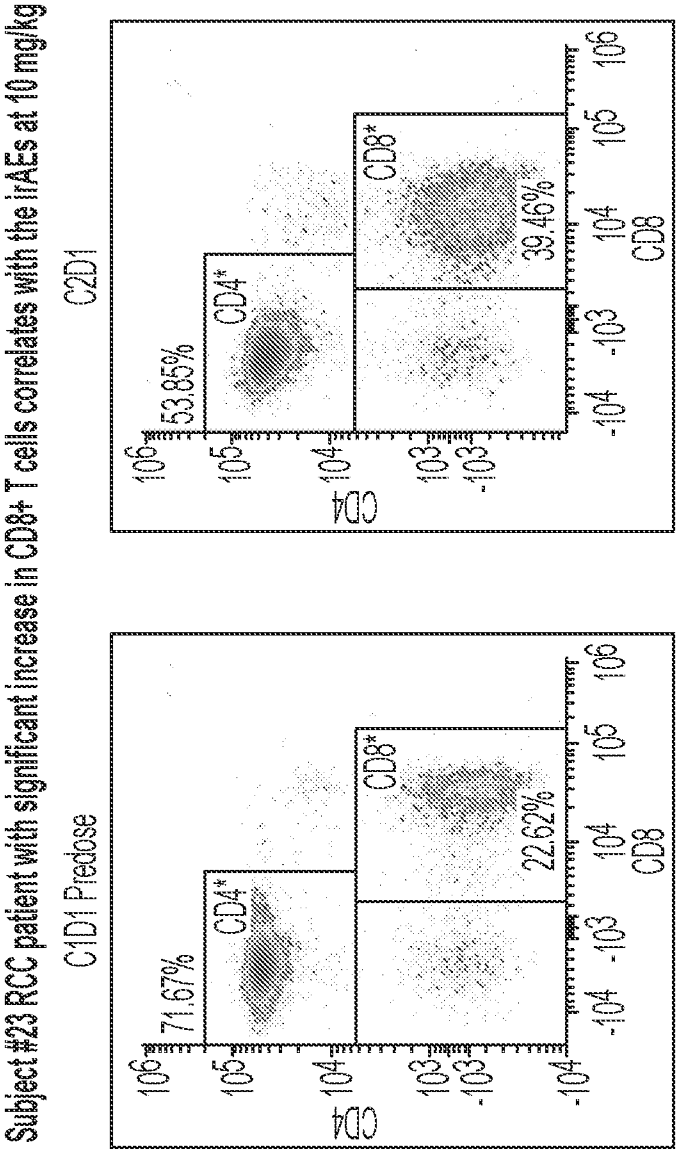
Figure 15D:
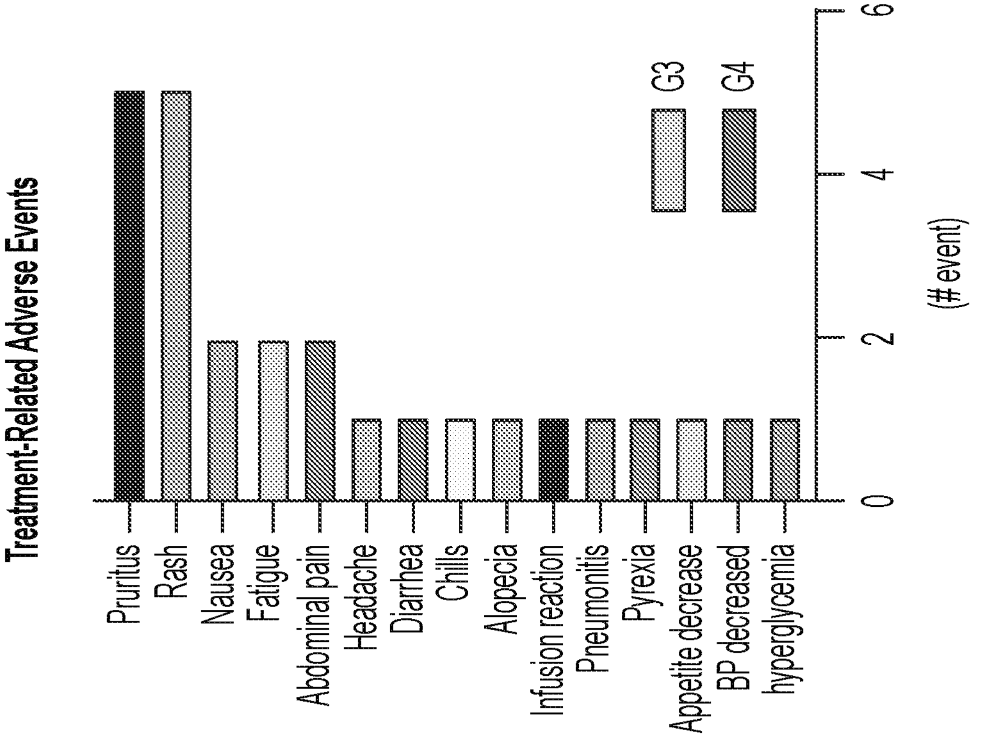

To date, 25 patients with advanced/metastatic solid tumors were treated with TY21580 at nine dose escalation cohorts (i.e., 0.003 mg/kg, 0.01 mg/kg, 0.03 mg/kg, 0.3 mg/kg, 1.0 mg/kg, 3.0 mg/kg, 6.0 mg/kg, and 10 mg/kg, n=24 patients) and 6 mg/kg expansion (n=1). These patients have advanced metastatic disease and have been treated across 15 different tumor types, 68% of which are IO insensitive tumors. (FIG. 15B). TY21580 has been well tolerated up to 10 mg/kg, once every three weeks (Q3W), with no DLT and no dose-dependent toxicities identified (FIG. 15D). Currently, patients are enrolling at the next higher dose level, 20 mg/kg, to continue dose escalation following the amended protocol and 6.0 mg/kg dose expansion.

Pharmacokinetics

Figure 16:
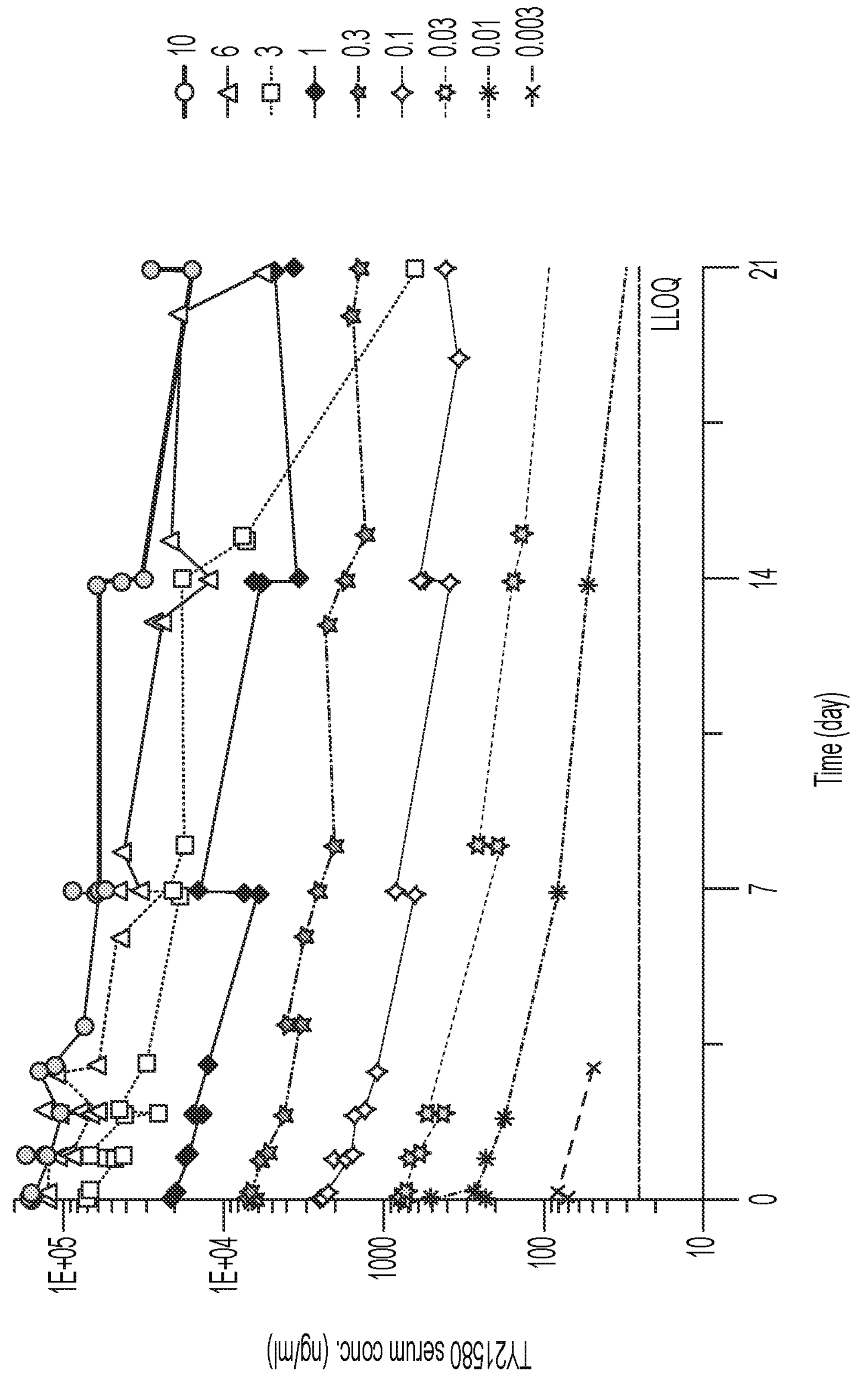
FIG. 16 shows the serum pharmacokinetics of TY21580. The x-axis shows the day after dose, the y-axis shows the measured drug concentration in patient serum, and the lines represent different doses.

TY21580 shows a dose-proportional increase in drug exposure with a half-life of approximately 10 days (estimated at about 10±5 days up to 10 mg/kg). FIG. 16 shows the serum pharmacokinetics of TY21580 after IV infusion, as assessed by non-compartmental analysis and population PK modeling approaches.

Pharmacodynamics Results

Pharmacodynamic results are presented in FIGS. 17-26. Blood samples of patients at serial visit points were collected for pharmacodynamic study in order to monitor the dynamic changes of cytokines and immune-related soluble proteins. Blood was collected at six visit time points, Cycle 1 Day 1 pre-dose, Cycle 1 Day 1 4 hr, Cycle 1 Day 2, Cycle 1 Day 8, Cycle 1 Day 15, and Cycle 2 Day 1. Serum was prepared following standard protocols. An MSD panel was designed to investigate whether there is a dose-dependent change in the abundance of five cytokines, IFN-γ, IL-2, IL-6, IL-10, and TNF-α, in the peripheral blood during TY21580 treatment. In addition, serum levels of four soluble proteins, sCTLA-4, sPD-L1, sCD25, and CXCL11, were measured.

Figure 17A:
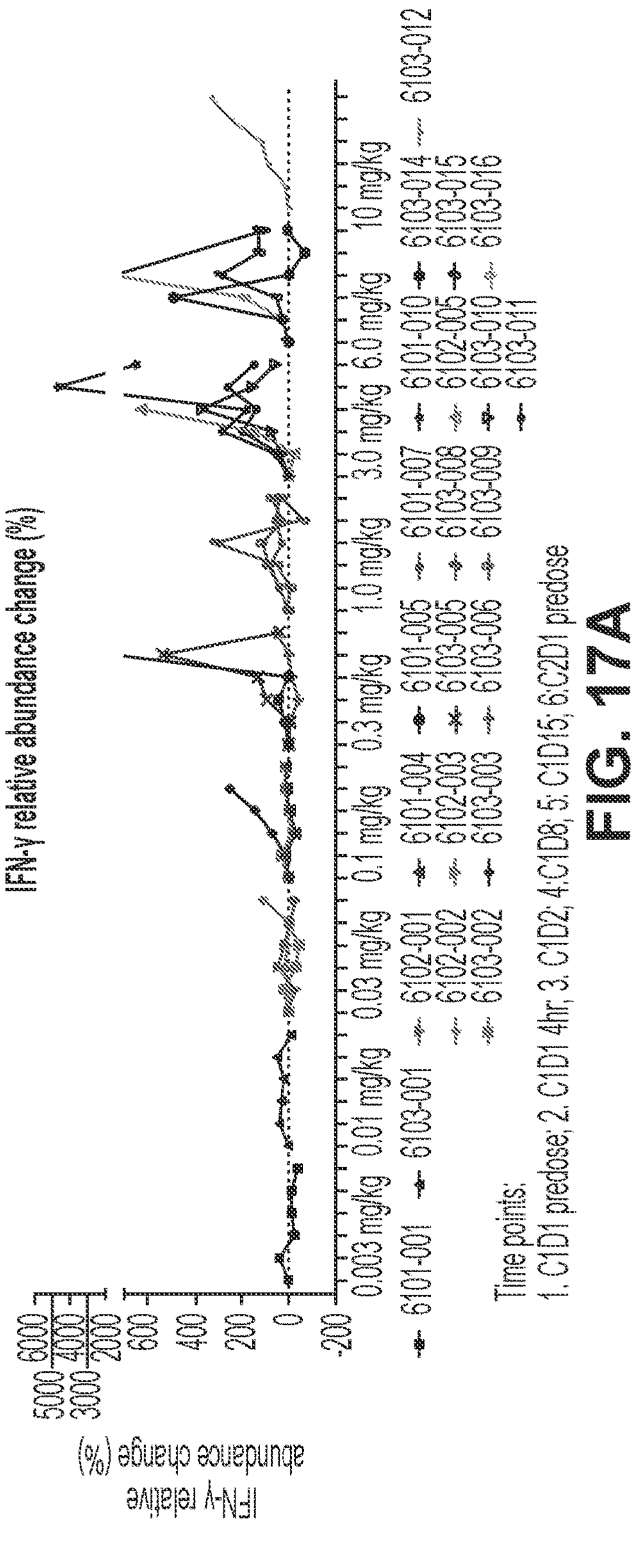
FIGS. 17A-17C show kinetics of serum IFN-γ levels in patients treated with TY21580.
Figure 17B:
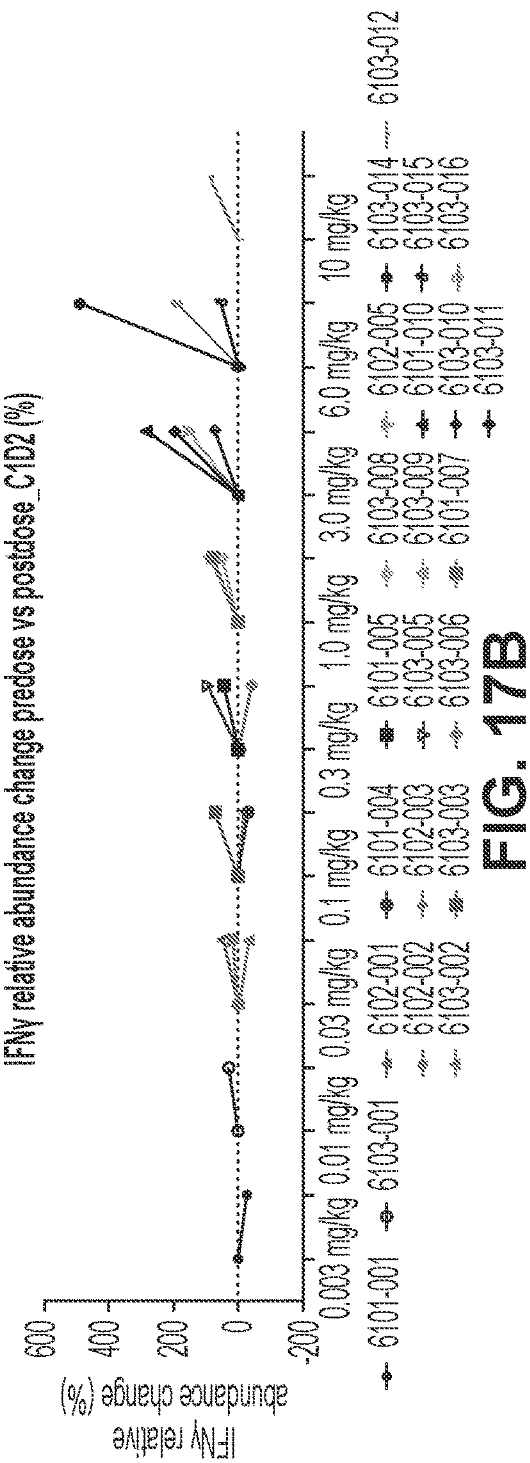
Figure 17C:
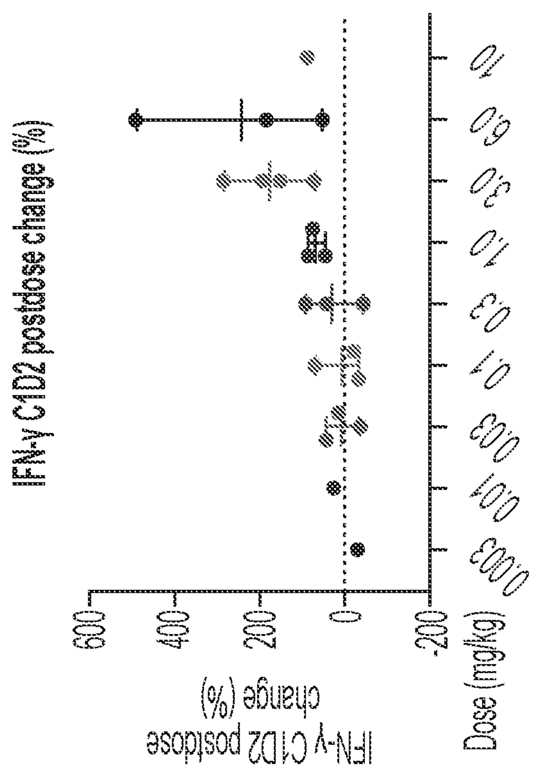

FIG. 17A shows a dose dependent change in serum IFN-γ concentration in patients treated with TY21580, with IFN-γ levels increasing significantly in the first two days after dosing for most patients. These kinetics reflect immune system activation and may correlate with the antibody concentration in patients' blood. The change in absolute concentration of each analyte was compared to baseline, which shows a clear dose-dependent response of IFN-γ to TY21580 treatment at doses up to 6 mg/kg (FIG. 17B). In addition, quantifying changes in IFN-γ serum concentration at C1D2 from baseline level (C1D1 pre-dose) within each dose group showed the increase in IFN-γ abundance to be dose dependent at 0.1 mg/kg and higher (FIG. 17C), which indicates the immune system is activated upon TY21580 treatment. These data are consistent with one proposed mechanism of TY21580 action, in which TY21580 activates the immune system through relief of CTLA-4-mediated immunosuppression.

Figure 18A:
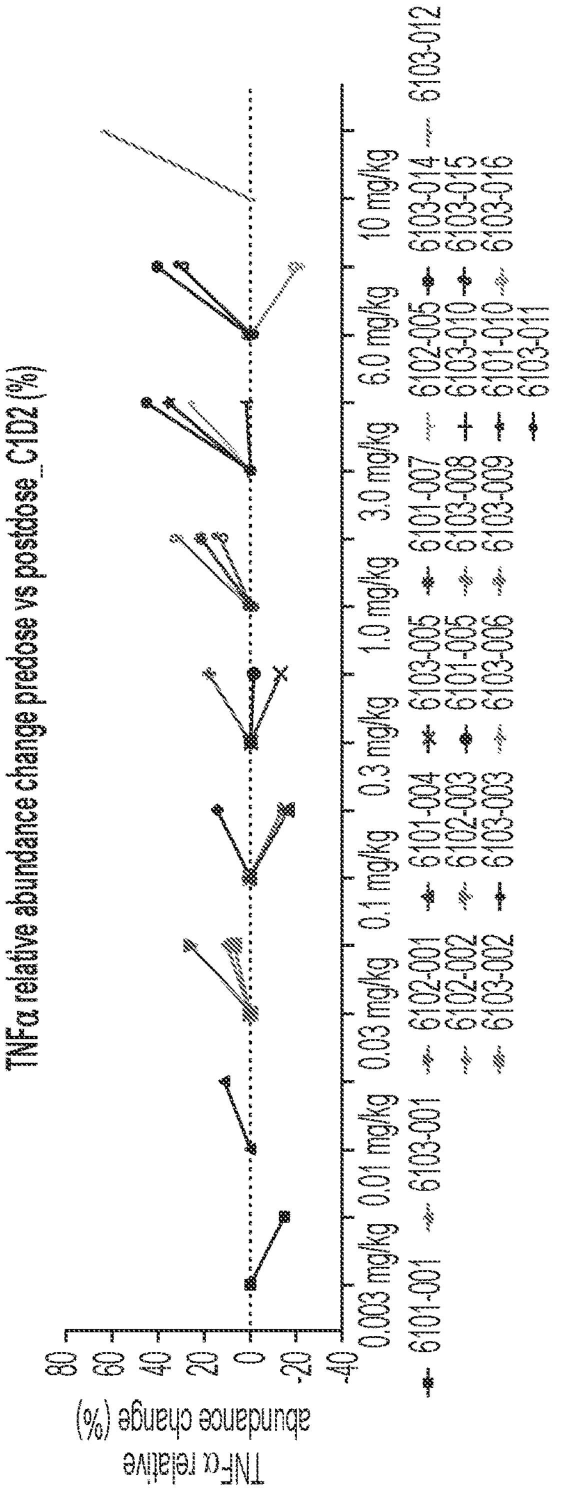
FIGS. 18A-18B show changes of TNFα in patients treated with TY21580.
Figure 18B:
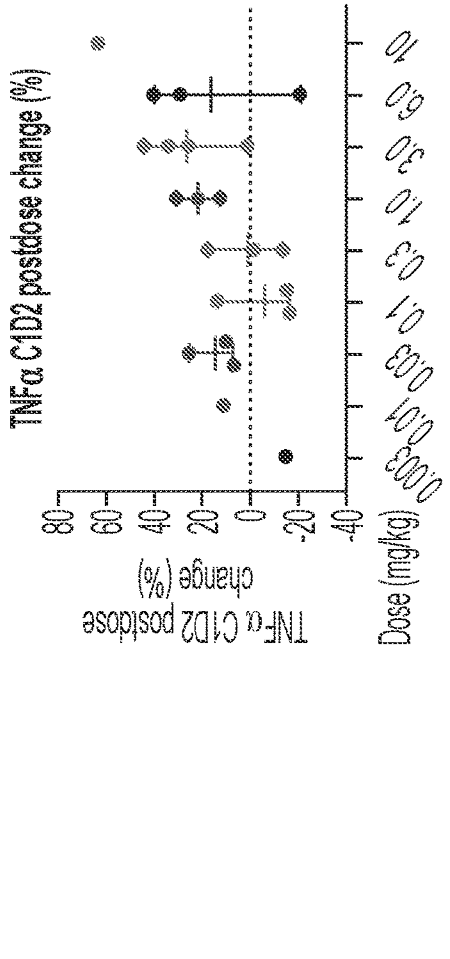

TNFα concentrations were also measured in patients treated with TY2180 and changes were plotted relative to baseline levels. FIG. 18 show a dose dose-dependent increase in TNFα levels following treatment with TY2180.

Figure 19A:
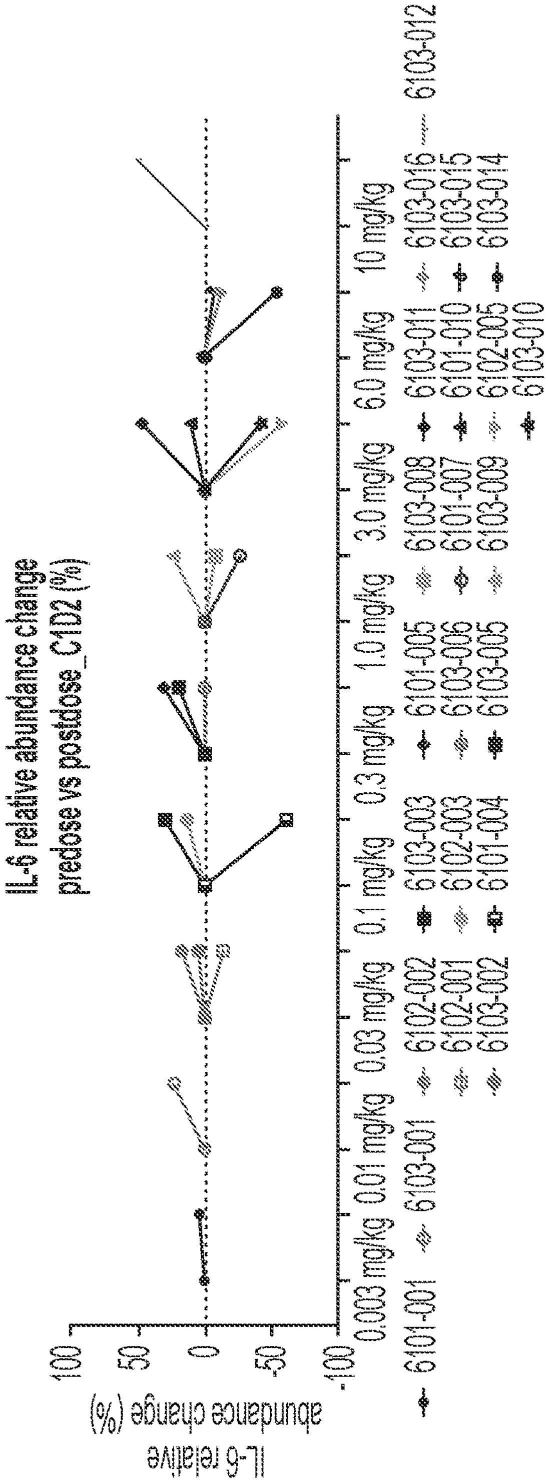
FIGS. 19A and 19B show changes of IL-6 in patients treated with TY21580.
Figure 19B:
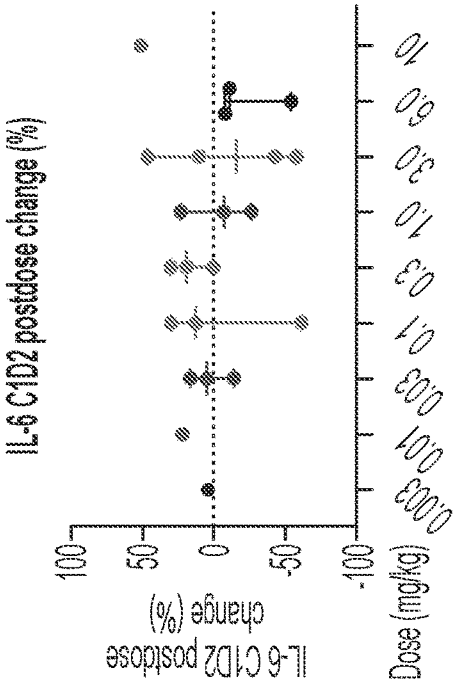
Figure 20A:
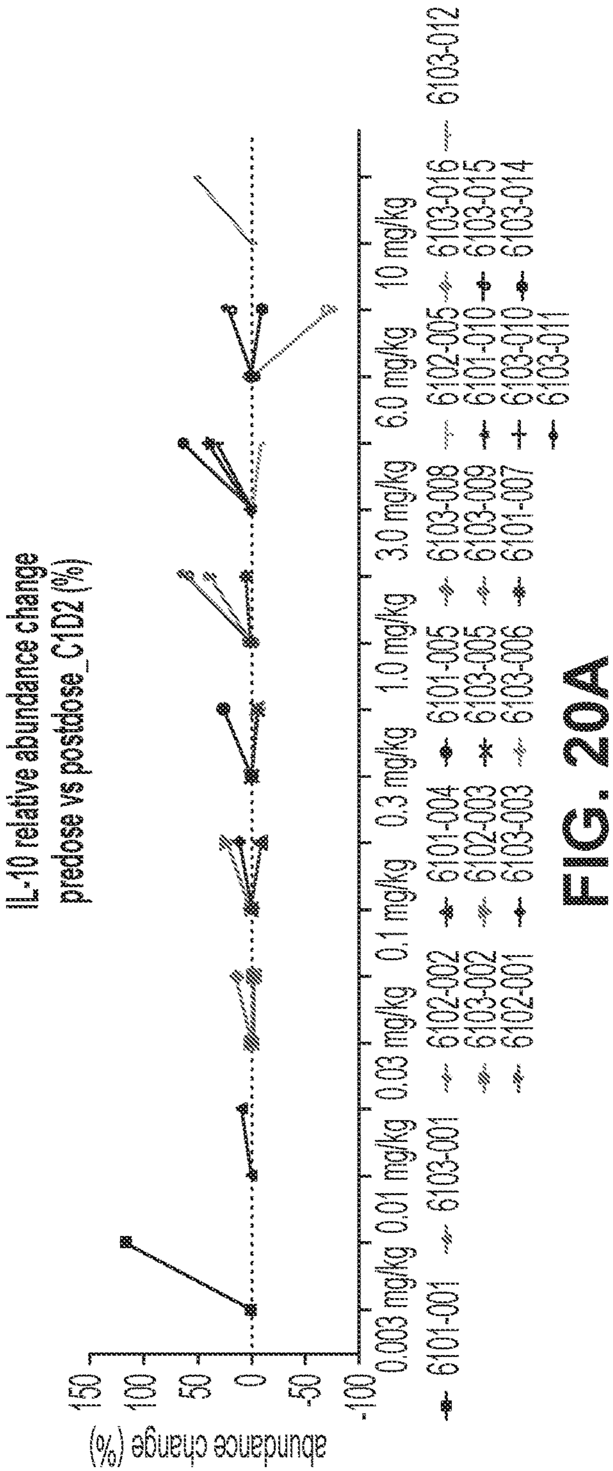
FIG. 20A shows the change in relative abundance of IL-6 to baseline in patients treated with TY21580. The x-axis shows the dose cohorts, the y-axis shows the percent change, and the lines represent values from different subjects.
Figure 20B:
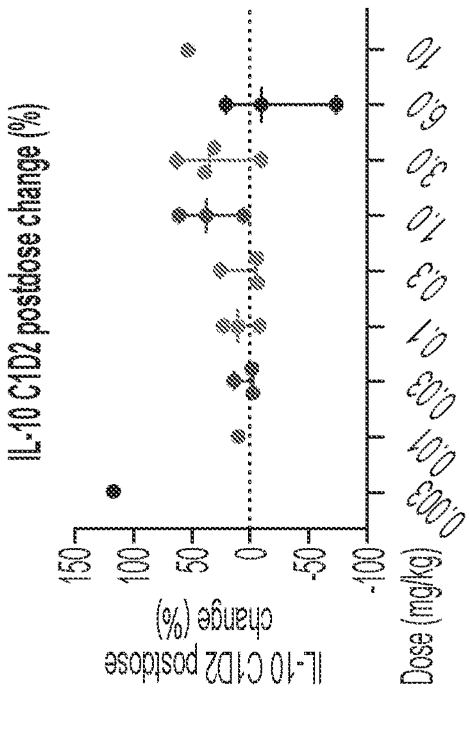

In addition, IL-6 (FIG. 19), IL-10 (FIG. 20), and IL-2 (data not shown) were measured in patients treated with TY2180. FIG. 19 show no observable dose-dependent change in IL-6 concentration in patients treated with TY21580. Serum concentration of IL-2 was below the assay detection limit in most patients.

Figure 21A:
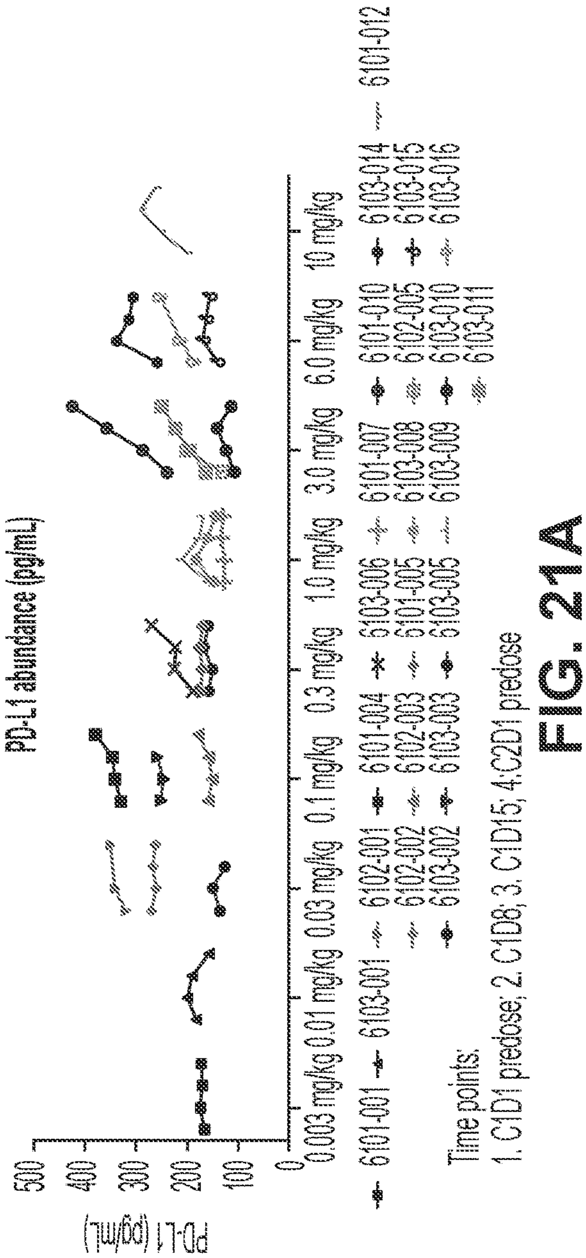
FIG. 21A-21C show changes of sPD-L1 in patients treated with TY21580.
Figure 21B:
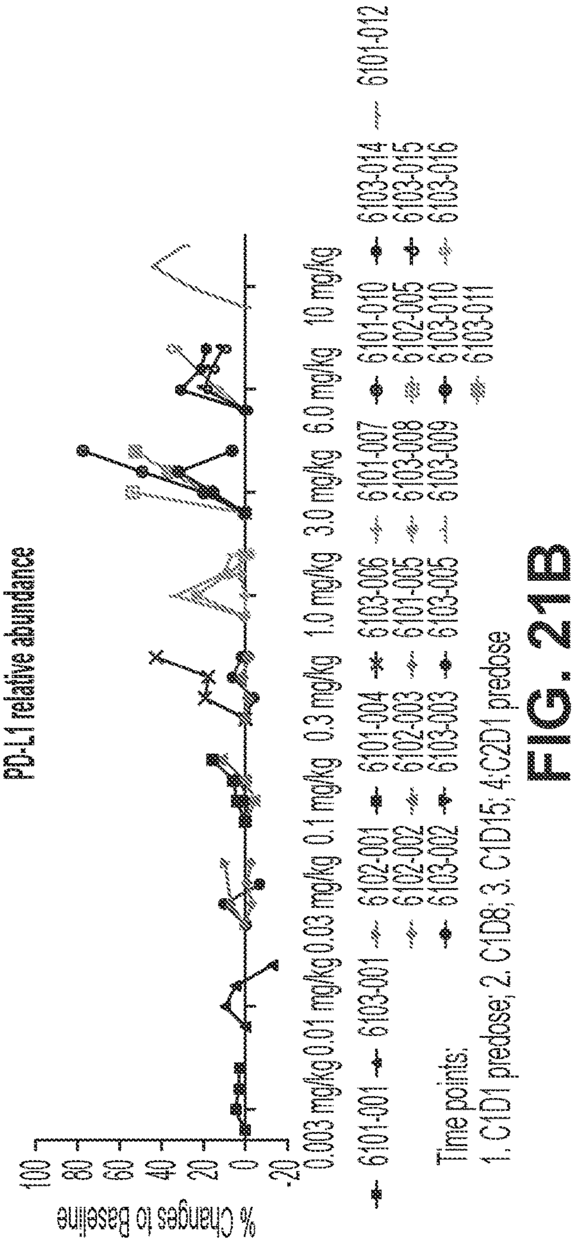
Figure 21C:
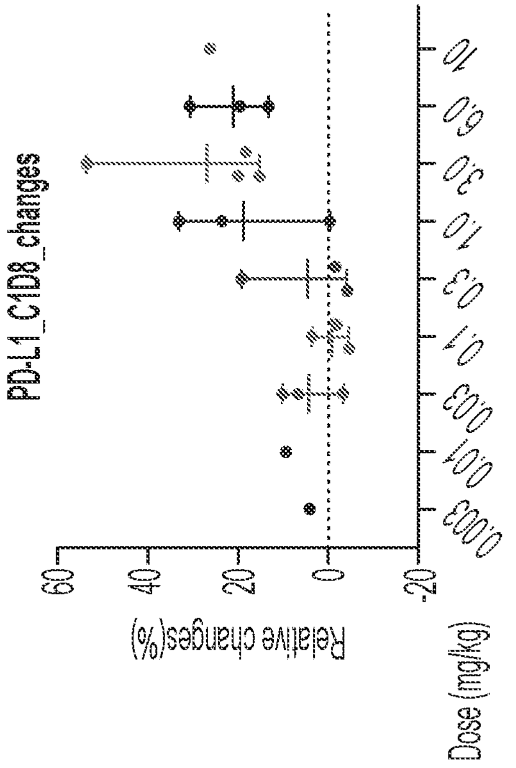

The serum concentration of soluble PD-L1 was also measured in patients treated with TY21580 at serial visit time points (FIG. 21A) and FIG. 21B shows changes in sPD-L1 abundance relative to baseline in response to treatment. Changes of sPD-L1 abundance in each dose group is shown in FIG. 21C. sPD-L1 levels increased significantly in patients dosed with 3 mg/kg and higher, which might indicate a clinical response.

Figure 22A:
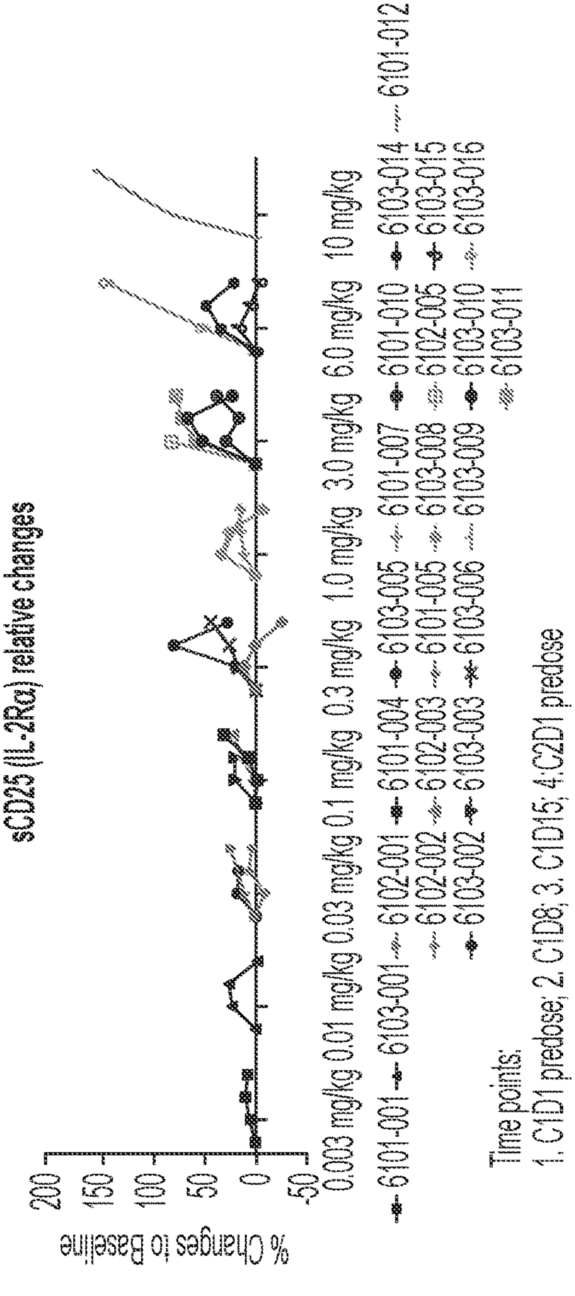
FIGS. 22A and 22B show changes of sCD25 in patients treated with TY21580.
Figure 22B:
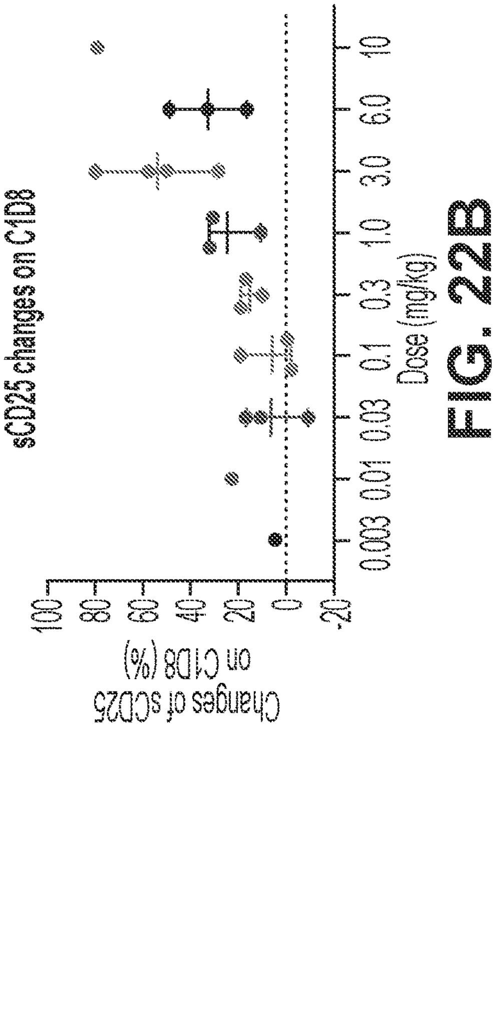

FIG. 22 shows a dose dependent increase in soluble CD25 at C1D8 as compared to baseline levels.

Figure 23A:
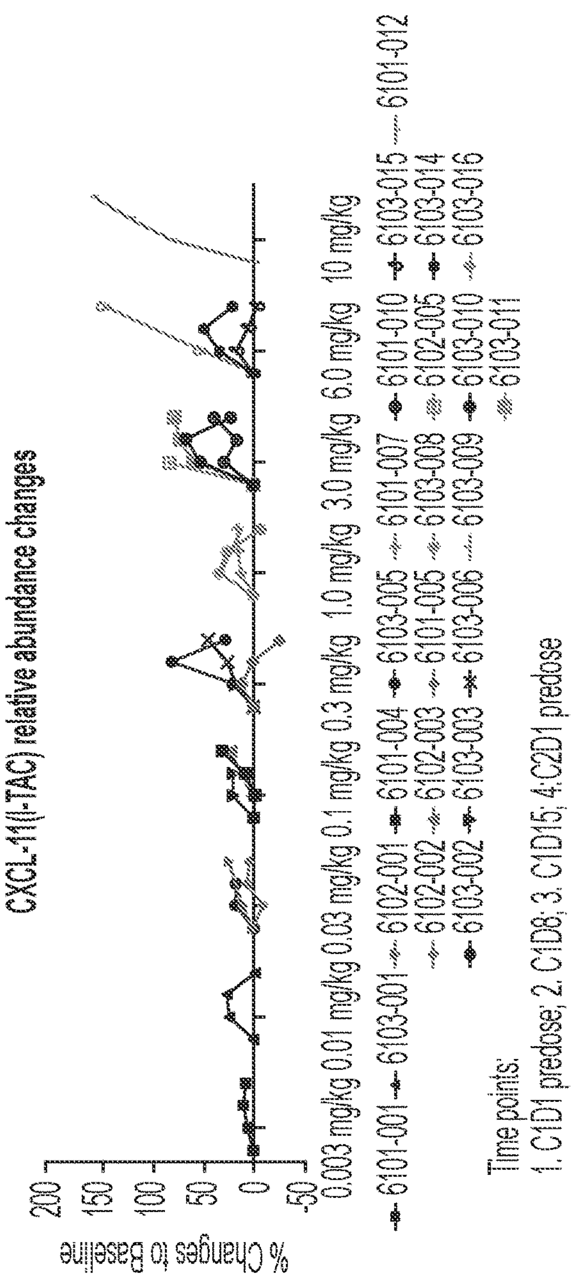
FIGS. 23A and 23B show changes of CXCL-11 in patients treated with TY21580.
Figure 23B:
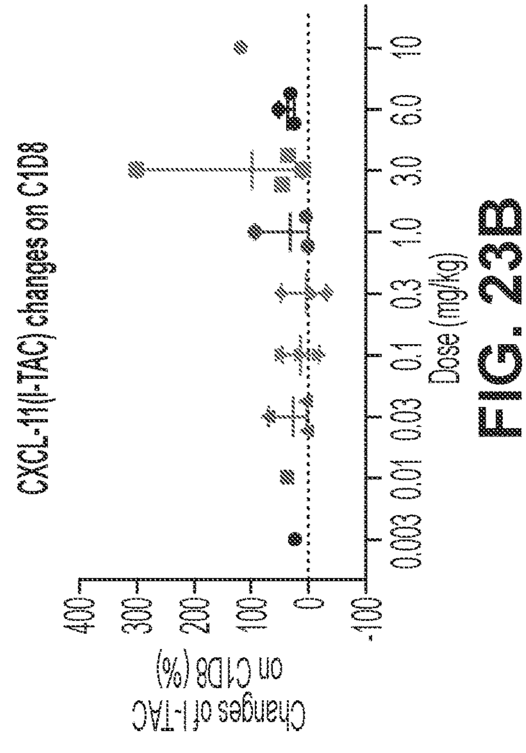

The serum concentration of soluble CXCL11 was also measured in patients treated with TY21580 at serial visit time points, and FIG. 23 shows what appears to be a dose-dependent increase in response following TY21580 treatment. These data show that CXCL11 abundance increases significantly in patients who received a dose equal to or exceeding 0.3 mg/kg.

Whole blood collected from patients was also used to assess T cell and NK cell counts in patients treated with TY21580.

Figure 24A:
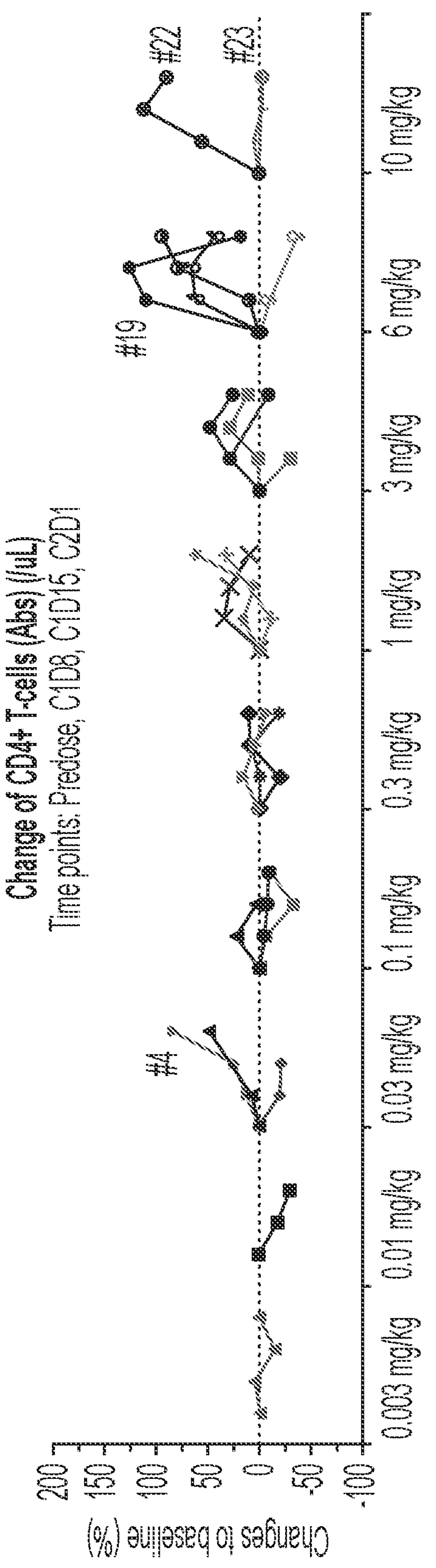
FIG. 24A-24E show changes of CD4+ T cells in patients treated with TY21580.
Figure 24B:
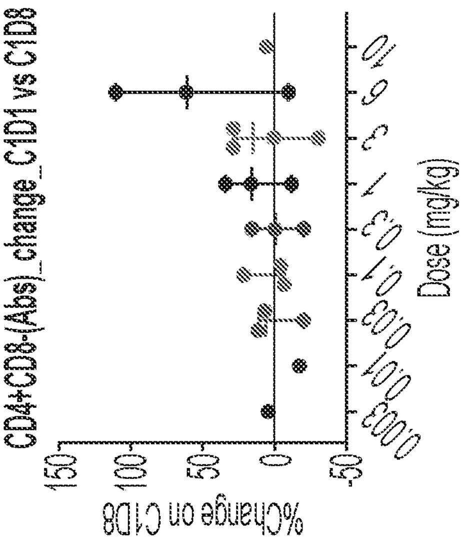
Figure 24C:
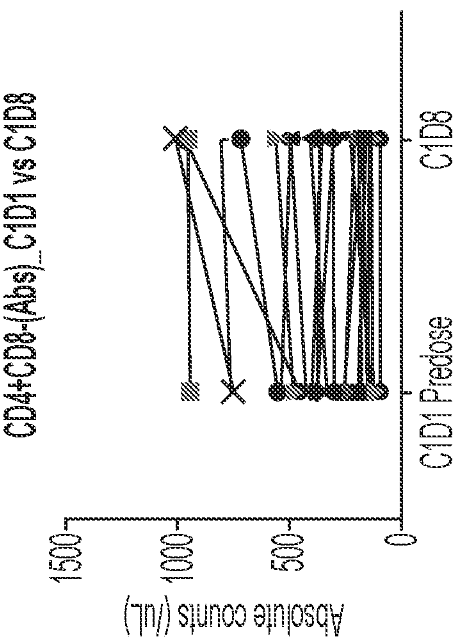
Figure 24D:
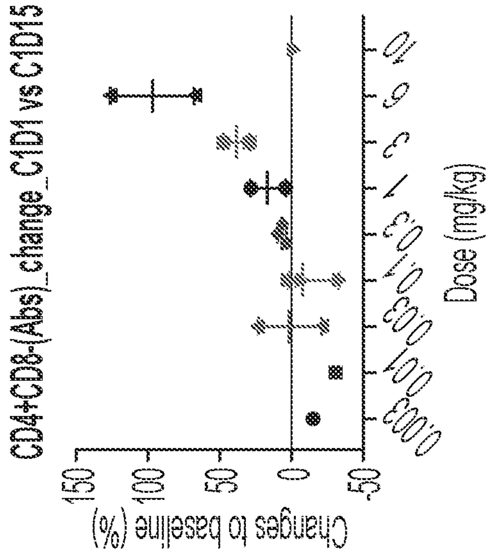
Figure 24E:
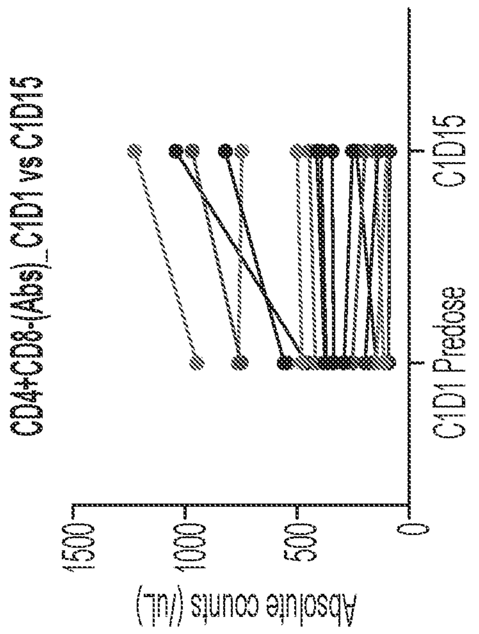

CD4+CD8− T cells were quantified in whole blood collected from patients treated with TY21580 at C1D1 (pre-dose), C1D8, C1D15, and C2D1 time points. A dose-dependent increase of CD4+ cells was measured by absolute count, which was particularly notable at the 3 mg/kg and 6 mg/kg doses (FIG. 24A). FIGS. 24B-24E compare changes in CD4+ T cell counts between baseline and C1D8 (FIGS. 24B and 24C) and baseline and C1D8 (FIGS. 24D and 24E), with FIGS. 24B and 24D showing the relative change compared to baseline, and FIGS. 24C and 24E showing the change in absolute counts per μL. A dose-dependent increase in absolute count of CD8+ T cells was also measured, as seen in FIG. 25. These dose-dependent increases in absolute count of CD4+ and CD8+ T cells indicates the immune system is activated upon TY21580 treatment. This data also shows that even two weeks following treatment (C1D15), TY21580 showed consistent anti-tumor efficacy.

Figure 26B:
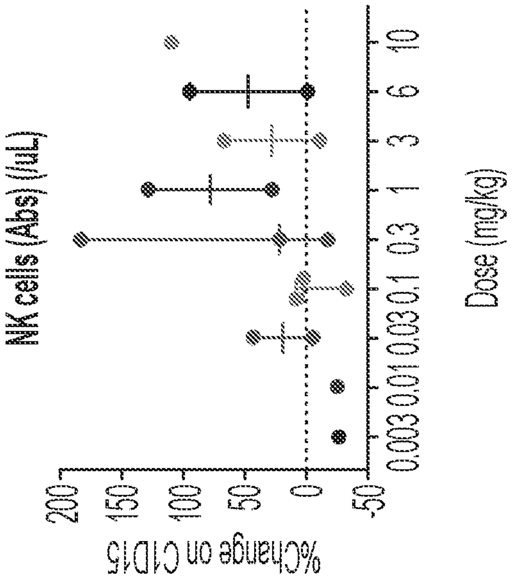
FIGS. 26A and 26B show changes of NK cells in patients treated with TY21580.
Figure 26A:
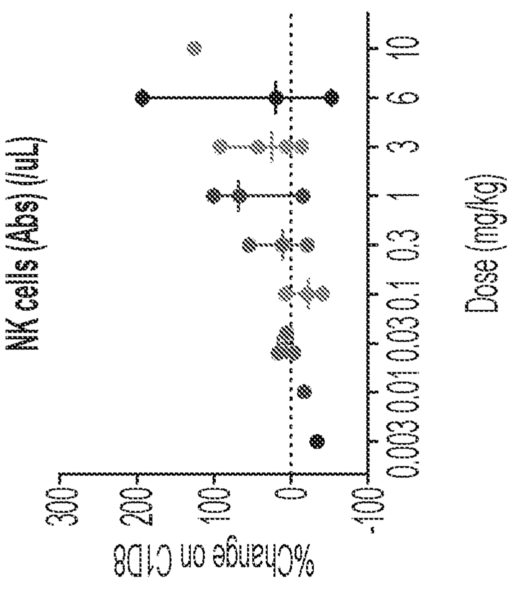
Figure 27:
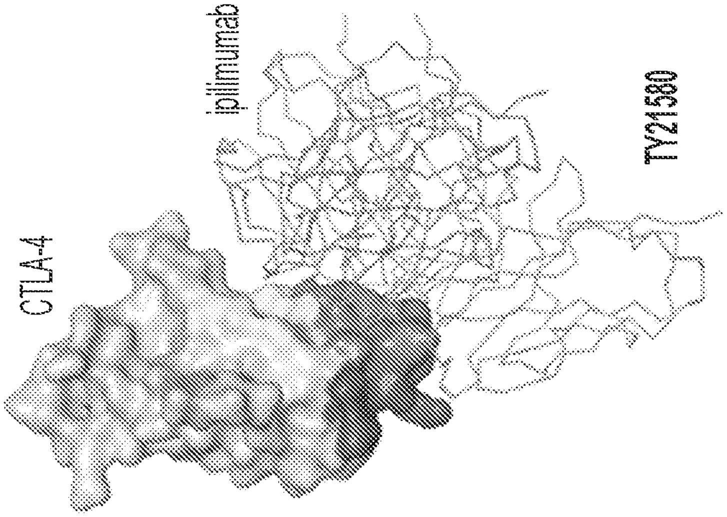
FIG. 27 shows a 3D structure of CTLA4 and its interations with Ipilimumab and TY21580.
Figure 28:
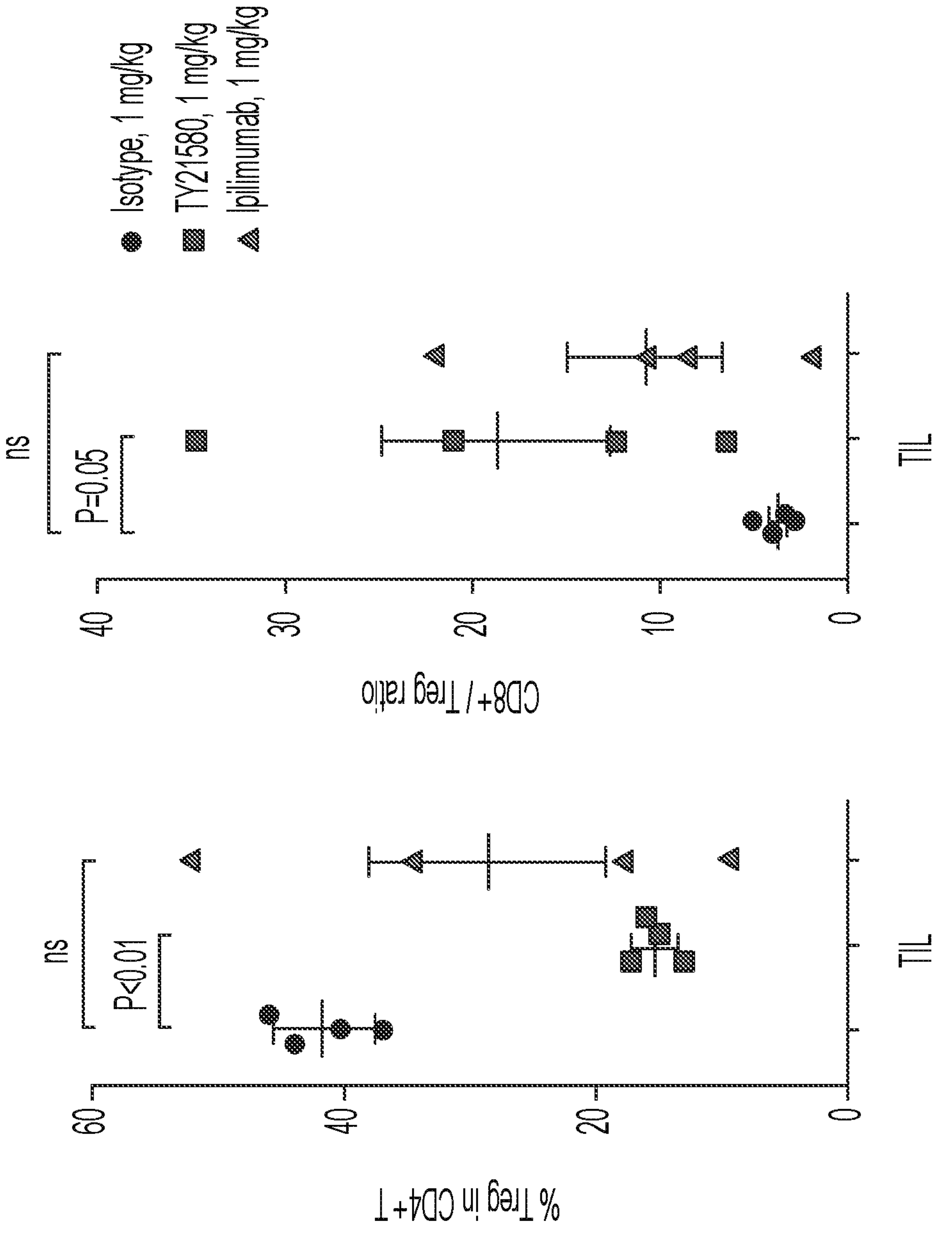
FIG. 28 shows Treg depletion and CD8/Treg rations in the tumor-infiltrating lymphocytes (TIL) of treated MC38 tumors in hCTLA4 knock-in background.

NK cell counts were also determined in patients treated with TY21580, with FIG. 26 showing the change in absolute cell counts per μL at C1D8 and C1D15.

Interim Efficacy Data

Subject #23 is a 74 year-old male with renal cell carcinoma who relapsed on nivolumab and is enrolled in the 10 mg/kg cohort. CD8+ T cells increased in this subject after the 1st cycle of treatment (FIGS. 15C and 25A), showing that TY21580 is highly active for triggering T cell activation.

Subject #22 is a 77 year-old male with pancreatic cancer in the 10 mg/kg cohort who has undergone three previous therapies. This subject has two target lesions, one in the pancreas and one in the liver with baseline measurements of 35 mm for the pancreas lesion and 15 mm for the liver lesion. The first tumor assessment was performed on this patient after two cycles of TY21580 treatment. This assessment shows the pancreas lesion has shrunk to 29 mm and the liver lesion has shrunk to 10 mm, reflecting a 22% reduction in target lesion size (Table 4).

TABLE 4

Tumor shrinkage in Subject #22 (pancreatic cancer)

| Patient #22 | | Baseline | 1st tumor assessment |
|---|---|---|---|
| Target lesions | TL1-Pancreas | 35 mm | 29 mm |
| | TL-2 Liver | 15 mm | 10 mm |
| Non-target lesion | Portal vein lymph node | Present | Disappear |
| Change in target lesions | | −22% | |

Figure 25A:
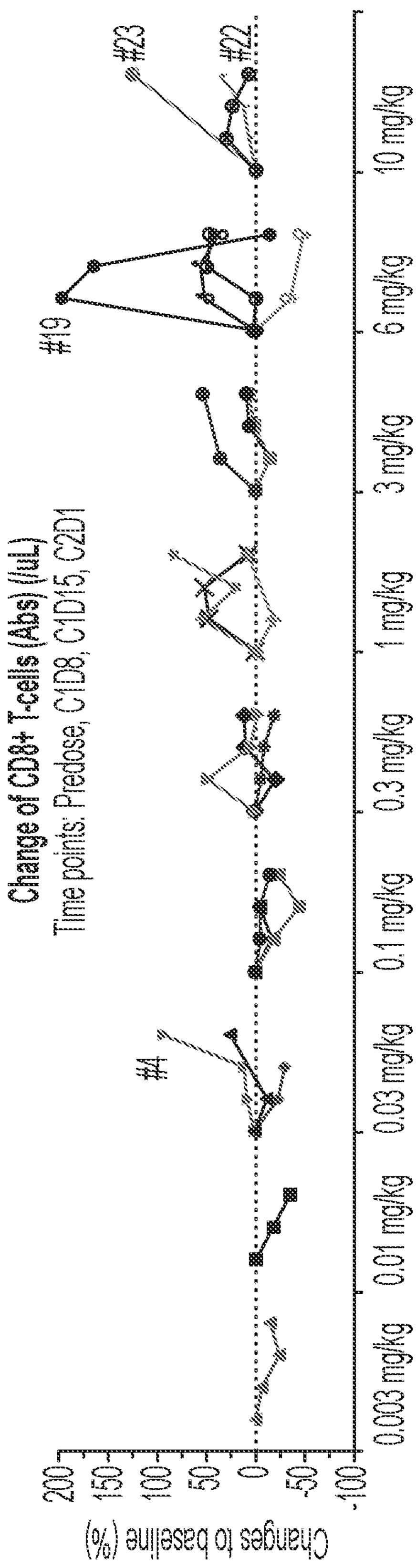
FIG. 25A-25E show changes of CD8+ T cells in patients treated with TY21580.
Figure 25C:
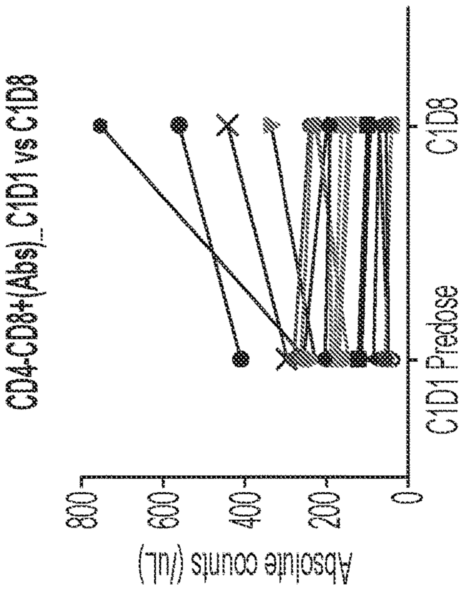
Figure 25B:
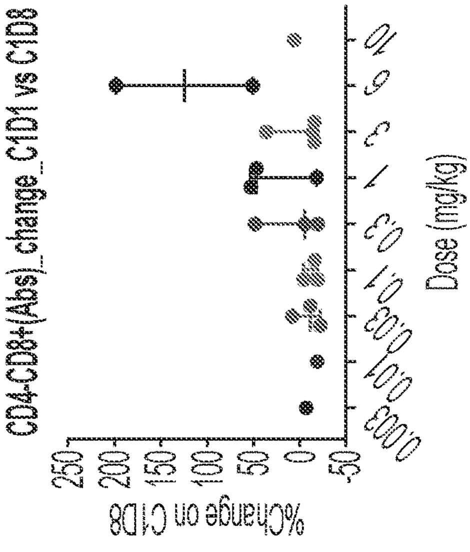
Figure 25E:
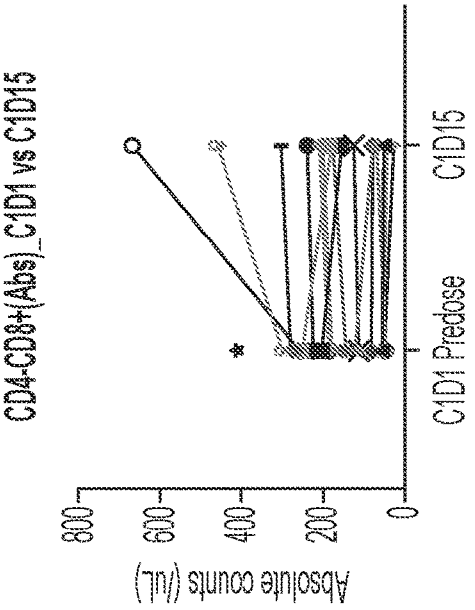
Figure 25D:
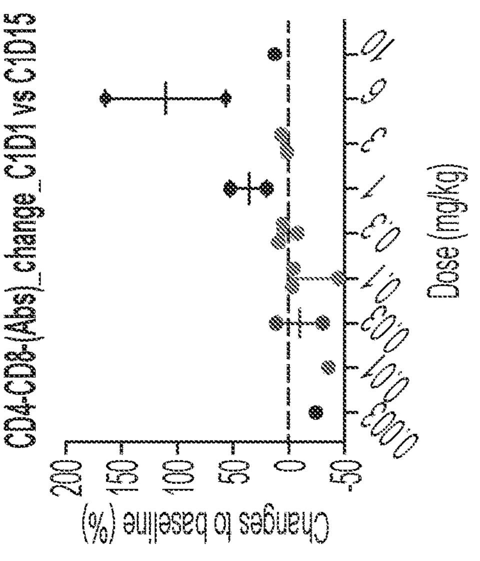

Prolonged stable disease is also observed in 17% (4/24) of patients, all of whom had received multiple prior treatments and had "cold tumors" (i.e., tumors that T cells cannot penetrate because the tumor has not been recognized by the immune system, or provoked an immune response). Notably, all four patients have increased CD8 and/or CD4 T cells, with Subjects #4 and #19 having significantly increased CD8 T cells. (FIGS. 24A and 25A).

Example 2. Dose Selection Criteria for TY21580

The serum pharmacokinetics (PK) of TY21580 monotherapy after IV infusion was assessed using Non-compartmental Analysis (NCA by Phoenix WinNonlin version 8.3) and population PK modeling (by NONMEM® 7.5) approaches.

Figure 29:
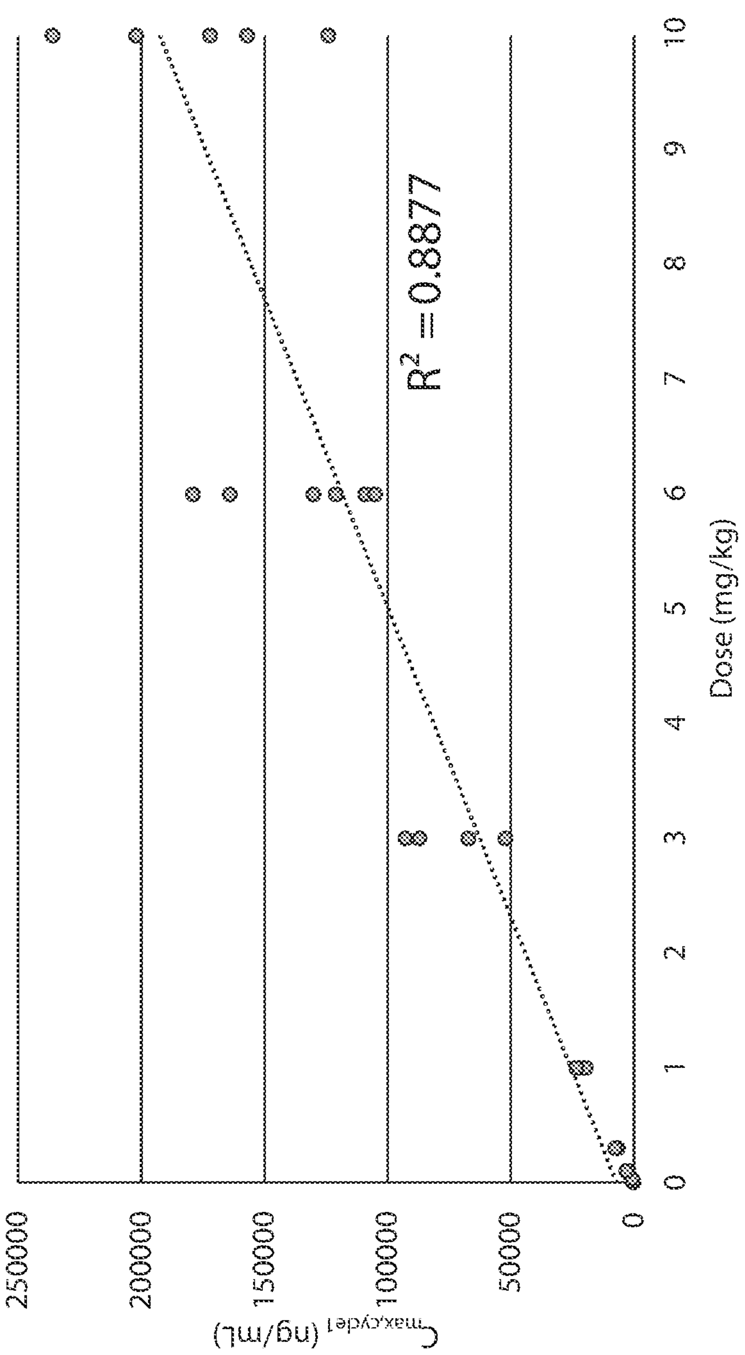
FIG. 29 shows the plasma $C_{max}$ of TY21580 at various doses levels following IV administration of TY21580 to human subjects.
Figure 30:
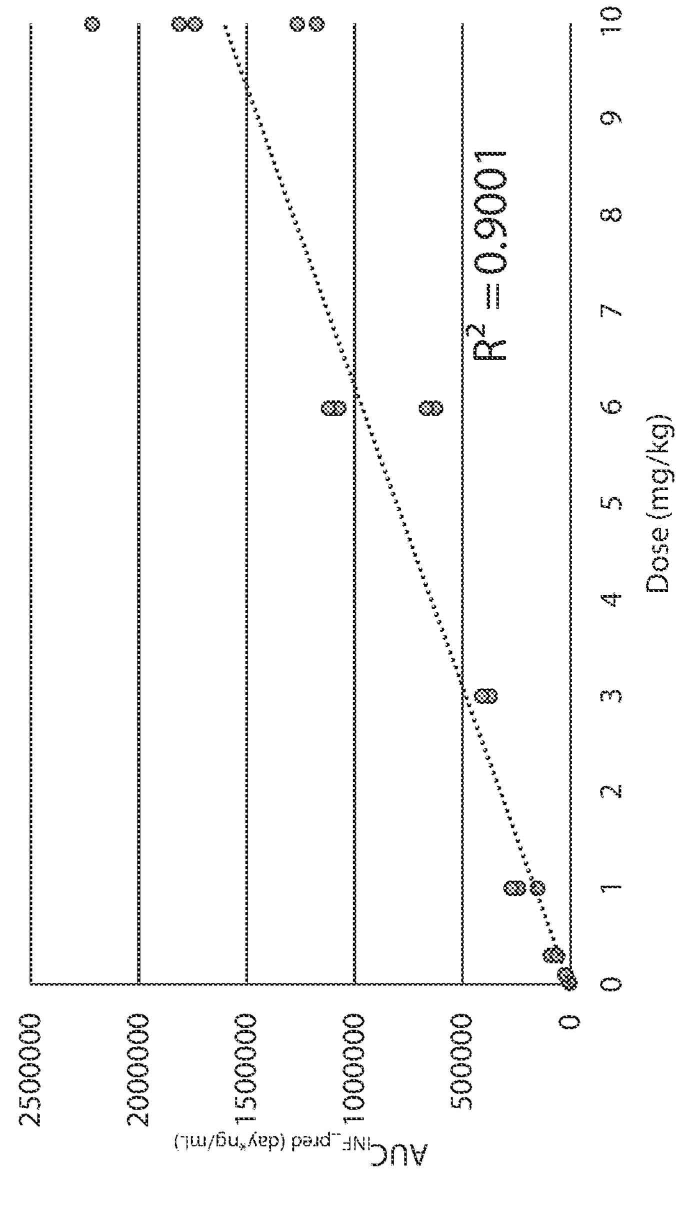
FIG. 30 shows the predicted $AUC_{(0-\infty)}$ of TY21580 at various doses levels following IV administration of TY21580 to human subjects.

Dose-dependent increase in serum exposure was observed. The maximum serum concentration post IV infusion ($C_{max,cycle\ 1}$) has an approximately linear relationship with dose (e.g., 0.003 to 10 mg/kg, $R^2$=0.89, FIG. 29). Predicted drug exposure $AUC_{0\text{-}infinity}$ based on cycle 1 PK ($AUC_{INF\_pred}$) has an approximately linear relationship with dose (e.g., 0.01 to 10 mg/kg, $R^2$=0.90, FIG. 30).

Cycle 1 terminal half-life (mean±standard deviation) of TY21580 in serum is estimated as ~10±3 days from 0.01 to 10 mg/kg. No apparent dose-dependency was observed. This set of PK analysis, including $C_{max}$, AUC and half-life indicated that for TY21580, no significant target-mediated drug disposition (TMDD) was observed from 0.01 to 10 mg/kg. A 2-compartment linear population PK model was developed and can describe the PK data reasonably well. Body-weight (BW) is highly correlated with the model-estimated central of volume of distribution (Vc) and is considered as a meaningful covariate (e.g., exponent value >0.8). For patients with PK data from multiple treatment cycles (Q3W, once every three-week dosing), limited accumulation (e.g., <2-fold) for pre-dose PK ($C_{trough,repeat\ dose}$) and $C_{max,repeat\ dose}$ was observed in most patients, consistent with PK model-estimated half-life and predicted mean accumulation ratios (e.g., ~1.3-fold) with Q3W dosing.

Potentially efficacious human doses based on observed PK vs. in vitro data were explored. $EC_{90s}$ of TY21580 in various binding assays generally are >3-5 µg/mL, consistent with functional readouts and could be targeted as minimal tumor tissue steady-state pre-dose concentrations (i.e. $C_{trough,ss}$) These $EC_{90s}$ correlate with a theoretical receptor occupancy (RO) of ~90%. As an example, ~5 µg/mL (~34.5 nM) was chosen as a representative integrated $EC_{90}$ value based on key available in vitro data (e.g., binding, functional readout for T cell activation and ADCC.) This $EC_{90}$ corresponds to 172-345 nM in the systemic circulation considering a likely 10-20% tumor tissue drug distribution for a target without significant TMDD. At a 10 mg/kg dose of TY21580, the mean observed serum trough concentration of TY21580 on day 21 in the first cycle is still around the lowest targeted systemic concentration (e.g., 172 nM, assuming 20% tumor drug distribution). These PK data, together with simulated PK at steady state (FIG. 31, showing that the $C_{trough}$ conc. at 504 hour of the dosing cycle at 10 mg/kg, e.g., 212 nM, is close to the middle range of the target conc.), monotherapy clinical PD biomarker data, and safety/efficacy data support 10 mg/kg once every three weeks (Q3W) IV dosing as a likely efficacious/saturating monotherapy dose.

Figure 31:
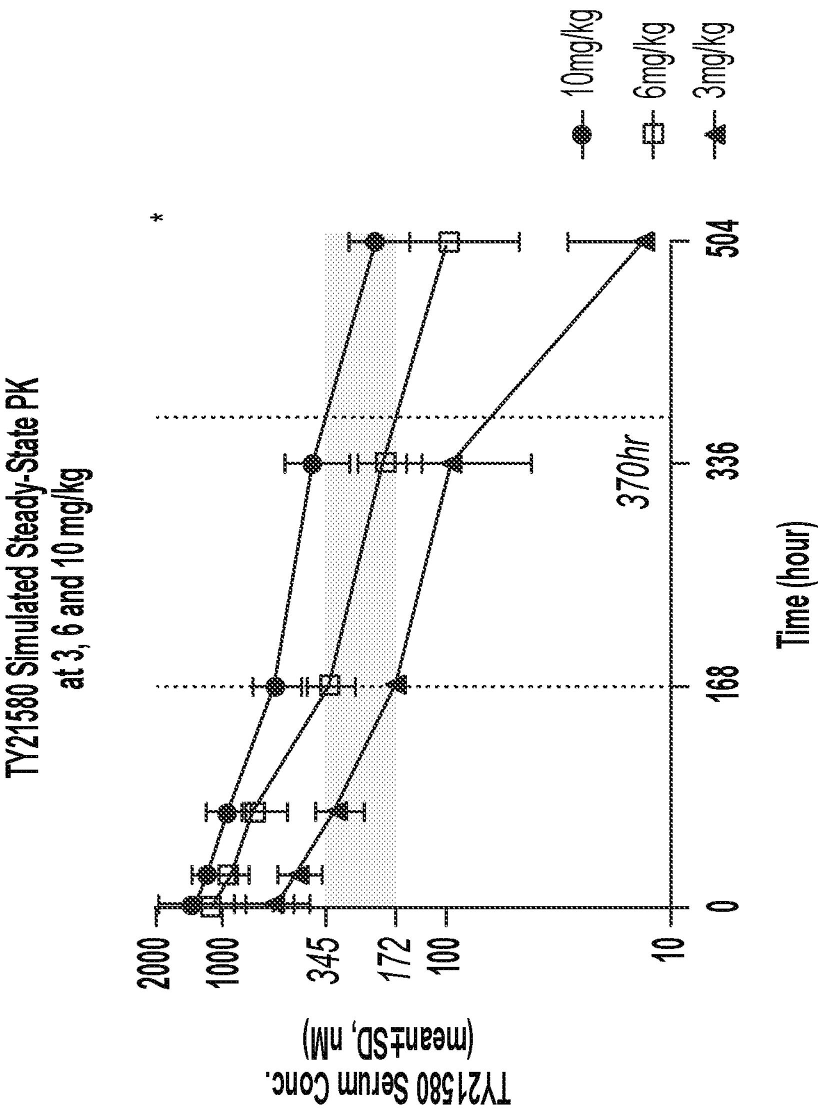
FIG. 31 shows a dimulated PK study used to predict serum concentration levels at various doses of TY21580 administered to human subjects.

Considering the predicted mean accumulation ratios of TY21580 (e.g., ~1.3-fold) with Q3W dosing, at 6 or 3 mg/kg, mean predicted day 14 or day 7 serum concentrations of TY21580 would be around or slightly above the lowest targeted systemic concentration (e.g., 172 nM), respectively (FIG. 31). Therefore, at steady state with 3 mg/kg Q3W dosing, the estimated time (e.g., ~168 hours, FIG. 31) above the lowest target conc. is ~33% of the total cycle duration, and may be sufficient to allow for optimal therapeutic index. Alternatively, at steady state with 6 mg/kg Q3W dosing, the estimated time (e.g., ~370 hours, FIG. 31) above the lowest target concentration is >70% of the total cycle duration.

What is claimed is:

1. A method of reducing the size of a solid tumor in a human cancer patient, comprising administering to the subject an effective amount of an anti-CTLA4 antibody, wherein the subject is resistant to or has relapsed from a prior therapy, wherein the prior therapy is an inhibitor of CTLA4, PD-1, or a PD-1 ligand, wherein the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75, and wherein the cancer is colon cancer, colorectal cancer, liver cancer, urothelial cancer, renal cell carcinoma, pancreatic cancer, lung cancer, brain cancer, kidney cancer, skin cancer, or breast cancer.

2. The method of claim 1, wherein the inhibitor of a PD-1 ligand is an anti-PD-1 antibody comprising pembrolizumab or nivolumab.

3. The method of claim 1, wherein the anti-CTLA4 antibody comprises a heavy chain variable region comprising the amino acid sequence of SEQ ID NO: 87, and a light chain variable region comprising the amino acid sequence of SEQ ID NO: 100.

4. The method of claim 1, wherein the anti-CTLA4 antibody comprises a heavy chain comprising the amino acid sequence of SEQ ID NO: 125 or SEQ ID NO: 126 and a light chain comprising the amino acid sequence of SEQ ID NO: 127.

5. The method of claim 1, wherein the cancer is colon cancer or colorectal cancer.

6. A method of reducing the size of a solid tumor in a human cancer patient, comprising administering to the subject an effective amount of an anti-CTLA4 antibody, wherein the anti-CTLA4 antibody is administered at a dose of from 3 mg/kg to 20 mg/kg, wherein the anti-CTLA4 antibody is administered about once every three weeks, and wherein the anti-CTLA4 antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75, and wherein the cancer is colon cancer, colorectal cancer, liver cancer, urothelial cancer, renal cell carcinoma, pancreatic cancer, lung cancer, brain cancer, kidney cancer, skin cancer, or breast cancer.

7. The method of claim 6, wherein the anti-CTLA4 antibody is administered at a dose of from 6 mg/kg to 15 mg/kg.

8. The method of claim 6, wherein the anti-CTLA4 antibody is administered at a dose of 6 mg/kg.

9. The method of claim 6, wherein the anti-CTLA4 antibody is administered at a dose of 10 mg/kg.

10. The method of claim 6, wherein the anti-CTLA4 antibody is administered at a dose of 15 mg/kg.

11. The method of claim 6, wherein the anti-CTLA4 antibody is administered at a dose of 20 mg/kg.

12. The method of claim 6, wherein the anti-CTLA4 antibody comprises a heavy chain variable region comprising the amino acid sequence of SEQ ID NO: 87, and a light chain variable region comprising the amino acid sequence of SEQ ID NO: 100.

13. The method of claim 6, wherein the anti-CTLA4 antibody comprises a heavy chain comprising the amino acid sequence of SEQ ID NO: 125 or SEQ ID NO: 126 and a light chain comprising the amino acid sequence of SEQ ID NO: 127.

14. The method of claim 6, wherein the anti-CTLA4 antibody is administered at a dose that provides a steady state serum trough concentration of from 50 nM to 700 nM in systemic circulation when measured at the last day of a dosing cycle.

15. The method of claim 6, wherein the anti-CTLA4 antibody is administered at a dose that provides a steady state serum trough concentration of from 100 nM to 500 nM in systemic circulation when measured at the last day of a dosing cycle.

16. The method of claim 6, wherein the anti-CTLA4 antibody is administered at a dose that provides a steady state serum trough concentration of from 100 nM to 400 nM in systemic circulation when measured at the last day of a dosing cycle.

17. The method of claim 6, wherein the subject receives at least 4 cycles of treatment with the anti-CTLA4 antibody.

18. The method of claim 6, wherein the cancer is resistant or refractory to a prior therapy, wherein the therapy is an anti-PD-1 antibody or an anti-CTLA4 antibody.

19. The method of claim 18, wherein the anti-PD-1 antibody is pembrolizumab or nivolumab.

20. The method of claim 6, wherein the cancer is colon cancer or colorectal cancer.

* * * * *

SEQUENCE LISTING

```
<160> NUMBER OF SEQ ID NOS: 139

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Phe or Tyr
<220> FEATURE:
<221> NAME/KEY: VARIANT
<222> LOCATION: 5
<223> OTHER INFORMATION: Xaa = Asp or Gly
<220> FEATURE:
<221> NAME/KEY: VARIANT
<222> LOCATION: 7
<223> OTHER INFORMATION: Xaa = Ala, Gly or Trp

<400> SEQUENCE: 1

Xaa Thr Phe Ser Xaa Tyr Xaa Ile His Trp Val
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Thr
```

<220> FEATURE:
<221> NAME/KEY: VARIANT
<222> LOCATION: 7, 8
<223> OTHER INFORMATION: Xaa = His or Tyr
<220> FEATURE:
<221> NAME/KEY: VARIANT
<222> LOCATION: 10
<223> OTHER INFORMATION: Xaa = Ala, Asp, or Ser

<400> SEQUENCE: 2

Tyr Ser Ile Xaa Ser Gly Xaa Xaa Trp Xaa Trp Ile
1 5 10

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Xaa = Gly or Ser

<400> SEQUENCE: 3

Phe Ser Leu Ser Thr Gly Gly Val Ala Val Xaa Trp Ile
1 5 10

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Glu
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 14
<223> OTHER INFORMATION: Xaa = Pro or Gln

<400> SEQUENCE: 4

Ile Gly Xaa Ile Xaa His Ser Gly Ser Thr Tyr Tyr Ser Xaa Ser Leu
1 5 10 15

Lys Ser Arg Val
20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ile or Trp
<220> FEATURE:
<221> NAME/KEY: VARIANT
<222> LOCATION: 8, 10
<223> OTHER INFORMATION: Xaa = Gly or Ser
<220> FEATURE:
<221> NAME/KEY: VARIANT
<222> LOCATION: 12
<223> OTHER INFORMATION: Xaa = Lys or Asn

<400> SEQUENCE: 5

Ile Gly Xaa Ile Ser Pro Ser Xaa Gly Xaa Thr Xaa Tyr Ala Gln Lys
1 5 10 15

Phe Gln Gly Arg Val
20

<210> SEQ ID NO 6
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ala, Gly, or Ser
<220> FEATURE:
<221> NAME/KEY: VARIANT
<222> LOCATION: 7
<223> OTHER INFORMATION: Xaa = Ser or Tyr
<220> FEATURE:
<221> NAME/KEY: VARIANT
<222> LOCATION: 9
<223> OTHER INFORMATION: Xaa = Gly or Ser
<220> FEATURE:
<221> NAME/KEY: VARIANT
<222> LOCATION: 10
<223> OTHER INFORMATION: Xaa = Ser or Thr

<400> SEQUENCE: 6

Val Ser Xaa Ile Ser Gly Xaa Gly Xaa Xaa Thr Tyr Tyr Ala Asp Ser
1 5 10 15

Val Lys Gly Arg Phe
20

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Gly, Arg, or Ser
<220> FEATURE:
<221> NAME/KEY: VARIANT
<222> LOCATION: 4
<223> OTHER INFORMATION: Xaa = Ala, Ile, or Tyr
<220> FEATURE:
<221> NAME/KEY: VARIANT
<222> LOCATION: 5
<223> OTHER INFORMATION: Xaa = Asp, Val, or Tyr
<220> FEATURE:
<221> NAME/KEY: VARIANT
<222> LOCATION: 6
<223> OTHER INFORMATION: Xaa = Ala, Glu, or Tyr
<220> FEATURE:
<221> NAME/KEY: VARIANT
<222> LOCATION: 9
<223> OTHER INFORMATION: Xaa = Ile or Tyr

<400> SEQUENCE: 7

Ala Arg Xaa Xaa Xaa Xaa Phe Asp Xaa
1 5

<210> SEQ ID NO 8
<211> LENGTH: 10
<212> TYPE: PRT
<213> ORGANISM: Artificial Sequence
<220> FEATURE:

<223> OTHER INFORMATION: Synthetic Construct
<220> FEATURE:
<221> NAME/KEY: VARIANT
<222> LOCATION: 3
<223> OTHER INFORMATION: Xaa = Asp or Leu
<220> FEATURE:
<221> NAME/KEY: VARIANT
<222> LOCATION: 5
<223> OTHER INFORMATION: Xaa = Phe or Tyr
<220> FEATURE:
<221> NAME/KEY: VARIANT
<222> LOCATION: 10
<223> OTHER INFORMATION: Xaa = Val or Tyr

<400> SEQUENCE: 8

```
Ala Arg Xaa Gly Xaa Gly Tyr Phe Asp Xaa
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Leu or Arg
<220> FEATURE:
<221> NAME/KEY: VARIANT
<222> LOCATION: 4
<223> OTHER INFORMATION: Xaa = Ile or Pro
<220> FEATURE:
<221> NAME/KEY: VARIANT
<222> LOCATION: 5
<223> OTHER INFORMATION: Xaa = Ala or Tyr
<220> FEATURE:
<221> NAME/KEY: VARIANT
<222> LOCATION: 6
<223> OTHER INFORMATION: Xaa = Ser or Thr
<220> FEATURE:
<221> NAME/KEY: VARIANT
<222> LOCATION: 8
<223> OTHER INFORMATION: Xaa = Thr or Tyr
<220> FEATURE:
<221> NAME/KEY: VARIANT
<222> LOCATION: 9
<223> OTHER INFORMATION: Xaa = Ala or Tyr

<400> SEQUENCE: 9

```
Ala Arg Xaa Xaa Xaa Xaa Ala Xaa Xaa Phe Asp Tyr
1               5                   10
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ile or Val
<220> FEATURE:
<221> NAME/KEY: VARIANT
<222> LOCATION: 5
<223> OTHER INFORMATION: Xaa = Ala or His
<220> FEATURE:
<221> NAME/KEY: VARIANT
<222> LOCATION: 6
<223> OTHER INFORMATION: Xaa = Pro or Ser
<220> FEATURE:
<221> NAME/KEY: VARIANT
<222> LOCATION: 13
<223> OTHER INFORMATION: Xaa = Asp or Tyr
<220> FEATURE:
<221> NAME/KEY: VARIANT
<222> LOCATION: 17
<223> OTHER INFORMATION: Xaa = Phe or Val

<400> SEQUENCE: 10

Ala Arg Asp Xaa Xaa Xaa Gly Ser Ser Gly Tyr Tyr Xaa Gly Phe Asp
1               5                   10                  15

Xaa

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5, 7
<223> OTHER INFORMATION: Xaa = Gly or Ser
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 9
<223> OTHER INFORMATION: Xaa = Ser or Tyr
<220> FEATURE:
<221> NAME/KEY: VARIANT
<222> LOCATION: 11
<223> OTHER INFORMATION: Xaa = Ala or Asn

<400> SEQUENCE: 11

Arg Ala Ser Gln Xaa Xaa Xaa Ser Xaa Leu Xaa
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 7
<223> OTHER INFORMATION: Xaa = Phe, Arg, or Ser
<220> FEATURE:
<221> NAME/KEY: VARIANT
<222> LOCATION: 8
<223> OTHER INFORMATION: Xaa = Gly or Ser
<220> FEATURE:
<221> NAME/KEY: VARIANT
<222> LOCATION: 10
<223> OTHER INFORMATION: Xaa = Phe or Tyr

<400> SEQUENCE: 12

Arg Ala Ser Gln Xaa Val Xaa Xaa Arg Xaa Leu Ala
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 9
<223> OTHER INFORMATION: Xaa = Asp, Phe, His, or Tyr
<220> FEATURE:
<221> NAME/KEY: VARIANT
<222> LOCATION: 11
<223> OTHER INFORMATION: Xaa = Phe, Ile, or Lys
<220> FEATURE:
<221> NAME/KEY: VARIANT
<222> LOCATION: 15
<223> OTHER INFORMATION: Xaa = Ala, Asp, or His

<400> SEQUENCE: 13

```
Arg Ala Ser Xaa Ser Val Asp Phe Xaa Gly Xaa Ser Phe Leu Xaa
1               5                   10                  15
```

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ala or Asp
<220> FEATURE:
<221> NAME/KEY: VARIANT
<222> LOCATION: 4
<223> OTHER INFORMATION: Xaa = Asn, Ser or Thr
<220> FEATURE:
<221> NAME/KEY: VARIANT
<222> LOCATION: 5
<223> OTHER INFORMATION: Xaa = Leu or Arg
<220> FEATURE:
<221> NAME/KEY: VARIANT
<222> LOCATION: 6
<223> OTHER INFORMATION: Xaa = Ala, Glu, or Gln
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 9
<223> OTHER INFORMATION: Xaa = Ile or Val

<400> SEQUENCE: 14

```
Xaa Ala Ser Xaa Xaa Xaa Xaa Gly Xaa
1               5
```

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Glu, Gln, or Val
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 5
<223> OTHER INFORMATION: Xaa = Ala, Gly, His, Arg, or Ser
<220> FEATURE:
<221> NAME/KEY: VARIANT
<222> LOCATION: 6

<223> OTHER INFORMATION: Xaa = Asp, Leu, Ser, or Tyr
<220> FEATURE:
<221> NAME/KEY: VARIANT
<222> LOCATION: 7
<223> OTHER INFORMATION: Xaa = Glu, Gly, Pro, Gln, or Ser
<220> FEATURE:
<221> NAME/KEY: VARIANT
<222> LOCATION: 8
<223> OTHER INFORMATION: Xaa = Leu, Thr, Val, or Trp
<220> FEATURE:
<221> NAME/KEY: VARIANT
<222> LOCATION: 10
<223> OTHER INFORMATION: Xaa = Phe, Leu, Pro, Trp, or Tyr

<400> SEQUENCE: 15

Tyr Cys Xaa Xaa Xaa Xaa Xaa Xaa Pro Xaa Thr
1 5 10

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 6
<223> OTHER INFORMATION: Xaa = Asp or Tyr
<220> FEATURE:
<221> NAME/KEY: VARIANT
<222> LOCATION: 7
<223> OTHER INFORMATION: Xaa = Gln or Tyr

<400> SEQUENCE: 16

Tyr Cys Gln Gln Xaa Xaa Xaa Trp Pro Pro Trp Thr
1 5 10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 6
<223> OTHER INFORMATION: Xaa = Thr or Val
<220> FEATURE:
<221> NAME/KEY: VARIANT
<222> LOCATION: 11
<223> OTHER INFORMATION: Xaa = Glu or Val

<400> SEQUENCE: 17

Tyr Cys Gln Xaa Tyr Xaa Ser Ser Pro Pro Xaa Tyr Thr
1 5 10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Phe Thr Phe Ser Asp Tyr Ala Ile His Trp Val
1 5 10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19

Tyr Ser Ile Thr Ser Gly Tyr Tyr Trp Ala Trp Ile
1 5 10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Phe Thr Phe Ser Asp Tyr Gly Ile His Trp Val
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Tyr Ser Ile Ser Ser Gly Tyr His Trp Asp Trp Ile
1 5 10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Phe Thr Phe Ser Asp Tyr Trp Ile His Trp Val
1 5 10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Tyr Ser Ile Ser Ser Gly Tyr His Trp Ser Trp Ile
1 5 10

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

Phe Ser Leu Ser Thr Gly Gly Val Ala Val Ser Trp Ile
1 5 10

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Phe Ser Leu Ser Thr Gly Gly Val Ala Val Gly Trp Ile
1 5 10

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Phe Thr Phe Ser Gly Tyr Ala Ile His Trp Val
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Tyr Thr Phe Ser Gly Tyr Gly Ile His Trp Val
1 5 10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Tyr Thr Phe Ser Gly Tyr Ala Ile His Trp Val
1 5 10

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Tyr Ser Ile Thr Ser Gly His Tyr Trp Ser Trp Ile
1 5 10

<210> SEQ ID NO 30
<211> LENGTH: 21
<212> TYPE: PRT
<213> ORGANISM: Artificial Sequence
<220> FEATURE:
<223> OTHER INFORMATION: Synthetic Construct

<400> SEQUENCE: 30

Ile Gly Ile Ile Ser Pro Ser Ser Gly Ser Thr Asn Tyr Ala Gln Lys
1 5 10 15

Phe Gln Gly Arg Val
20

<210> SEQ ID NO 31
<211> LENGTH: 21
<212> TYPE: PRT
<213> ORGANISM: Artificial Sequence
<220> FEATURE:
<223> OTHER INFORMATION: Synthetic Construct

<400> SEQUENCE: 31

Val Ser Ser Ile Ser Gly Ser Gly Ser Thr Thr Tyr Tyr Ala Asp Ser
1 5 10 15

Val Lys Gly Arg Phe
20

<210> SEQ ID NO 32
<211> LENGTH: 20
<212> TYPE: PRT
<213> ORGANISM: Artificial Sequence
<220> FEATURE:
<223> OTHER INFORMATION: Synthetic Construct

<400> SEQUENCE: 32

Ile Gly Glu Ile Tyr His Ser Gly Ser Thr Tyr Tyr Ser Pro Ser Leu
1 5 10 15

Lys Ser Arg Val
20

<210> SEQ ID NO 33
<211> LENGTH: 21
<212> TYPE: PRT
<213> ORGANISM: Artificial Sequence
<220> FEATURE:
<223> OTHER INFORMATION: Synthetic Construct

<400> SEQUENCE: 33

Val Ser Gly Ile Ser Gly Tyr Gly Gly Ser Thr Tyr Tyr Ala Asp Ser
1 5 10 15

Val Lys Gly Arg Phe
20

<210> SEQ ID NO 34
<211> LENGTH: 21
<212> TYPE: PRT
<213> ORGANISM: Artificial Sequence
<220> FEATURE:
<223> OTHER INFORMATION: Synthetic Construct

<400> SEQUENCE: 34

Ile Gly Trp Ile Ser Pro Ser Gly Gly Gly Thr Lys Tyr Ala Gln Lys
1 5 10 15

Phe Gln Gly Arg Val
20

<210> SEQ ID NO 35
<211> LENGTH: 20
<212> TYPE: PRT
<213> ORGANISM: Artificial Sequence
<220> FEATURE:

<223> OTHER INFORMATION: Synthetic Construct

<400> SEQUENCE: 35

Leu Ala Arg Ile Asp Trp Asp Asp Asp Lys Tyr Tyr Ser Thr Ser Leu
1 5 10 15

Lys Ser Arg Leu
20

<210> SEQ ID NO 36
<211> LENGTH: 21
<212> TYPE: PRT
<213> ORGANISM: Artificial Sequence
<220> FEATURE:
<223> OTHER INFORMATION: Synthetic Construct

<400> SEQUENCE: 36

Val Ser Ala Ile Ser Gly Tyr Gly Ser Thr Thr Tyr Tyr Ala Asp Ser
1 5 10 15

Val Lys Gly Arg Phe
20

<210> SEQ ID NO 37
<211> LENGTH: 21
<212> TYPE: PRT
<213> ORGANISM: Artificial Sequence
<220> FEATURE:
<223> OTHER INFORMATION: Synthetic Construct

<400> SEQUENCE: 37

Ile Gly Ile Ile Ser Pro Ser Gly Gly Gly Thr Lys Tyr Ala Gln Lys
1 5 10 15

Phe Gln Gly Arg Val
20

<210> SEQ ID NO 38
<211> LENGTH: 21
<212> TYPE: PRT
<213> ORGANISM: Artificial Sequence
<220> FEATURE:
<223> OTHER INFORMATION: Synthetic Construct

<400> SEQUENCE: 38

Ile Gly Ile Ile Ser Pro Ser Gly Gly Ser Thr Lys Tyr Ala Gln Lys
1 5 10 15

Phe Gln Gly Arg Val
20

<210> SEQ ID NO 39
<211> LENGTH: 20
<212> TYPE: PRT
<213> ORGANISM: Artificial Sequence
<220> FEATURE:
<223> OTHER INFORMATION: Synthetic Construct

<400> SEQUENCE: 39

Ile Gly Asp Ile Ser His Ser Gly Ser Thr Tyr Tyr Ser Gln Ser Leu
1 5 10 15

Lys Ser Arg Val
20

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Ala Arg Asp Ile His Ser Gly Ser Ser Gly Tyr Tyr Tyr Gly Phe Asp
1 5 10 15

Val

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Ala Arg Asp Gly Phe Gly Tyr Phe Asp Tyr
1 5 10

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Ala Arg Asp Val Ala Pro Gly Ser Ser Gly Tyr Tyr Asp Gly Phe Asp
1 5 10 15

Phe

<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Ala Arg His Ser Tyr Tyr Gly Ser Gly Asn Phe Asp Tyr
1 5 10

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Ala Arg Gly Ala Tyr Glu Phe Asp Tyr
1 5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Ala Arg Ser Tyr Val Tyr Phe Asp Tyr
1 5

<210> SEQ ID NO 46

<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Ala Arg Arg Ile Ala Thr Ala Thr Tyr Phe Asp Tyr
1 5 10

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Ala Arg Leu Pro Tyr Ser Ala Tyr Ala Phe Asp Tyr
1 5 10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Ala Arg His Pro Phe Ala Tyr
1 5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Ala Arg Arg Ile Asp Ala Phe Asp Ile
1 5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ala Arg Leu Tyr Asp Val Ala Tyr
1 5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Ala Arg Leu Gly Tyr Gly Tyr Phe Asp Val
1 5 10

<210> SEQ ID NO 52
<211> LENGTH: 11

<212> TYPE: PRT
<213> ORGANISM: Artificial Sequence
<220> FEATURE:
<223> OTHER INFORMATION: Synthetic Construct

<400> SEQUENCE: 52

Ala Arg Gly Ser Arg Thr Gly Tyr Phe Asp Tyr
1 5 10

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Arg Ala Ser Glu Ser Val Asp Phe Phe Gly Ile Ser Phe Leu Ala
1 5 10 15

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Ser Ala Ser Ser Ser Val Ser Tyr Val Tyr
1 5 10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Arg Ala Ser Gln Gly Ile Gly Ser Ser Leu Ala
1 5 10

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Arg Ala Ser Glu Ser Val Asp Phe Phe Gly Lys Ser Phe Leu His
1 5 10 15

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Arg Ala Ser Gln Ser Val Ser Ser Arg Phe Leu Ala
1 5 10

<210> SEQ ID NO 58
<211> LENGTH: 12
<212> TYPE: PRT

<213> ORGANISM: Artificial Sequence
<220> FEATURE:
<223> OTHER INFORMATION: Synthetic Construct

<400> SEQUENCE: 58

Arg Ala Ser Gln Ser Val Arg Gly Arg Phe Leu Ala
1 5 10

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Arg Ala Ser Gln Thr Val Phe Ser Arg Tyr Leu Ala
1 5 10

<210> SEQ ID NO 60
<211> LENGTH: 11
<212> TYPE: PRT
<213> ORGANISM: Artificial Sequence
<220> FEATURE:
<223> OTHER INFORMATION: Synthetic Construct

<400> SEQUENCE: 60

Arg Ala Ser Gln Gly Val Ser Ser Tyr Leu Ala
1 5 10

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Arg Ala Ser Gln Ser Val Asp Phe Tyr Gly Ile Ser Phe Leu Asp
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Ser Val Asp Phe Asp Gly Phe Ser Phe Leu His
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Arg Ala Ser Gln Ser Val Asp Phe His Gly Lys Ser Phe Leu His
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Synthetic Construct

<400> SEQUENCE: 64

Arg Ala Ser Gln Ser Val Asp Phe Tyr Gly Ile Ser Phe Leu His
1 5 10 15

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Arg Ala Ser Gln Ser Ile Ser Ser Tyr Leu Asn
1 5 10

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Asp Ala Ser Asn Arg Ala Thr Gly Ile
1 5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Asp Ala Ser Ser Leu Glu Ser Gly Val
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Asp Ala Ser Asn Leu Glu Thr Gly Val
1 5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Ala Ala Ser Thr Leu Gln Ser Gly Val
1 5

<210> SEQ ID NO 70
<211> LENGTH: 13
<212> TYPE: PRT
<213> ORGANISM: Artificial Sequence
<220> FEATURE:

<223> OTHER INFORMATION: Synthetic Construct

<400> SEQUENCE: 70

Tyr Cys Gln His Tyr Thr Ser Ser Pro Pro Val Tyr Thr
1 5 10

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Tyr Cys Val Gln Gly Leu Gln Thr Pro Trp Thr
1 5 10

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Tyr Cys Gln Gln Tyr Asp Gln Trp Pro Pro Trp Thr
1 5 10

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Tyr Cys Gln Gln Ser Tyr Ser Trp Pro Pro Thr
1 5 10

<210> SEQ ID NO 74
<211> LENGTH: 11
<212> TYPE: PRT
<213> ORGANISM: Artificial Sequence
<220> FEATURE:
<223> OTHER INFORMATION: Synthetic Construct

<400> SEQUENCE: 74

Tyr Cys Gln Gln Ser Tyr Pro Thr Pro Leu Thr
1 5 10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Tyr Cys Gln Gln Ser Ser Ser Trp Pro Pro Thr
1 5 10

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Tyr Cys Gln Gln Ser Tyr Tyr Trp Pro Pro Trp Thr
1 5 10

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Tyr Cys Gln His His Tyr Gly Thr Pro Leu Thr
1 5 10

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

Tyr Cys Gln Gln Tyr Val Ser Ser Pro Pro Glu Tyr Thr
1 5 10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Tyr Cys Gln Gln Arg Asp Ser Trp Pro Tyr Thr
1 5 10

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Tyr Cys Glu Gln Ser Leu Glu Val Pro Phe Thr
1 5 10

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Tyr Cys Val Gln Ala Leu Gln Leu Pro Leu Thr
1 5 10

<210> SEQ ID NO 82
<211> LENGTH: 124
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Ile His Trp Val Arg Gln Ala Pro Gly Lys Gly Leu Glu Trp Ile
35 40 45

Gly Ile Ile Ser Pro Ser Ser Gly Ser Thr Asn Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Asp Ile His Ser Gly Ser Ser Gly Tyr Tyr Tyr Gly Phe Asp
100 105 110

Val Trp Gly Gln Gly Thr Leu Val Thr Val Ser Ser
115 120

<210> SEQ ID NO 83
<211> LENGTH: 118
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Ser Gly
20 25 30

Tyr Tyr Trp Ala Trp Ile Arg Gln Ala Pro Gly Lys Gly Leu Glu Trp
35 40 45

Val Ser Ser Ile Ser Gly Ser Gly Ser Thr Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg Asp Gly Phe Gly Tyr Phe Asp Tyr Trp Gly Gln Gly Thr
100 105 110

Leu Val Thr Val Ser Ser
115

<210> SEQ ID NO 84
<211> LENGTH: 123
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Gly Ile His Trp Val Arg Gln Ala Pro Gly Lys Gly Leu Glu Trp Ile
35 40 45

Gly Glu Ile Tyr His Ser Gly Ser Thr Tyr Tyr Ser Pro Ser Leu Lys
50 55 60

Ser Arg Val Thr Ile Ser Arg Asp Asn Ser Lys Asn Thr Leu Tyr Leu
65 70 75 80

Gln Leu Asn Ser Leu Arg Ala Glu Asp Thr Ala Val Tyr Tyr Cys Ala
85 90 95

Arg Asp Val Ala Pro Gly Ser Ser Gly Tyr Tyr Asp Gly Phe Asp Phe
100 105 110

Trp Gly Gln Gly Thr Leu Val Thr Val Ser Ser
115 120

<210> SEQ ID NO 85
<211> LENGTH: 121
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Ser Ser Gly
20 25 30

Tyr His Trp Asp Trp Ile Arg Gln Ala Pro Gly Lys Gly Leu Glu Trp
35 40 45

Val Ser Gly Ile Ser Gly Tyr Gly Gly Ser Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg His Ser Tyr Tyr Gly Ser Gly Asn Phe Asp Tyr Trp Gly
100 105 110

Gln Gly Thr Leu Val Thr Val Ser Ser
115 120

<210> SEQ ID NO 86
<211> LENGTH: 116
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Trp Ile His Trp Val Arg Gln Ala Pro Gly Lys Gly Leu Glu Trp Ile
35 40 45

Gly Trp Ile Ser Pro Ser Gly Gly Gly Thr Lys Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Gly Ala Tyr Glu Phe Asp Tyr Trp Gly Gln Gly Thr Leu Val
100 105 110

Thr Val Ser Ser
115

<210> SEQ ID NO 87
<211> LENGTH: 116
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Ser Ser Gly
20 25 30

Tyr His Trp Ser Trp Ile Arg Gln Ala Pro Gly Lys Gly Leu Glu Trp
35 40 45

Leu Ala Arg Ile Asp Trp Asp Asp Asp Lys Tyr Tyr Ser Thr Ser Leu
50 55 60

Lys Ser Arg Leu Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Ser Tyr Val Tyr Phe Asp Tyr Trp Gly Gln Gly Thr Leu Val
100 105 110

Thr Val Ser Ser
115

<210> SEQ ID NO 88
<211> LENGTH: 120
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Thr Gly
20 25 30

Gly Val Ala Val Ser Trp Ile Arg Gln Ala Pro Gly Lys Gly Leu Glu
35 40 45

Trp Ile Gly Glu Ile Tyr His Ser Gly Ser Thr Tyr Tyr Ser Pro Ser
50 55 60

Leu Lys Ser Arg Val Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg Arg Ile Ala Thr Ala Thr Tyr Phe Asp Tyr Trp Gly Gln
100 105 110

Gly Thr Leu Val Thr Val Ser Ser
115 120

<210> SEQ ID NO 89
<211> LENGTH: 121
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Val Ser Ala Ile Ser Gly Tyr Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Leu Pro Tyr Ser Ala Tyr Ala Phe Asp Tyr Trp Gly
            100                 105                 110

Gln Gly Thr Leu Val Thr Val Ser Ser
        115                 120

<210> SEQ ID NO 90
<211> LENGTH: 114
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg His Pro Phe Ala Tyr Trp Gly Gln Gly Thr Leu Val Thr Val
            100                 105                 110

Ser Ser

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Gly Ile His Trp Val Arg Gln Ala Pro Gly Lys Gly Leu Glu Trp Ile
        35                  40                  45

Gly Glu Ile Tyr His Ser Gly Ser Thr Tyr Tyr Ser Pro Ser Leu Lys
50 55 60

Ser Arg Val Thr Ile Ser Arg Asp Asn Ser Lys Asn Thr Leu Tyr Leu
65 70 75 80

Gln Leu Asn Ser Leu Arg Ala Glu Asp Thr Ala Val Tyr Tyr Cys Ala
85 90 95

Arg Arg Ile Asp Ala Phe Asp Ile Trp Gly Gln Gly Thr Leu Val Thr
100 105 110

Val Ser Ser
115

<210> SEQ ID NO 92
<211> LENGTH: 115
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Ser Gly Tyr
20 25 30

Ala Ile His Trp Val Arg Gln Ala Pro Gly Lys Gly Leu Glu Trp Ile
35 40 45

Gly Ile Ile Ser Pro Ser Gly Gly Gly Thr Lys Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Leu Tyr Asp Val Ala Tyr Trp Gly Gln Gly Thr Leu Val Thr
100 105 110

Val Ser Ser
115

<210> SEQ ID NO 93
<211> LENGTH: 117
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Ile His Trp Val Arg Gln Ala Pro Gly Lys Gly Leu Glu Trp Ile
35 40 45

Gly Ile Ile Ser Pro Ser Gly Gly Ser Thr Lys Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Leu Gly Tyr Gly Tyr Phe Asp Val Trp Gly Gln Gly Thr Leu
100 105 110

Val Thr Val Ser Ser
115

<210> SEQ ID NO 94
<211> LENGTH: 118
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Ser Gly
20 25 30

His Tyr Trp Ser Trp Ile Arg Gln Ala Pro Gly Lys Gly Leu Glu Trp
35 40 45

Ile Gly Asp Ile Ser His Ser Gly Ser Thr Tyr Tyr Ser Gln Ser Leu
50 55 60

Lys Ser Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Gly Ser Arg Thr Gly Tyr Phe Asp Tyr Trp Gly Gln Gly Thr
100 105 110

Leu Val Thr Val Ser Ser
115

<210> SEQ ID NO 95
<211> LENGTH: 114
<212> TYPE: PRT
<213> ORGANISM: Artificial Sequence
<220> FEATURE:
<223> OTHER INFORMATION: Synthetic Construct

<400> SEQUENCE: 95

Asp Ile Gln Leu Thr Gln Ser Pro Ser Ser Leu Ser Ala Ser Val Gly
1 5 10 15

Asp Arg Val Thr Ile Thr Cys Arg Ala Ser Glu Ser Val Asp Phe Phe
20 25 30

Gly Ile Ser Phe Leu Ala Trp Tyr Gln Gln Lys Pro Gly Lys Ala Pro
35 40 45

Lys Leu Leu Ile Tyr Asp Ala Ser Asn Arg Ala Thr Gly Ile Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Tyr Thr
85 90 95

Ser Ser Pro Pro Val Tyr Thr Phe Gly Gln Gly Thr Lys Val Glu Ile
100 105 110

Lys Arg

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Asp Ile Gln Leu Thr Gln Ser Pro Ser Ser Leu Ser Ala Ser Val Gly
1 5 10 15

Asp Arg Val Thr Ile Thr Cys Ser Ala Ser Ser Ser Val Ser Tyr Val
20 25 30

Tyr Trp Tyr Gln Gln Lys Pro Gly Lys Ala Pro Lys Leu Leu Ile Tyr
35 40 45

Asp Ala Ser Ser Leu Glu Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys Val Gln Gly Leu Gln Thr Pro Trp Thr
85 90 95

Phe Gly Gln Gly Thr Lys Val Glu Ile Lys Arg
100 105

<210> SEQ ID NO 97
<211> LENGTH: 109
<212> TYPE: PRT
<213> ORGANISM: Artificial Sequence
<220> FEATURE:
<223> OTHER INFORMATION: Synthetic Construct

<400> SEQUENCE: 97

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Gly Ser Ser
20 25 30

Leu Ala Trp Tyr Gln Gln Lys Pro Gly Lys Ala Pro Lys Leu Leu Ile
35 40 45

Tyr Asp Ala Ser Asn Arg Ala Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asp Gln Trp Pro Pro
85 90 95

Trp Thr Phe Gly Gln Gly Thr Lys Val Glu Ile Lys Arg
100 105

<210> SEQ ID NO 98
<211> LENGTH: 112
<212> TYPE: PRT
<213> ORGANISM: Artificial Sequence
<220> FEATURE:
<223> OTHER INFORMATION: Synthetic Construct

<400> SEQUENCE: 98

Asp Ile Gln Leu Thr Gln Ser Pro Ser Ser Leu Ser Ala Ser Val Gly
1 5 10 15

Asp Arg Val Thr Ile Thr Cys Arg Ala Ser Glu Ser Val Asp Phe Phe
20 25 30

Gly Lys Ser Phe Leu His Trp Tyr Gln Gln Lys Pro Gly Lys Ala Pro
35 40 45

Lys Leu Leu Ile Tyr Asp Ala Ser Asn Leu Glu Thr Gly Val Pro Ser
50 55 60

Arg Phe Ser Gly Ser Gly Ser Gly Thr Asp Phe Thr Leu Thr Ile Ser
65 70 75 80

```
Ser Leu Gln Pro Glu Asp Phe Ala Thr Tyr Tyr Cys Gln Gln Ser Tyr
                85                  90                  95

Ser Trp Pro Pro Thr Phe Gly Gln Gly Thr Lys Val Glu Ile Lys Arg
            100                 105                 110


<210> SEQ ID NO 99
<211> LENGTH: 109
<212> TYPE: PRT
<213> ORGANISM: Artificial Sequence
<220> FEATURE:
<223> OTHER INFORMATION: Synthetic Construct

<400> SEQUENCE: 99

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Pro Thr Pro
                85                  90                  95

Leu Thr Phe Gly Gln Gly Thr Lys Val Glu Ile Lys Arg
            100                 105


<210> SEQ ID NO 100
<211> LENGTH: 109
<212> TYPE: PRT
<213> ORGANISM: Artificial Sequence
<220> FEATURE:
<223> OTHER INFORMATION: Synthetic Construct

<400> SEQUENCE: 100

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Ser Trp Pro
                85                  90                  95

Pro Thr Phe Gly Gln Gly Thr Lys Val Glu Ile Lys Arg
            100                 105


<210> SEQ ID NO 101
<211> LENGTH: 110
<212> TYPE: PRT
<213> ORGANISM: Artificial Sequence
<220> FEATURE:
<223> OTHER INFORMATION: Synthetic Construct
```

<400> SEQUENCE: 101

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Val Phe Ser Arg
            20                  25                  30

Tyr Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Tyr Trp Pro
                85                  90                  95

Pro Trp Thr Phe Gly Gln Gly Thr Lys Val Glu Ile Lys Arg
            100                 105                 110
```

<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Val Glu Ile Lys Arg
            100                 105
```

<210> SEQ ID NO 103
<211> LENGTH: 114
<212> TYPE: PRT
<213> ORGANISM: Artificial Sequence
<220> FEATURE:
<223> OTHER INFORMATION: Synthetic Construct

<400> SEQUENCE: 103

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln Tyr Val
                85                  90                  95

Ser Ser Pro Pro Glu Tyr Thr Phe Gly Gln Gly Thr Lys Val Glu Ile
            100                 105                 110

Lys Arg


<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Asp
            20                  25                  30

Gly Phe Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Asp
                85                  90                  95

Ser Trp Pro Tyr Thr Phe Gly Gln Gly Thr Lys Val Glu Ile Lys Arg
            100                 105                 110


<210> SEQ ID NO 105
<211> LENGTH: 112
<212> TYPE: PRT
<213> ORGANISM: Artificial Sequence
<220> FEATURE:
<223> OTHER INFORMATION: Synthetic Construct

<400> SEQUENCE: 105

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
            20                  25                  30

Gly Lys Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Glu Gln Ser Leu
                85                  90                  95

Glu Val Pro Phe Thr Phe Gly Gln Gly Thr Lys Val Glu Ile Lys Arg
            100                 105                 110


<210> SEQ ID NO 106
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 106

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Ala Leu
                85                  90                  95

Gln Leu Pro Leu Thr Phe Gly Gln Gly Thr Lys Val Glu Ile Lys Arg
            100                 105                 110
```

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Val Glu Ile Lys Arg
            100                 105
```

<210> SEQ ID NO 108
<211> LENGTH: 120
<212> TYPE: PRT
<213> ORGANISM: Artificial Sequence
<220> FEATURE:
<223> OTHER INFORMATION: Synthetic Construct

<400> SEQUENCE: 108

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80
```

-continued

```
Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu
        115                 120
```

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<211> LENGTH: 445
<212> TYPE: PRT
<213> ORGANISM: Artificial Sequence
<220> FEATURE:
<223> OTHER INFORMATION: Synthetic Construct

<400> SEQUENCE: 125

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 126
<211> LENGTH: 446
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60
```

```
Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 127
<211> LENGTH: 215
<212> TYPE: PRT
<213> ORGANISM: Artificial Sequence
<220> FEATURE:
<223> OTHER INFORMATION: Synthetic Construct

<400> SEQUENCE: 127

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Ser Trp Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 128
<211> LENGTH: 446
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Ser Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Gly Tyr Gly Tyr Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 129
<211> LENGTH: 447
<212> TYPE: PRT
<213> ORGANISM: Artificial Sequence
<220> FEATURE:
<223> OTHER INFORMATION: Synthetic Construct

<400> SEQUENCE: 129

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Ile His Trp Val Arg Gln Ala Pro Gly Lys Gly Leu Glu Trp Ile
35 40 45

```
Gly Ile Ile Ser Pro Ser Gly Gly Ser Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Gly Tyr Gly Tyr Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 130
<211> LENGTH: 218
<212> TYPE: PRT

<213> ORGANISM: Artificial Sequence
<220> FEATURE:
<223> OTHER INFORMATION: Synthetic Construct

<400> SEQUENCE: 130

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Ala Leu
                85                  90                  95

Gln Leu Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 131
<211> LENGTH: 447
<212> TYPE: PRT
<213> ORGANISM: Artificial Sequence
<220> FEATURE:
<223> OTHER INFORMATION: Synthetic Construct

<400> SEQUENCE: 131

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Tyr Trp Ala Trp Ile Arg Gln Ala Pro Gly Lys Gly Leu Glu Trp
        35                  40                  45

Val Ser Ser Ile Ser Gly Ser Gly Ser Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Gly Phe Gly Tyr Phe Asp Tyr Trp Gly Gln Gly Thr
            100                 105                 110
```

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 132
<211> LENGTH: 213
<212> TYPE: PRT
<213> ORGANISM: Artificial Sequence
<220> FEATURE:
<223> OTHER INFORMATION: Synthetic Construct

<400> SEQUENCE: 132

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Val
            20                  25                  30
```

```
Tyr Trp Tyr Gln Gln Lys Pro Gly Lys Ala Pro Lys Leu Leu Ile Tyr
        35                  40                  45

Asp Ala Ser Ser Leu Glu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Val Gln Gly Leu Gln Thr Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 133
<211> LENGTH: 448
<212> TYPE: PRT
<213> ORGANISM: Artificial Sequence
<220> FEATURE:
<223> OTHER INFORMATION: Synthetic Construct

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Tyr Trp Ala Trp Ile Arg Gln Ala Pro Gly Lys Gly Leu Glu Trp
        35                  40                  45

Val Ser Ser Ile Ser Gly Ser Gly Ser Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Gly Phe Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 134
<211> LENGTH: 443
<212> TYPE: PRT
<213> ORGANISM: Artificial Sequence
<220> FEATURE:
<223> OTHER INFORMATION: Synthetic Construct

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95
```

Ala Arg His Pro Phe Ala Tyr Trp Gly Gln Gly Thr Leu Val Thr Val
100 105 110

Ser Ser Ala Ser Thr Lys Gly Pro Ser Val Phe Pro Leu Ala Pro Ser
115 120 125

Ser Lys Ser Thr Ser Gly Gly Thr Ala Ala Leu Gly Cys Leu Val Lys
130 135 140

Asp Tyr Phe Pro Glu Pro Val Thr Val Ser Trp Asn Ser Gly Ala Leu
145 150 155 160

Thr Ser Gly Val His Thr Phe Pro Ala Val Leu Gln Ser Ser Gly Leu
165 170 175

Tyr Ser Leu Ser Ser Val Val Thr Val Pro Ser Ser Ser Leu Gly Thr
180 185 190

Gln Thr Tyr Ile Cys Asn Val Asn His Lys Pro Ser Asn Thr Lys Val
195 200 205

Asp Lys Lys Val Glu Pro Lys Ser Cys Asp Lys Thr His Thr Cys Pro
210 215 220

Pro Cys Pro Ala Pro Glu Leu Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser His Glu Asp Pro Glu Val Lys Phe
260 265 270

Asn Trp Tyr Val Asp Gly Val Glu Val His Asn Ala Lys Thr Lys Pro
275 280 285

Arg Glu Glu Gln Tyr Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Ala Leu Pro Ala Pro Ile Glu Lys Thr Ile Ser Lys Ala
325 330 335

Lys Gly Gln Pro Arg Glu Pro Gln Val Tyr Thr Leu Pro Pro Ser Arg
340 345 350

Asp Glu Leu Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly
435 440

<210> SEQ ID NO 135
<211> LENGTH: 444
<212> TYPE: PRT
<213> ORGANISM: Artificial Sequence
<220> FEATURE:
<223> OTHER INFORMATION: Synthetic Construct

<400> SEQUENCE: 135

Glu Val Gln Leu Val Glu Ser Gly Gly Gly Leu Val Gln Pro Gly Gly
1 5 10 15

-continued

Ser Leu Arg Leu Ser Cys Ala Ala Ser Gly Phe Thr Phe Ser Gly Tyr
20 25 30

Ala Ile His Trp Val Arg Gln Ala Pro Gly Lys Gly Leu Glu Trp Ile
35 40 45

Gly Ile Ile Ser Pro Ser Gly Gly Gly Thr Lys Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg His Pro Phe Ala Tyr Trp Gly Gln Gly Thr Leu Val Thr Val
100 105 110

Ser Ser Ala Ser Thr Lys Gly Pro Ser Val Phe Pro Leu Ala Pro Ser
115 120 125

Ser Lys Ser Thr Ser Gly Gly Thr Ala Ala Leu Gly Cys Leu Val Lys
130 135 140

Asp Tyr Phe Pro Glu Pro Val Thr Val Ser Trp Asn Ser Gly Ala Leu
145 150 155 160

Thr Ser Gly Val His Thr Phe Pro Ala Val Leu Gln Ser Ser Gly Leu
165 170 175

Tyr Ser Leu Ser Ser Val Val Thr Val Pro Ser Ser Ser Leu Gly Thr
180 185 190

Gln Thr Tyr Ile Cys Asn Val Asn His Lys Pro Ser Asn Thr Lys Val
195 200 205

Asp Lys Lys Val Glu Pro Lys Ser Cys Asp Lys Thr His Thr Cys Pro
210 215 220

Pro Cys Pro Ala Pro Glu Leu Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser His Glu Asp Pro Glu Val Lys Phe
260 265 270

Asn Trp Tyr Val Asp Gly Val Glu Val His Asn Ala Lys Thr Lys Pro
275 280 285

Arg Glu Glu Gln Tyr Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Ala Leu Pro Ala Pro Ile Glu Lys Thr Ile Ser Lys Ala
325 330 335

Lys Gly Gln Pro Arg Glu Pro Gln Val Tyr Thr Leu Pro Pro Ser Arg
340 345 350

Asp Glu Leu Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Lys Leu Thr Val Asp Lys Ser Arg Trp Gln Gln
405 410 415

```
Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 136
<211> LENGTH: 220
<212> TYPE: PRT
<213> ORGANISM: Artificial Sequence
<220> FEATURE:
<223> OTHER INFORMATION: Synthetic Construct

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Val
                85                  90                  95

Ser Ser Pro Pro Glu Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 137
<211> LENGTH: 444
<212> TYPE: PRT
<213> ORGANISM: Artificial Sequence
<220> FEATURE:
<223> OTHER INFORMATION: Synthetic Construct

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Ala Ile His Trp Val Arg Gln Ala Pro Gly Lys Gly Leu Glu Trp Ile
        35                  40                  45
```

```
Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Tyr Asp Val Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 138
<211> LENGTH: 445

<212> TYPE: PRT
<213> ORGANISM: Artificial Sequence
<220> FEATURE:
<223> OTHER INFORMATION: Synthetic Construct

<400> SEQUENCE: 138

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Tyr Asp Val Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

-continued

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 139
<211> LENGTH: 218
<212> TYPE: PRT
<213> ORGANISM: Artificial Sequence
<220> FEATURE:
<223> OTHER INFORMATION: Synthetic Construct

<400> SEQUENCE: 139

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
            20                  25                  30

Gly Lys Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Glu Gln Ser Leu
                85                  90                  95

Glu Val Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```